US012774494B2

(12) United States Patent
Schwartz et al.

(10) Patent No.: US 12,774,494 B2
(45) Date of Patent: Oct. 27, 2026

(54) METHODS FOR PREDICTING RISK OF INTERSTITIAL PNEUMONIA

(71) Applicant: THE REGENTS OF THE UNIVERSITY OF COLORADO, A BODY CORPORATE, Denver, CO (US)

(72) Inventors: David A. Schwartz, Denver, CO (US); Tasha E. Fingerlin, Aurora, CO (US); Weiming Zhang, Aurora, CO (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 259 days.

(21) Appl. No.: 18/631,414

(22) Filed: Apr. 10, 2024

(65) Prior Publication Data

US 2024/0271215 A1 Aug. 15, 2024

Related U.S. Application Data

(60) Division of application No. 16/928,436, filed on Jul. 14, 2020, now Pat. No. 11,976,328, which is a division of application No. 14/813,559, filed on Jul. 30, 2015, now Pat. No. 10,752,952, which is a continuation of application No. PCT/US2014/016601, filed on Feb. 14, 2014.

(60) Provisional application No. 61/764,986, filed on Feb. 14, 2013.

(51) Int. Cl.
*C12Q 1/68* (2018.01)
*C12Q 1/6883* (2018.01)
*G01N 33/68* (2006.01)

(52) U.S. Cl.
CPC ....... *C12Q 1/6883* (2013.01); *G01N 33/6893* (2013.01); *C12Q 2600/156* (2013.01); *C12Q 2600/158* (2013.01); *G01N 2800/12* (2013.01); *G01N 2800/50* (2013.01); *G01N 2800/52* (2013.01); *G01N 2800/60* (2013.01)

(58) Field of Classification Search
None
See application file for complete search history.

(56) References Cited

U.S. PATENT DOCUMENTS

| | | | |
|---|---|---|---|
| 5,143,854 | A | 9/1992 | Pirrung et al. |
| 6,514,750 | B2 | 2/2003 | Bordenkircher et al. |
| 6,942,837 | B2 | 9/2005 | Frye et al. |
| 7,211,443 | B2 | 5/2007 | Woudenberg et al. |
| 7,235,406 | B1 | 6/2007 | Woudenberg et al. |
| 10,752,952 | B2 | 8/2020 | Schwartz et al. |
| 11,976,328 | B2 | 5/2024 | Schwartz et al. |
| 2002/0197646 | A1 | 12/2002 | Nogee et al. |
| 2012/0034214 | A1 | 2/2012 | Ho |
| 2016/0060701 | A1 | 3/2016 | Schwartz et al. |
| 2021/0040560 | A1 | 2/2021 | Schwartz et al. |

FOREIGN PATENT DOCUMENTS

| | | | |
|---|---|---|---|
| WO | 2011094345 | A1 | 8/2011 |
| WO | 2014127290 | A2 | 8/2014 |

OTHER PUBLICATIONS

Sharif et al; Arthritis and Rheumatism, Oct. 2011, vol. 63, abstract No. 2429.*
Assassi et al; Arthritis Research & Therapy, vol. 12, pp. 1-11, 2010.*
Hsu et al; Arthritis and Rheumatism, vol. 63, Mar. 2011, pp. 783-794.*
Extended European Search Report received for European Patent Application No. 17169995.2, mailed on Sep. 29, 2017, 9 pages.
Partial European Search Report received for European Application No. 14751579.5, mailed on Jun. 27, 2016, 6 pages.
Partial European Search Report received for European Application No. 22159018.5, Mailed on Jun. 22, 2022, 12 pages.
International Search Report and Written Opinion received for PCT Application No. PCT/US2014/016601, mailed on Sep. 22, 2014, 19 pages.
*Homo sapiens* Mucin 5B, Oligomeric Mucus/gel-forming (MUC5B), Refseqgene on Chromosome 11, NCBI Accession No. NG_031880.1, Feb. 18, 2021, 20 pages.
*Homo sapiens*, Database dbSNP No. rs3778337, 2012, 5 pages.
*Homo sapiens*, Database dbSNP No. rs10484326, 2012, 5 pages.
*Homo sapiens*, Database dbSNP No. rs2076295, 2012, 6 pages.
Submitted SNP details for rs12610495, dbSNP, NCBI, NLM, 2009.
Submitted SNP details for rs2109069, dbSNP, NCBI, NLM, 2009.
Assassi et al. (2010) "Predictors of Interstitial Lung Disease in Early Systemic Sclerosis: A Prospective Longitudinal Study of the Genisos Cohort", Arthritis Research & Therapy, 12(5):R1669 (11 pages).
Coche et al. (Feb. 2001) "Non-specific Interstitial Pneumonia Showing a "Crazy Paving" Pattern on High Resolution CT", The British Journal of Radiology, 74(878):189-191.
Fingerlin et al. (Jun. 2013) "Genome-wide Association Study Identifies Multiple Susceptibility Loci for Pulmonary Fibrosis", Nature Genetics, 45(6):613-620.
Genbank "*Homo sapiens* MUC2 gene, Virtual Transcript, partial sequence, genomic survey sequence", Accession No. DQ036653.1, 2 pages.
Golubicic et al. (2006) "Clinical Atlas of Interstitial Lung Disease", Acute Interstitial Pneumonia, ed:61-63.
Johnston, Mark (1998) "Gene Chips: Array of Hope for Understanding Gene Regulation", Current Biology, 8(5):R171-R174.
Larson et al. (Sep. 19, 2007) "Framingham Heart Study 100K project: genome-wide associations for cardiovascular disease outcomes", BMC Medical Genetics, 8(Suppl 1):9 pages.
(Continued)

*Primary Examiner* — Jehanne S Sitton
(74) *Attorney, Agent, or Firm* — Baker Botts L.L.P.

(57) ABSTRACT

Disclosed are biomarkers, methods and assay systems for the identification of poor prognosis of interstitial pneumonia (pulmonary fibrosis) in an individual diagnosed with suspected of having interstitial pneumonia.

16 Claims, 42 Drawing Sheets

(56) References Cited

OTHER PUBLICATIONS

Levy et al. (May 18, 2010) "Genome-Wide Association Identifies OBFC1 as a Locus Involved In Human Leukocyte Telomere Biology", Proceedings of the National Academy of Sciences of the United States of America, 107(20):9293-9298.

Mathai et al. (May 15, 2016) "Desmoplakin Variants Are Associated with Idiopathic Pulmonary Fibrosis", American Journal of Respiratory and Critical Care Medicine, 193(10):1151-1160.

Mushiroda et al. (Oct. 2008) "A Genome-Wide Association Study Identifies an Association of a Common Variant in TERT with Susceptibility to Idiopathic Pulmonary Fibrosis", Journal of Medical Genetics, 45(10):654-656.

Database dbSNP ss67222984, for rs2076295; NCBI, NLM, 2006, located at <https://www.ncbi.nlm.nih.gov/projects/SNP/snp ss.cgi?subsnp id=67222984>, 4 pages.

Database dbSNP ss153847632, for rs2076295, NCBI, NLM, 2009, located at <https://www.ncbi.nlm.nih.gov/projects/SNP/snp_ss.cgi?subsnp_id=153847632), 02 pages.

Peljto et al. (May 18, 2012) "Risk Variant for ILD does not Influence Systemic Sclerosis (SSc) Associated ILD", American Thoracic Society International Conference Abstract, A6605 page.

Peljto et al. (Dec. 1, 2012) "The Pulmonary Fibrosis-Associated MUC5B Promoter Polymorphism Does Not Influence the Development of Interstitial Pneumonia in Systemic Sclerosis", Chest, American College of Chest Physicians, 142(6):1584-1588.

Pinto et al. (2012) "Identification of New Cancer Biomarkers Based on Aberrant Mucin Glycoforms by in Situ Proximity Ligation", Journal of Cellular and Molecular Medicine, 16(7):1474-1484.

Rampazzo et al. (Oct. 8, 2002) "Mutation in Human Desmoplakin Domain Binding to Plakoglobin Causes a Dominant Form of Arrhythmogenic Right Ventricular Cardiomyopathy", American Journal of Human Genetics, 71(5):1200-1206.

Richards et al. (Apr. 16, 2008) "Oligonucleotide-Stabilized Ag Nanocluster Fluorophores", Journal of the American Chemical Society, 130(15):5038-5039.

Riise et al. (Apr. 1992) "A Bronchoscopic Brush Biopsy Study of Large Airway Mucosal Pathology in Smokers With Chronic Bronchitis and in Healthy Nonsmokers", European Respiratory Journal, 5(4):382-386.

Riise et al. (Aug. 1996) "Bronchial Brush Biopsies For Studies of Epithelial Inflammation in Stable Asthma and Nonobstructive Chronic Bronchitis", European Respiratory Journal, 9(8):1665-1671.

Ritter et al. (Nov. 29, 2005) "Characterization of Toll-Like Receptors In Primary Lung Epithelial Cells: Strong Impact Of The TLR3 Ligand Poly(I:C) On The Regulation of Toll-Like Receptors, Adaptor Proteins and Inflammatory Response", Journal of Inflammation, 2(16):15 Pages.

Roozbeh et al. (Oct. 2011) "A Functional IRF5 Variant Predicts Prognosis in Patients with Systemic Sclerosis", Arthritis and Rheumatism, abstract No. 2429, 63:1 page.

Seibold et al. (2011) "A Common MUC5B Promoter Polymorphism and Pulmonary Fibrosis", The New England Journal of Medicine, 364(16): 1503-1512.

Sharif et al. (Mar. 22, 2012) "IRF5 Polymorphism Predicts Prognosis in Patients with Systemic Sclerosis", Annals of the Rheumatic Diseases, 71(7):1197-1202.

Smelaya et al. (Apr. 2011) "Genetic Polymorphism and the Rate of Development of Complications in Pneumonia of Varying Genesis", General Reanimatology, 7(2):10-16.

Tazelaar et al. (Mar. 2011) "Desquamative Interstitial Pneumonia", Histopathology, 58(4):509-516.

Thery et al. (Apr. 2006) "Isolation and Characterization of Exosomes From Cell Culture Supernatants and Biological Fluids", Current Protocols in Cell Biology, Chapter 3:Unit 3.22 (pp. 29).

Vosch et al. (Jul. 31, 2007) "Strongly Emissive Individual Dna-encapsulated Ag Nanoclusters As Single-molecule Fluorophores", Proceedings of the National Academy of Sciences of the United States of America, 104(31):12616-12621.

Wells et al. (Oct. 2003) "Respiratory Bronchiolitis-associated Interstitial Lung Disease", Seminars in Respiratory and Critical Care Medicine, 24(5):585-594.

White et al. (Jul. 2007) "Bronchiolitis Obliterans Organizing Pneumonia", Critical Care Nurse, 27(3):53-66.

Yang et al. (Oct. 2012) "Desmoplakin Acts as a Tumor Suppressor by Inhibition of the Wnt/β-catenin Signaling Pathway in Human Lung Cancer", Carcinogenesis, 33(10):1863-1870.

* cited by examiner

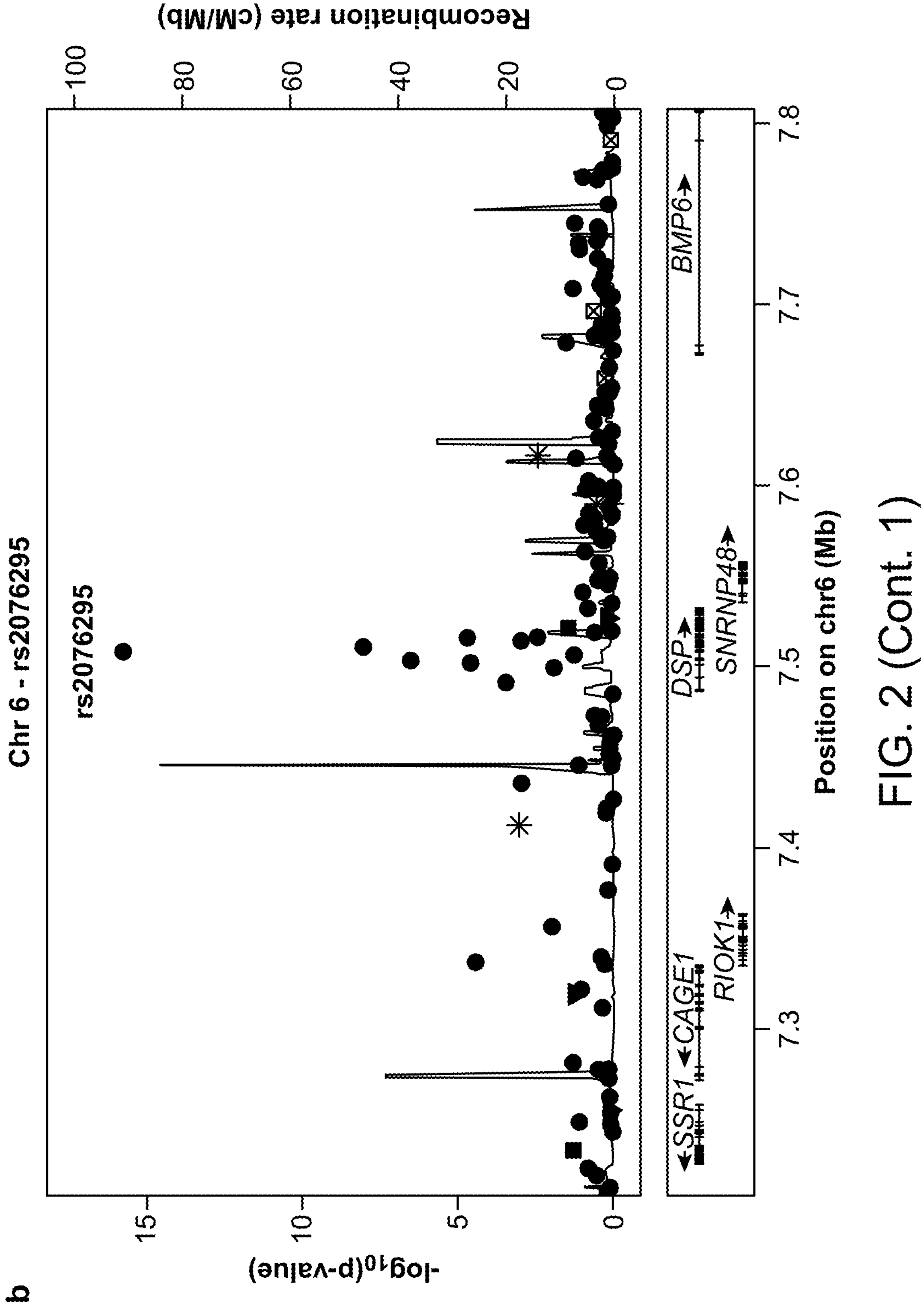
FIG. 2 (Cont. 1)

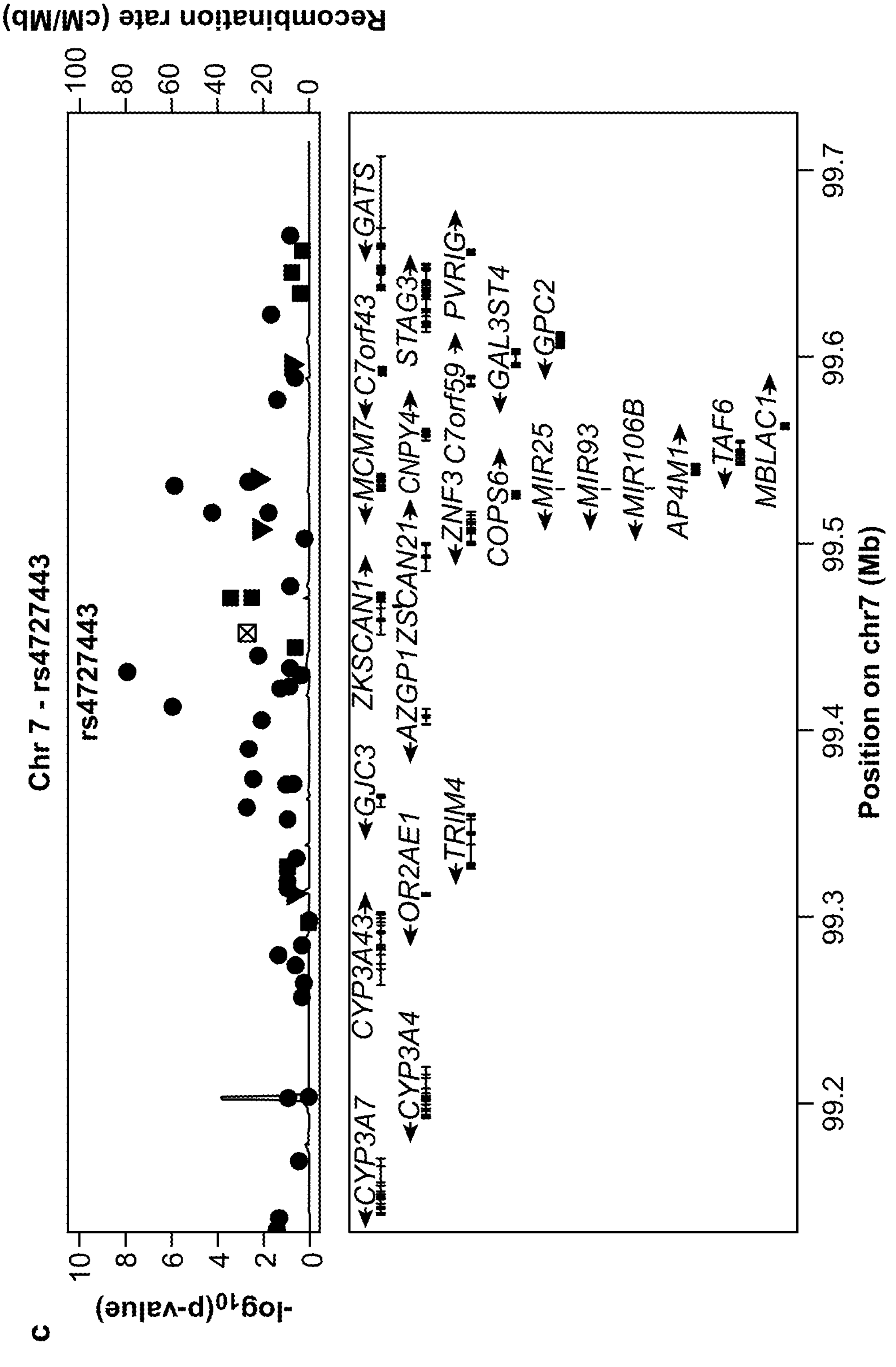
FIG. 2 (Cont. 2)

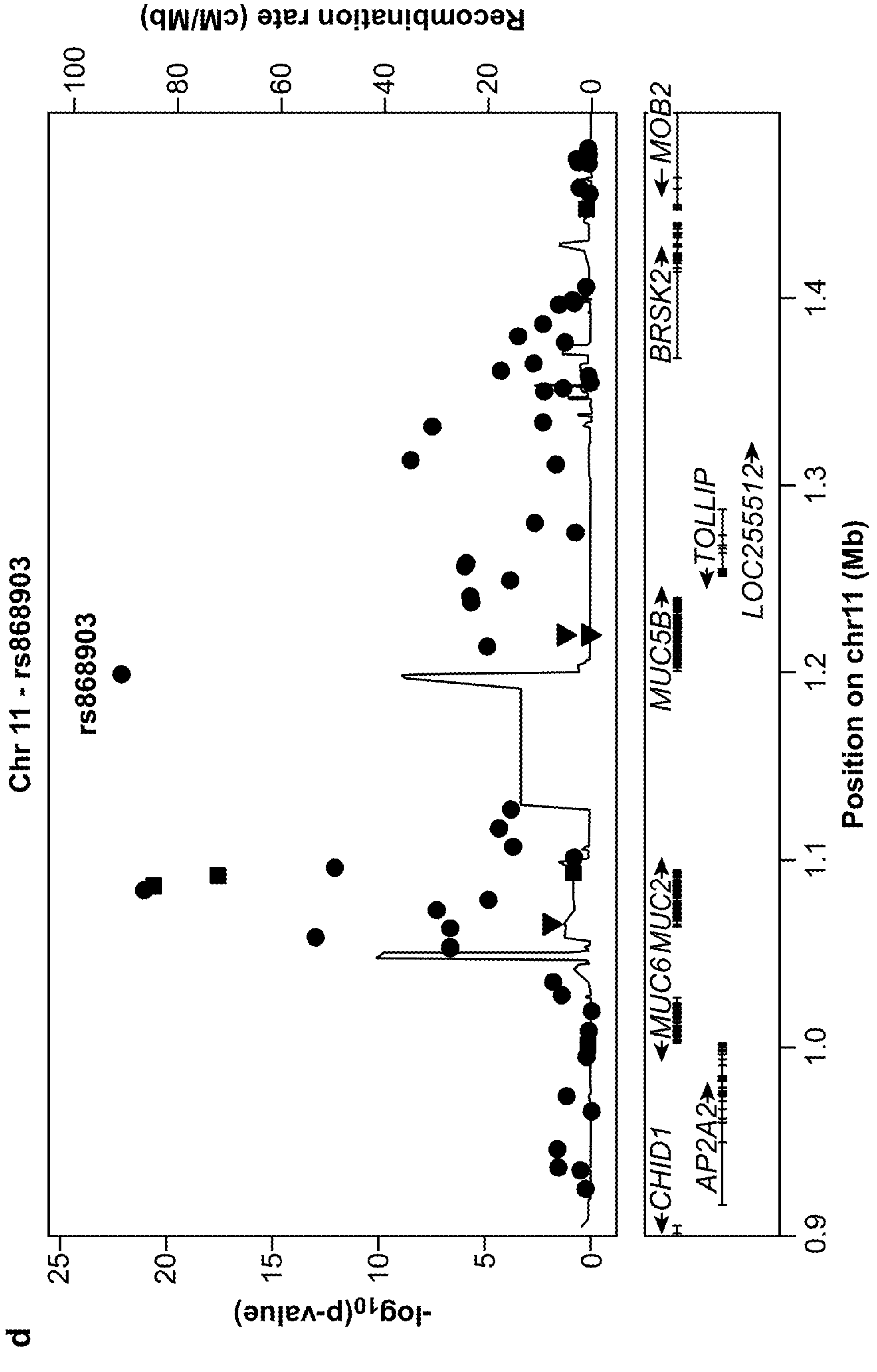
FIG. 2 (Cont. 3)

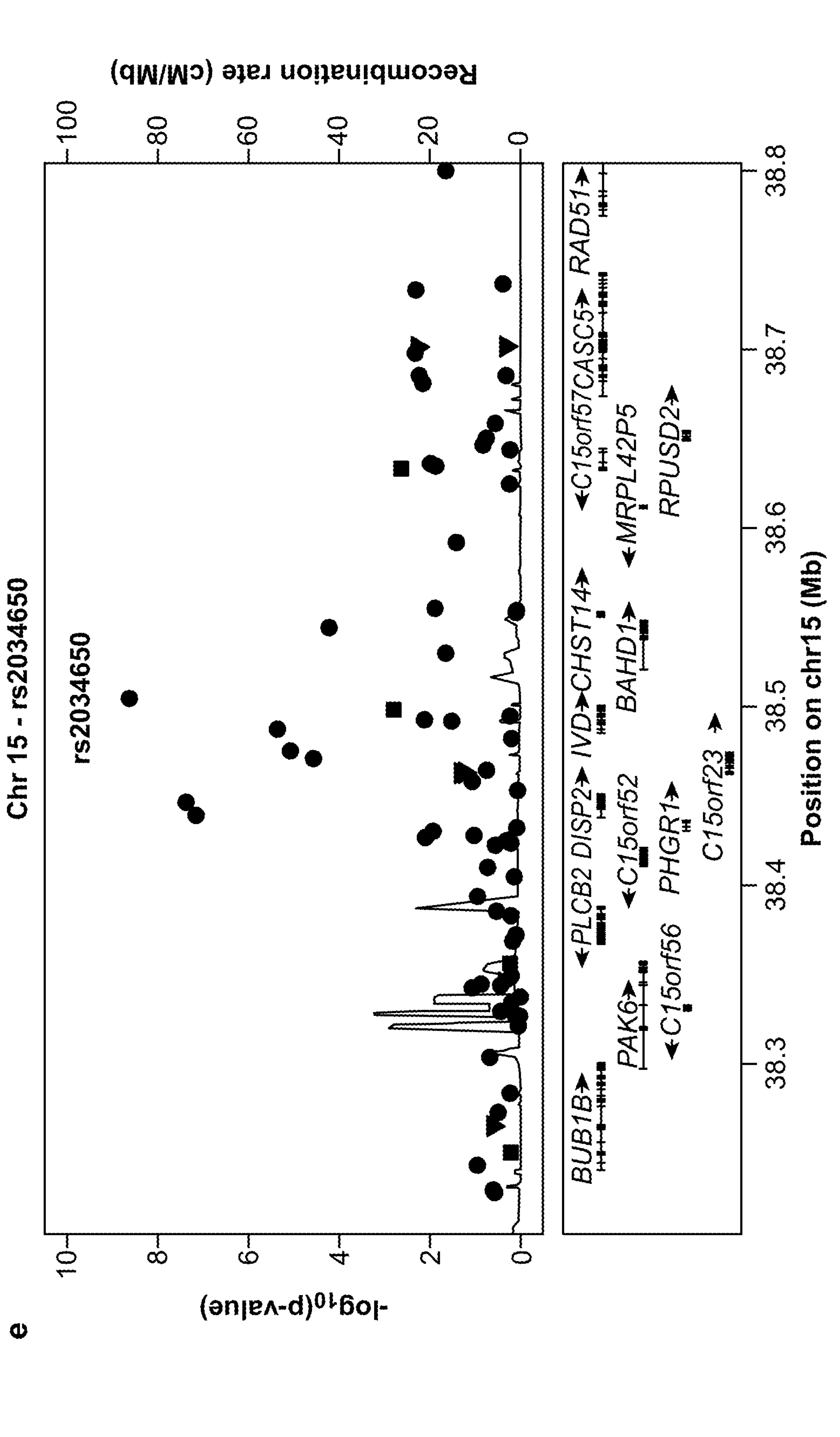
FIG. 2 (Cont. 4)

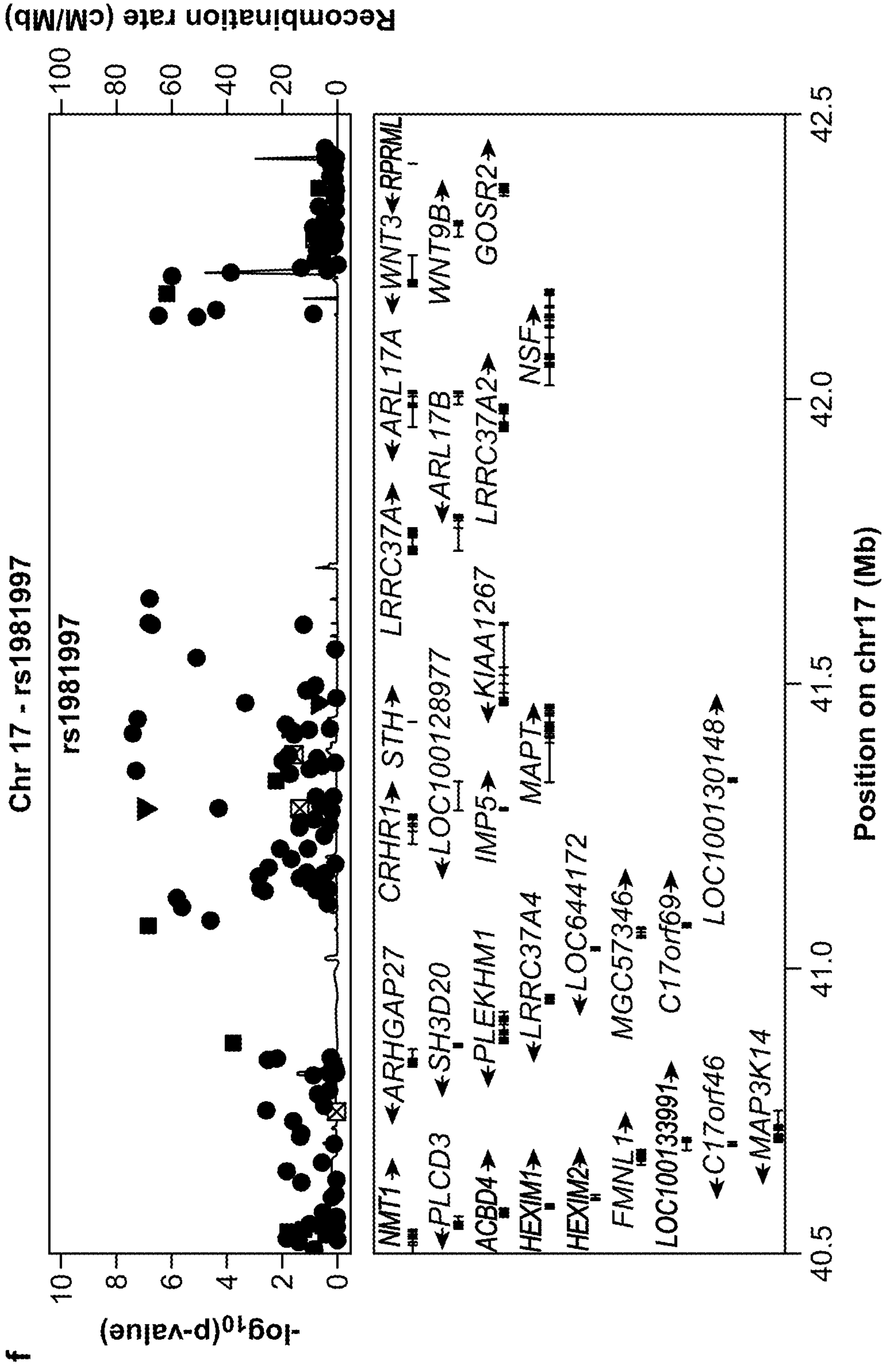
FIG. 2 (Cont. 5)

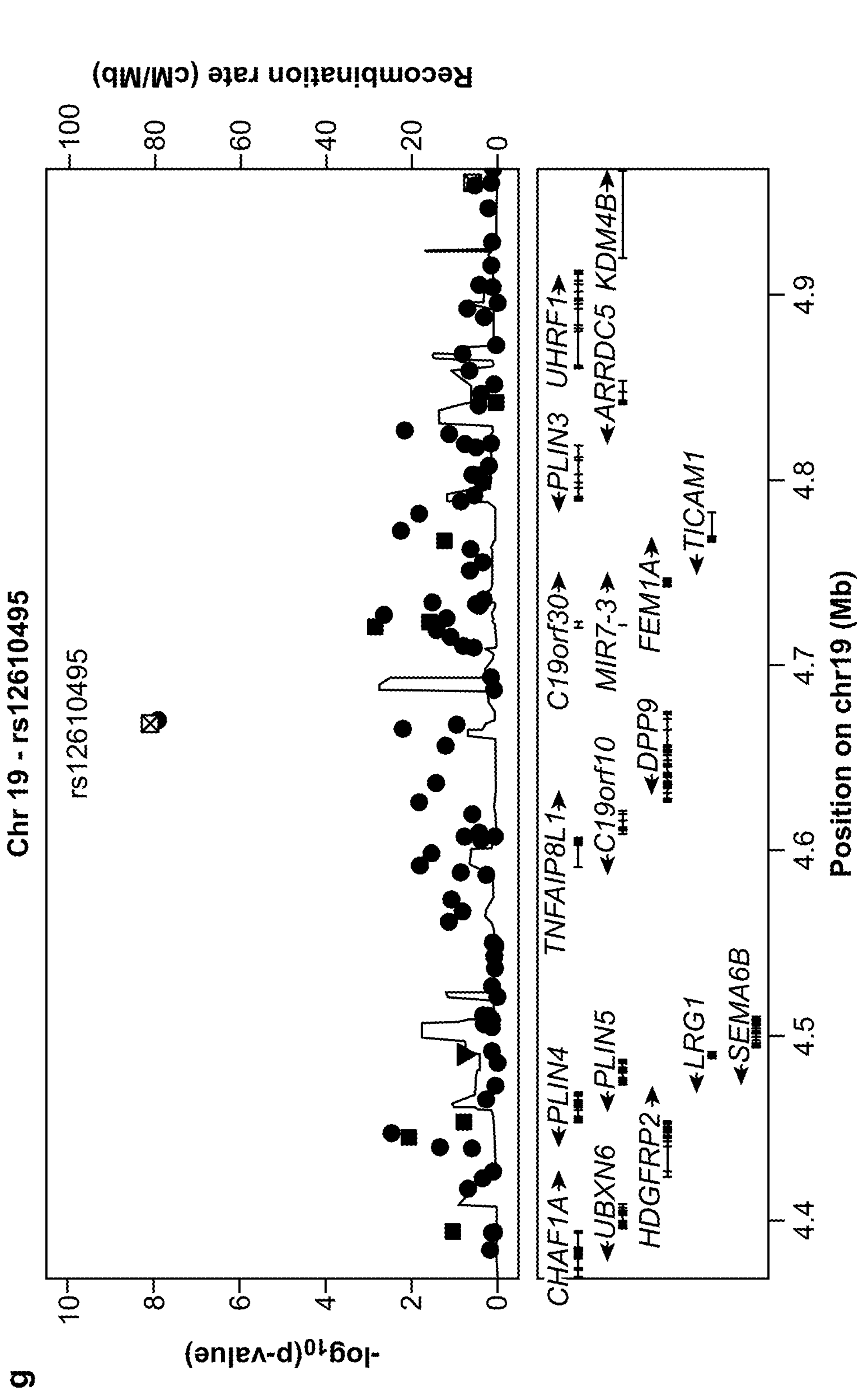
FIG. 2 (Cont. 6)

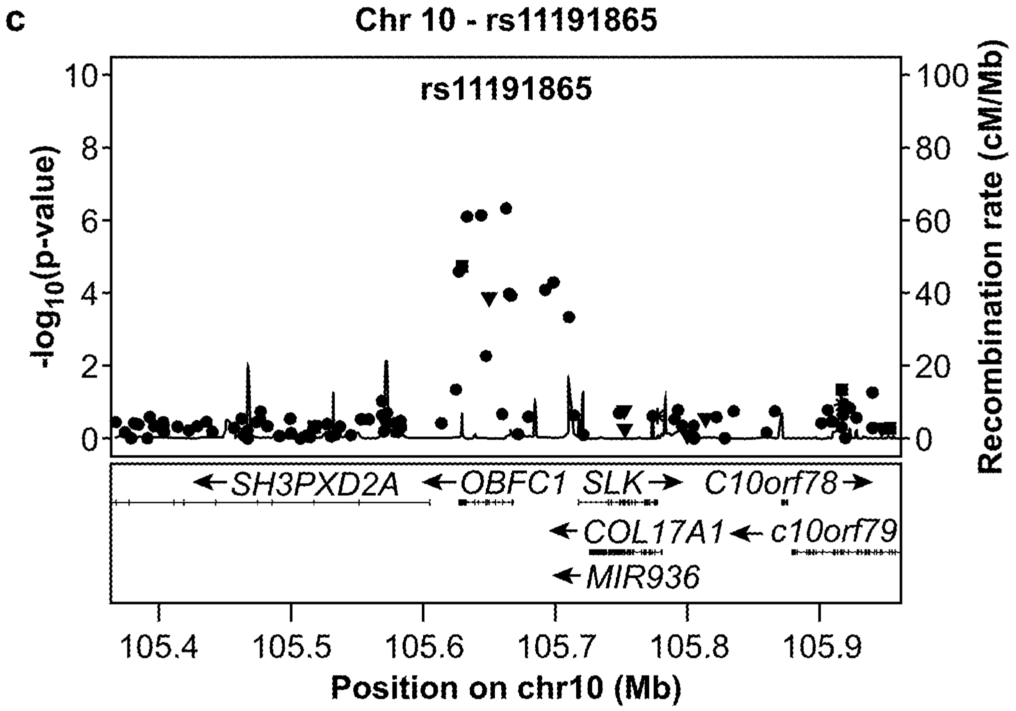
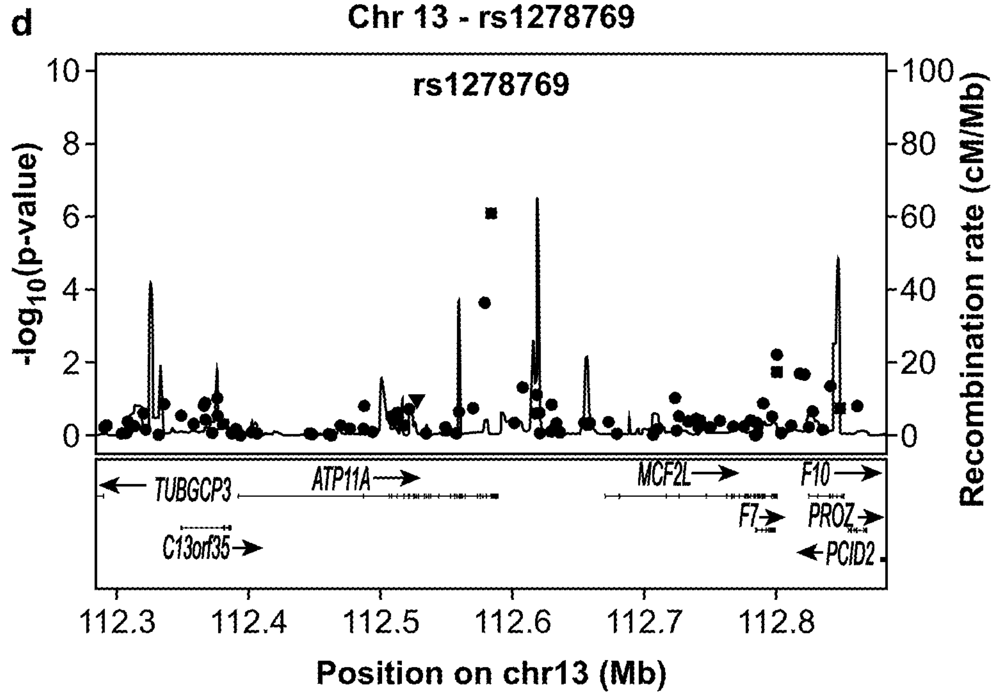
FIG. 3 (Cont.)

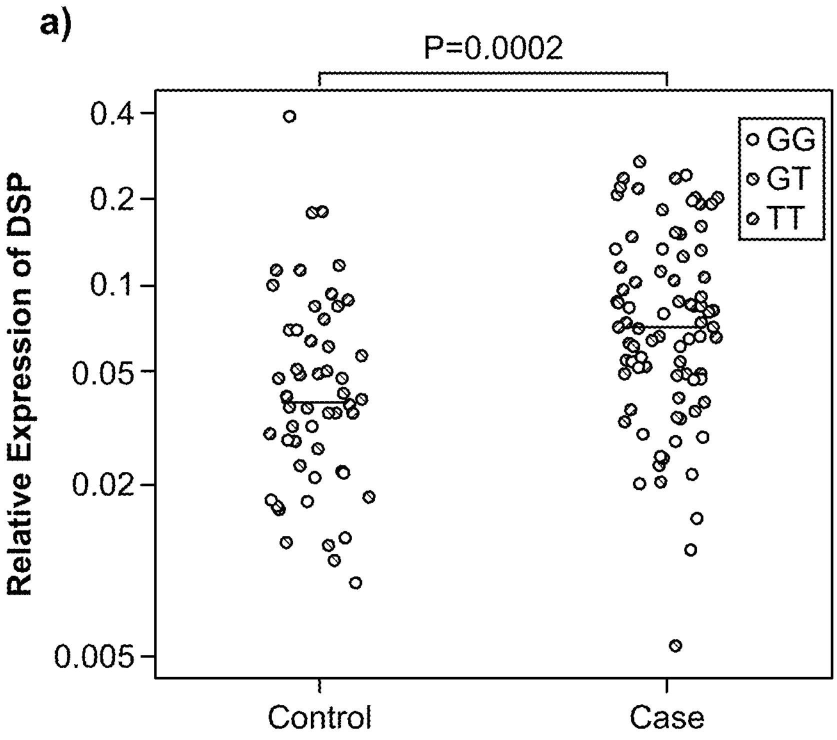
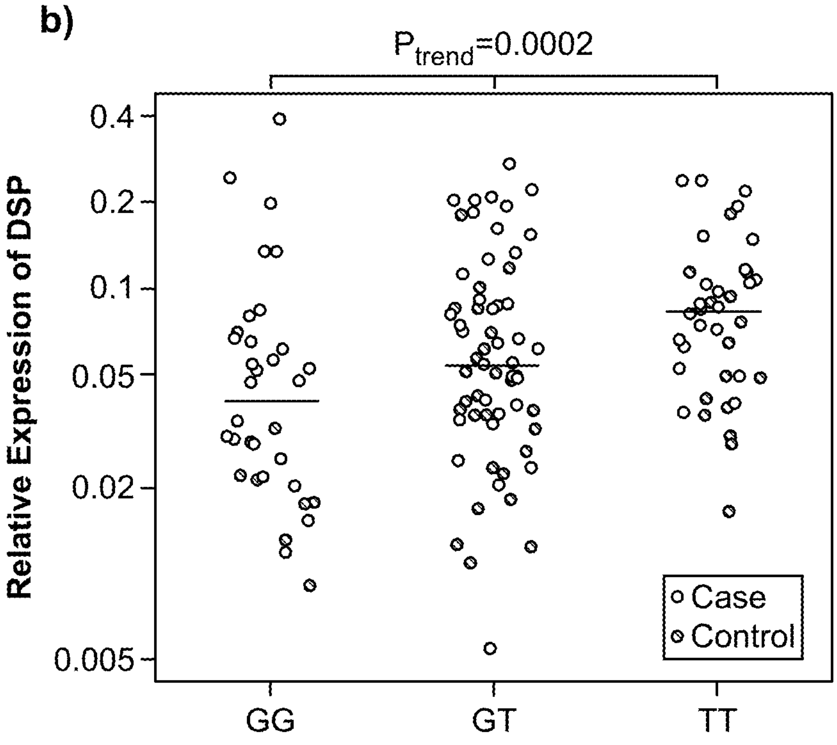
FIG. 4

MUC5B Promoter SNP and FIP/IPF

| | GG | GT | TT |
|---|---|---|---|
| Controls | 272 (82%) | 58 (18%) | 2 (1%) |
| FIP Cases | 35 (41%) | 46 (53%) | 5 (6%) |
| IPF Cases | 186 (34%) | 332 (60%) | 37 (7%) |

Odds Ratios

| | GT | TT |
|---|---|---|
| FIP Cases | 6.2 (3.7-10.4) | 19.4 (3.6-103.9) |
| IPF Cases | 8.4 (6.0-11.7) | 27.0 (6.4-113.6) |

Confirmation of MUC5B Promoter SNP and IPF

| | Pittsburgh | | Chicago | | All Subjects | |
|---|---|---|---|---|---|---|
| | IPF (n=272) | Control (n=166) | IPF (n=95) | Control (n=636) | IPF (n=367) | Control (n=803) |
| Minor allele (T) | 33.27% | 10.84% | 35.79% | 11.16% | 33.90% | 11.10% |
| Allelic Association (P-Value) | $8.6 \times 10^{-14}$ | | 1.8 x 10-19 | | $4.1 \times 10^{-40}$ | |
| Genotype | | | | | | |
| GG | 108 (39.7%) | 132 (79.5%) | 36 (37.9%) | 504 (79.3%) | 144 (39.2%) | 636 (79.3%) |
| GT | 147 (54.0%) | 32 (19.3%) | 50 (52.6%) | 122 (19.2%) | 197 (53.7%) | 154 (19.2%) |
| TT | 18 (6.3%) | 2 (1.2%) | 9 (9.5%) | 10 (1.5$) | 26 (7.1%) | 12 (1.5%) |
| Genotype Association (P-Value) | $3.9 \times 10^{-15}$ | | $1.0 \times 10^{-17}$ | | $8.9 \times 10^{-41}$ | |
| OR (95% CI) | | | | | | |
| GT vs. GG | 5.6 (3.5-8.9) | | 5.7 (3.6-9.2) | | 5.7 (4.3-7.5) | |
| TT vs GG | 10.4 (2.3-46.0) | | 12.6 (4.8-33.0) | | 9.6 (4.7-19.4) | |
| HEW (p-value) | 0.0003 | 0.9691 | 0.1572 | 0.407 | 0.0002 | 0.4472 |

**Stock. *Thorax* 2013 (in press)**
OR=4.9 (3.4-7.0); P=$2.0 \times 10^{-17}$

Naftali Kaminski and Skip Garcia Zhang.
***NEJM* 2011; 364:1576**

FIG. 10

*MUC5B* Promoter SNP is Associated with Improved Survival [InterMune (N=438) vs. Chicago (N=148)]

| | *MUC5B* | Intermune (17% deaths) | | Chicago (43% deaths) | |
|---|---|---|---|---|---|
| Univariable | | HR (95% CI) | P value | HR (95% CI) | P value |
| | GT | 0.50 (0.2-0.8) | 0.001 | 0.49 (0.3-0.8) | 0.004 |
| | TT | 0.25 (0.1-0.6) | | 0.24 (0.1-0.6) | |

FIG. 12

*MUC5B* Promoter SNP and Pulmonary Fibrosis in the Framingham Population

N=60 (24%) N=20 (8%) N=6 (2%)

*MUC5B* Promoter SNP and Pulmonary Fibrosis in the Framingham Population [N=254 over 50 y/o]

| High Resolution Chest CT Scan | Wild Type (N=128) | Heterozygote (N=120) | Homozygote (N=6) | Odds Ratio per variant T allele (95% CI) |
|---|---|---|---|---|
| Interstitial Lung Abnormalities | 16% | 29% | 83% | 2.5 (1.4-4.4) |
| Definite Pulmonary Fibrosis | 4% | 15% | 50% | 4.9 (1.7-13.8) |
| Advanced Pulmonary Fibrosis | <1% | 4% | 33% | 9.0 (1.0-81.8) |

- ≈3% > 50 years of age have pulmonary fibrosis
- ≈15% of individuals with the *MUC5B* variant will have pulmonary fibrosis in the general population (biomarker)
- *MUC5B* variant is associated with increasing radiologic evidence of pulmonary fibrosis

FIG. 21

GWAS in fibrosing IIP [Discovery Cases]

| | Genotyped Population (N=1914) | |
|---|---|---|
| | Sporadic | Familial |
| IPF | 1055 (55%) | 445 (24%) |
| NSIP | 51 (3%) | 60 (3%) |
| COP | 3 (<1%) | 3 (<1%) |
| RB-ILD | 8 (<1%) | 3 (<1%) |
| DIP | 5 (<1%) | 0 |
| Unclassified | 226 (12%) | 55 (3%) |

GWAS in fibrosing IIP [Replication Population]

| | Genotyped Population (N=1027) | | Replication Population (N=876) | |
|---|---|---|---|---|
| | Sporadic | Familial | Sporadic | Familial |
| IPF | 881 (86%) | 32 (3%) | 749 (86%) | 25 (3%) |
| NSIP | 66 (6%) | 1 (<1%) | 58 (7%) | 1 (<1%) |
| COP | 6 (1%) | 0 | 5 (1%) | 0 |
| RB-ILD | 3 (<1%) | 0 | 2 (<1%) | 0 |
| DIP | 6 (1%) | 0 | 5 (1%) | 0 |
| Unclassified | 31 (3%) | 1 (<1%) | 30 (3%) | 1 (<1%) |

1890 NHW Controls – COPDGene

FIG. 27

Effect of Ancestry on Chromosome 17q21

| SNP | Discovery GWAS | | Replication Population | | Controlled for H1/H2 Haplotypes | |
|---|---|---|---|---|---|---|
| | OR (95% CI) | *P-value* | OR (95% CI) | *P-value* | OR (95% CI) | *P-value* |
| rs17690703 | 0.78 (0.71, 0.86) | $3.4\times10^{-05}$ | 0.75 (0.65,0.86) | $5.0\times10^{-05}$ | 1.23 (0.98,1.56) | 0.08 |
| rs415430 | 0.72 (0.65, 0.80) | $7.9\times10^{-07}$ | 0.72 (0.62,0.84) | $3.9\times10^{-05}$ | 1.17 (0.79,1.7) | 0.35 |
| rs1981997 | 0.71 (0.64,0.78) | $2.5\times10^{-08}$ | 0.67 (0.58,0.79) | $4.7\times10^{-07}$ | 1.97 (0.81,1.58) | 0.46 |
| rs2532274 | 0.72 (0.65, 0.80) | $1.3\times10^{-07}$ | 0.70 (0.60,0.81) | $3.0\times10^{-06}$ | 1.39 (0.79,1.12) | 0.49 |
| rs2532269 | 0.71 (0.64, 0.79) | $9.6\times10^{-08}$ | 0.66 (0.57,0.77) | $1.6\times10^{-07}$ | 0.62 (0.79,2.45) | 0.26 |
| rs2668692 | 0.71 (0.64, 0.79) | $1.0\times10^{-07}$ | 0.67 (0.58,0.78) | $3.4\times10^{-07}$ | 0.39 (0.20,1.98) | 0.42 |
| rs169201 | 0.71 (0.64, 0.79) | $2.3\times10^{-07}$ | 0.70 (0.60,0.82) | $9.0\times10^{-06}$ | 0.39 (1.09,1.93) | 0.01 |
| rs199533 | 0.72 (0.64, 0.80) | $5.2\times10^{-07}$ | 0.70 (0.59,0.81) | $6.2\times10^{-06}$ | 0.44 (1.08,1.66) | 0.01 |

FIG. 31

MUC5B Promoter SNP (rs35705950) and IIP

| SNP | Joint Analysis | |
|---|---|---|
| | OR (95% CI) | *P-value* |
| rs35705950 | 4.51 (3.91, 5.21) | $7.2x10^{-95}$ |

FIG. 32

METHODS FOR PREDICTING RISK OF INTERSTITIAL PNEUMONIA

CROSS-REFERENCES TO RELATED APPLICATIONS

This application is a division of U.S. patent application Ser. No. 16/928,436, filed Jul. 14, 2020, which is a division of U.S. patent application Ser. No. 14/813,559, filed Jul. 30, 2015, now U.S. Pat. No. 10,752,952, issued Aug. 25, 2020, which is a continuation of International Application No. PCT/US2014/016601, filed Feb. 14, 2014, which claims priority to U.S. Provisional Application No. 61/764,986, filed Feb. 14, 2013, the disclosure of which are incorporated herein in their entirety.

STATEMENT OF GOVERNMENTAL SUPPORT

This invention was made with Government support under grant numbers R01-HL095393, R01-HL097163, P01-HL092870, RC2-HL101715, U01-HL089897, U01-HL089856, U01-HL108642, and P50-HL0894932 awarded by the National Heart, Lung and Blood Institute and grant number 1101BX001534 awarded by the Veterans Administration. The Government has certain rights in this invention.

FIELD OF THE INVENTION

The present disclosure generally relates to biomarkers, methods and assay kits for identifying and evaluating the prognosis of individuals with or suspected of having interstitial lung disease.

BACKGROUND OF THE INVENTION

The idiopathic interstitial pneumonias (IIPs) represent a group of lung diseases commonly characterized by pulmonary fibrosis or progressive scarring of the alveolar interstitium which can lead to significant morbidity and mortality due to hypoxemic respiratory insufficiency. While some forms of pulmonary fibrosis are associated with known environmental exposures (e.g. asbestos), drug toxicity, radiation exposures, or collagen vascular diseases (e.g. scleroderm(a), the IIPs have no known etiology. The most common and severe IIP is idiopathic pulmonary fibrosis (IPF) which has a median survival of 2-3 years after diagnosis. There are no IPF pharmacologic therapies approved for use in the United States, and lung transplantation is the only intervention to prolong life. Although all IIPs have a variable clinical course, they often progress to end-stage lung disease and death. While it appears that the risk of IIP is likely determined by multiple genetic variants and environmental toxins, the causes of IIP are only beginning to emerge.

There is a need for identification of genetic variants, acting independently or in combination, that are indicative of different histologic types of interstitial lung diseases, as well as methods of identifying these genetic variants in an individual, diagnosed with, or suspected of being predisposed to the development of, interstitial lung disease. Provided herein are solutions to these and other problems in the art.

BRIEF SUMMARY OF THE INVENTION

Provided herein are methods and materials for determining whether a subject (i.e. individual) has or is at risk of developing an interstitial lung disease such as interstitial pneumonia (e.g., FIP, IPF, or IIP). Also provided are methods of determining the prognosis of an individual diagnosed with or suspected of having an interstitial lung disease (e.g. an individual with a familial history of interstitial pneumoni (a). In some embodiments, the interstitial lung disease is a fibrotic interstitial pneumonia such as idiopathic pulmonary fibrosis or familial interstitial pneumonia. In some embodiments, the individual is a human.

Also provided herein are methods of detecting a genetic variant (e.g. a single nucleotide polymorphism) in a human subject with an interstitial lung disease. The method includes detecting a polymorphism described below in a biological sample of the human subject. In some embodiments, the method includes obtaining and/or assaying the biological sample. As described below, in some embodiments, the polymorphism is rs868903, rs7934606, rs6421972, rs7480563, rs7942850, rs4077759, rs2334659, rs7122936, rs2301160, rs3829223 or rs2857476. In some embodiments, the genetic variant is selected from any one of the SNPs listed in Tables 1 and 2.

Also provided herein are methods of treating an interstitial lung disease in a human subject in need of such treatment, e.g., in an subject diagnosed as having or likely having an interstitial lung disease using the methods described herein. The method includes detecting a genetic variant as described below in a biological sample of the human subject and administering an effective amount of an interstitial lung disease treatment. In some embodiments, the method includes obtaining and/or assaying the biological sample. As described below, in some embodiments, the genetic variant is the polymorphism rs868903, rs7934606, rs6421972, rs7480563, rs7942850, rs4077759, rs2334659, rs7122936, rs2301160, rs3829223 and/or rs2857476. In some embodiments, the genetic variant is selected from any one of the SNPs listed in Tables 1 and 2.

One embodiment of the disclosure relates to a method that includes detecting one or more genetic variants (e.g. a polymorphism in a marker gene or plurality of marker genes) in a biological sample from an individual. The polymorphisms are selected from rs2736100, rs2076295, rs3778337, rs4727443, rs868903, rs7934606, rs6421972, rs7480563, rs7942850, rs4077759, rs2334659, rs7122936, rs2034650, rs1992272, rs1981997, rs17563986, rs8070723, rs12610495, rs2109069, rs1379326, rs1881984, rs10936599, rs1997392, rs6793295, rs2609255, rs2853676, rs10484326, rs10748858, rs2067832, rs11191865, rs2301160, rs3829223, rs2857476, rs1278769, rs1007177, rs10518693, rs393152, rs12373139, rs17690703, rs2532274, rs2532269, rs2668692, rs169201, rs199533, and rs415430.

In a related embodiment, the polymorphism is selected from the group consisting of rs2736100, rs2076295, rs3778337, rs4727443, rs868903, rs7934606, rs6421972, rs7480563, rs7942850, rs4077759, rs2334659, rs7122936, rs2034650, rs1992272, rs1981997, rs17563986, rs8070723, rs12610495, and rs2109069. In some embodiments, the detecting comprises detecting at least 1, 2, 3, 4, 5, 6, 7, 8, 9, 10, 11, 12, 13, 14, 15, 16, 17, 18 or 19 of these polymorphisms in any combination.

In related embodiments, the polymorphism is selected from the group consisting of rs868903, rs7934606, rs6421972, rs7480563, rs7942850, rs4077759, rs2334659, rs7122936, rs2301160, rs3829223, and rs2857476. In some embodiments, the detecting comprises detecting at least 1, 2, 3, 4, 5, 6, 7, 8, 9, 10, or 11 of these polymorphisms in any combination.

In related embodiments, the polymorphism is selected from the group consisting rs2736100, rs868903, rs1881984 and rs2853676. In some embodiments, the detecting comprises detecting at least 1, 2, 3, or 4 of these polymorphisms in any combination.

In related embodiments, the polymorphism is rs868903.

In a related embodiment, the polymorphism is selected from the group consisting of rs1379326, rs1881984, rs10936599, rs1997392, rs6793295, rs2609255, rs2853676, rs10484326, rs10748858, rs2067832, rs11191865, rs2301160, rs3829223, rs2857476, rs1278769, rs1007177, rs10518693, rs393152, rs12373139, rs17690703, rs2532274, rs2532269, rs2668692, rs169201, rs199533, and rs415430. In some embodiments, the detecting comprises detecting at least 1, 2, 3, 4, 5, 6, 7, 8, 9, 10, 11, 12, 13, 14, 15, 16, 17, 18, 19, 20, 21, 22, 23, 24, 25, 26, 27, 28, or 29 of these polymorphisms in any combination.

In related embodiments, the method includes detecting one or more additional polymorphisms in the biological sample from the individual wherein the polymorphism is rs35705950.

In related embodiments, the individual may be homozygous for one or more of the polymorphisms recited above. In other related embodiments, the individual may be heterozygous for one or more of the polymorphisms recited above.

In each of these embodiments, the detection of at least one of the polymorphisms is indicative of an individual that has a modified risk of developing interstitial lung disease (e.g. the individual has an elevated or reduced risk of developing interstitial lung diseas(e).

In some embodiments, the individual is at elevated risk of developing sporadic interstitial lung disease. In some embodiments, the individual is at elevated risk of developing familial interstitial lung disease. In some embodiments, the individual is at elevated risk of developing idiopathic pulmonary fibrosis (IPF). In other embodiments, the individual is at reduced risk of developing sporadic IIP. In some embodiments, the individual is at reduced risk of developing familial IIP. In some embodiments, the individual is at reduced risk of developing idiopathic pulmonary fibrosis (IPF).

In these embodiments, the detection of at least one of the polymorphisms may be indicative of the progression of the individual's interstitial lung disease. In some embodiments, the detection of at least one of the polymorphisms may be indicative of a lack of progression of the interstitial lung disease, or a slow progression of the interstitial lung diseasein the individual. In some embodiments, the detection of at least one of the polymorphisms may be indicative of a rapid progression of the interstitial lung diseasein the individual.

In each of these embodiments, the presence of one or more of the polymorphisms may be compared to a control, such as a standard set or reference group of polymorphisms that have been associated with the risk of developing an interstitial lung disease, a diagnosis of a specific interstitial lung disease, a progression of interstitial lung disease, a clinical outcome of interstitial lung diseasein an individual, or responsiveness to a treatment of interstitial lung disease, as determined according to a statistical procedure for risk prediction.

In one embodiment of this method, the presence of the polymorphisms can be detected by obtaining a genomic DNA sample from the individual and determining the presence or absence of the polymorphism at the specific locus. In some embodiments, the presence or absence of the polymorphism is determined by at least one method selected from multiplexed locus-specific PCR amplification, multiplexed single-based extension (SB(E) from locus-specific amplicons, and multiplexed resolution of SBE products using matrix-assisted laser desorption/ionization time-of-flight (MALDI-TOF) mass spectrometry.

In another embodiment of this method, the presence of the marker is determined by obtaining RNA from the biological sample (e.g. tissue sampl(e); generating cDNA from the RNA; optionally amplifying the cDNA with probes or primers for genetic locations containing the polymorphisms; determining the presence or absence of at least one of the polymorphisms in the biological sample.

These methods may include comparing the presence of one or more of the polymorphisms in the biological sample to a standard set of one or more polymorphism(s) that has been correlated with the development of an interstitial lung disease or the progression of the disease in a diagnosed individual (e.g. one of stable IIP disease or slow, severe or rapidly progressing IIP), or a control or standard set of one or more polymorphism(s) that has been correlated with not developing interstitial lung disease or not developing pathological symptoms of the disease, such as lung scarring (fibrosis). In this embodiment, the individual is identified as at modified risk (e.g. at elevated or reduced risk) to develop or progress (e.g. progress rapidly, slowly or not progress) with the development of interstitial lung disease or pathological manifestations of the interstitial lung disease disease (lung scarring (fibrosis)) if the presence of the one or more polymorphisms matches the standard set of one or more polymorphism(s) that has been correlated with the risk of developing interstitial lung disease or the severity or extent of progression of the interstitial lung disease disease. Alternatively, the individual may be predicted to have a reduced risk or not develop interstitial lung disease disease or not clinically progress with pathological manifestations of the interstitial lung disease disease, if the presence of the one or more polymorphisms does not match the standard set of one or more polymorphism(s).

An embodiment of these methods of determining if an individual is at elevated or reduced risk of developing interstitial lung disease, or is at elevated or reduced risk of progressing rapidly with the development of lung scarring (fibrosis), includes detecting the presence of at least one polymorphism selected from the polymorphism(s) listed above, such as any one or more of the SNPs listed in Tables 1 and 2, e.g., rs35705950, rs868903, rs2736100, rs2853676, rs1881984, rs2736100, rs2609255, rs10484326, rs2076295, rs10748858, rs2067832, rs11191865, rs1278769, rs12610495, and rs2109069. The presence of at least one of the polymorphisms is indicative of whether an individual will develop or progress (e.g. progress rapidly) with the development of lung scarring (fibrosis) and interstitial lung disease.

These embodiments may include performing a follow-up step with the individual, such as a clinical evaluation, a computed tomogram of the chest (CT scan of the chest) and review by a radiologist.

Another embodiment of the present disclosure is an assay system for predicting the need for treatment (e.g., palliative therapy or lung transplant) in an individual diagnosed with interstitial lung disease. The assay system includes a means to detect the presence of at least one polymorphism selected from the group consisting of rs35705950, rs868903, rs2736100, rs2853676, rs1881984, rs2736100, rs2609255, rs10484326, rs2076295, rs10748858, rs2067832, rs11191865, rs1278769, rs12610495, and rs2109069. In one embodiment of the assay system, the means to detect the polymorphisms includes a nucleic acid probe having at least 10 to 50 contiguous nucleic acids of the nucleic acid sequence comprising the polymorphism. The nucleic acid probes are preferably disposed on an assay surface that may include a chip, array, or fluidity card. The assay system can include a control selected from information containing a predetermined polymorphism or set of polymorphisms that has been correlated with the risk of developing interstitial lung disease, or the progression of interstitial lung disease or increased or decreased life expectancy in interstitial lung disease patients.

In any one of the embodiments of the present disclosure, the step of detecting can include, but is not limited to, using a nucleotide probe that hybridizes to at least one genetic location comprising the polymorphism. In one aspect, the probe may be a chimeric probe (e.g., that hybridizes to more than one of the polymorphism locations). In another aspect, the step of detecting can include detecting the number of copies of the polymorphism in one or more cells in the biological sample (i.e., determining whether the individual is heterozygous or homozygous in the polymorphism).

In one aspect of this embodiment, the step of comparing comprises comparing the presence of one or more of the polymorphisms in the biological sample to a control set of the polymorphisms from patients with rapidly progressing interstitial lung disease, or a control set of the polymorphisms from patients with slow or no progression of interstitial lung disease.

In any one of the embodiments of the disclosure, an individual may be selected for their risk of developing and interstitial lung disease or for diagnosis or prognosis (e.g. whether predicted to not progress or to progress slowly or rapidly with pathological characteristics of interstitial lung disease, such as lung scarring) through evaluation of a clinical covariate including histological appearance and/or marker(s) in the individual's lung tissue.

Also provided herein are methods of detecting a level of expression of one or more marker genes (e.g., biomarkers) in a human subject with an interstitial lung disease. The method includes detecting a level of one or more marker genes described below in a biological sample of the human subject. In some embodiments, the method includes obtaining and/or assaying the biological sample. As described below, in some embodiments, the marker gene is TERT, MUC2, TOLLIP, DSP, DISP2, MAPT, DPP9, CSMD1, MYNN, LRRC34, FAM13A, OBFC1, ATPIIA, IVD, CRHR1, IMP5, LOC100128977, KIAA1267, NSF, WNT3, C17orf69, or homologs or variants thereof. In some embodiments, the marker gene is selected from TERT, MUC2, TOLLIP, homologs, and variants thereof.

Also provided herein are methods of treating an interstitial lung disease in a subject in need of such treatment. The method includes detecting a level of one or more marker genes described below in a biological sample of the human subject and administering an effective amount of an interstitial lung disease treatment. In some embodiments, the method includes obtaining and/or assaying the biological sample. As described below, in some embodiments, the marker gene is TERT, MUC2, TOLLIP, DSP, DISP2, MAPT, DPP9, CSMD1, MYNN, LRRC34, FAM13A, OBFC1, ATPIIA, IVD, CRHR1, IMP5, LOC100128977, KIAA1267, NSF, WNT3, C17orf69, or homologs or variants thereof.

One embodiment of the disclosure relates to a method that includes detecting a level of gene expression (e.g. expression of RNA or protein) of a marker gene or plurality of marker genes in a biological sample from an individual. The marker gene(s) are selected from a marker gene having at least 95% sequence identity with a sequence selected from: TERT (telomerase reverse transcriptase; NC_000005.9; AY407349); TOLLIP (toll interacting protein; NC_000011.9; AY419805), MUC2 (mucin 2, oligomeric mucus/gel-forming; NC_000011.9; DQ036653), DSP (desmoplakin; NC_000006.11; DQ030635), DISP2 (dispatched homolog 2; NC_000015.9), MAPT (microtubule-associated protein tau; NC_000017.10; AY413628), DPP9 (dipeptidyl-peptidase 9; NC_000019.9; DQ053109), CSMD1 (CUB and Sushi multiple domains 1; NC_000008.10; DQ037810), MYNN (myoncurin; NC_000003.11; AY407169), LRRC34 (leucine rich repeat containing 34; NC_000003.11), FAM13A (family with sequence similarity 13, member A; NC_000004.11), OBFC1 (oligonucleotide/oligosaccharide-binding fold containing 1; NC_000010.10), ATP11A (ATPase, class VI, type 11A; NC_000013.10), IVD (isovaleryl-CoA dehydrogenase; NC_000015.9; AY418331), CRHR1 (corticotropin releasing hormone receptor 1; NC_000017.10; AY414327), IMP5 (importin 5; NC_000013.10), LOC100128977 (MAPT antisense RNA 1; NC_000017.10), KIAA1267 (KAT8 regulatory NSL complex subunit 1; NC_000017.10; NG_032784), NSF (N-ethylmalcimide-sensitive factor; NC_000017.10), WNT3 (wingless-type MMTV integration site family, member 3; NC_000017.10; AY413892), C17orf69 (CRHR1 intronic transcript 1 (non-protein coding; NC_000017.10). In some embodiments, the marker gene has at least 95% sequence identity over a span of at least 10, 15, 20, 25, 30, 50, 70, 80, 100, 200, or more contiguous nucleotides of the selected gene. In some embodiments, the marker gene is a homologs or variant of at least one of the above that, while distinct from the selected marker gene, includes the same genetic variation.

In a related embodiment, the marker gene(s) are selected from a marker gene having at least 95% sequence identity with a sequence selected from a plurality of marker genes comprising MUC5B and at least one marker gene having at least 95% sequence identity (e.g., at least 96, 97, 98, 99, or 100% identity over a span of at least 10, 15, 20, 25, 30, 50, 70, 80, 100, 200, or more contiguous nucleotides) with a sequence selected from the group consisting of TERT, DSP, MUC2, DISP2, MAPT, DPP9, CSMD1, MYNN, LRRC34, FAM13A, OBFC1, TOLLIP, ATPIIA, IVD, CRHR1, IMP5, LOC100128977, KIAA1267, NSF, WNT3, C17orf69. Again, the marker gene can be a homolog or variant of the selected marker gene that includes the same genetic variant.

In a related embodiment, the marker gene(s) are selected from a marker gene having at least 95% sequence identity (e.g., at least 96, 97, 98, 99, or 100% identity) over a span of at least 10, 15, 20, 25, 30, 50, 70, 80, 100, 200, or more contiguous nucleotides with a sequence selected from a plurality of marker genes comprising the gene set of TERT, DSP, MUC2, DISP2, MAPT, DPP9, or homologs or variants thereof. In a related embodiment, the marker gene(s) are selected from a marker gene having at least 95% sequence identity with a sequence selected from a plurality of marker genes comprising the gene set of TERT, MUC2, TOLLIP, or homologs or variants thereof.

In a related embodiment, the marker gene(s) are selected from a marker gene having at least 95% sequence identity (e.g., at least 96, 97, 98, 99, or 100% identity) with a sequence selected from a plurality of marker genes comprising the gene set of TERT, DSP, MUC2, DISP2, MAPT, DPP9, CSMD1, MYNN, LRRC34, FAM13A, OBFC1, TOLLIP, ATP11A, IVD, CRHR1, IMP5, LOC100128977, KIAA1267, NSF, WNT3, C17orf69, or homologs or variants thereof. In related embodiments, the methods may further include detecting a level of gene expression (e.g. expression of RNA or protein) of one or more additional marker genes in the biological sample from the individual. The additional marker gene(s) are selected from a marker gene having at least 95% sequence identity (e.g., at least 96, 97, 98, 99, or 100% identity) with a sequence selected from MUC5B and TERC, SFTPC and SFTPA2. In related embodiments, the additional marker gene is MUC5B.

In a related embodiment, the detection of the level of expression of the marker gene(s) may be conducted by detection of polypeptides encoded by the marker genes and/or fragments of polypeptides of the marker genes, and/or a polynucleotide (e.g. mRN(A) which is fully complementary to at least a portion of the marker genes.

In some embodiments, the detection of an elevated gene expression of the markers is indicative of an individual that has an elevated risk of developing interstitial lung disease. In some embodiments, the individual is at risk of developing sporadic IIP. In some embodiments, the individual is at risk of developing familial IIP. In some embodiments, the individual is at risk of developing idiopathic pulmonary fibrosis (IPF).

In some embodiments, the genes detected in these methods share 100% sequence identity with the corresponding marker genes.

In each of these embodiments, the levels of at least one of the plurality of markers may be determined and compared to a standard level or reference range of gene expression that may be determined according to a statistical procedure for risk prediction.

In one embodiment of this method, the presence of the polypeptides may be detected using a reagent that specifically binds to the polypeptide, or a fragment thereof. In one embodiment, the reagent is selected from the group consisting of an antibody, an antibody derivative, and an antibody fragment.

In another embodiment of this method, the presence of the marker is determined by obtaining RNA from a subject's tissue sample; generating cDNA from the RNA; amplifying the cDNA with probes or primers for marker genes; obtaining from the amplified cDNA the expression levels of the genes or gene expression products in the sample.

These methods may include comparing the expression level of the marker gene or plurality of marker genes, in the biological sample to a control level of the marker gene(s) including: a control level of the marker gene that has been correlated with diagnosis with or development of, or progression of, interstitial lung disease. In these embodiments, the individual is predicted to develop or progress with the pathological manifestations of interstitial lung disease (such as lung scarring (fibrosis)), if the expression level of the marker gene in the individual's biological sample is statistically similar to, or greater than, the control level of expression of the marker gene that has been correlated with the incidence of interstitial lung disease or with developing interstitial lung disease, or progressive interstitial lung disease. Alternatively, the individual is predicted to not develop or may be predicted to not progress or to progress slowly with the development of interstitial lung disease if the level of the marker gene in the individual's biological sample is statistically less than the control level of the marker gene that has been correlated with the incidence of interstitial lung disease or with developing interstitial lung disease, or progressive interstitial lung disease.

Additionally, or as an alternative, these embodiments may include comparing the expression level of the marker gene or plurality of marker genes, in the biological sample to a level of the marker gene(s) in a second individual that has developed or has a progressive interstitial lung disease. In this embodiment, the individual is predicted to develop or have a progressive interstitial lung disease if the expression level of the marker gene in the individual's biological sample is statistically similar to, or greater than, the level of expression of the marker gene(s) in the second individual. Alternatively, the individual is predicted to not develop or not have a progressive interstitial lung disease, if the level of the marker gene in the individual's biological sample is less than the level of expression of the marker gene(s) in the second individual.

An embodiment of these methods of determining if an individual will develop or will progress rapidly with the development of lung scarring (fibrosis) and interstitial lung disease includes detecting a level of gene expression of a gene having at least 95% sequence identity with each of MUC5B, DSP and DPP9, or homologs or variants thereof, in a biological sample from an individual. In some embodiments, the genes detected preferably share 100% sequence identity with the corresponding marker genes. The method may also be conducted by detecting a level of polypeptides encoded by the genes, and/or fragments of polypeptides, and/or a polynucleotide which is fully complementary to the genes. In this embodiment, an elevated level of expression of the plurality of markers is indicative of whether an individual that will develop or progress rapidly with the development of lung scarring (fibrosis) and interstitial lung disease.

Another embodiment of the disclosure is a method of monitoring the progression of interstitial lung disease in a subject by measuring the expression level of one or more (e.g. a plurality of) the marker genes set forth above in a first biological sample obtained from the subject and comparing the expression level to a control. In related embodiments, a method is provided of monitoring the progression of interstitial lung disease in a subject by measuring the expression level of a plurality of marker genes in a first biological sample obtained from the subject, measuring the level of the plurality of markers in a second biological sample obtained from the subject, and comparing the level of the marker measured in the first sample with the level of the marker measured in the second sample. In this embodiment, the plurality of marker gene(s) are selected from a marker gene having at least 95% sequence identity with a sequence selected from a marker gene as set forth above. Alternatively, in this embodiment, the plurality of marker gene(s) are selected from a marker gene having at least 95% sequence identity with a sequence selected from MUC5B, DSP and DPP9 or homologs or variants thereof. Preferably, the second biological sample is obtained from the subject at a time later than the first biological sample is obtained. Alternatively, the first biological sample and the second biological sample are obtained from the subject more than once, over a range of times.

In a related embodiment, the detection of the level of expression of the marker gene(s) may be conducted by detection of polypeptides encoded by the marker genes, and/or fragments of polypeptides of the marker genes, and/or a polynucleotide which is fully complementary to at least a portion of the marker genes. In some embodiments, the genes detected in these methods share 100% sequence identity with the corresponding marker genes.

These embodiments may include performing a follow-up step, such as computed tomogram of the chest (CT scan of the chest) and review by a radiologist.

Another embodiment of the disclosure is a method of assessing the efficacy of a treatment for interstitial lung disease in a subject by comparing the level of expression of a gene marker measured in a first sample obtained from the subject with a control value associated with developing or progression of interstitial lung disease. Another embodiment of the disclosure is a method of assessing the efficacy of a treatment for interstitial lung disease in a subject by comparing the level of expression of a gene marker measured in a first sample obtained from the subject with the expression level of the gene marker in a second sample obtained from the subject at a later time, and performing a follow-up step such as computed tomogram of the chest (CT scan of the chest) or review of a lung sample by a radiologist. In this embodiment, a decrease in the level of the marker in the second sample relative to the first sample is an indication that the treatment is efficacious for treating interstitial lung disease in the subject. In some embodiments, the first sample is collected before a treatment has been administered to the subject, and the second sample is obtained after the treatment has been administered to the subject. In another embodiment, the samples are obtained and the comparing is repeated over a range of times. In this embodiment, the plurality of marker gene(s) are selected from a marker gene having at least 95% sequence identity with a sequence selected from a marker gene described above. Alternatively, in this embodiment, the plurality of marker gene(s) are selected from a marker gene having at least 95% sequence identity with a sequence selected from MUC5B, DSP and DPP9 or homologs or variants thereof.

In a related embodiment, the detection of the level of expression of the marker gene(s) may be conducted by detection of polypeptides encoded by the marker genes, and/or fragments of polypeptides of the marker genes, and/or a polynucleotide which is fully complementary to at least a portion of the marker genes. In some embodiments, the genes detected in these methods share 100% sequence identity with the corresponding marker genes.

Another embodiment of the present disclosure is an assay system for predicting the need for lung transplant in an individual diagnosed with interstitial lung disease. The assay system includes a means to detect the expression of a marker gene or plurality of marker genes having at least 95% sequence identity with a sequences selected from MUC5B, DSP and DPP9, or homologs or variants thereof. In some embodiments, the genes detected in these methods share 100% sequence identity with the corresponding marker gene.

In one embodiment of the assay system, the means to detect includes a nucleic acid probe having at least 10 to 50 (e.g., 10, 15, 20, 25, 30, 10-50, 20-40, 10-100, 50-100, etc.) contiguous nucleic acids of the marker gene(s), or complementary nucleic acid sequences thereof. In another embodiment of the assay system, the means to detect includes binding ligands that specifically detect polypeptides encoded by the marker genes. These binding ligands may include antibodies, antigen-binding antibody derivatives or antigen-binding antibody fragments. The nucleic acid probes and/or binding ligands can be disposed on an assay surface such as a bead, microfluidic surface, chip, array, or fluidity card.

The assay system can include a control selected from information containing a predetermined control level of the marker gene that has been correlated with progression or life expectancy in interstitial lung disease patients.

In any one of the embodiments of the present disclosure, the step of detecting can include, but is not limited to, using a nucleotide probe that hybridizes to at least one of the marker gene(s). In one aspect, the probe may be a chimeric probe (e.g., that hybridizes to more than one of the biomarker genes). In another aspect, the step of detecting can include detecting the number of copies of the biomarker genes per cell in one or more cells in the biological sample, and/or detecting marker gene amplification per cell in one or more cells in the biological sample. In embodiments, the step of detecting gene expression is performed by TaqMan® Gene Signature Array, as described in U.S. Pat. Nos. 6,514,750, 6,942,837, 7,211,443, and 7,235,406, each of which is incorporated by reference in its entirety.

In one aspect of this embodiment, the step of comparing comprises comparing the biomarker level in the biological sample to a control level of the biomarker in one or more control samples from patients with rapidly progressing interstitial lung disease. In one aspect, the control level of the biomarker is the level that has been correlated with slow or no progression of interstitial lung disease.

In any one of the embodiments of the disclosure, the selection of an individual predicted to develop or have a progressive interstitial lung disease may include evaluation of a clinical covariate including histological appearance and/or marker(s) in the individual's lung tissue.

Further provided are methods for determining whether a human subject has or is at risk of developing interstitial lung disease comprising: detecting in a biological sample from the subject, at least one of: (a) presence of a genetic variant selected from the group consisting of: rs2736100, rs2076295, rs3778337, rs4727443, rs868903, rs7934606, rs6421972, rs7480563, rs7942850, rs4077759, rs2334659, rs7122936, rs2034650, rs1992272, rs1981997, rs17563986, rs8070723, rs12610495, rs2109069, rs1379326, rs1881984, rs10936599, rs1997392, rs6793295, rs2609255, rs2853676, rs10484326, rs10748858, rs2067832, rs11191865, rs2301160, rs3829223, rs2857476, rs1278769, rs1007177, rs10518693, rs393152, rs12373139, rs17690703, rs2532274, rs2532269, rs2668692, rs169201, rs199533, and rs415430; (b) level of gene expression of a marker gene or plurality of marker genes selected from the group consisting of: a marker gene having at least 95% sequence identity with a sequence selected from the group consisting of TERT, DSP, MUC2, DISP2, MAPT, DPP9, CSMD1, MYNN, LRRC34, FAM13A, OBFC1, TOLLIP, ATPIIA, IVD, CRHR1, IMP5, LOC100128977, KIAA1267, NSF, WNT3, C17orf69, or homologs or variants thereof; (c) polypeptides encoded by the marker genes of (b); (d) fragments of polypeptides of (c); and (c) a polynucleotide which is fully complementary to at least a portion of a marker gene of (b); wherein the presence of the at least one genetic variant, polypeptide, fragment, and/or complementary polynucleotide, and/or increased or reduced gene expression of the marker gene indicates that the subject has or is at risk of developing interstitial lung disease.

In some embodiments, the presence of a genetic variant is determined by PCR. In some embodiments, the presence of the genetic variant is determined by detection of a Förster resonance energy transfer (FRET). In some embodiments, the presence of the genetic variant is determined by detecting the presence or expression level of a polypeptide, e.g., using an antibody, an antigen-binding antibody derivative, and an antigen-binding antibody fragment specific for the polypeptide. In some embodiments, the interstitial lung disease is a fibrotic lung disease, idiopathic pulmonary fibrosis (IPF), familial interstitial pneumonia (FIP), or idiopathic interstitial pneumonia (IIP).

Also provided are methods for monitoring the progression of interstitial lung disease in a human subject, comprising (i) measuring expression levels of a plurality of gene markers in a first biological sample obtained from the subject, wherein the plurality of markers comprise a plurality of markers selected from the group consisting of: (a) a marker gene having at least 95% sequence identity with a sequence selected from the group consisting of TERT, DSP, MUC2, DISP2, MAPT, DPP9, CSMD1, MYNN, LRRC34, FAM13A, OBFC1 TOLLIP, ATP11A, IVD, CRHR1, IMP5, LOC100128977, KIAA1267, NSF, WNT3, C17orf69, or homologs or variants thereof; (b) polypeptides encoded by the marker genes of (a); (c) fragments of polypeptides of (b); and (d) a polynucleotide which is fully complementary to at least a portion of a marker gene of (a); (ii) measuring expression levels of the plurality of markers in a second biological sample obtained from the subject; and (iii) comparing the expression level of the marker measured in the first sample with the level of the marker measured in the second sample. In some embodiments, the method further comprises measuring the expression level of the plurality of markers in at least one additional biological sample obtained from the subject at least one additional time, and comparing the expression level of the markers measured in the first and second samples with the level of the marker measured in the at least one additional sample. In some embodiments, the method further comprises recommending treatment for interstitial lung disease when the expression level of the marker in the second sample is higher than that of the first sample. In some embodiments, the interstitial lung disease is fibrotic lung disease, idiopathic pulmonary fibrosis (IPF), familial interstitial pneumonia (FIP), or idiopathic interstitial pneumonia.

Also provided are methods of assessing the efficacy of treatment for interstitial lung disease in a human subject, the method comprising: (i) determining the expression level of a marker measured in a first sample obtained from the subject at a time to, wherein the marker is selected from the group consisting of (a) a marker gene having at least 95% sequence identity with a sequence selected from the group consisting of TERT, DSP, MUC2, DISP2, MAPT, DPP9, CSMD1, MYNN, LRRC34, FAM13A, OBFC1, TOLLIP, ATP11A, IVD, CRHR1, IMP5, LOC100128977, KIAA1267, NSF, WNT3, C17orf69, or homologs or variants thereof; (b) polypeptides encoded by the marker genes of (a); (c) fragments of polypeptides of (b); and (d) a polynucleotide which is fully complementary to at least a portion of a marker gene of (a); (ii) determining the expression level of the marker in a second sample obtained from the subject at a later time $t_1$; and (iii) performing a follow-up step selected from performing a CT scan of the chest and performing a pathological examination of lung tissues from the subject; wherein a decrease in the expression level of the marker in the second sample relative to the first sample is an indication that the treatment is efficacious for treating interstitial lung disease in the subject. In some embodiments, the time to is before the treatment has been administered to the subject, and the time $t_1$ is after the treatment has been administered to the subject. In some embodiments, the time $t_0$ is after the treatment has been administered to the subject, and the time $t_1$ is later than time $t_0$ after the treatment has been administered to the subject. In some embodiments, the treatment is administered multiple times. In some embodiments, the comparing is repeated for biological samples obtained from the subject over a range of times.

Further provided are assay systems for predicting response to therapy for interstitial lung disease in a human subject comprising a means to detect at least one of: (a) presence of a genetic variant selected from the group consisting of: rs2736100, rs2076295, rs3778337, rs4727443, rs868903, rs7934606, rs6421972, rs7480563, rs7942850, rs4077759, rs2334659, rs7122936, rs2034650, rs1992272, rs1981997, rs17563986, rs8070723, rs12610495, rs2109069, rs1379326, rs1881984, rs10936599, rs1997392, rs6793295, rs2609255, rs2853676, rs10484326, rs10748858, rs2067832, rs11191865, rs2301160, rs3829223, rs2857476, rs1278769, rs1007177, rs10518693, rs393152, rs12373139, rs17690703, rs2532274, rs2532269, rs2668692, rs169201, rs199533, and rs415430; and (b) level of gene expression of a marker gene or plurality of marker genes selected from the group consisting of: a marker gene having at least 95% sequence identity with a sequence selected from the group consisting of TERT, DSP, MUC2, DISP2, MAPT, DPP9, CSMD1, MYNN, LRRC34, FAM13A, OBFC1, TOLLIP, ATP11A, IVD, CRHR1, IMP5, LOC100128977, KIAA1267, NSF, WNT3, C17orf69, or homologs or variants thereof; (c) polypeptides encoded by the marker genes of (b); (d) fragments of polypeptides of (c); and (c) a polynucleotide which is fully complementary to at least a portion of a marker gene of (b). In some embodiments, the means to detect comprises nucleic acid probes comprising at least 10 to 50 contiguous nucleic acids of the marker polymorphisms or gene(s), or complementary nucleic acid sequences thereof. In some embodiments, the means to detect comprises nucleic acid primers or probes that hybridize to a sequence adjacent to or comprising the genetic variant(s) of (a). In some embodiments, at least one of the primers or probes is labeled with a Förster resonance energy transfer (FRET) acceptor, and at least one of the primers or probes is labeled with a FRET donator. In some embodiments, the means to detect comprises binding ligands that specifically detect polypeptides encoded by the marker genes (e.g., an antibody, antigen-binding antibody derivative or antigen-binding antibody fragment). In some embodiments, the means to detect comprises at least one of nucleic acid probe and/or binding ligands disposed on an assay surface (e.g., chip, array, bead, microfluidic surface, or fluidity car(d). In some embodiments, the probes comprise complementary nucleic acid sequences to at least 10 to 50 contiguous nucleic acids of the marker genes.

Further provided are kits for predicting, diagnosing, or prognosing interstitial lung disease. In some embodiments, the kit comprises at least one nucleic acid probe or primer for detecting a genetic variant in a gene selected from the group consisting of: TERT, DSP, MUC2, DISP2, MAPT, DPP9, CSMD1, MYNN, LRRC34, FAM13A, OBFC1, TOLLIP, MUC5B, ATP11A, IVD, CRHR1, IMP5, LOC100128977, KIAA1267, NSF, C17orf69, and WNT3. In some embodiments, the kit includes reagents for amplifying the selected genetic variant(s), e.g., primers that amplify a nucleic acid in the selected gene, polymerase (e.g., a thermostable polymerase such as Taq or other DNA or RNA polymeras(e), buffers, etc. In some embodiments, the at least one probe or primer is complementary to a variant nucleotide (e.g., the recessive SNP) of the genetic variant. In some embodiments, the at least one probe or primer is complementary to (hybridizes to) the selected genetic variant polynucleotide sequence or an amplification product thereof. In some embodiments, at least one probe or primer is labeled. In some embodiments, the label is a fluorescent label, or a FRET acceptor or donor. In some embodiments, the kit comprises at least one probe or primer labeled with a Förster resonance energy transfer (FRET) acceptor, and at least one probe or primer labeled with a FRET donor. In some embodiments, the kit includes at least one probe or primer each for detecting a genetic variant in at least 2, 3, 4, 5, 6, 7, 8, 9, 10, 11, 12, 13, 14, 15, 16, 17, 18, 19, 20, 21, or 22 of the above genes in any combination. In some embodiments, the at least one nucleic acid probe or primer is included on an array, bead, microfluidic surface, or chip. In some embodiments, the kit includes at least one control sample, e.g., comprising a nucleic acid with the dominant allele of the at least one selected genetic variant, or comprising a nucleic acid with the polymorphic allele of the at least one selected genetic variant.

Further provided are kits for predicting, diagnosing, or prognosing interstitial lung disease comprising at least one nucleic acid probe or primer for detecting a genetic variant selected from the group consisting of: rs2736100, rs2076295, rs3778337, rs4727443, rs868903, rs7934606, rs6421972, rs7480563, rs7942850, rs4077759, rs2334659, rs7122936, rs2034650, rs1992272, rs1981997, rs17563986, rs8070723, rs12610495, rs2109069, rs1379326, rs1881984, rs10936599, rs1997392, rs6793295, rs2609255, rs2853676, rs10484326, rs10748858, rs2067832, rs11191865, rs2301160, rs3829223, rs2857476, rs1278769, rs1007177, rs10518693, rs393152, rs12373139, rs17690703, rs2532274, rs2532269, rs2668692, rs169201, rs199533, and rs415430. In some embodiments, the kit includes reagents for amplifying the nucleic acid comprising the genetic variant (e.g., PCR primers on either side of the polymorphic nucleotide, polymerase, buffer, etc.). In some embodiments, the at least one probe or primer is complementary to a variant nucleotide (e.g., SNP) of the genetic variant. In some embodiments, the at least one probe or primer is complementary to (hybridizes to) the selected genetic variant polynucleotide sequence or an amplification product thereof. In some embodiments, at least one probe or primer is labeled. In some embodiments, the label is a fluorescent label, or a FRET acceptor or donor. In some embodiments, the kit comprises at least one probe or primer labeled with a Förster resonance energy transfer (FRET) acceptor, and at least one probe or primer labeled with a FRET donor. In some embodiments, the kit includes at least one probe or primer each for detecting a genetic variant in at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 of the above genetic variants in any combination. In some embodiments, the at least one nucleic acid probe or primer is included on an array, bead, microfluidic surface, or chip. In some embodiments, the kit includes at least one control sample, e.g., comprising a nucleic acid with the dominant allele of the at least one selected genetic variant, or comprising a nucleic acid with the polymorphic allele of the at least one selected genetic variant.

Further provided are in vitro complexes formed in detecting a biomarker (e.g. genetic variant) associated with interstitial lung disease (e.g., fibrotic lung disease, idiopathic pulmonary fibrosis (IPF), familial interstitial pneumonia (FIP), or idiopathic interstitial pneumonia (IIP)). The interstitial lung disease can be fibrotic lung disease. The interstitial lung disease can be IPF. The interstitial lung disease can be FIP. The interstitial lung disease can be IIP. In some embodiments, the complex comprises a first nucleic acid probe hybridized to a genetic variant nucleic acid, wherein the genetic variant nucleic acid comprises a genetic variant TERT, DSP, MUC2, DISP2, MAPT, DPP9, CSMD1, MYNN, LRRC34, FAM13A, OBFC1, TOLLIP, MUC5B, ATP11A, IVD, CRHR1, IMP5, LOC100128977, KIAA1267, NSF, WNT3, or C17orf69 gene sequence, wherein said genetic variant nucleic acid is extracted from a human subject having or suspected of having an interstitial lung disease or is an amplification product of a nucleic acid extracted from a human subject having or suspected of having an interstitial lung disease. In some embodiments, the complex further comprises a second labeled nucleic acid probe hybridized to said genetic variant nucleic acid. In some embodiments, the first labeled nucleic acid probe comprises a first label and said second labeled nucleic acid probe comprises a second label, wherein said first and second label are capable of Förster resonance energy transfer (FRET). In some embodiments, the complex further comprises a polymerase (e.g., a thermostable polymerase, or other DNA or RNA polymeras(e) or ligase. In some embodiments, the complex further comprises a nucleic acid primer hybridized to the genetic variant nucleic acid.

Other features and advantages of the disclosure will become apparent to one of skill in the art from the following detailed description.

BRIEF DESCRIPTION OF THE DRAWINGS

FIG. 4 shows relative expression of DSP in lung tissue from 100 cases and 94 controls (a) relative expression by case/control status (b) relative expression by genotype at rs2076295 in DSP.

FIG. 10 shows confirmation of relevance of the MUC5B promoter SNP rs3570950 in various study groups.

FIG. 12 shows the increased duration of survival associated with interstitial lung disease patients carrying the rs3570950 SNP in different study groups.

FIG. 21 shows increased likelihood of interstitial lung disease in patients carrying at least one variant rs3570950 allele.

FIG. 27 shows the relative frequency of fibrotic conditions in genotyped and replication populations.

FIG. 31 shows the odds ratios (ORs) and P-values for the effect of ancestry on various SNPs on chromosome 17q21.

FIG. 32 shows the ORs and P-value for the association of the MUC5B promoter SNP with interstitial lung disease.

DETAILED DESCRIPTION

Figure 1:
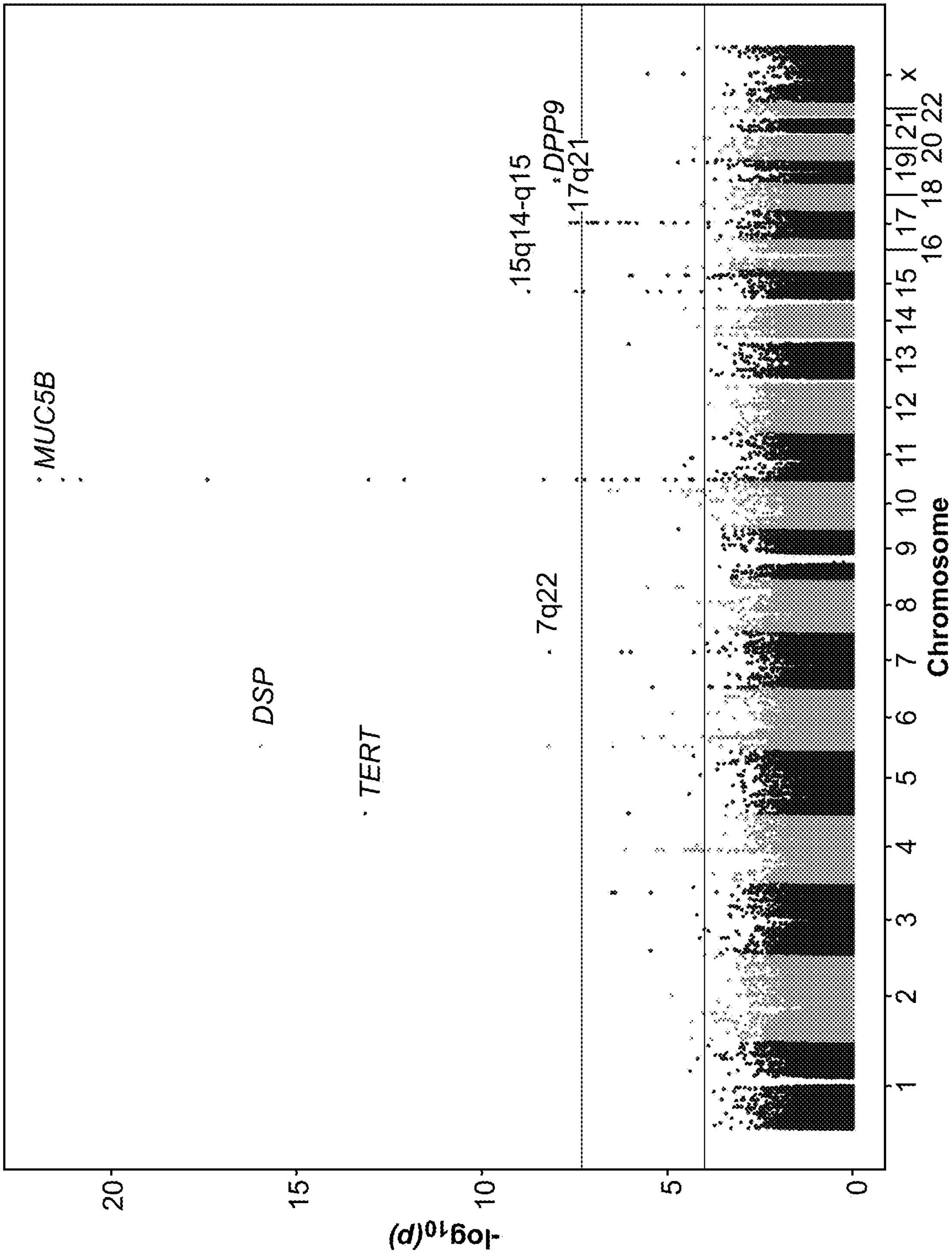
FIG. 1 shows GWAS results at 439,828 SNPs with 1616 cases and 4683 controls under additive model. SNPs above red line were genome-wide significant at P<5×10-8. These SNPs and SNPs between red and blue lines, corresponding to 5×10-8<P-value<0.0001 were selected for follow-up in 876 cases and 1890 controls.

Unless defined otherwise, technical and scientific terms used herein have the same meaning as commonly understood by a person of ordinary skill in the art. See, e.g., Lackie, Dictionary of Cell and Molecular Biology, Elsevier (4$^{th}$ ed. 2007); Sambrook et al., Molecular Cloning, A Laboratory Manual, Cold Springs Harbor Press (Cold Springs Harbor, N Y 1989). The term "a" or "an" is intended to mean "one or more." The term "comprise" and variations thereof such as "comprises" and "comprising," when preceding the recitation of a step or an element, are intended to mean that the addition of further steps or elements is optional and not excluded. The following definitions are provided to facilitate understanding of certain terms used frequently herein and are not meant to limit the scope of the present disclosure.

The terms "subject," "patient," "individual," etc. are not intended to be limiting and can be generally interchanged. That is, an individual described as a "patient" does not necessarily have a given disease, but may be merely seeking medical advice.

A "control," "control sample," "standard control," or "control value" refers to a sample that serves as a reference, usually a known reference, for comparison to a test sample. For example, a test sample can be taken from a patient suspected of having a given pulmonary disease and compared to samples from a known pulmonary disease patient, known polymorphism carrier, or a known normal (non-diseas(e) individual. A control can also represent an average value gathered from a population of similar individuals, e.g., pulmonary disease patients or healthy individuals with a similar medical background, same age, weight, etc. A control value can also be obtained from the same individual, e.g., from an earlier-obtained sample, prior to disease, or prior to treatment. One of skill will recognize that controls can be designed for assessment of any number of parameters.

One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

The term "nucleic acid" refers to deoxyribonucleotides or ribonucleotides and polymers thereof in either single- or double-stranded form, and complements thereof. "Nucleic acid" or "oligonucleotide" or "polynucleotide" or grammatical equivalents used herein means at least two nucleotides covalently linked together. Oligonucleotides are typically from about 5, 6, 7, 8, 9, 10, 12, 15, 25, 30, 40, 50 or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. The term "nucleotide" typically refers to a single unit of a polynucleotide, i.e., a monomer. Nucleotides can be ribonucleotides, deoxyribonucleotides, or modified versions thereof.

As used herein, a "genetic variant" refers to a mutation, single nucleotide polymorphism (SNP), deletion variant, missense variant, insertion variant, inversion, or copy number variant. A genetic variant can be used as a biomarker, and can result in increased or decreased expression levels, or differential modification.

The term "biomarker" refers to a biometric that can be detected in a biological sample (or sample derived from or processed from a biological sampl(e) and compared to a control sample as indicative of a particular condition. Examples of biomarkers include genetic variants, increased or decreased expression levels (determined by detection of chromatin opening, transcription product, or translation product), and differential modification (e.g., methylation of nucleic acids, or phosphorylation, glycosylation, or multimerization of proteins). A "marker gene" is a gene affected by a biomarker. That is, a marker gene can include a genetic variation in its genomic form, be expressed at a higher or lower level, or be differentially modified as indicative of a particular condition, e.g., interstitial lung disease.

The terms "probe" or "primer" refer to one or more nucleic acid fragments whose specific hybridization to a sample can be detected. A probe or primer can be of any length depending on the particular technique it will be used for. For example, PCR primers are generally between 10 and 40 nucleotides in length, while nucleic acid probes for, e.g., a Southern blot, can be more than a hundred nucleotides in length. The probe or primers can be unlabeled or labeled as described below so that its binding to a target sequence can be detected (e.g., with a FRET donor or acceptor label). The probe or primer can be designed based on one or more particular (preselecte(d) portions of a chromosome, e.g., one or more clones, an isolated whole chromosome or chromosome fragment, or a collection of polymerase chain reaction (PCR) amplification products. The length and complexity of the nucleic acid fixed onto the target element is not critical to the invention. One of skill can adjust these factors to provide optimum hybridization and signal production for a given hybridization and detection procedures, and to provide the required resolution among different genes or genomic locations.

Probes and primers can also be immobilized on a solid surface (e.g., nitrocellulose, glass, quartz, fused silica slides), as in an array. Techniques for producing high density arrays can also be used for this purpose (see, e.g., Fodor (1991) Science 767-773; Johnston (1998) Curr. Biol. 8: R171-R174; Schummer (1997) Biotechniques 23: 1087-1092; Kern (1997) Biotechniques 23: 120-124; U.S. Pat. No. 5,143,854). One of skill will recognize that the precise sequence of particular probes and primers can be modified from the target sequence to a certain degree to produce probes that are "substantially identical" or "substantially complementary to" a target sequence, but retain the ability to specifically bind to (i.e., hybridize specifically to) the same targets from which they were derived.

A probe or primer is "capable of detecting" a genetic variant if it is complementary to a region that covers or is adjacent to the genetic variant. For example, to detect a SNP, primers can be designed on either side of the SNP, and primer extension used to determine the identity of the nucleotide at the position of the SNP. In some embodiments, FRET-labeled primers are used (at least one labeled with a FRET donor and at least one labeled with a FRET acceptor) so that FRET signal will be detected only upon hybridization of both primers. In some embodiments, a probe is used in conditions such that it hybridizes only to a genetic variant, or only to a dominant sequence.

Again, in the context of nucleic acids, the term "capable of hybridizing to" refers to a polynucleotide sequence that forms Watson-Crick bonds with a complementary sequence. One of skill will understand that the percent complementarity need not be 100% for hybridization to occur, depending on the length of the polynucleotides, length of the complementary region (e.g. 5, 10, 15, 20, 25, 30, 35, 40, 45, 50, 60, 70, 80, 90, 100, or more bases in length), and stringency of the conditions. For example, a polynucleotide (e.g., primer or prob(e) can be capable of binding to a polynucleotide having 60%, 65%, 70%, 75%, 80%, 85%, 90%, 91%, 92%, 93%, 94%, 95%, 96%, 97%, 98%, 99% or 100% complementarity over the stretch of the complementary region. In the context of detecting genetic variants, the tolerated percent complementarity or number of mismatches will vary depending on the technique used for detection (see below).

In the context of nucleic acids, the term "amplification product" refers to a nucleic acid (e.g., polynucleotid(e) that results from an amplification reaction, e.g., PCR and variations thereof, rtPCR, strand displacement reaction (SDR), ligase chain reaction (LCR), transcription mediated amplification (TM(A), or Qbeta replication. A thermally stable polymerase, e.g., Taq, can be used to avoid repeated addition of polymerase throughout amplification procedures that involve cyclic or extreme temperatures (e.g., PCR and its variants).

The terms "label," "detectable moiety," "detectable agent," and like terms refer to a composition detectable by spectroscopic, photochemical, biochemical, immunochemical, chemical, or other physical means. For example, useful labels include fluorescent dyes, luminescent agents, radioisotopes (e.g., 32P, 3H), electron-dense reagents, enzymes, biotin, digoxigenin, or haptens and proteins or other entities which can be made detectable, e.g., by affinity. Any method known in the art for conjugating a nucleic acid or other biomolecule to a label may be employed, e.g., using methods described in Hermanson, Bioconjugate Techniques 1996, Academic Press, Inc., San Diego. The term "tag" can be used synonymously with the term "label," but generally refers to an affinity-based moiety, e.g., a "His tag" for purification, or a "strepavidin tag" that interacts with biotin.

A "labeled" molecule (e.g., nucleic acid, protein, or antibody) is one that is bound, either covalently, through a linker or a chemical bond, or noncovalently, through ionic, van der Waals, electrostatic, or hydrogen bonds to a label such that the presence of the molecule may be detected by detecting the presence of the label bound to the molecule.

Förster resonance energy transfer (abbreviated FRET), also known as fluorescence resonance energy transfer, is a mechanism describing energy transfer between two chromophores. A donor chromophore (FRET donor), initially in its electronic excited state, can transfer energy to an acceptor chromophore (FRET acceptor), which is typically less than 10 nm away, through nonradiative dipole-dipole coupling. The energy transferred to the FRET acceptor is detected as an emission of light (energy) when the FRET donor and acceptor are in proximity. A "FRET signal" is thus the signal that is generated by the emission of light from the acceptor. The efficiency of Förster resonance energy transfer between a donor and an acceptor dye separated by a distance of R is given by $E=1/[1+(R/R_0)^6]$ with $R_0$ being the Förster radius of the donor-acceptor pair at which $E=½$. $R_0$ is about 50-60 Å for some commonly used dye pairs (e.g., Cy3-Cy5). FRET signal varies as the distance to the $6^{th}$ power. If the donor-acceptor pair is positioned around $R_0$, a small change in distance ranging from 1 Å to 50 Å can be measured with the greatest signal to noise. With current technology, 1 ms or faster parallel imaging of many single FRET pairs is achievable.

A "FRET pair" refers to a FRET donor and FRET acceptor pair that are capable of FRET detection.

The terms "fluorophore," "dye," "fluorescent molecule," "fluorescent dye," "FRET dye" and like terms are used synonymously herein unless otherwise indicated.

As used herein, the terms "treat" and "prevent" are not intended to be absolute terms. Treatment can refer to any delay in onset, reduction in the frequency or severity of symptoms, amelioration of symptoms, improvement in patient comfort and/or respiratory function, etc. The effect of treatment can be compared to an individual or pool of individuals not receiving a given treatment, or to the same patient prior to, or after cessation of, treatment.

The term "prevent" refers to a decrease in the occurrence of pulmonary disease symptoms in a patient. As indicated above, the prevention may be complete (no detectable symptoms) or partial, such that fewer symptoms are observed than would likely occur absent treatment.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

The term "diagnosis" refers to a relative probability that a pulmonary disease is present in the subject. Similarly, the term "prognosis" refers to a relative probability that a certain future outcome may occur in the subject. For example, in the context of the present invention, prognosis can refer to the likelihood that an individual will develop a pulmonary disease, or the likely severity of the disease (e.g., severity of symptoms, rate of functional decline, survival, etc.). The terms are not intended to be absolute, as will be appreciated by any one of skill in the field of medical diagnostics.

The terms "correlating" and "associated," in reference to determination of a pulmonary disease risk factor, refers to comparing the presence or amount of the risk factor (e.g., dysregulation or genetic variation in a mucin gen(e) in an individual to its presence or amount in persons known to suffer from, or known to be at risk of, the pulmonary disease, or in persons known to be free of pulmonary disease, and assigning an increased or decreased probability of having/developing the pulmonary disease to an individual based on the assay result(s).

The present inventors have discovered polymorphisms and gene expression profiles that are important contributors to risk of IIP. These findings include eight novel genetic risk loci (4q22, 6p24, 7922, 10q24, 13q34, 15q14-15, 17q21, and 19p13), and the role of risk variants in three previously reported genes/loci (TERC [3q26], TERT [5p15], and MUC5B [11p15]) in IIP. Prior to this discovery, the only two genes with a reproducibly IIP-associated common variant were TERT and MUC5B. In aggregate, the common risk variants associated with IIP suggest that this disease is primarily mediated by defects in host defense, cell-cell adhesion, and early cell senescence. These findings can be used to guide intervention trials and treatment in this complex disease.

According to one definition, a biological marker is "a characteristic that is objectively measured and evaluated as an indicator of normal biologic processes, pathogenic processes, or pharmacological responses to therapeutic interventions." NIH Biomarker Definitions Working Group (1998). Biological markers can also include patterns or ensembles of characteristics indicative of particular biological processes ("panel of markers"). The marker measurement can be increased or decreased to indicate a particular biological event or process. In addition, if a marker measurement typically changes in the absence of a particular biological process, a constant measurement can indicate occurrence of that process.

Marker measurements may be of the absolute values (e.g., the molar concentration of a molecule in a biological sample or the presence or absence of a polymorphism) or relative values (e.g., the relative concentration of two molecules in a biological sampl(e). The quotient or product of two or more measurements also may be used as a marker. For example, some physicians use the total blood cholesterol as a marker of the risk of developing coronary artery disease, while others use the ratio of total cholesterol to HDL cholesterol.

In the disclosure, the markers are primarily used for diagnostic and prognostic purposes. However they may also be used for therapeutic, drug screening and individual stratification purposes (e.g., to group individuals into a number of "subsets" for evaluation), as well as other purposes described herein, including evaluation the effectiveness of an interstitial lung disease therapeutic.

The practice of the disclosure employs, unless otherwise indicated, conventional methods of analytical biochemistry, microbiology, molecular biology and recombinant DNA generally known techniques within the skill of the art. Such techniques are explained fully in the literature. (See, e.g., Sambrook et al. Molecular Cloning: A Laboratory Manual. 3rd, ed., Cold Spring Harbor Laboratory, Cold Spring Harbor Laboratory Press, Cold Spring Harbor, N Y, 2000; DNA Cloning: A Practical Approach, Vol. I & II (Glover, ed.); Oligonucleotide Synthesis (Gait, ed., Current Edition); Nucleic Acid Hybridization (Hames & Higgins, eds., Current Edition); Transcription and Translation (Hames & Higgins, eds., Current Edition); CRC Handbook of Parvoviruses, Vol. I & II (Tijessen, ed.); Fundamental Virology, 2nd Edition, Vol. I & II (Fields and Knipe, eds.)).

The terminology used herein is for describing particular embodiments and is not intended to be limiting. As used herein, the singular forms "a," "and" and "the" include plural referents unless the content and context clearly dictate otherwise. Thus, for example, a reference to "a marker" includes a combination of two or more such markers. Unless defined otherwise, all scientific and technical terms are to be understood as having the same meaning as commonly used in the art to which they pertain. For the purposes of the present disclosure, the following terms are defined below.

As used herein, the term "marker" includes polypeptide markers and polynucleotide markers. For clarity of disclosure, aspects of the disclosure will be described with respect to "polypeptide markers" and "polynucleotide markers." However, statements made herein with respect to "polypeptide markers" are intended to apply to other polypeptides of the disclosure. Likewise, statements made herein with respect to "polynucleotide" markers are intended to apply to other polynucleotides of the disclosure, respectively. Thus, for example, a polynucleotide described as encoding a "polypeptide marker" is intended to include a polynucleotide that encodes: a polypeptide marker, a polypeptide that has substantial sequence identity to a polypeptide marker, modified polypeptide markers, fragments of a polypeptide marker, precursors of a polypeptide marker and successors of a polypeptide marker, and molecules that comprise a polypeptide marker, homologous polypeptide, a modified polypeptide marker or a fragment, precursor or successor of a polypeptide marker (e.g., a fusion protein).

As used herein, the term "polypeptide" refers to a polymer of amino acid residues that has at least 5 contiguous amino acid residues, e.g., 5, 6, 7, 8, 9, 10, 11 or 12 or more amino acids long, including each integer up to the full length of the polypeptide. A polypeptide may be composed of two or more polypeptide chains. A polypeptide includes a protein, a peptide, an oligopeptide, and an amino acid. A polypeptide can be linear or branched. A polypeptide can comprise modified amino acid residues, amino acid analogs or non-naturally occurring amino acid residues and can be interrupted by non-amino acid residues. Included within the definition are amino acid polymers that have been modified, whether naturally or by intervention, e.g., formation of a disulfide bond, glycosylation, lipidation, methylation, acetylation, phosphorylation, or by manipulation, such as conjugation with a labeling component. Also included are antibodies produced by a subject in response to overexpressed polypeptide markers.

As used herein, a "fragment" of a polypeptide refers to a plurality of amino acid residues that is shorter than the full-length polypeptide. For example, a fragment of a given polypeptide can comprise at least 5 contiguous amino acid residues, at least 10 contiguous amino acid residues, at least 20 contiguous amino acid residues or at least 30 contiguous amino acid residues of the full length the polypeptide. As used herein, a “fragment” of polynucleotide refers to a polymer of nucleic acid residues comprising a nucleic acid sequence that has at least 5, 10, or 15 contiguous nucleic acid residues, at least 30 contiguous nucleic acid residues, at least 60 contiguous nucleic acid residues, or at least 90% of a sequence of the polynucleotide. In some embodiments, the fragment represents a domain (e.g., a functional domain) of the full-length polypeptide. In some embodiments, the fragment represents the full-length polypeptide minus a given domain. In some embodiments, the fragment is an antigenic fragment, and the size of the fragment will depend upon factors such as whether the epitope recognized by an antibody is a linear epitope or a conformational epitope. Thus, some antigenic fragments will consist of longer segments while others will consist of shorter segments (e.g. 5, 6, 7, 8, 9, 10, 11 or 12 or more amino acids long, including each integer up to the full length of the polypeptid(e). Those skilled in the art are well versed in methods for selecting antigenic fragments bound by antigen-binding antibodies, antibody derivatives, and antibody fragments.

In some embodiments, a polypeptide marker is a member of a biological pathway. As used herein, the term “precursor” or “successor” refers to molecules that precede or follow the polypeptide marker or polynucleotide marker in the biological pathway. Thus, once a polypeptide marker or polynucleotide marker is identified as a member of one or more biological pathways, the present disclosure can include additional precursor or successor members of the biological pathway. Such identification of biological pathways and their members is within the skill of one in the art.

As used herein, the term “polynucleotide” refers to a single nucleotide or a polymer of nucleic acid residues of any length. The polynucleotide may contain deoxyribonucleotides, ribonucleotides, and/or their analogs and may be double-stranded or single stranded. A polynucleotide can comprise modified nucleic acids (e.g., methylate(d), nucleic acid analogs or non-naturally occurring nucleic acids and can be interrupted by non-nucleic acid residues. For example a polynucleotide includes a gene, a gene fragment, cDNA, isolated DNA, mRNA, tRNA, rRNA, isolated RNA of any sequence, recombinant polynucleotides, primers, probes, plasmids, and vectors. Included within the definition are nucleic acid polymers that have been modified, whether naturally or by intervention.

As used herein, a component (e.g., a marker) is referred to as “differentially expressed” in one sample as compared to another sample when the method used for detecting the component provides a different level or activity when applied to the two samples. A component is referred to as “increased” in the first sample if the method for detecting the component indicates that the level or activity of the component is higher in the first sample than in the second sample (or if the component is detectable in the first sample but not in the second sampl(e). Conversely, a component is referred to as “decreased” in the first sample if the method for detecting the component indicates that the level or activity of the component is lower in the first sample than in the second sample (or if the component is detectable in the second sample but not in the first sampl(e). In particular, marker is referred to as “increased” or “decreased” in a sample (or set of samples) obtained from an interstitial lung disease subject (or a subject who is suspected of having interstitial lung disease, or is at risk of developing interstitial lung diseas(e) if the level or activity of the marker is higher or lower, respectively, compared to the level of the marker in a sample (or set of samples) obtained from a non-interstitial lung disease subject, or a reference value or range.

The markers identified as being expressed in interstitial lung disease are of significant biologic interest. A case-control genome-wide association study (GWAS; 1616 cases and 4683 controls) and replication study (876 cases and 1890 controls) of IIP was conducted. All types of fibrotic IIP were included in the case group since: (a) distinguishing among the IIP diagnoses is often problematic due to substantial clinical, pathological, and radiological overlap; and (b) there is strong evidence for shared genetic susceptibility. Both familial and sporadic IIPs were also included in the case group because the MUC5B, TERT, TERC, and SFTPC variants provide evidence that sporadic IIP is genetically similar to the familial form of this disease. The results indicate that IIPs are caused by multiple genetic variants, acting independently or in combination, and that the same genetic variants can lead to different histologic types of IIP.

As explained in detail below, when polymorphism and gene expression profiles were compared with clinical parameters and the common risk variants associated with IIP, the results indicate that this disease is primarily mediated by defects in host defense, cell-cell adhesion, and early cell senescence. These findings can be used to guide intervention trials in this complex disease.

In addition to the discovery of biomarkers that can be used individually or in any combination in assays and kits for the diagnosis of, prognosis of, or other evaluation or study of interstitial lung disease, the biomarkers not previously recognized to play a role in the disease process of interstitial lung disease can now be studied in more detail and/or be used as targets for the discovery of other modulators of disease or therapeutic agents. The markers of the disclosure include the polymorphisms: rs1379326, rs1881984, rs10936599, rs1997392, rs6793295, rs2609255, rs2853676, rs10484326, rs10748858, rs2067832, rs11191865, rs2301160, rs3829223, rs2857476, rs1278769, rs1007177, rs10518693, rs393152, rs12373139, rs17690703, rs2532274, rs2532269, rs2668692, rs169201, rs199533, and rs415430. The markers of the disclosure also include elevated gene expression in the genes: TERT, DSP, MUC2, DISP2, MAPT, DPP9, CSMD1, MYNN, LRRC34, FAM13A, OBFC1, TOLLIP, ATP11A, IVD, CRHR1, IMP5, LOC100128977, KIAA1267, NSF, WNT3, and C17orf69.

Given the name of the gene, the protein (also referred to herein as the “full protein”; indicated as “Protein”), and other peptide fragments of such measured proteins may be obtained (by whatever means), and such other peptide fragments are included within the scope of the disclosure. The methods of the present disclosure may be used to evaluate fragments of the products of the expression of the listed genes as well as molecules that contain an entire listed molecule, or at least a significant portion thereof (e.g., measured unique epitop(e), and modified versions of the markers. Accordingly, such fragments, larger molecules and modified versions are included within the scope of the disclosure.

Homologs and alleles of the markers of the disclosure can be identified by conventional techniques. As used herein, a homolog to a gene or polypeptide, e.g., from a human or other animal, has a high degree of structural and functional similarity to the identified gene or polypeptide. Identification of human and other organism homologs of polypeptide markers identified herein will be familiar to those of skill in the art. In general, nucleic acid hybridization is a suitable method for identification of homologous sequences of another species (e.g., human, cow, sheep), which correspond to a known sequence. Standard nucleic acid hybridization procedures can be used to identify related nucleic acid sequences of selected percent identity. For example, one can construct a library of cDNAs reverse transcribed from the mRNA of a selected tissue (e.g., colon) and use the nucleic acids that encode polypeptides identified herein to screen the library for related nucleotide sequences. The screening preferably is performed using high-stringency conditions (described elsewhere herein) to identify those sequences that are closely related by sequence identity. Nucleic acids so identified can be translated into polypeptides and the polypeptides can be tested for activity.

Additionally, the present disclosure includes polynucleotides and polypeptides that have substantially similar sequence identity to the markers of the present disclosure. As used herein, two polynucleotides or polypeptides have "substantial sequence identity" when there is at least about 70% sequence identity, at least about 80% sequence identity, at least about 90% sequence identity, at least about 95% sequence identity, at least about 99% sequence identity, or 100% sequence identity between their amino acid sequences, or when polynucleotides (e.g., polynucleotides encoding the polypeptides) are capable of forming a stable duplex with each other under stringent hybridization conditions. In the context of the present disclosure, a genetic variant can be detected in a marker gene, even if the marker gene has more than one site of genetic variation. That is, a selected genetic variant can be detected in test sample, e.g., from an individual suspected of having interstitial lung disease, by determining the sequence of a marker gene comprising the genetic variant, and compared to the sequence of the marker gene from a control or control population. The test and control full-length marker gene sequences might include more than one genetic variant, and thus may differ from each other, i.e., may not be 100% identical. One of skill will recognize that the genetic variant can be detected in a sequence that is less than the full length marker gene sequence, e.g., using PCR to amplify a fragment of the marker gene that includes the genetic variant site or a probe that is complementary to a sequence that includes the genetic variant site. Where the aspects or embodiments refer to sequence identity, that sequence identity can be with respect to a portion of the sequence as disclosed herein (e.g. 5, 10, 15, 20, 25, 30, 35, 40, 45, 50, 60, 70, 80, 90, 100, or more nucleic acid bases or amino acids in length).

Conservative amino acid substitutions may be made in polypeptides to provide functionally equivalent variants of the foregoing polypeptides, i.e., the variants retain the functional capabilities of the polypeptides. As used herein, a "conservative amino acid substitution" refers to an amino acid substitution that does not alter the relative charge or size characteristics of the protein in which the amino acid substitution is made. Variants can be prepared according to methods for altering polypeptide sequences known to one of ordinary skill in the art. For example, upon determining that a peptide is an interstitial lung disease-associated polypeptide, one can make conservative amino acid substitutions to the amino acid sequence of the peptide, and still have the polypeptide retain its specific antibody-binding characteristics. Additionally, one skilled in the art will realize that allelic variants and SNPs will give rise to substantially similar polypeptides and the same or substantially similar polypeptide fragments.

A number of comparison studies were performed to identify the markers using various groups of interstitial lung disease and non-interstitial lung disease (e.g., "control") individuals. The tables list markers that were found to be present or differentially expressed with statistical significance. Accordingly, these biomarkers are indicators of interstitial lung disease and disease progression. Where a polypeptide marker was found to be statistically significant in a plurality of studies, the data associated with the observations of highest statistical significance is presented. Accordingly, in one aspect, the disclosure provides polypeptide biomarkers of interstitial lung disease. In another embodiment, the disclosure provides a polypeptide having substantial sequence identity with a polypeptide marker. In another embodiment, the disclosure provides a molecule that comprises a foregoing polypeptide or polynucleotide. As used herein, a compound is referred to as "isolated" when it has been separated from at least one component with which it is naturally associated. For example, a polypeptide can be considered isolated if it is separated from contaminants including metabolites, polynucleotides and other polypeptides. Isolated molecules can be either prepared synthetically or purified from their natural environment. Standard quantification methodologies known in the art can be employed to obtain and isolate the molecules of the disclosure.

Some variation is inherent in the measurements of the physical and chemical characteristics of the markers. The magnitude of the variation depends to some extent on the reproductively of the separation means and the specificity and sensitivity of the detection means used to make the measurement. Preferably, the method and technique used to measure the markers is sensitive and reproducible.

The data set forth in the Tables reflects the method that was used to detect the markers. When a sample is processed and analyzed as described in the Example, the retention time of the marker is about the value stated for the marker; that is, within about 10% of the value stated, within about 5% of the value stated, or within about 1% of the value stated, and the marker has a mass to charge ratio of about the value stated for the marker; that is, within about 10% of the value stated, within about 5% of the value stated, or within about 1% of the value stated.

Another embodiment of the present disclosure relates to an assay system including a plurality of antibodies, or antigen binding fragments thereof, or aptamers for the detection of the expression of biomarkers differentially expressed in individuals with interstitial lung disease. The plurality of antibodies, or antigen binding fragments thereof, or aptamers consists of antibodies, or antigen binding fragments thereof, or aptamers that selectively bind to proteins differentially expressed in individuals with interstitial lung disease, and that can be detected as protein products using antibodies or aptamers. In addition, the plurality of antibodies, or antigen binding fragments thereof, or aptamers comprises antibodies, or antigen binding fragments thereof, or aptamers that selectively bind to proteins or portions thereof (peptides) encoded by any of the genes from the tables provided herein.

Certain embodiments of the present disclosure utilize a plurality of biomarkers that have been identified herein as being present or differentially expressed in subjects with interstitial lung disease. As used herein, the terms "patient," "a subject who has interstitial lung disease, "subject having interstitial pneumonia," "interstitial lung disease patient," "interstitial pneumonia subject," etc. are intended to refer to subjects who have been diagnosed with interstitial lung disease (e.g., IIP, IPF, FIP). The terms "non-subject," "normal individual," "a subject who does not have interstitial lung disease," etc. are intended to refer to a subject who has not been diagnosed with interstitial lung disease. A non-interstitial lung disease subject may be healthy and have no other disease, or they may have a disease other than interstitial lung disease.

The plurality of biomarkers within the above-limitation includes at least two or more biomarkers (e.g., at least 2, 3, 4, 5, 6, and so on, in whole integer increments, up to all of the disclosed biomarkers), and includes any combination of such biomarkers. Such biomarkers are selected from any of the polymorphisms or polypeptides listed in the tables provided herein, and polypeptides encoded by any of the genes listed in the Tables. In some embodiments, the plurality of biomarkers used in the present disclosure includes at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or all of the biomarkers that have been demonstrated to be predictive of the development of or progression of or clinical outcome of an individual diagnosed with or suspected of having interstitial lung disease such as interstitial pneumonia.

The polypeptide and polynucleotide markers of the disclosure are useful in methods for diagnosing interstitial lung disease, determining the extent and/or severity of the disease, monitoring progression of the disease, response to therapy, and/or need for a lung transplant. The markers are also useful in methods for treating interstitial lung disease and for evaluating the efficacy of treatment for the disease. Such methods can be performed in human and non-human subjects. The markers may also be used as pharmaceutical compositions or in kits. The markers may also be used to screen candidate compounds that modulate their expression. The markers may also be used to screen candidate drugs for treatment of interstitial lung disease. Such screening methods can be performed in human and non-human subjects.

Polypeptide markers may be isolated by any suitable method known in the art. Native polypeptide markers can be purified from natural sources by standard methods known in the art (e.g., chromatography, centrifugation, differential solubility, immunoassay). In one embodiment, polypeptide markers may be isolated from a serum sample using the chromatographic methods disclosed herein. In another embodiment, polypeptide markers may be isolated from a sample by contacting the sample with substrate-bound antibodies or aptamers that specifically bind to the marker.

The polynucleotide markers may be found in genomic DNA, cDNA, or mRNA transcripts and may include polynucleotides that encode the polypeptides of the disclosure. In one embodiment, the disclosure provides polynucleotides that encode a polypeptide marker, or a molecule that comprises such a polypeptide. In another embodiment, the disclosure provides polynucleotides that encode a polypeptide having substantial sequence identity with a polypeptide marker, or a molecule that comprises such a polypeptide.

In another embodiment, the disclosure provides polynucleotides that encode a polypeptide that is a fragment, precursor, successor or modified version of a marker, or a molecule that comprises such polypeptide.

In another embodiment, the disclosure provides polynucleotides that have substantial sequence similarity to a polynucleotide that encodes a polypeptide that is a fragment, precursor, successor or modified version of a marker, or a molecule that comprises such polypeptide. Two polynucleotides have "substantial sequence identity" when there is at least about 70% sequence identity, at least about 80% sequence identity, at least about 90% sequence identity, at least about 95% sequence identity or at least 99% sequence identity between their amino acid sequences or when the polynucleotides are capable of forming a stable duplex with each other under stringent hybridization conditions. Such conditions are described elsewhere herein. As described above with respect to polypeptides, the disclosure includes polynucleotides that are allelic variants, the result of SNPs, or that in alternative codons to those present in the native materials as inherent in the degeneracy of the genetic code.

In some embodiments, the polynucleotides described may be used as surrogate markers of interstitial lung disease. Thus, for example, if the level of a polypeptide marker is increased in interstitial lung disease subjects, an increase in the mRNA that encodes the polypeptide marker may be interrogated rather than the polypeptide marker (e.g., to diagnose interstitial lung disease in a subject).

Polynucleotide markers may be isolated by any suitable method known in the art. Native polynucleotide markers may be purified from natural sources by standard methods known in the art. In one embodiment, a polynucleotide marker may be isolated from a mixture by contacting the mixture with substrate bound probes that are complementary to the polynucleotide marker under hybridization conditions.

Alternatively, polynucleotide markers may be synthesized by any suitable chemical or recombinant method known in the art. In one embodiment, for example, the makers can be synthesized using the methods and techniques of organic chemistry. In another embodiment, a polynucleotide marker can be produced by polymerase chain reaction (PCR).

The present disclosure also encompasses molecules which specifically bind the polypeptide or polynucleotide markers of the present disclosure. In one aspect, the disclosure provides molecules that specifically bind to a polypeptide marker or a polynucleotide marker. As used herein, the term "specifically binding," refers to the interaction between binding pairs (e.g., an antibody and an antigen or aptamer and its target). In some embodiments, the interaction has an affinity constant of at most $10^{-6}$ moles/liter, at most $10^{-7}$ moles/liter, or at most $10^{-8}$ moles/liter. In other embodiments, the phrase "specifically binds" refers to the specific binding of one protein to another (e.g., an antibody, fragment thereof, or binding partner to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen binding fragment thereof in the absence of the antigen is considered to be background. Binding can be measured using a variety of methods standard in the art including enzyme immunoassays (e.g., ELIS (A), immunoblot assays, etc.).

The binding molecules include antibodies, aptamers and antibody fragments. As used herein, the term "antibody" refers to an immunoglobulin molecule capable of binding an epitope present on an antigen. The term is intended to encompasses not only intact immunoglobulin molecules such as monoclonal and polyclonal antibodies, but also bi-specific antibodies, humanized antibodies, chimeric antibodies, anti-idiopathic (anti-I(D) antibodies, single-chain antibodies, Fab fragments, F(ab') fragments, fusion proteins and any modifications of the foregoing that comprise an antigen recognition site of the required specificity. As used herein, an aptamer is a non-naturally occurring nucleic acid having a desirable action on a target. A desirable action includes, but is not limited to, binding of the target, catalytically changing the target, reacting with the target in a way which modifies/alters the target or the functional activity of the target, covalently attaching to the target as in a suicide inhibitor, facilitating the reaction between the target and another molecule. In some embodiments, the action is specific binding affinity for a target molecule, such target molecule being a three dimensional chemical structure other than a polynucleotide that binds to the nucleic acid ligand through a mechanism which predominantly depends on Watson/Crick base pairing or triple helix binding, wherein the nucleic acid ligand is not a nucleic acid having the known physiological function of being bound by the target molecule.

In one aspect, the disclosure provides antibodies or aptamers that specifically bind to a SNP marker, or to a molecule that comprises a foregoing component (e.g., a protein comprising a polypeptide encoded by a marker gen(c).

In another embodiment, the disclosure provides antibodies or aptamers that specifically bind to a polypeptide having substantial sequence identity with a marker gene, or to a molecule that comprises a foregoing polypeptide.

In another embodiment, the disclosure provides antibodies or aptamers that specifically bind to a polypeptide marker or a polynucleotide marker that is structurally different from a marker specifically identified in the tables provided herein but has the same (or nearly the sam(e) function or properties, or to a molecule that comprises a foregoing component.

Another embodiment of the present disclosure relates to a plurality of aptamers, antibodies, or antigen binding fragments thereof, for the detection of the expression of biomarkers differentially expressed in individuals with interstitial pneumonia. The plurality of aptamers, antibodies, or antigen binding fragments thereof, consists of antibodies, or antigen binding fragments thereof, that selectively bind to proteins differentially expressed in individuals with interstitial lung disease, and that can be detected as protein products using antibodies. In addition, the plurality of aptamers, antibodies, or antigen binding fragments thereof, comprises antibodies, or antigen binding fragments thereof, that selectively bind to proteins or portions thereof (peptides) encoded by any of the genes from the tables provided herein.

According to the present disclosure, a plurality of aptamers, antibodies, or antigen binding fragments thereof, refers to at least 2, and more preferably at least 3, and more preferably at least 4, and more preferably at least 5, and more preferably at least 6, and more preferably at least 7, and more preferably at least 8, and more preferably at least 9, and more preferably at least 10, and so on, in increments of one, up to any suitable number of antibodies, or antigen binding fragments thereof, including, in some embodiments, antibodies representing all of the biomarkers described herein, or antigen binding fragments thereof.

Certain antibodies that specifically bind polypeptide markers polynucleotide markers of the disclosure already may be known and/or available for purchase from commercial sources. In any event, the antibodies of the disclosure may be prepared by any suitable means known in the art. For example, antibodies may be prepared by immunizing an animal host with a marker or an immunogenic fragment thereof (conjugated to a carrier, if necessary). Adjuvants (e.g., Freund's adjuvant) optionally may be used to increase the immunological response. Sera containing polyclonal antibodies with high affinity for the antigenic determinant can then be isolated from the immunized animal and purified.

Alternatively, antibody-producing tissue from the immunized host can be harvested and a cellular homogenate prepared from the organ can be fused to cultured cancer cells. Hybrid cells which produce monoclonal antibodies specific for a marker can be selected. Alternatively, the antibodies of the disclosure can be produced by chemical synthesis or by recombinant expression. For example, a polynucleotide that encodes the antibody can be used to construct an expression vector for the production of the antibody. The antibodies of the present disclosure can also be generated using various phage display methods known in the art.

Antibodies or aptamers that specifically bind markers of the disclosure can be used, for example, in methods for detecting biomarkers of this disclosure using methods and techniques well-known in the art. In some embodiments, for example, the antibodies are conjugated to a detection molecule or moiety (e.g., a dye, and enzym(e) and can be used in ELISA or sandwich assays to detect markers of the disclosure.

In another embodiment, antibodies or aptamers against a polypeptide marker or polynucleotide marker of the disclosure can be used to assay a tissue sample (e.g., a thin cortical slic(e) for the marker. The antibodies or aptamers can specifically bind to the marker, if any, present in the tissue sections and allow the localization of the marker in the tissue. Similarly, antibodies or aptamers labeled with a radioisotope may be used for in vivo imaging or treatment applications.

Another aspect of the disclosure provides compositions comprising a polypeptide or polynucleotide marker of the disclosure, a binding molecule that is specific for a polypeptide or polynucleotide marker (e.g., an antibody or an aptamer), an inhibitor of a polypeptide or polynucleotide marker, or other molecule that can increase or decrease the level or activity of a polypeptide marker or polynucleotide marker. Such compositions may be pharmaceutical compositions formulated for use as a therapeutic.

Alternatively, the disclosure provides a composition that comprises a component that is a fragment, modification, precursor or successor of a marker of the invention, or to a molecule that comprises a foregoing component.

In another embodiment, the disclosure provides a composition that comprises a polynucleotide that binds to a polypeptide or a molecule that comprises a foregoing polynucleotide.

In another embodiment, the disclosure provides a composition that comprises an antibody or aptamer that specifically binds to a polypeptide or a molecule that comprises a foregoing antibody or aptamer.

Methods for Detecting a Genetic Variant

The present disclosure also provides methods of detecting the biomarkers of the present disclosure. The practice of the present disclosure employs, unless otherwise indicated, conventional methods of analytical biochemistry, microbiology, molecular biology and recombinant DNA techniques within the skill of the art. Such techniques are explained fully in the literature. (See, e.g., Sambrook, J. et al. Molecular Cloning: A Laboratory Manual. 3rd, ed., Cold Spring Harbor Laboratory, Cold Spring Harbor Laboratory Press, Cold Spring Harbor, N Y, 2000; DNA Cloning: A Practical Approach, Vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition); CRC Handbook of Parvoviruses, Vol. I & II (P.

Tijessen, ed.); Fundamental Virology, 2nd Edition, Vol. I & II (B. N. Fields and D. M. Knipe, eds.)).

The methods of the invention are not limited to any particular way of detecting the presence or absence of a genetic variant (e.g. SNP) and can employ any suitable method to detect the presence or absence of a variant(s), of which numerous detection methods are known in the art. Dynamic allele-specific hybridization (DASH) can be used to detect a genetic variant. DASH genotyping takes advantage of the differences in the melting temperature in DNA that results from the instability of mismatched base pairs. The process can be vastly automated and encompasses a few simple principles. Thus, the aspects and embodiments described herein provide methods for assessing the presence or absence of SNPs in a sample (e.g. biological sampl(e) from a subject suspected of having or developing an interstitial lung disease (e.g., because of family history). In certain embodiments, one or more SNPs are screened in one or more samples from a subject. The SNPs can be associated with one or more genes, e.g., one or more genes or other genes associated with mucous secretions as disclosed herein Typically, the target genomic segment is amplified and separated from non-target sequence, e.g., through use of a biotinylated primer and chromatography. A probe that is specific for the particular allele is added to the amplification product. The probe can be designed to hybridize specifically to a variant sequence or to the dominant allelic sequence. The probe can be either labeled with or added in the presence of a molecule that fluoresces when bound to double-stranded DNA. The signal intensity is then measured as temperature is increased until the Tm can be determined. A non-matching sequence (either genetic variant or dominant allelic sequence, depending on probe design), will result in a lower than expected Tm.

DASH genotyping relies on a quantifiable change in Tm, and is thus capable of measuring many types of mutations, not just SNPs. Other benefits of DASH include its ability to work with label free probes and its simple design and performance conditions.

Molecular beacons can also be used to detect a genetic variant. This method makes use of a specifically engineered single-stranded oligonucleotide probe. The oligonucleotide is designed such that there are complementary regions at each end and a probe sequence located in between. This design allows the probe to take on a hairpin, or stem-loop, structure in its natural, isolated state. Attached to one end of the probe is a fluorophore and to the other end a fluorescence quencher. Because of the stem-loop structure of the probe, the fluorophore is in close proximity to the quencher, thus preventing the molecule from emitting any fluorescence. The molecule is also engineered such that only the probe sequence is complementary to the targeted genomic DNA sequence.

If the probe sequence of the molecular beacon encounters its target genomic DNA sequence during the assay, it will anneal and hybridize. Because of the length of the probe sequence, the hairpin segment of the probe will be denatured in favor of forming a longer, more stable probe-target hybrid. This conformational change permits the fluorophore and quencher to be free of their tight proximity due to the hairpin association, allowing the molecule to fluoresce.

If on the other hand, the probe sequence encounters a target sequence with as little as one non-complementary nucleotide, the molecular beacon will preferentially stay in its natural hairpin state and no fluorescence will be observed, as the fluorophore remains quenched. The unique design of these molecular beacons allows for a simple diagnostic assay to identify SNPs at a given location. If a molecular beacon is designed to match a wild-type allele and another to match a mutant of the allele, the two can be used to identify the genotype of an individual. If only the first probe's fluorophore wavelength is detected during the assay then the individual is homozygous to the wild type. If only the second probe's wavelength is detected then the individual is homozygous to the mutant allele. Finally, if both wavelengths are detected, then both molecular beacons must be hybridizing to their complements and thus the individual must contain both alleles and be heterozygous.

A microarray can also be used to detect genetic variants. Hundreds of thousands of probes can be arrayed on a small chip, allowing for many genetic variants or SNPs to be interrogated simultaneously. Because SNP alleles only differ in one nucleotide and because it is difficult to achieve optimal hybridization conditions for all probes on the array, the target DNA has the potential to hybridize to mismatched probes. This can be addressed by using several redundant probes to interrogate each SNP. Probes can be designed to have the SNP site in several different locations as well as containing mismatches to the SNP allele. By comparing the differential amount of hybridization of the target DNA to each of these redundant probes, it is possible to determine specific homozygous and heterozygous alleles.

Restriction fragment length polymorphism (RFLP) can be used to detect genetic variants and SNPs. RFLP makes use of the many different restriction endonucleases and their high affinity to unique and specific restriction sites. By performing a digestion on a genomic sample and determining fragment lengths through a gel assay it is possible to ascertain whether or not the enzymes cut the expected restriction sites. A failure to cut the genomic sample results in an identifiably larger than expected fragment implying that there is a mutation at the point of the restriction site which is rendering it protected from nuclease activity.

PCR- and amplification-based methods can be used to detect genetic variants. For example, tetra-primer PCR employs two pairs of primers to amplify two alleles in one PCR reaction. The primers are designed such that the two primer pairs overlap at a SNP location but each matches perfectly to only one of the possible alleles. As a result, if a given allele is present in the PCR reaction, the primer pair specific to that allele will produce product but not the alternative allele with a different allelic sequence. The two primer pairs can be designed such that their PCR products are of a significantly different length allowing for easily distinguishable bands by gel electrophoresis, or such that they are differently labeled.

Primer extension can also be used to detect genetic variants. Primer extension first involves the hybridization of a probe to the bases immediately upstream of the SNP nucleotide followed by a 'mini-sequencing' reaction, in which DNA polymerase extends the hybridized primer by adding a base that is complementary to the SNP nucleotide. The incorporated base that is detected determines the presence or absence of the SNP allele. Because primer extension is based on the highly accurate DNA polymerase enzyme, the method is generally very reliable. Primer extension is able to genotype most SNPs under very similar reaction conditions making it also highly flexible. The primer extension method is used in a number of assay formats, and can be detected using e.g., fluorescent labels or mass spectrometry.

Primer extension can involve incorporation of either fluorescently labeled ddNTP or fluorescently labeled deoxynucleotides (dNTP). With ddNTPs, probes hybridize to the target DNA immediately upstream of SNP nucleotide, and a single, ddNTP complementary to the SNP allele is added to the 3' end of the probe (the missing 3'-hydroxyl in didioxy-nucleotide prevents further nucleotides from being adde(d). Each ddNTP is labeled with a different fluorescent signal allowing for the detection of all four alleles in the same reaction. With dNTPs, allele-specific probes have 3' bases which are complementary to each of the SNP alleles being interrogated. If the target DNA contains an allele complementary to the 3' base of the probe, the target DNA will completely hybridize to the probe, allowing DNA polymerase to extend from the 3' end of the probe. This is detected by the incorporation of the fluorescently labeled dNTPs onto the end of the probe. If the target DNA does not contain an allele complementary to the probe's 3' base, the target DNA will produce a mismatch at the 3' end of the probe and DNA polymerase will not be able to extend from the 3' end of the probe.

The iPLEX® SNP genotyping method takes a slightly different approach, and relies on detection by mass spectrometer. Extension probes are designed in such a way that many different SNP assays can be amplified and analyzed in a PCR cocktail. The extension reaction uses ddNTPs as above, but the detection of the SNP allele is dependent on the actual mass of the extension product and not on a fluorescent molecule. This method is for low to medium high throughput, and is not intended for whole genome scanning.

Primer extension methods are, however, amenable to high throughput analysis. Primer extension probes can be arrayed on slides allowing for many SNPs to be genotyped at once. Broadly referred to as arrayed primer extension (APEX), this technology has several benefits over methods based on differential hybridization of probes. Comparatively, APEX methods have greater discriminating power than methods using differential hybridization, as it is often impossible to obtain the optimal hybridization conditions for the thousands of probes on DNA microarrays (usually this is addressed by having highly redundant probes).

Oligonucleotide ligation assays can also be used to detect genetic variants. DNA ligase catalyzes the ligation of the 3' end of a DNA fragment to the 5' end of a directly adjacent DNA fragment. This mechanism can be used to interrogate a SNP by hybridizing two probes directly over the SNP polymorphic site, whereby ligation can occur if the probes are identical to the target DNA. For example, two probes can be designed; an allele-specific probe which hybridizes to the target DNA so that its 3' base is situated directly over the SNP nucleotide and a second probe that hybridizes the template upstream (downstream in the complementary stran (d) of the SNP polymorphic site providing a 5' end for the ligation reaction. If the allele-specific probe matches the target DNA, it will fully hybridize to the target DNA and ligation can occur. Ligation does not generally occur in the presence of a mismatched 3' base. Ligated or unligated products can be detected by gel electrophoresis, MALDI-TOF mass spectrometry or by capillary electrophoresis.

The 5'-nuclease activity of Taq DNA polymerase can be used for detecting genetic variants. The assay is performed concurrently with a PCR reaction and the results can be read in real-time. The assay requires forward and reverse PCR primers that will amplify a region that includes the SNP polymorphic site. Allele discrimination is achieved using FRET, and one or two allele-specific probes that hybridize to the SNP polymorphic site. The probes have a fluorophore linked to their 5' end and a quencher molecule linked to their 3' end. While the probe is intact, the quencher will remain in close proximity to the fluorophore, eliminating the fluorophore's signal. During the PCR amplification step, if the allele-specific probe is perfectly complementary to the SNP allele, it will bind to the target DNA strand and then get degraded by 5'-nuclease activity of the Taq polymerase as it extends the DNA from the PCR primers. The degradation of the probe results in the separation of the fluorophore from the quencher molecule, generating a detectable signal. If the allele-specific probe is not perfectly complementary, it will have lower melting temperature and not bind as efficiently. This prevents the nuclease from acting on the probe.

Förster resonance energy transfer (FRET) detection can be used for detection in primer extension and ligation reactions where the two labels are brought into close proximity to each other. It can also be used in the 5'-nuclease reaction, the molecular beacon reaction, and the invasive cleavage reactions where the neighboring donor/acceptor pair is separated by cleavage or disruption of the stem-loop structure that holds them together. FRET occurs when two conditions are met. First, the emission spectrum of the fluorescent donor dye must overlap with the excitation wavelength of the acceptor dye. Second, the two dyes must be in close proximity to each other because energy transfer drops off quickly with distance. The proximity requirement is what makes FRET a good detection method for a number of allelic discrimination mechanisms.

A variety of dyes can be used for FRET, and are known in the art. The most common ones are fluorescein, cyanine dyes (Cy3 to Cy7), rhodamine dyes (e.g. rhodamine 6G), the Alexa series of dyes (Alexa 405 to Alexa 730). Some of these dyes have been used in FRET networks (with multiple donors and acceptors). Optics for imaging all of these require detection from UV to near IR (e.g. Alex 405 to Cy7), and the Atto series of dyes (Atto-Tec GmbH). The Alexa series of dyes from Invitrogen cover the whole spectral range. They are very bright and photostable.

Example dye pairs for FRET labeling include Alexa-405/Alex-488, Alexa-488/Alexa-546, Alexa-532/Alexa-594, Alexa-594/Alexa-680, Alexa-594/Alexa-700, Alexa-700/Alexa-790, Cy3/Cy5, Cy3.5/Cy5.5, and Rhodamine-Green/Rhodamine-Red, etc. Fluorescent metal nanoparticles such as silver and gold nanoclusters can also be used (Richards et al. (2008) J Am Chem Soc 130:5038-39; Vosch et al. (2007) Proc Natl Acad Sci USA 104:12616-21; Petty and Dickson (2003) J Am Chem Soc 125:7780-81 Available filters, dichroics, multichroic mirrors and lasers can affect the choice of dye.

Methods for Detecting Markers, Including Polynucleotide and Polypeptide Expression Levels The markers of the disclosure may be detected by any method known to those of skill in the art, including without limitation LC-MS, GC-MS, immunoassays, hybridization and enzyme assays. The detection may be quantitative or qualitative. A wide variety of conventional techniques are available, including mass spectrometry, chromatographic separations, 2-D gel separations, binding assays (e.g., immunoassays), competitive inhibition assays, and so on. Any effective method in the art for measuring the presence/absence, level or activity of a polypeptide or polynucleotide is included in the disclosure. It is within the ability of one of ordinary skill in the art to determine which method would be most appropriate for measuring a specific marker. Thus, for example, a ELISA assay may be best suited for use in a physician's office while a measurement requiring more sophisticated instrumentation may be best suited for use in a clinical laboratory. Regardless of the method selected, it is important that the measurements be reproducible.

The markers of the disclosure can be measured by mass spectrometry, which allows direct measurements of analytes with high sensitivity and reproducibility. A number of mass spectrometric methods are available. Electrospray ionization (ESI), for example, allows quantification of differences in relative concentration of various species in one sample against another; absolute quantification is possible by normalization techniques (e.g., using an internal standar(d). Matrix-assisted laser desorption ionization (MALDI) or the related SELDI® technology (Ciphergen, Inc.) also could be used to make a determination of whether a marker was present, and the relative or absolute level of the marker. Mass spectrometers that allow time-of-flight (TOF) measurements have high accuracy and resolution and are able to measure low abundant species, even in complex matrices like serum or CSF.

For protein markers, quantification can be based on derivatization in combination with isotopic labeling, referred to as isotope coded affinity tags ("ICAT"). In this and other related methods, a specific amino acid in two samples is differentially and isotopically labeled and subsequently separated from peptide background by solid phase capture, wash and release. The intensities of the molecules from the two sources with different isotopic labels can then be accurately quantified with respect to one another. Quantification can also be based on the isotope dilution method by spiking in an isotopically labeled peptide or protein analogous to those being measured. Furthermore, quantification can also be determined without isotopic standards using the direct intensity of the analyte comparing with another measurement of a standard in a similar matrix.

In addition, one- and two-dimensional gels have been used to separate proteins and quantify gels spots by silver staining, fluorescence or radioactive labeling. These differently stained spots have been detected using mass spectrometry, and identified by tandem mass spectrometry techniques.

In one embodiment, the markers are measured using mass spectrometry in connection with a separation technology, such as liquid chromatography-mass spectrometry or gas chromatography-mass spectrometry. In particular, coupling reverse-phase liquid chromatography to high resolution, high mass accuracy ESI time-of-flight (TOF) mass spectroscopy allows spectral intensity measurement of a large number of biomolecules from a relatively small amount of any complex biological material. Analyzing a sample in this manner allows the marker (characterized by a specific RT and m/z) to be determined and quantified.

As will be appreciated by one of skill in the art, many other separation technologies may be used in connection with mass spectrometry. For example, a wide selection of separation columns is commercially available. In addition, separations may be performed using custom chromatographic surfaces (e.g., a bead on which a marker specific reagent has been immobilize(d). Molecules retained on the media subsequently may be eluted for analysis by mass spectrometry.

Analysis by liquid chromatography-mass spectrometry produces a mass intensity spectrum, the peaks of which represent various components of the sample, each component having a characteristic mass-to-charge ratio (m/z) and retention time (RT). The presence of a peak with the m/z and RT of a marker indicates that the marker is present. The peak representing a marker may be compared to a corresponding peak from another spectrum (e.g., from a control sampl(e) to obtain a relative measurement. Any normalization technique in the art (e.g., an internal standar(d) may be used when a quantitative measurement is desired. "Deconvoluting" software is available to separate overlapping peaks. The retention time depends to some degree on the conditions employed in performing the liquid chromatography separation. Suitable conditions, those used to obtain the retention times that appear in the Tables, are set forth in the Example. The mass spectrometer preferably provides high mass accuracy and high mass resolution. The mass accuracy of a well-calibrated Micromass TOF instrument, for example, is reported to be approximately 5 mDa, with resolution m/Δm exceeding 5000.

In some embodiments, the level of the markers may be determined using a standard immunoassay, such as sandwiched ELISA using matched antibody pairs and chemiluminescent detection. Commercially available or custom monoclonal or polyclonal antibodies are typically used. However, the assay can be adapted for use with other reagents that specifically bind to the marker. Standard protocols and data analysis are used to determine the marker concentrations from the assay data.

A number of the assays discussed above employ a reagent that specifically binds to the marker. Any molecule that is capable of specifically binding to a marker is included within the disclosure. In some embodiments, the binding molecules are antibodies or antibody fragments. In other embodiments, the binding molecules are non-antibody species, such as aptamers. Thus, for example, the binding molecule may be an enzyme for which the marker is a substrate. The binding molecules may recognize any epitope of the targeted markers.

As described above, the binding molecules may be identified and produced by any method accepted in the art. Methods for identifying and producing antibodies and antibody fragments specific for an analyte are well known. Examples of other methods used to identify the binding molecules include binding assays with random peptide libraries (e.g., phage display) and design methods based on an analysis of the structure of the marker.

The markers of the disclosure also may be detected or measured using a number of chemical derivatization or reaction techniques known in the art. Reagents for use in such techniques are known in the art, and are commercially available for certain classes of target molecules.

Finally, the chromatographic separation techniques described above also may be coupled to an analytical technique other than mass spectrometry such as fluorescence detection of tagged molecules, NMR, capillary UV, evaporative light scattering or electrochemical detection.

Measurement of the relative amount of an RNA or protein marker of the disclosure may be by any method known in the art (see, e.g., Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N Y, 1989; and Current Protocols in Molecular Biology, eds. Ausubel et al. John Wiley & Sons: 1992). Typical methodologies for RNA detection include RNA extraction from a cell or tissue sample, followed by hybridization of a labeled probe (e.g., a complementary polynucleotid(e) specific for the target RNA to the extracted RNA, and detection of the probe (e.g., Northern blotting). Typical methodologies for protein detection include protein extraction from a cell or tissue sample, followed by hybridization of a labeled probe (e.g., an antibody) specific for the target protein to the protein sample, and detection of the probe. The label group can be a radioisotope, a fluorescent compound, an enzyme, or an enzyme co-factor. Detection of specific protein and polynucleotides may also be assessed by gel electrophoresis, column chromatography, direct sequencing, or quantitative PCR (in the case of polynucleotides) among many other techniques well known to those skilled in the art.

Detection of the presence or number of copies of all or a part of a marker gene of the disclosure may be performed using any method known in the art. Typically, it is convenient to assess the presence and/or quantity of a DNA or cDNA by Southern analysis, in which total DNA from a cell or tissue sample is extracted, is hybridized with a labeled probe (e.g., a complementary DNA molecul(e), and the probe is detected. The label group can be a radioisotope, a fluorescent compound, an enzyme, or an enzyme co-factor. Other useful methods of DNA detection and/or quantification include direct sequencing, gel electrophoresis, column chromatography, and quantitative PCR, as is known by one skilled in the art.

Polynucleotide similarity can be evaluated by hybridization between single stranded nucleic acids with complementary or partially complementary sequences. Such experiments are well known in the art. High stringency hybridization and washing conditions, as referred to herein, refer to conditions which permit isolation of nucleic acid molecules having at least about 80% nucleic acid sequence identity with the nucleic acid molecule being used to probe in the hybridization reaction (i.e., conditions permitting about 20% or less mismatch of nucleotides).

Very high stringency hybridization and washing conditions, as referred to herein, refer to conditions which permit isolation of nucleic acid molecules having at least about 90% nucleic acid sequence identity with the nucleic acid molecule being used to probe in the hybridization reaction (i.e., conditions permitting about 10% or less mismatch of nucleotides). As discussed above, one of skill in the art can use the formulae in Meinkoth et al., ibid. to calculate the appropriate hybridization and wash conditions to achieve these particular levels of nucleotide mismatch. Such conditions will vary, depending on whether DNA:RNA or DNA:DNA hybrids are being formed. Calculated melting temperatures for DNA:DNA hybrids are 10° C. less than for DNA:RNA hybrids. In particular embodiments, stringent hybridization conditions for DNA:DNA hybrids include hybridization at an ionic strength of 6× SSC (0.9 M $Na^+$) at a temperature of between about 20° C. and about 35° C. (lower stringency), more preferably, between about 28° C. and about 40° C. (more stringent), and even more preferably, between about 35° C. and about 45° C. (even more stringent), with appropriate wash conditions. In particular embodiments, stringent hybridization conditions for DNA:RNA hybrids include hybridization at an ionic strength of 6× SSC (0.9 M $Na^+$) at a temperature of between about 30° C. and about 45° C., more preferably, between about 38° C. and about 50° C., and even more preferably, between about 45° C. and about 55° C., with similarly stringent wash conditions. These values are based on calculations of a melting temperature for molecules larger than about 100 nucleotides, 0% formamide and a G+C content of about 40%. Alternatively, Tm can be calculated empirically as set forth in Sambrook et al., supra, pages 9.31 to 9.62. In general, the wash conditions should be as stringent as possible, and should be appropriate for the chosen hybridization conditions. For example, hybridization conditions can include a combination of salt and temperature conditions that are approximately 20-25° C. below the calculated $T_m$ of a particular hybrid, and wash conditions typically include a combination of salt and temperature conditions that are approximately 12-20° C. below the calculated Tm of the particular hybrid. One example of hybridization conditions suitable for use with DNA:DNA hybrids includes a 2-24 hour hybridization in 6× SSC (50% formamid(e) at about 42° C., followed by washing steps that include one or more washes at room temperature in about 2× SSC, followed by additional washes at higher temperatures and lower ionic strength (e.g., at least one wash as about 37° C. in about 0.1×-0.5× SSC, followed by at least one wash at about 68° C. in about 0.1×-0.5× SS(C). Other hybridization conditions, and for example, those most useful with nucleic acid arrays, will be known to those of skill in the art.

Diagnosis, Monitoring, and Treatment of Interstitial Lung Disease

The present disclosure includes methods of diagnosing interstitial lung diseases such as interstitial pneumonia, idiopathic interstitial pneumonia, familial interstitial pneumonia, idiopathic pulmonary fibrosis, etc, stratifying patients amongst different types of interstitial lung disease, and/or ruling out other types of lung disease that cause similar symptoms and show similar abnormalities on chest radiographs, and related methods. In general, it is expected that the biomarkers described herein will be measured in combination with other signs, symptoms and clinical tests of interstitial lung disease, such as radiographs, pathological evaluation of lung tissue, or interstitial lung disease biomarkers reported in the literature. Likewise, more than one of the biomarkers of the present disclosure may be measured in combination. Measurement of the biomarkers of the disclosure along with any other markers known in the art, including those not specifically listed herein, falls within the scope of the present disclosure. Markers appropriate for this embodiment include those that have been identified as present or increased in samples obtained from biological, and especially lung, samples compared with samples from normal or control samples. Other markers appropriate for this embodiment include fragments, precursors, successors and modified versions of such markers, polypeptides having substantial sequence identity to such markers. Other appropriate markers for this embodiment will be apparent to one of skill in the art in light of the disclosure herein.

The term “interstitial lung disease” or “ILD” is used herein according to its plain and ordinary meaning in the art. Interstitial lung diseases are lung diseases affecting the interstitium. ILDs may be characterized by shortness of breath, chronic coughing, fatigue and weakness, loss of appetite and/or rapid with loss. Where an aspect or embodiment herein refers to ILD, the ILD may be IIP. Where an aspect or embodiment herein refers to ILD, the ILD may be FIP. Where an aspect or embodiment herein refers to ILD, the ILD may be IPF. Where an aspect or embodiment herein refers to ILD, the ILD may be IIP. Additional fibrotic pulmonary diseases include Acute Interstitial Pneumonia (AIP), Respiratory Bronchiolitis-associated Interstitial Lung Disease (RBIL(D), Desquamative Interstitial Pneumonia (DIP), Non-Specific Interstitial Pneumonia (NSIP), Bronchiolitis obliterans, with Organizing Pneumonia (BOOP). AIP is a rapidly progressive and histologically distinct form of interstitial pneumonia. The pathological pattern is an organizing form of diffuse alveolar damage (DA(D) that is also found in acute respiratory distress syndrome (ARDS) and other acute interstitial pneumonias of known causes (see Clinical Atlas of Interstitial Lung Disease (2006 ed.) pp 61-63).

RBILD is characterized by inflammatory lesions of the respiratory bronchioles in cigarette smokers. The histologic appearance of RBILD is characterized by the accumulation of pigmented macrophages within the respiratory bronchioles and the surrounding airspaces, variably, peribronchial fibrotic alveolar septal thickening, and minimal associated mural inflammation (see Wells et al. (2003) Sem Respir. Crit. Care Med. vol. 24).

DIP is a rare interstitial lung disease characterized by the accumulation of macrophages in large numbers in the alveolar spaces associated with interstitial inflammation and/or fibrosis. The macrophages frequently contain light brown pigment. Lymphoid nodules are common, as is a sparse but distinct eosinophil infiltrate. DIP is most common in smokers (see Tazelaar et al. (Sep. 21, 2010) Histopathology).

NSIP is characterized pathologically by uniform interstitial inflammation and fibrosis appearing over a short period of time. NSIP differs from other interstitial lung diseases in that it has a generally good prognosis. In addition, the temporal uniformity of the parenchymal changes seen in NSIP contrasts greatly with the temporal heterogeneity of usual interstitial pneumonia (see Coche et al. (2001) Brit J Radiol 74:189).

BOOP, unlike NSIP, can be fatal within days of first acute symptoms. It is characterized by rapid onset of acute respiratory distress syndrome; therefore, clinically, rapidly progressive BOOP can be indistinguishable from acute interstitial pneumonia. Histological features include clusters of mononuclear inflammatory cells that form granulation tissue and plug the distal airways and alveolar spaces. These plugs of granulation tissue may form polyps that migrate within the alveolar ducts or may be focally attached to the wall. (see White & Ruth-Saad (2007) Crit. Care Nurse 27:53).

Further details about the characteristics and therapies available for these diseases can be found, e.g., on the website of the American Lung Association at lungusa.org/lung-disease/pulmonary-fibrosis. Diagnostic indicators of pulmonary disorders include biopsy (e.g., VATS or surgical lung biopsy), high resolution computed tomography (HRT(C) or breathing metrics, such as forced expiratory volume (FEV1), vital capacity (V(C), forced vital capacity (FV(C), and FEV1/FVC.

The idiopathic interstitial pneumonias (IIP) can include idiopathic pulmonary fibrosis and familial interstitial pneumonia (FIP). Idiopathic interstitial pneumonias (IIP) are a subset of diffuse interstitial lung diseases of unknown etiology (the term "idiopathic" indicates unknown origin). IIPs are characterized by expansion of the interstitial compartment (i.e., that portion of the lung parenchyma sandwiched between the epithelial and endothelial basement membranes) with an infiltrate. The infiltrate may be accompanied by fibrosis, either in the form of abnormal collagen deposition or proliferation of fibroblasts capable of collagen synthesis.

Idiopathic Pulmonary Fibrosis (IPF) occurs in thousands of people worldwide with a doubling of prevalence over the past 10 years. Onset of IPF occurs around 50 to 70 years of age and starts with progressive shortness of breath and hypoxemia. IPF median survival is around 3-5 years. The etiology and pathogenesis of the condition is not well understood. About 5-20 percent of all cases of IPF have a family history and inheritance appears to be autosomal dominant.

Provided herein are methods for determining whether a subject has interstitial lung disease. In another aspect, the disclosure provides methods for diagnosing interstitial lung disease in a subject. These methods comprise obtaining a biological sample from a subject suspected of having interstitial pneumonia, or at risk for developing interstitial lung disease, detecting the presence or level or activity of one or more biomarkers in the sample, and comparing the result to the present, level or activity of the marker(s) in a sample obtained from a control or normal subject, or to a reference range or value. As used herein, the term "biological sample" includes a sample from any body fluid or tissue (e.g., mucus, whole blood, peripheral blood mononuclear cells (PBMCs), serum, plasma, blood, cerebrospinal fluid, urine, saliva, lung tissu(e).

One of skill in the art will understand that a blood sample or a check swab is expected to carry the same genetic sequence information as a lung cell. For detection of a given expression level, pulmonary tissue samples and other biological fluids are typically used. Biological samples can include a pulmonary mucosal sample or biological fluid such as blood or blood components (plasma, serum), sputum, mucus, urine, saliva, etc. A pulmonary mucosal sample can be obtained using methods known in the art, e.g., a bronchial epithelial brush or exhaled breath condensate. Additional methods include bronchial biopsy, bronchial wash, bronchoalveolar lavage, whole lung lavage, transendoscopic biopsy, translaryngoscopic catheter, and transtracheal wash. A review of commonly used techniques, including comparisons and safety issues, is provided in Busse et al. (2005) Am J Respir Crit Care Med 172:807-816. For lavage techniques, a bronchoscope can be inserted to the desired level of the airway. A small volume of sterile, physiologically acceptable fluid (e.g., buffered salin(e) is released, and immediately aspirated. The wash material contains cells from the mucosa and upper epithelia (Riise et al. (1996) Eur Resp J9:1665). For use of a bronchial epithelial brush, a sterile, non-irritating (e.g., nylon) cytology brush can be used. Multiple brushings can be taken to ensure representative sampling. The brush is then agitated in physiologically acceptable fluid, and the cells and debris separated using routine methods (Riise et al. (1992) Eur Resp J 5:382). Cellular components can be isolated using methods known in the art, e.g., centrifugation. Similarly, subcellular components (e.g., exosomes or vesicles) can be isolated using known methods or commercial separation products (available from BioCat, System Bio, Bioscientific, etc.). An exemplary method is described e.g., by Thery et al. (2006) Current Prot. Cell Biol.

Typically, the standard biomarker level or reference range is obtained by measuring the same marker or markers in a set of normal controls. Measurement of the standard biomarker level or reference range need not be made contemporaneously; it may be a historical measurement. Preferably the normal control is matched to the individual with respect to some attribute(s) (e.g., ag(c). Depending upon the difference between the measured and standard level or reference range, the individual can be diagnosed as having interstitial lung disease or as not having interstitial lung disease. In some embodiments, interstitial lung disease is diagnosed in the individual if the expression level of the biomarker or biomarkers in the individual sample is statistically more similar to the expression level of the biomarker or biomarkers that has been associated with interstitial lung disease than the expression level of the biomarker or biomarkers that has been associated with the normal controls.

What is presently referred to as interstitial lung disease includes a number of related, but distinguishable conditions. Classifications can be made, and these types may be further distinguished into subtypes. Any and all of the various forms of interstitial lung disease are intended to be within the scope of the present disclosure. Indeed, by providing a method for subsetting individuals based on biomarker measurement level, the compositions and methods of the present disclosure may be used to uncover and define various forms of the disease.

The methods of the present disclosure may be used to make the diagnosis of interstitial pneumonia, independently from other information such as the individual's symptoms or the results of other clinical or paraclinical tests. However, the methods of the present disclosure may be used in conjunction with such other data points.

Because a diagnosis is rarely based exclusively on the results of a single test, the method canbe used to determine whether a subject is more likely than not to have interstitial lung disease, or is more likely to have interstitial lung disease than to have another disease, based on the difference between the measured and standard level or reference range of the biomarker. Thus, for example, an individual with a putative diagnosis of interstitial lung disease may be diagnosed as being "more likely" or "less likely" to have interstitial lung disease in light of the information provided by a method of the present disclosure. If a plurality of biomarkers are measured, at least one and up to all of the measured biomarkers must differ, in the appropriate direction, for the subject to be diagnosed as having (or being more likely to hav(e) interstitial lung disease. In some embodiments, such difference is statistically significant.

The biological sample may be of any tissue or fluid, including a serum or tissue sample, but other biological fluids or tissue may be used. Possible biological fluids include, but are not limited to, mucus, whole blood, peripheral blood mononuclear cells (PBMCs), plasma, urine, saliva and lung tissue. In some embodiments, the level of a marker may be compared to the level of another marker or some other component in a different tissue, fluid or biological "compartment." Thus, a differential comparison may be made of a marker in tissue and serum. It is also within the scope of the disclosure to compare the level of a marker with the level of another marker or some other component within the same compartment.

As will be apparent to those of ordinary skill in the art, the above description is not limited to making an initial diagnosis of interstitial lung disease, but also is applicable to confirming a provisional diagnosis of interstitial lung disease or "ruling out" such a diagnosis. Furthermore, an increased or decreased level or activity of the marker(s) in a sample obtained from a subject suspected of having interstitial lung disease, or at risk for developing interstitial lung disease (e.g., with a genetic predisposition), is indicative that the subject has or is at risk for developing interstitial lung disease.

Based on the diagnosis, a practitioner can further determine a course of treatment for interstitial lung disease. Therapy options are limited, but can include palliative measures, decongestants, pain killers, immunosuppression, lung transplantation. In addition, based on the present disclosure, treatment can include targeted gene or antibody therapy directed to reduce or correct expression of the disclosed biomarkers to more normal levels. Treatment can be adjusted over time depending on the continued monitoring of the subject, e.g., measurement of expression levels of the presently disclosed biomarkers, or other measures such as radiology, oxygen capacity, comfort levels, etc.

The disclosure also provides a method for determining a subject's risk of developing interstitial lung disease, the method comprising obtaining a biological sample from a subject, detecting the presence, level or activity of a marker in the sample, and comparing the result to the presence, level or activity of the marker in a sample obtained from a non-interstitial lung disease subject, or to a reference range or value wherein the presence, or an increase or decrease of the marker is correlated with the risk of developing interstitial lung disease.

The disclosure also provides methods for determining the stage or severity of interstitial lung disease, the method comprising obtaining a biological sample from a subject, detecting the presence, level or activity of a marker in the sample, and comparing the result to the present, level or activity of the marker in a sample obtained from a normal or control subject, or to a reference range or value wherein the presence, or an increase or decrease of the marker is correlated with the stage or severity of the disease.

In another aspect, the disclosure provides methods for monitoring the progression of the disease in a subject who has interstitial lung disease, the method comprising obtaining a first biological sample from a subject, detecting the level or activity of a marker in the sample, and comparing the result to the level or activity of the marker in a second sample obtained from the subject at a later time, or to a reference range or value wherein an increase of the marker is correlated with progression of the disease.

A significant difference in the elevation of the measured value of one or more of the gene markers indicates that the individual has (or is more likely to have, or is at risk of having, or is at risk of developing, or is at increased risk of developing progressiv(e) interstitial lung disease. If only one biomarker is measured, then that value must increase to indicate interstitial lung disease. If more than one biomarker is measured, then a diagnosis of interstitial pneumonia can be indicated by a change in only one biomarker, all biomarkers, or any number in between. In some embodiments, multiple markers are measured, and a diagnosis of interstitial lung disease is indicated by changes in multiple markers. For example, a panel of markers may include markers that are increased in level or activity in interstitial lung disease subject samples as compared to non-interstitial lung disease subject samples. Measurements can be of (i) a biomarker of the present disclosure, (ii) a biomarker of the present disclosure and another factor known to be associated with interstitial lung disease (e.g., CT scan); (iii) a plurality of biomarkers of the present disclosure, (iv) a plurality of biomarkers comprising at least one biomarker of the present disclosure and at least one biomarker reported in the literature; (v) a biomarker or a plurality of biomarkers of the present disclosure and at least one clinical covariate that may include the individual's age, pathological evaluation results, and (vi) any combination of the foregoing. Furthermore, the amount of change in a biomarker level may be an indication of the relative likelihood of the progression of the disease.

The marker(s) may be detected in any biological sample obtained from the subject, by any suitable method known in the art (e.g., immunoassays, hybridization assay). Preferably, the marker(s) are detected in a sample of whole blood obtained from the individual.

In an alternative embodiment of the disclosure, a method is provided for monitoring interstitial lung disease in an individual over time to determine whether the disease is progressing. The specific techniques used in implementing this embodiment are similar to those used in the embodiments described above. The method is performed by obtaining a biological sample, such as serum or lung tissue, from the subject at a certain time ($t_1$); measuring the level of at least one of the biomarkers in the biological sample; and comparing the measured level with the level measured with respect to a biological sample obtained from the subject at an earlier time ($t_0$). Depending upon the difference between the measured levels, it can be seen whether the marker level has increased, decreased, or remained constant over the interval ($t_1$-$t_0$). A further deviation of a marker in the direction indicating interstitial pneumonia, or the measurement of additional increased interstitial lung disease markers, would suggest a progression of the disease during the interval. Subsequent sample acquisitions and measurements can be performed as many times as desired over a range of times $t_2$ to $t_n$.

The ability to monitor an individual by making serial marker level determinations would represent a valuable clinical tool. Rather than the limited "snapshot" provided by a single test, such monitoring would reveal trends in marker levels over time. In addition to indicating a progression of the disease, tracking the marker levels in an individual could be used to predict exacerbations or indicate the clinical course of the disease. For example, as will be apparent to one of skill in the art, the biomarkers of the present disclosure could be further investigated to distinguish between any or all of the known forms of interstitial lung disease or any later described types or subtypes of the disease. In addition, the sensitivity and specificity of any method of the present disclosure could be further investigated with respect to distinguishing interstitial lung disease from other diseases or to predict relapse or remission.

In an analogous manner, administration a drug or drug combination can be evaluated or re-evaluated in light of the assay results of the present disclosure. For example, the drug(s) can be administered differently to different subject populations, and measurements corresponding to administration analyzed to determine if the differences in the inventive biomarker signature before and after drug administration are significant. Results from the different drug regiments can also be compared with each other directly. Alternatively, the assay results may indicate the desirability of one drug regimen over another, or indicate that a specific drug regimen should or should not be administered to an interstitial pneumonia individual. In one embodiment, the finding of elevated levels of the marker genes of the present disclosure in an interstitial lung disease individual is indicative of a poor prognosis. In another embodiment, the absence of elevated levels of the marker genes of the present disclosure in an interstitial lung disease individual is indicative of a good prognosis.

In another aspect, the disclosure provides methods for screening candidate compounds for use as therapeutic compounds in the treatment of interstitial lung disease. In one embodiment, the method comprises screening candidate compounds for those that provide clinical progress following administration to an interstitial lung disease patient from which a lung sample has been shown to have elevated levels of the markers of the present disclosure.

In an analogous manner, the markers of the present disclosure can be used to assess the efficacy of a therapeutic intervention in a subject. The same approach described above would be used, except a suitable treatment would be started, or an ongoing treatment would be changed, before the second measurement (i.e., after to and before $t_1$). The treatment can be any therapeutic intervention, such as drug administration, dietary restriction or surgery, and can follow any suitable schedule over any time period as appropriate for the intervention. The measurements before and after could then be compared to determine whether or not the treatment had an effect. As will be appreciated by one of skill in the art, the determination may be confounded by other superimposed processes (e.g., an exacerbation of the disease during the same perio(d).

In a further embodiment, the markers may be used to screen candidate drugs, for example, in a clinical trial, to determine whether a candidate drug is effective in treating interstitial lung disease. At time to, a biological sample is obtained from each subject in population of subjects diagnosed with interstitial pneumonia. Next, assays are performed on each subject's sample to measure levels of a biological marker. In some embodiments, only a single marker is monitored, while in other embodiments, a combination of markers, up to the total number of markers provided herein, is monitored. Next, a predetermined dose of a candidate drug is administered to a portion or sub-population of the same subject population. Drug administration can follow any suitable schedule over any time period. In some cases, varying doses are administered to different subjects within the sub-population, or the drug is administered by different routes. At time $t_1$, after drug administration, a biological sample is acquired from the sub-population and the same assays are performed on the biological samples as were previously performed to obtain measurement values. As before, subsequent sample acquisitions and measurements can be performed as many times as desired over a range of times $t_2$ to $t_n$. In such a study, a different sub-population of the subject population serves as a control group, to which a placebo is administered. The same procedure is then followed for the control group: obtaining the biological sample, processing the sample, and measuring the biological markers to obtain a measurement chart.

Specific doses and delivery routes can also be examined. The method is performed by administering the candidate drug at specified dose or delivery routes to subjects with interstitial lung disease; obtaining biological samples, such as serum or tissue, from the subjects; measuring the level of at least one of the biomarkers in each of the biological samples; and, comparing the measured level for each sample with other samples and/or a standard level. Typically, the standard level is obtained by measuring the same marker or markers in the subject before drug administration. Depending upon the difference between the measured and standard levels, the drug can be considered to have an effect on interstitial lung disease. If multiple biomarkers are measured, at least one and up to all of the biomarkers must change, in the expected direction, for the drug to be considered effective. Preferably, multiple markers must change for the drug to be considered effective, and preferably, such change is statistically significant.

As will be apparent to those of ordinary skill in the art, the above description is not limited to a candidate drug, but is applicable to determining whether any therapeutic intervention is effective in treating interstitial lung disease.

In a typical embodiment, a subject population having interstitial lung disease is selected for the study. The population is typically selected using standard protocols for selecting clinical trial subjects. For example, the subjects are generally healthy, are not taking other medication, and are evenly distributed in age and sex. The subject population can also be divided into multiple groups; for example, different sub-populations may be suffering from different types or different degrees of the disorder to which the candidate drug is addressed. The stratification of the individual population may be made based on the levels of biomarkers of the present disclosure.

In general, a number of statistical considerations must be made in designing the trial to ensure that statistically significant changes in biomarker measurements can be detected following drug administration. The amount of change in a biomarker depends upon a number of factors, including strength of the drug, dose of the drug, and treatment schedule. It will be apparent to one skilled in statistics how to determine appropriate subject population sizes. Preferably, the study is designed to detect relatively small effect sizes.

The subjects optionally may be "washed out" from any previous drug use for a suitable period of time. Washout removes effects of any previous medications so that an accurate baseline measurement can be taken. At time to, a biological sample is obtained from each subject in the population. Next, an assay or variety of assays is performed on each subject's sample to measure levels of particular biomarkers of the disclosure. The assays can use conventional methods and reagents, as described above. If the sample is blood, then the assays typically are performed on either serum or plasma. For other fluids or tissues, additional sample preparation steps are included as necessary before the assays are performed. The assays measure values of at least one of the biological markers described herein. In some embodiments, only a single marker is monitored, while in other embodiments, a combination of factors, up to the total number of markers, is monitored. The markers can also be monitored in conjunction with other measurements and factors associated with interstitial lung disease (e.g., MRI imaging). The number of biological markers whose values are measured depends upon, for example, the availability of assay reagents, biological fluid, and other resources.

Next, a predetermined dose of a candidate drug is administered to a portion or sub-population of the same subject population. Drug administration can follow any suitable schedule over any time period, and the sub-population can include some or all of the subjects in the population. In some cases, varying doses are administered to different subjects within the sub-population, or the drug is administered by different routes. Suitable doses and administration routes depend upon specific characteristics of the drug. At time $t_1$, after drug administration, another biological sample (the "$t_1$ sample") is acquired from the sub-population. Typically, the sample is the same type of sample and processed in the same manner as the sample acquired from the subject population before drug administration (the "to sample"). The same assays are performed on the $t_1$ sample as on the $t_0$ sample to obtain measurement values. Subsequent sample acquisitions and measurements can be performed as many times as desired over a range of times $t_2$ to $t_n$.

Typically, a different sub-population of the subject population is used as a control group, to which a placebo is administered. The same procedure is then followed for the control group: obtaining the biological sample, processing the sample, and measuring the biological markers to obtain measurement values. Additionally, different drugs can be administered to any number of different sub-populations to compare the effects of the multiple drugs. As will be apparent to those of ordinary skill in the art, the above description is a highly simplified description of a method involving a clinical trial. Clinical trials have many more procedural requirements, and it is to be understood that the method is typically implemented following all such requirements.

Paired measurements of the various biomarkers are now available for each subject. The different measurement values are compared and analyzed to determine whether the biological markers changed in the expected direction for the drug group but not for the placebo group, indicating that the candidate drug is effective in treating the disease. In some embodiments, such change is statistically significant. The measurement values at time ty for the group that received the candidate drug are compared with standard measurement values, preferably the measured values before the drug was given to the group, i.e., at time to. Typically, the comparison takes the form of statistical analysis of the measured values of the entire population before and after administration of the drug or placebo. Any conventional statistical method can be used to determine whether the changes in biological marker values are statistically significant. For example, paired comparisons can be made for each biomarker using either a parametric paired t-test or a non-parametric sign or sign rank test, depending upon the distribution of the data.

In addition, tests may be performed to ensure that statistically significant changes found in the drug group are not also found in the placebo group. Without such tests, it cannot be determined whether the observed changes occur in all individuals and are therefore not a result of candidate drug administration.

The gene marker expression values are higher in samples taken from individuals having interstitial lung disease. A significant decrease in the measured value of one or more of the gene expression markers indicates that the drug is effective. If only one biomarker is measured, then that value must decrease to indicate drug efficacy. If more than one biomarker is measured, then drug efficacy can be indicated by change in only one biomarker, all biomarkers, or any number in between. In some embodiments, multiple markers are measured, and drug efficacy is indicated by changes in multiple markers. Measurements can be of both biomarkers of the present disclosure and other measurements and factors associated with interstitial lung disease. Furthermore, the amount of decrease in a gene biomarker level may be an indication of the relatively efficacy of the drug.

In addition to determining whether a particular drug is effective in treating interstitial lung disease, biomarkers of the disclosure can also be used to examine dose effects of a candidate drug. There are a number of different ways that varying doses can be examined. For example, different doses of a drug can be administered to different subject populations, and measurements corresponding to each dose analyzed to determine if the differences in the inventive biomarkers before and after drug administration are significant. In this way, a minimal dose required to effect a change can be estimated. In addition, results from different doses can be compared with each other to determine how each biomarker behaves as a function of dose. Based on the results of drug screenings, the markers of the disclosure may be used as theragnostics; that is, they can be used to individualize medical treatment.

Kits

In another aspect, the disclosure provides a kit for detecting polynucleotide or polypeptide marker(s) of the present disclosure. The kit may be prepared as an assay system including any one of assay reagents, assay controls, protocols, exemplary assay results, or combinations of these components designed to provide the user with means to evaluate the expression level of the marker(s) of the present disclosure.

In another aspect, the disclosure provides a kit for diagnosing interstitial lung disease in an individual including reagents for detecting at least one polypeptide or polynucleotide marker in a biological sample from a subject.

The kits of the disclosure may comprise one or more of the following: an antibody, wherein the antibody specifically binds with a polypeptide marker, a labeled binding partner to the antibody, a solid phase upon which is immobilized the antibody or its binding partner, a polynucleotide probe that can hybridize to a polynucleotide marker, pairs of primers that under appropriate reaction conditions can prime amplification of at least a portion of a polynucleotide marker or a polynucleotide encoding a polypeptide marker (e.g., by PCR), instructions on how to use the kit, and a label or insert indicating regulatory approval for diagnostic or therapeutic use.

The disclosure further includes polynucleotide or polypeptide microarrays comprising polypeptides of the disclosure, polynucleotides of the disclosure, or molecules, such as antibodies, which specifically bind to the polypeptides or polynucleotides of the present disclosure. In this aspect of the disclosure, standard techniques of microarray technology are utilized to assess expression of the polypeptides biomarkers and/or identify biological constituents that bind such polypeptides. Protein microarray technology is well known to those of ordinary skill in the art and is based on, but not limited to, obtaining an array of identified peptides or proteins on a fixed substrate, binding target molecules or biological constituents to the peptides, and evaluating such binding. Polynucleotide arrays, particularly arrays that bind polypeptides of the disclosure, also can be used for diagnostic applications, such as for identifying subjects that have a condition characterized by expression of polypeptide biomarkers, e.g., interstitial lung disease.

The assay systems of the present disclosure can include a means for detecting in a sample of lung cells a level of amplification of the marker gene(s) and/or a level of polysomy of the marker gene(s). The assay system preferably also includes one or more controls. The controls may include: (i) a control sample for detecting interstitial lung disease in an individual; (ii) a control sample for detecting the absence of interstitial lung disease; and, (iii) information containing a predetermined control level of gene markers to be measured with regard to the diagnosis of or progression of interstitial lung disease.

In another embodiment, a means for detecting the expression level of the marker(s) of the disclosure can generally be any type of reagent that can include, but are not limited to, antibodies and antigen binding fragments thereof, peptides, binding partners, aptamers, enzymes, and small molecules. Additional reagents useful for performing an assay using such means for detection can also be included, such as reagents for performing immunohistochemistry or another binding assay.

The means for detecting of the assay system of the present disclosure can be conjugated to a detectable tag or detectable label. Such a tag can be any suitable tag which allows for detection of the reagents used to detect the gene or protein of interest and includes, but is not limited to, any composition or label detectable by spectroscopic, photochemical, electrical, optical or chemical means. Useful labels in the present disclosure include: biotin for staining with labeled streptavidin conjugate, magnetic beads (e.g., Dynabeads™), fluorescent dyes (e.g., fluorescein, texas red, rhodamine, green fluorescent protein, and the lik(e), radiolabels (e.g., $^{3}H$, $^{125}I$, $^{35}S$, $^{14}C$, or $^{32}P$), enzymes (e.g., horse radish peroxidase, alkaline phosphatase and others commonly used in an ELIS(A), and colorimetric labels such as colloidal gold or colored glass or plastic (e.g., polystyrene, polypropylene, latex, etc.) beads.

In addition, the means for detecting of the assay system of the present disclosure can be immobilized on a substrate. Such a substrate can include any suitable substrate for immobilization of a detection reagent such as would be used in any of the previously described methods of detection. Briefly, a substrate suitable for immobilization of a means for detecting includes any solid support, such as any solid organic, biopolymer or inorganic support that can form a bond with the means for detecting without significantly affecting the activity and/or ability of the detection means to detect the desired target molecule. Exemplary organic solid supports include polymers such as polystyrene, nylon, phenol-formaldehyde resins, and acrylic copolymers (e.g., polyacrylamid(e). The kit can also include suitable reagents for the detection of the reagent and/or for the labeling of positive or negative controls, wash solutions, dilution buffers and the like. The assay system can also include a set of written instructions for using the system and interpreting the results.

The assay system can also include a means for detecting a control marker that is characteristic of the cell type being sampled can generally be any type of reagent that can be used in a method of detecting the presence of a known marker (at the nucleic acid or protein level) in a sample, such as by a method for detecting the presence of a biomarker of this disclosure. Specifically, the means is characterized in that it identifies a specific marker of the cell type being analyzed that positively identifies the cell type. For example, in an interstitial lung disease assay, it is desirable to screen lung cells for the level of the biomarker expression and/or biological activity. Therefore, the means for detecting a control marker identifies a marker that is characteristic of a lung cell, so that the cell is distinguished from other cell types. Such a means increases the accuracy and specificity of the assay of the present disclosure. Such a means for detecting a control marker include, but are not limited to: a probe that hybridizes under stringent hybridization conditions to a nucleic acid molecule encoding a protein marker; PCR primers which amplify such a nucleic acid molecule; an aptamer that specifically binds to a conformationally-distinct site on the target molecule; and/or an antibody, antigen binding fragment thereof, or antigen binding peptide that selectively binds to the control marker in the sample. Nucleic acid and amino acid sequences for many cell markers are known in the art and can be used to produce such reagents for detection.

In some embodiments, the kit includes (or consists essentially of) primers or at least one probe capable of detecting a genetic variant, e.g., as described above, depending on the detection method selected. In some embodiments, the kit includes primers or at least one probe capable of detecting a genetic variant in a region selected from the group consisting of 5p15, 6p24, 7q22, 11p15, 15q14-15, 17q21, 19p13, and 8p23. In some embodiments, the kit includes primers or at least one probe capable of detecting at least one genetic variant in 6p24 (e.g., rs2076295 or rs3778337). In some embodiments, the kit includes primers or at least one probe capable of detecting at least one genetic variant in 7922 (e.g., rs4727443). In some embodiments, the kit includes primers or at least one probe capable of detecting at least one genetic variant in 11p15 (e.g., rs868903, rs7934606, rs6421972, rs7480563, rs7942850, rs4077759, rs2334659, rs2334659, rs7122936). In some embodiments, the kit includes primers or at least one probe capable of detecting at least one genetic variant in 5p15 (e.g., rs2736100). In some embodiments, the kit includes primers or at least one probe capable of detecting at least one genetic variant in 15q14-15(e.g., rs2034650, rs1992272). In some embodiments, the kit includes primers or at least one probe capable of detecting at least one genetic variant in 17q21 (e.g., rs1981997, rs17563986, rs8070723). In some embodiments, the kit includes primers or at least one probe capable of detecting at least one genetic variant in 19p13 (e.g., rs12610495, rs2109069). In some embodiments, the kit includes primers or at least one probe capable of detecting at least one genetic variant in 8p23 (e.g., rs1379326). In some embodiments, the kit includes primers or probes capable of detecting more than one (e.g., 2, 3, 4, 5, 5-10, 10-20, or mor(e) genetic variant in 5p15, 6p24, 7q22, 11p15, 15q14-15, 17q21, 19p13, and 8p23 in any combination.

In some embodiments, the primers and/or probes are labeled, e.g., with fluorescent labels or FRET labels. In some embodiments, the primers and/or probes are unlabeled. In some embodiments, the kit includes primers and/or probes that detect both a variant allelic sequence and the dominant allelic sequence at a selected genetic variant site, e.g., with different labels, or designed to generate amplification or primer extension products with different masses.

In some embodiments, the kit further includes at least one control sample, e.g., sample(s) with dominant allele(s) at the selected genetic variation site(s), or sample(s) with variant allele(s) at the selected genetic variation site(s).

In Vitro Complexes

Provided herein are nucleic acid complexes, e.g., formed in in vitro assays to indicate the presence of a genetic variant sequence. One of skill will understand that a nucleic acid complex can also be formed to detect the presence of a dominant allelic sequence, depending on the design of the probe or primer, e.g., in assays to distinguish homozygous and heterozygous subjects.

In some embodiments, the complex comprises a first nucleic acid hybridized to a genetic variant nucleic acid, wherein the genetic variant nucleic acid is a genetic variant in a region selected from 5p15, 6p24, 7922, 11p15, 15q14-15, 17q21, 19p13, and 8p23, or in a gene selected from TERT, DSP, MUC2, DISP2, MAPT, DPP9, CSMD1, MYNN, LRRC34, FAM13A, OBFC1, TOLLIP, MUC5B, ATP11A, IVD, CRHR1, IMP5, LOC100128977, KIAA1267, NSF, and WNT3. In some embodiments, the genetic variant nucleic acid is an amplification product. In some embodiments, the genetic variant nucleic acid is on genomic DNA, e.g., from a subject that has or is suspected of having an interstitial lung disease. In some embodiments, the first nucleic acid is an amplification product or a primer extension product. In some embodiments, the first nucleic acid is labeled. In some embodiments, the nucleic acid complex further comprises a second nucleic acid hybridized to the genetic variant nucleic acid. In some embodiments, the second nucleic acid is labeled e.g., with a FRET or other fluorescent label. In some embodiments, the first and second nucleic acids form a FRET pair when hybridized to a genetic variant sequence.

In some embodiments, the nucleic acid complex further comrprises an enzyme, such as a DNA polymerase (e.g., standard DNA polymerase or thermostable polymerase such as Taq) or ligase.

The present disclosure includes but is not limited to the following embodiments:

1. A method for determining if an individual is predicted to develop and/or progress rapidly with an interstitial pneumonia comprising: detecting in a biological sample from the individual, at least one of: (a) the presence of a marker polymorphism selected from the group consisting of: rs2736100, rs2076295, rs3778337, rs4727443, rs868903, rs7934606, rs6421972, rs7480563, rs7942850, rs4077759, rs2334659, rs7122936, rs2034650, rs1992272, rs1981997, rs17563986, rs8070723, rs12610495, rs2109069, rs1379326, rs1881984, rs10936599, rs1997392, rs6793295, rs2609255, rs2853676, rs10484326, rs10748858, rs2067832, rs11191865, rs2301160, rs3829223, rs2857476, rs1278769, rs1007177, rs10518693, rs393152, rs12373139, rs17690703, rs2532274, rs2532269, rs2668692, rs169201, rs199533, and rs415430; and, (b) a level of gene expression of a marker gene or plurality of marker genes selected from the group consisting of: a marker gene having at least 95% sequence identity with at least one sequence selected from the group consisting of MUC5B, TERT, DSP, MUC2, DISP2, MAPT, DPP9, CSMD1, MYNN, LRRC34, FAM13A, OBFC1, TOLLIP, ATP11A, IVD, CRHR1, IMP5, LOC100128977, KIAA1267, NSF, WNT3, C17orf69, or homologs or variants thereof; (c) polypeptides encoded by the marker genes of (b); (d) fragments of polypeptides of (c); and (e) a polynucleotide which is fully complementary to at least a portion of a marker gene of (b); wherein the presence of the plurality of markers is indicative of whether an individual will develop interstitial pneumonia or develop a progressive IIP disease.
2. The method of embodiment 1, wherein the genes detected share 100% sequence identity with the corresponding marker gene in (b).
3. The method of embodiment 1, wherein the presence or level of at least one of the plurality of markers is determined and compared to a standard level or reference set.
4. The method of embodiment 1, wherein the standard level or reference set is determined according to a statistical procedure for risk prediction.
5. The method of embodiment 4, wherein the statistical procedure for risk prediction comprises using the sum of the gene expression of the marker or markers or the presence or absence of a set of markers, weighted by a Proportional Hazards coefficient.
6. The method of embodiment 1, wherein the presence of the at least one marker is determined by detecting the presence or absence or expression level of a polypeptide.
7. The method of embodiment 6, wherein the method further comprises detecting the presence of the polypeptide using a reagent that specifically binds to the polypeptide or a fragment thereof.
8. The method of embodiment 7, wherein the reagent is selected from the group consisting of an antibody, an antibody derivative, and an antibody fragment.
9. The method of embodiment 1, wherein the presence of the marker is determined by obtaining the sequence of genomic DNA at the locus of the polymorphism.
10. The method of embodiment 1, wherein the presence of the marker is determined by obtaining RNA from the biological sample; generating cDNA from the RNA; amplifying the cDNA with probes or primers for marker genes; obtaining from the amplified cDNA the expression levels of the genes or gene expression products in the sample.
11. The method of any of embodiment 1, wherein the individual is a human.
12. The method of any of embodiment 1, further comprising: (a) comparing the expression level of the marker gene or plurality of marker genes in the biological sample to a control level of the marker gene(s) selected from the group consisting of: a control level of the marker gene that has been correlated with interstitial lung disease, the risk of developing IIP, or having a progressive interstitial pneumonia; and a control level of the marker that has been correlated with slow or no progression of interstitial lung disease or interstitial pneumonia, or low risk of developing an IIP; and (b) selecting the individual as being predicted to progress rapidly in the development of interstitial pneumonia, if the expression level of the marker gene in the individual's biological sample is statistically similar to, or greater than, the control level of expression of the marker gene that has been correlated with interstitial lung disease or rapid progression of interstitial pneumonia, or (c) selecting the individual as being predicted to not develop interstitial pneumonia, or to progress slowly, if the level of the marker gene in the individual's biological sample is statistically less than the control level of the marker gene that has been correlated with interstitial lung disease or rapid progression of interstitial pneumonia.

13. The method of embodiment 1, further comprising: comparing the presence of a polymorphism, in the biological sample to a set of genetic variants or polymorphic markers from an individual or control group having developed interstitial pneumonia, and, selecting the individual as being predicted to develop or to progress with interstitial pneumonia if the polymorphic markers present in the biological sample are identical to or statistically similar to a set of polymorphic markers from the individual or control group or, selecting the individual as being predicted to develop or rapidly progress with interstitial pneumonia, if the polymorphic markers present in the biological sample are not identical to or statistically similar to the set of genetic variants or polymorphic markers from the individual or control group.

14. A method for monitoring the progression of interstitial lung disease or interstitial pneumonia in a subject, comprising: i) measuring expression levels of a plurality of gene markers in a first biological sample obtained from the subject, wherein the plurality of markers comprise a plurality of markers selected from the group consisting of: a marker gene having at least 95% sequence identity with a sequence selected from the group consisting of MUC5B, TERT, DSP, MUC2, DISP2, MAPT, DPP9, CSMD1, MYNN, LRRC34, FAM13A, OBFC1, TOLLIP, ATP11A, IVD, CRHR1, IMP5, LOC100128977, KIAA1267, NSF, WNT3, C17orf69, or homologs or variants thereof; (b) polypeptides encoded by the marker genes of (a); (c) fragments of polypeptides of (d); and (c) a polynucleotide which is fully complementary to at least a portion of a marker gene of (b); (ii) measuring expression levels of the plurality of markers in a second biological sample obtained from the subject; and (iii) comparing the expression level of the marker measured in the first sample with the level of the marker measured in the second sample.

15. The method of embodiment 14, wherein the marker genes detected share 100% sequence identity with the corresponding marker gene in (a).

16. The method of embodiment 14, further comprising performing a follow-up step selected from the group consisting of CT scan of the chest and pathological examination of lung tissues from the subject.

17. The method of embodiment 14, wherein the first biological sample from the subject is obtained at a time to, and the second biological sample from the subject is obtained at a later time $t_1$.

18. The method of embodiment 14, wherein the first biological sample and the second biological sample are obtained from the subject are obtained more than once over a range of times.

19. A method of assessing the efficacy of a treatment for interstitial lung disease or interstitial pneumonia in a subject, the method comprising comparing: i) the expression level of a marker measured in a first sample obtained from the subject at a time to, wherein the marker is selected from the group consisting of (a) a marker gene having at least 95% sequence identity with a sequence selected from the group consisting of TERT, DSP, MUC2, DISP2, MAPT, DPP9, CSMD1, MYNN, LRRC34, FAM13A, OBFC1, TOLLIP, ATP11A, IVD, CRHR1, IMP5, LOC100128977, KIAA1267, NSF, WNT3, C17orf69, or homologs or variants thereof; (b) polypeptides encoded by the marker genes of (a) (c) fragments of polypeptides of (b); and (d) a polynucleotide which is fully complementary to at least a portion of a marker gene of (a); ii) the level of the marker in a second sample obtained from the subject at time $t_1$; and, (iii) performing a follow-up step selected from CT scan of the chest and pathological examination of lung tissues from the subject; wherein a decrease in the level of the marker in the second sample relative to the first sample is an indication that the treatment is efficacious for treating interstitial pneumonia in the subject.

20. The method of embodiment 19, wherein the genes detected share 100% sequence identity with the corresponding marker gene in (a).

21. The method of embodiment 19, wherein the time to is before the treatment has been administered to the subject, and the time $t_1$ is after the treatment has been administered to the subject.

22. The method of embodiment 19, wherein the comparing is repeated over a range of times.

23. An assay system for predicting individual prognosis therapy for interstitial pneumonia comprising a means to detect at least one of: (a) the presence of a marker polymorphism selected from the group consisting of: rs2736100, rs2076295, rs3778337, rs4727443, rs868903, rs7934606, rs6421972, rs7480563, rs7942850, rs4077759, rs2334659, rs7122936, rs2034650, rs1992272, rs1981997, rs17563986, rs8070723, rs12610495, rs2109069, rs1379326, rs1881984, rs10936599, rs1997392, rs6793295, rs2609255, rs2853676, rs10484326, rs10748858, rs2067832, rs11191865, rs2301160, rs3829223, rs2857476, rs1278769, rs1007177, rs10518693, rs393152, rs12373139, rs17690703, rs2532274, rs2532269, rs2668692, rs169201, rs199533, and rs415430; and, (b) a level of gene expression of a marker gene or plurality of marker genes selected from the group consisting of: a marker gene having at least 95% sequence identity with a sequence selected from the group consisting of TERT, DSP, MUC2, DISP2, MAPT, DPP9, CSMD1, MYNN, LRRC34, FAM13A, OBFC1, TOLLIP, ATP11A, IVD, CRHR1, IMP5, LOC100128977, KIAA1267, NSF, WNT3, C17orf69, or homologs or variants thereof; (c) polypeptides encoded by the marker genes of (b); (d) fragments of polypeptides of (c); and (e) a polynucleotide which is fully complementary to at least a portion of a marker gene of (b).

24. The assay system of embodiment 23, wherein the means to detect comprises nucleic acid probes comprising at least 10 to 50 contiguous nucleic acids of the marker polymorphisms or gene(s), or complementary nucleic acid sequences thereof.

25. The assay system of embodiment 23, wherein the means to detect comprises binding ligands that specifically detect polypeptides encoded by the marker genes.
26. The assay system of embodiment 23, wherein the genes detected share 100% sequence identity with the corresponding marker gene in (b).
27. The assay system of embodiment 23, wherein the means to detect comprises at least one of nucleic acid probe and binding ligands disposed on an assay surface.
28. The assay system of embodiment 27, wherein the assay surface comprises a chip, array, or fluidity card.
29. The assay system of embodiment 28, wherein the probes comprise complementary nucleic acid sequences to at least 10 to 50 nucleic acid sequences of the marker genes.
30. The assay system of embodiment 28, wherein the binding ligands comprise antibodies or binding fragments thereof.
31. The assay system of embodiment 23, further comprising: a control selected from information containing a predetermined control level or set of genetic variants or polymorphic markers that has been correlated with diagnosis, development, progression, or life expectancy in interstitial lung disease or IIP patients.
32. A method of detecting a level of gene expression of one or more marker genes in a human subject with interstitial pneumonia, comprising: obtaining a biological sample from a human individual with interstitial pnuemonia; detecting the level of expression of a gene selected from TERT, MUC2, TOLLIP, MUC5B, DPP9, DSP, and homologs or variants thereof, in one or more cells from the biological sample from the individual.
33. The method of embodiment 32, further comprising detecting the level of expression of a gene selected from TERT, MUC2, TOLLIP, MUC5B, DPP9, DSP, and homologs or variants thereof, in one or more cells from the biological sample from the individual.
34. The method of embodiment 32, further comprising detecting the level of expression of a gene selected from MUC5B, TERC, SFTPC SFTPA2, and homologs or variants thereof in one or more cells from the biological sample from the individual.
35. A method of treating an interstitial pneumonia in a subject in need of such treatment, comprising: detecting a level of one or more marker genes selected from TERT, MUC2, TOLLIP, MUC5B, DPP9, DSP or homologs or variants thereof, in a biological sample obtained from the human subject; and, administering an effective amount of an interstitial pneumonia treatment.
36. The method of embodiment 35, further comprising detecting the level of expression of a gene selected from TERT, MUC2, TOLLIP, MUC5B, DPP9, DSP, and homologs or variants thereof, in one or more cells from the biological sample from the individual.
37. The method of embodiment 35, further comprising detecting the level of expression of a gene selected from MUC5B, TERC, SFTPC SFTPA2, and homologs or variants thereof, in one or more cells from the biological sample from the individual.

The Examples, which follow, are illustrative of specific embodiments of the disclosure, and various uses thereof. They are set forth for explanatory purposes only, and are not to be taken as limiting the disclosure.

EXAMPLES

Provided herein is a case-control genome-wide association study (GWAS; 1616 cases and 4683 controls) and replication study (876 cases and 1890 controls) of IIP individuals, including all types of fibrotic IIP. Different types of IIP were included in the study because: (a) distinguishing among the IIP diagnoses is often problematic due to substantial clinical, pathological, and radiological overlap; and (b) there is strong evidence for shared genetic susceptibility (e.g., over 40% of families with FIP have more than one type of IIP among the affected family members). Both familial and sporadic IIP individual samples were included in this GWAS study because the MUC5B, TERT, TERC, and SFTPC variants provide evidence that sporadic IIP is genetically similar to the familial form of this disease.

With the goal of identifying additional genetic risk factors that collectively further our understanding of IIP, the present inventors have completed a case-control genome-wide association study (GWAS; 1616 cases and 4683 controls) and replication study (876 cases and 1890 controls) of IIP. All types of fibrotic IIP were included in the case group. The inventors also included both familial and sporadic IIPs.

Study Populations

Case definition. We used standard criteria established by the American Thoracic Society/European Respiratory Society to determine diagnostic classification of all patients in the discovery and replication phases. We excluded cases with known explanations for development of fibrotic IIP including infections, systemic disorders, or relevant exposures (e.g. asbestos). To maximize power and minimize potential confounding by ancestry, we included only non-Hispanic white (NHW) participants in the GWAS and replication. All subjects gave written informed consent as part of IRB-approved protocols for their recruitment and the GWAS study was approved by the National Jewish Health IRB and Colorado Combined Institutional Review Board (COMIR(B).

GWAS Discovery. We genotyped 1914 patients with IIP from 7 cohorts (familial interstitial pneumonia [n=566], National Jewish Health IIP population [n=238], InterMune IPF trials [n=720], UCSF [n=66], Vanderbilt University IIP population [n=105], and the National Heart Lung and Blood Institute Lung Tissue Research Consortium [n=219]) and compared them to genotypes from 4683 out-of-study controls. After genotype quality control, we included 1616 cases in analyses.

A family with familial interstitial pneumonia (FIP) is defined by the presence of at least 2 cases of definite or probable IIP in individuals genetically related within 3 degrees. Recruitment of families based at three major referral centers (Vanderbilt University, Duke University and National Jewish Health) has been ongoing since 1999. We included only 1 IIP case among first degree relatives. The National Jewish Health IIP cohort consists of patients with sporadic IIP who were clinically evaluated and enrolled at National Jewish Health as part of ongoing research protocols associated with clinical care. Details of the recruitment criteria for the cases from the Intermune IPF γ-Interferon Intervention Trial have been described in detail. Briefly, eligible patients had IPF, were 40 to 79 years old with clinical symptoms for at least 3 months and evidence of disease progression within the previous 12 months. We included all available cases regardless of treatment assignment. The National Heart Lung and Blood Institute Lung Tissue Research Consortium (NHLBI LTR(C) was established to provide lung tissue and DNA for the research community. We included DNA from those subjects with a diagnosis of IIP.

We used de-identified control genotypes generated at Centre d'Étude du Polymorphisme Humain (CEPH) as part of other studies. Potential controls were those who were NHW, had been genotyped on the same platform as our cases, and were appropriately approved for use as controls in other studies. We selected a subset of controls, corresponding to approximately 3 controls for 1 case, based on genetic similarity to the cases that passed our genotyping quality control thresholds (see Statistical Analyses below).

Replication. We genotyped a total of 1027 NHW IIP cases and 2138 NHW controls for replication of the top SNPs from the GWAS. The replication controls were from individual replication groups (n=138) and a subset (n=2000) of the controls from the Chronic Obstructive Pulmonary Disease (COP(D) Gene Study. We selected controls to be frequency matched to the replication cases based on age and gender. After quality control, we included 876 cases and 1890 controls in analyses.

Expression. We measured gene expression on a subset of Lung Tissue Research Consortium and National Jewish Health IIP cases from the GWAS (n=100) and National Jewish Health controls (n=94). Whole-lung samples were obtained from International Institute for the Advancement of Medicine (Edison, NJ). Eligible cases and controls had sufficient RNA from lung tissue biopsy available for assay; cases with IPF were preferentially chosen over other IIP diagnoses. National Jewish Health controls also had genome-wide SNP data available.

DNA Preparation, Storage, and Quality Control

Genomic DNA was isolated from both whole blood and biopsied lung tissue on either the Autopure LS (Qiagen) or Qiacube (Qiagen) automation platform, respectively. Prior to extraction on the Qiacube using the DNAeasy kit, fibrotic lung tissues were first homogenized using Lysing Matrix D tubes and a FastPrep-24 benchtop homogenizer (MPBiomedicals). Following isolation, all DNA was assayed for concentration and purity on the NanoDrop ND-1000 Spectrophotometer. Samples were excluded if DNA was <50 ng/ul or had an A260/A280 ratio outside of the 1.7-2.0 range.

Prior to submission to the CNG, all samples were requantified using the Quant-iT PicoGreen dsDNA Assay Kit (Invitrogen), normalized with 1×TE, and aliquotted into individually barcoded screw-cap tubes. Due to volume limitations with liquid handling robots, an absolute minimum quantity for submission to the CNG was 30 ul at 50 ng/ul. If samples did not meet this minimum quantity, an alternate extraction was performed or the sample was withheld from the study.

Upon receipt of replication samples, they were transferred into 96-well robotics compatible plates, quantified with PicoGreen, and normalized with 1×TE. According to BMGC submission guidelines, 400 ng of DNA was submitted for each member of the GWAS and the replication cohorts. In an effort to minimize confounding by batch effects, samples were aliquotted into 96-well plates in a randomized fashion across all cohorts with two duplicates per plate using the Tecan Evo200 liquid handling robot.

Genome-Wide Genotyping

Barcoded DNA samples were received in standard tubes together with sample information, and were subjected to stringent quality control (Q(C). Concentration, fragmentation and response to PCR were determined. Samples from cases and controls were randomly distributed on 96-well plates. Processing was carried out under full LIMS control in a fully automated Illumina BeadLab equipped with 8 Tecan liquid handling robots, 6 Illumina BeadArray readers and 2 Illumina iScans. Genotyping was carried out using the Illumina Human610 quad array. Replication genotyping We genotyped 198 SNPs with P-values less than 0.0001 (see Statistical Analyses) in 1027 independent cases and 2000 COPDgene controls. We also genotyped the MUC5B promoter SNP rs35705950, which is not on the Illumina 660 Quad beadchip, to allow adjustment of chromosome 11p15 replication SNPs for rs35705950. In addition, to allow follow-up joint statistical tests (using raw genotypes from both GWAS cases and replication cases and controls) with adjustment for covariates that were not available on the out-of-study controls, we also genotyped a subset of GWAS cases. Details of the validation assays are described below. After genotyping quality control, we included 876 cases and 1890 controls in the replication analyses and 859 of the GWAS cases in the joint analyses.

Prior to genotyping, all samples were quality controlled by real-time Q-PCR quantitation ("QC1") and uniplex genotyping using Taqman ("QC2"). Samples that failed QC1 or QC2, although carried forward through genotyping, were later removed from analysis.

Validation genotyping was accomplished with a combination of multiplexed (Sequenom iPLEX) and uniplex (Taqman) assays. First, assay design for multiplexed Sequenom iPLEX genotyping was performed on an input set of 198 SNPs (Table 3), using a combination of web-based (AssayDesigner Suite, available at the website sequenom.com) and desktop (Assay Designer) software tools (Sequenom, San Diego). Of 198 input SNPs, 193 were efficiently placed into a set of 6 assays of the following plexities: 35, 35, 35, 35, 31, and 22 SNPs. Sequenom iPLEX genotyping is based on multiplexed locus-specific PCR amplification, multiplexed single-based extension (SB(E) from locus-specific amplicons, and multiplexed resolution of SBE products base calling using matrix-assisted laser desorption/ionization time-of-flight (MALDI-TOF) mass spectrometry.

Primers for the Sequenom assay were purchased from IDT (Coralville, low(a), and all steps of the iPLEX procedure were carried out using reagents and methods from Sequenom (San Diego, C(A) according to the manufacturer's instructions. Reactions were carried out in 384-well plates and analyzed using the Sequenom MassARRAY Analyzer 4 system with iPLEX Gold reagents and SpectroCHIP arrays. Results were analyzed using a combination of commercial software (Typer 4, Sequenom) and custom tools for data management. Of 193 assays in 6 multiplexes, 179 were successful in generating usable genotyping data.

The remaining 5 SNPs that were not successfully included in the original Sequenom iPLEX designs (rs2736100, rs35705950, rs13225346, rs10822856, rs10139381, rs10751635), as well as a sixth SNP (rs35705950) published in earlier studies, were genotyped using commercial Taqman assays (Life Technologies, San Diego, C(A). The dbSNP rs #s of these SNPs, as well as the commercial product IDs of the assays employed, are shown in Table 3. Reactions were carried out in 384-well plates and fluorescence read out using an Applied Biosystems ABI 7900HT Sequence Detection System (Applied Biosystems, Foster City, C(A).

Gene Expression

Total RNA was isolated from approximately 30 mg of snap-frozen or RNA-later preserved lung tissue using the Ambion mirVana kit (Life Technologies). RNA concentration was determined by Nanodrop ND-1000 (Thermo Scientifi(c) and RNA integrity was determined using the 2100 Bioanalyzer (Agilent). cDNA single strand conversions were performed using the Superscript III First-Strand Synthesis System (Invitrogen) and expression analysis was performed using pre-designed Taqman assays run on the Viia7 Real-Time PCR instrument (Life Technologies). (DPP9: Hs00373589; DSP: Hs00189422 and the DSP variant 1 assay is Hs00950584; FAM13A: Hs00208453; IVD: Hs01064832; MUC5B: Hs00861588; MUC2: Hs00149374; OBFC1: Hs00998588; WNT3: Hs00902257; WNT9B: Hs00916642; GAPDH: 4333764F). All assays were run in triplicate with GAPDH used as the endogenous control. As an additional control, one sample per plate was run in duplicate from the cDNA conversion step.

Statistical Analyses

Selection of out-of-study controls for GWAS discovery. An ancestry analysis was carried out using the EIGENSTRAT3.0 software. HapMap data and samples of reference Europeans were used as representatives of European, West African and East Asian populations to infer ancestry-informative principal components which were projected onto the case and control samples. Putative non-European samples were flagged as outliers and eliminated from subsequent analyses. We obtained controls with close genetic matching to cases from a large database of anonymous genotypes from Europeans. From this database, we selected a subset of the control genotype data so as to obtain three matching controls per case by using used an approach based on clustering with the support vector machine (R package "e1071") followed by application of a paired matching algorithm (R package "optmatch"). With this selection, the genomic inflation factor (evaluated with adjustment for population structure with the GEMMA softwar(e) was 0.99.

Removal of first degree relatives. We included only one individual among first degree relatives based on an estimated kinship coefficient ≥0.45. For estimation of the percent variation in disease risk explained by the GWAS SNPs which is sensitive to cryptic relatedness, we further removed only one individual among those with estimated kinship coefficient >0.025.

Exclusion of individuals and prioritization of SNPs for discovery GWAS. In addition to individuals excluded by the laboratory, we excluded individuals with 1) evidence for being a genetic outlier based on a pairwise identity-by-state (IBS) estimate with the 5th closest neighbor that was >4 standard deviations from the mean pairwise IBS estimate across all pairs, 2) unresolved sex mix-match between clinical and genomic data, 3) heterozygosity across the SNPs greater or less than 4 standard deviations from the mean heterozygosity across all individuals, and 4) genotype calls at less than 98% of SNPs that pass laboratory quality control. Based on this quality control, we excluded 298 cases and 165 controls. In addition to the laboratory quality control measures, we prioritized association signals for follow-up based on other criteria. We tested for differential missingness via a chi-squared test of proportions of missingness between cases and controls and departures from HWE via a 1-df goodness of fit test. We prioritized SNPs with 1) MAF>0.05, 2) HWE p-value>0.0001 in cases and controls evaluated separately, 3) p-value for differential missingness between cases and controls >0.001 if less than 2% missing and >0.05 if between 2% and 5% missing.

GWAS association testing. We tested for association between each SNP and IIP using an exact mixed model approach to account for both subtle relatedness and population stratification among our cases and controls that is implemented in the genome-wide efficient mixed-model association (GEMM(A) software package. We tested for association under an additive model for our primary analysis and subsequently took the minimum of the recessive and dominant model p-values if there was significant lack of fit to the additive model (p<0.05) from a linear regression that assumed independence among the samples (such a test is not currently implementable in the GEMMA softwar(e). We adjusted for sex in all models. We compared the distribution of p-values obtained under the additive model to that expected under the null hypothesis of no association across the genome and report the quantile-quantile (Q-Q plot) and genomic inflation factor (2) to verify the absence of systematic biases due to experimental or other confounding factors such as population stratification. We selected all SNPs with a p-value<0.0001 for follow-up in the replication populations and visually inspected genotype spectra for all 198 selected SNPs to assure genotype call quality. We calculated odds ratios and 95% confidence intervals (CIs) from a logistic regression model adjusted for sex that assumed independence among the cases and controls since the linear model in GEMMA uses the identity link rather than the log-odds link function. As such, the CIs may be slightly narrower than those based on the full mixed models.

Replication association. We tested for association between each replication SNP and IIP in the replication cases and controls using the freely available SNPGWA software (see URLs). We tested for association under the genetic model from the GWAS that gave the minimum p-value (143 under an additive model, 24 under a dominant model and 31 under a recessive model). A p-value<0.0025 was considered statistically significant replication for the 20 genome-wide significant GWAS SNPs. The p-values for the other 178 SNPs were used in the meta-analysis of the GWAS and replication cohorts.

Meta-analysis. To obtain a joint measure of association between each of the 181 successfully genotyped SNPs in the replication set and IIP, we performed a meta-analysis of the GWAS and replication results. We used the weighted inverse normal method. Let Zi (i=GWAS or replication) be the test statistic from the test of association in the ith study and let vi (i=GWAS or replication) be the corresponding weight. Here we took the weight to be the square root of the total sample size in the ith study since effect estimates from the GWAS and replication were not on the same scale. Note that this method explicitly accounts for the directionality of the association. Thus, highly significant associations with conflicting directions do not exhibit strong statistical association. We used METAL (available at the website sph.umich.edu/csg/abecasis/metal/) to perform our meta-analysis. SNPs with PJoint<5×10-8 were considered genome-wide statistically significant. We created locus-specific plots of the discovery GWAS results for all loci that were genome-wide significant in the meta-analysis.

Multi-SNP models. To assess the independence of effects of the genome-wide significant SNPs from the meta-analysis, we used logistic regression models within each locus using the combined case group (GWAS and replication) and the replication controls. Specifically, within each locus with a genome-wide significant SNP, we tested for association between IIP and each of the other validation panel SNPs within that locus after adjusting for the most significantly associated SNP in that locus (on chromosome 11p15, we adjusted for rs35705950). To assess the robustness of each SNP association to age effects in addition to sex, we tested for association between IIP and each SNP adjusted for age and sex.

Expression analyses. We tested for differential gene expression in the lung between 100 cases and 94 controls using a two-sample t-test. We also tested for differential expression by genotype using the combined case and control group via ANOVA across the three genotype groups unless there <5 individuals in a genotype group; we grouped the rare homozygote and heterozygote groups in that case. A p-value<0.05 was considered statistically significant.

Results

Genome-Wide Discovery

We genotyped 1914 self-reported non-Hispanic white fibrotic IIP cases on the Illumina 660 Quad beadchip. Of those, 14, 126, 8, and 150 were excluded based on being a genetic outlier, evidence for being a first degree relative of another case, high heterozygosity, or missing >2% of genotypes across all SNPs, respectively (see Statistical Methods); 1616 cases were included in analyses. Among 15,352 out-of study controls also genotyped on the Illumina 660 Quad beadchip, we used 4683 controls most genetically similar to our cases based on genome-wide identity-by-state comparisons.

Figure 5:
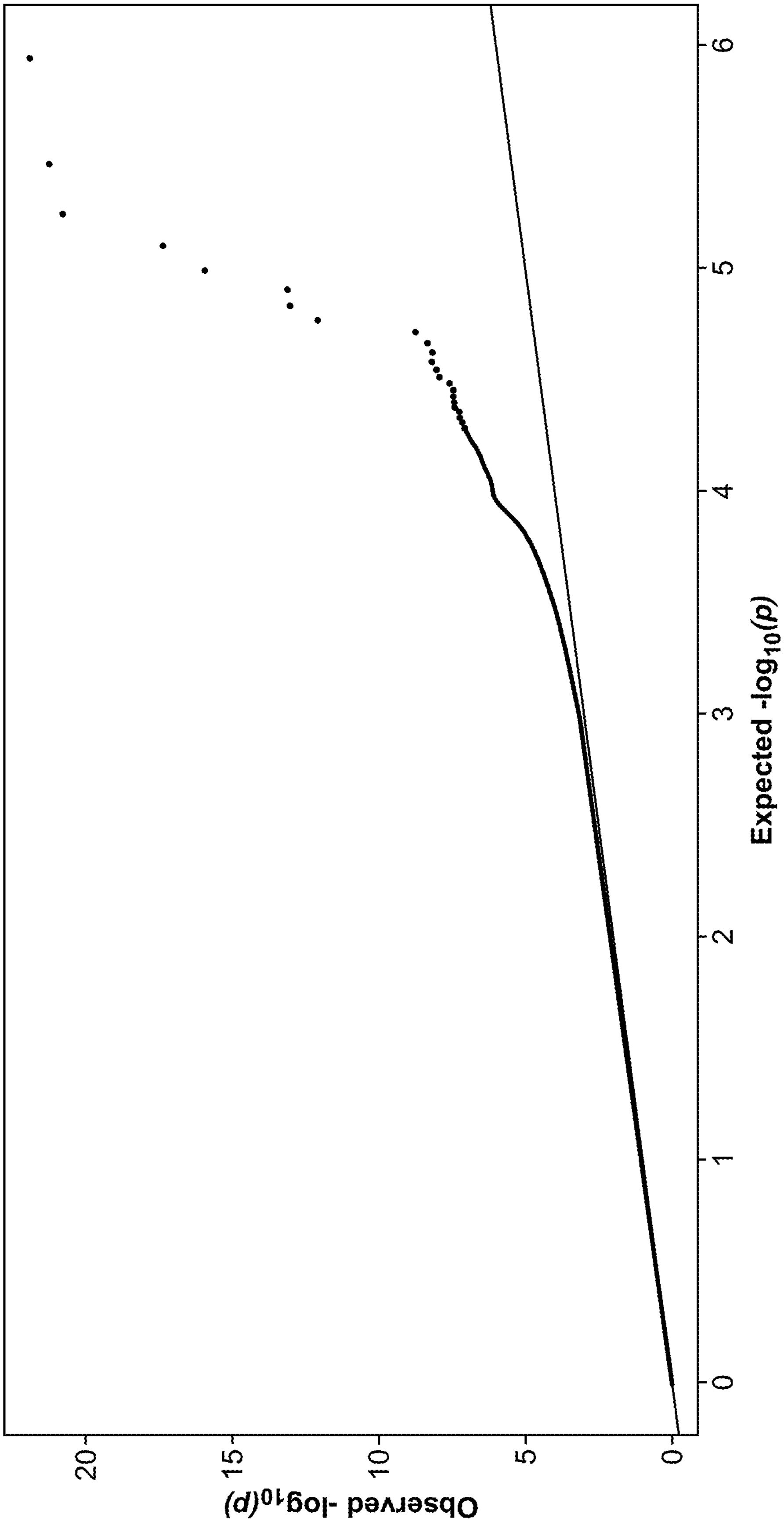
FIG. 5 shows a Quantile-Quantile (Q-Q) plot of observed vs. expected p value distribution for GWAS across 439,828 high quality SNPs.

We compared the cases of IIP and controls at 439,828 SNPs with 1) MAF >0.05, 2) HWE P-value>0.0001 in cases and controls evaluated separately, and 3) p-value for differential missingness between cases and controls >0.001 if less than 2% missing and >0.05 if between 2% and 5% missing. Neither the QQ-plot of p-values (FIG. 5) nor the estimated genomic inflation factor of 0.99 suggested any systematic biases, such as those related to population stratification. Under an additive model for the minor allele at each SNP, we identified 19 SNPs, representing 7 chromosomal locations, with genome-wide significant (P<5×10-8) associations (FIG. 1 and Table 1). We identified another genome-wide significant SNP (rs1379326) representing a unique locus, under a recessive model (Table 1).

Replication and Meta-Analysis

We selected the 20 genome-wide significant SNPs and an additional 178 SNPs with 5×10-8<P-value<0.0001 (SNPs between the top and bottom lines in FIG. 1; see Tables 3 and 4 for SNP location, genotype and HWE information and Table 5 for association information for all 198 SNPs) for genotyping in a replication cohort of 1027 cases of IIP and 2138 controls. After genotype quality control, we included 876 cases and 1890 controls successfully genotyped on 181 of the SNPs. 13 of the 20 genome-wide significant SNPs were associated with IIP in the replication cohort at P<0.0025, corresponding to conservative Bonferroni correction for 20 tests (Table 1, middle columns). Eighteen of the 20 genome-wide significant SNPs, representing 7 loci, from the GWAS (FIG. 2) were genome-wide significant in the meta-analysis (Table 1, last column). An additional 25 SNPs representing 9 chromosomal locations (5 overlapping with GWAS loci and 4 additional loci (FIG. 3)) were genome-wide significant in the meta-analysis (Table 1).

Figure 2:
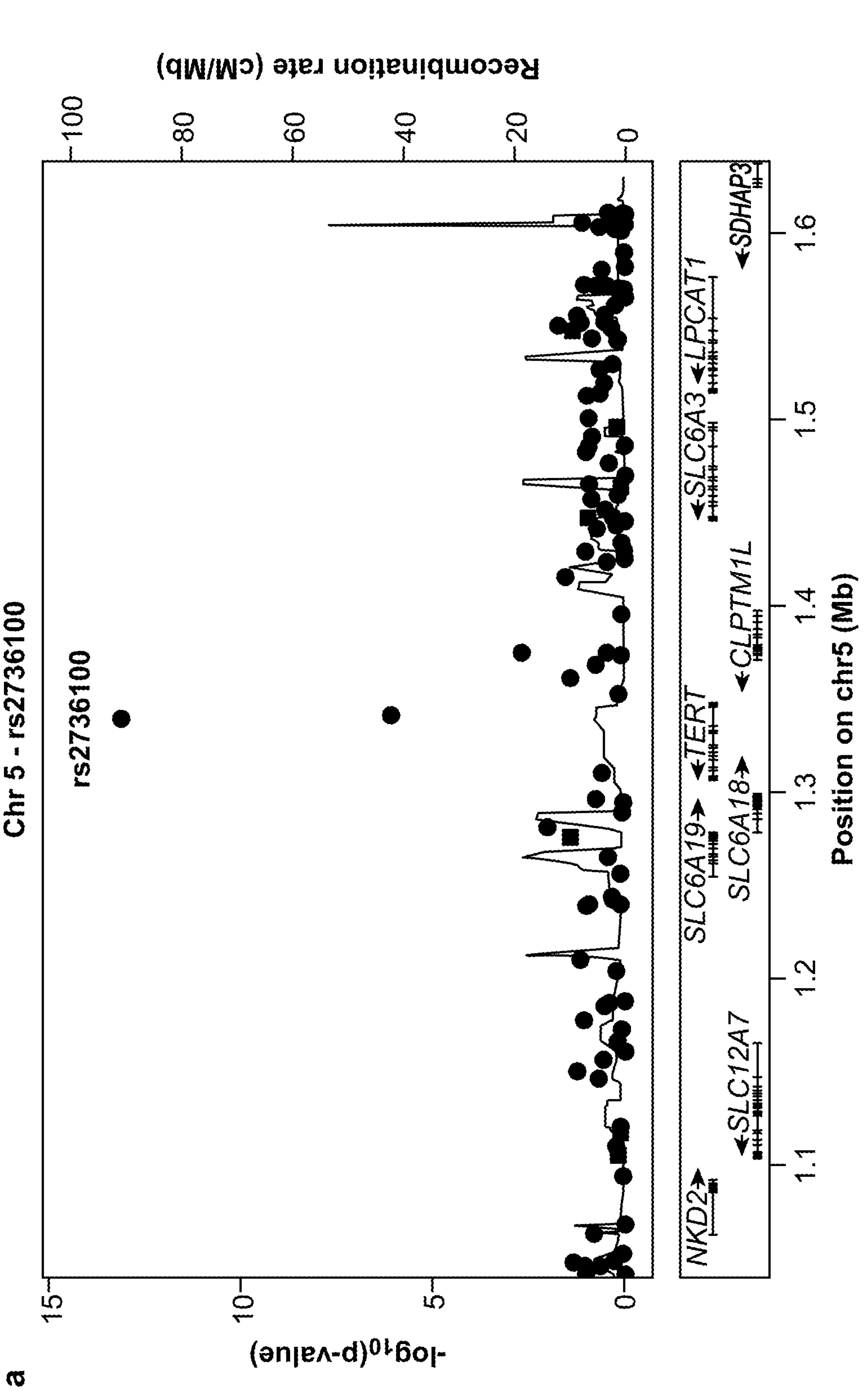
FIG. 2 shows locus-specific plots corresponding to discovery GWAS results for all loci reaching genome-wide significance in the GWAS discovery analysis and meta-analysis of the discovery and replication results.
Figure 3:
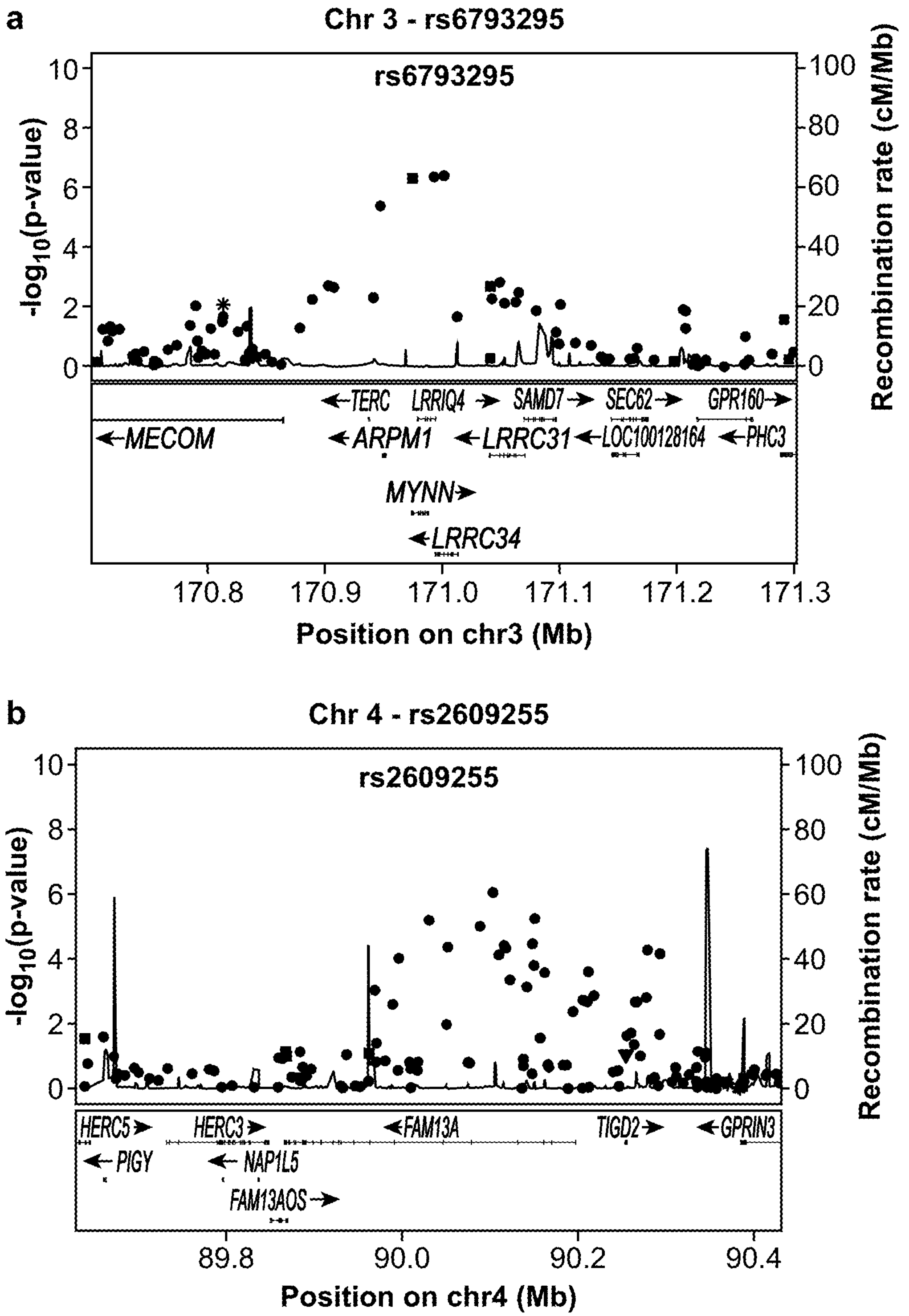
FIG. 3 shows locus-specific plots corresponding to discovery GWAS results for four additional loci reaching genome-wide significance after the meta-analysis of the discovery and replication results.
Figure 6:
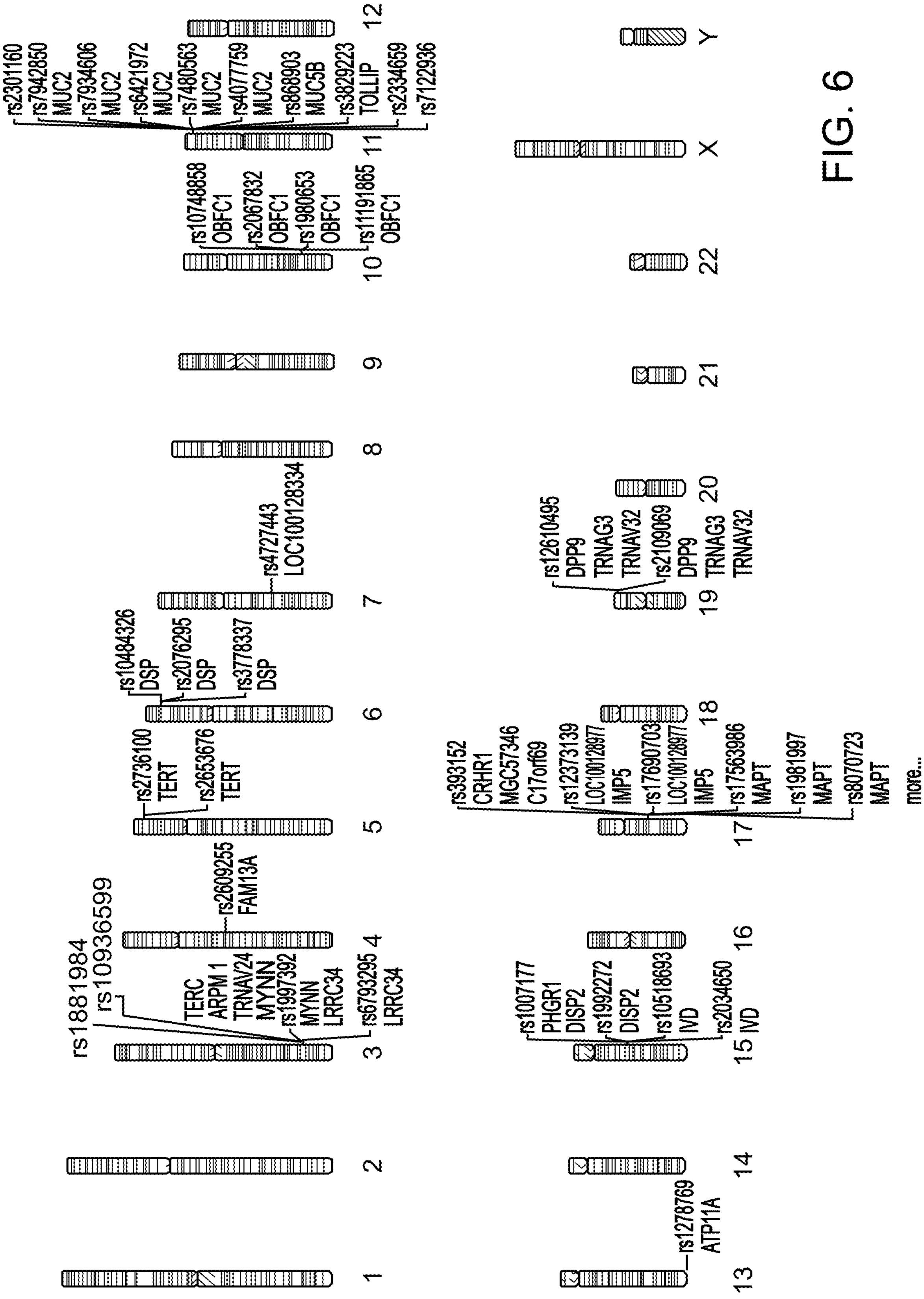
FIG. 6 shows the chromosomal locations, SNPs and genes for genome wide significant loci.
Figure 7:
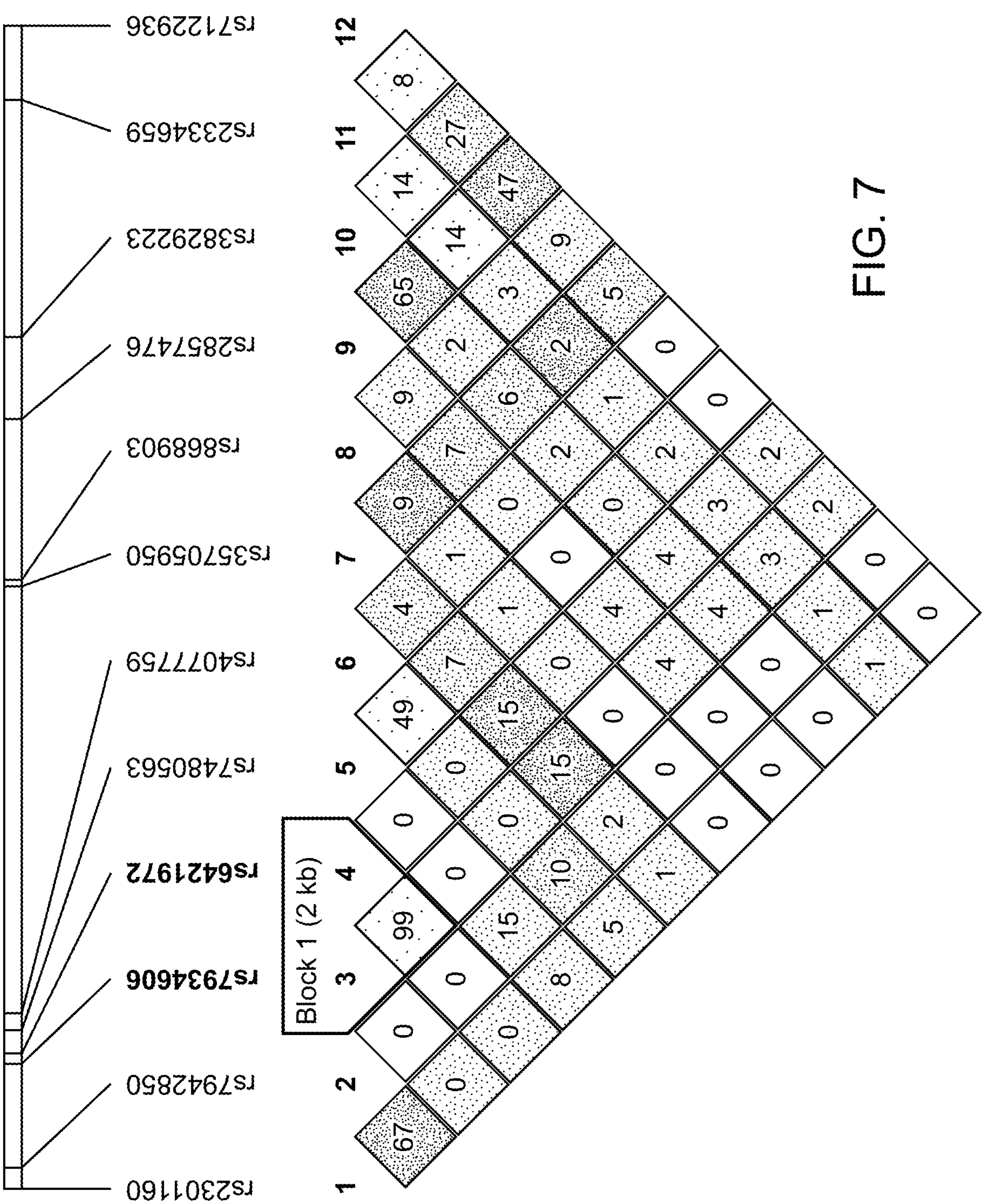
FIG. 7 shows the Linkage Disequilibrium among the genome-wide significant SNPs at 11p15 and rs35705950. Color indicates D'estimate=1, white a D'estimate=0. Numbers in squares correspond to r2*100. Estimates based on joint case and control genotypes as used in analyses for Table 2 and Table 6.
Figure 8:
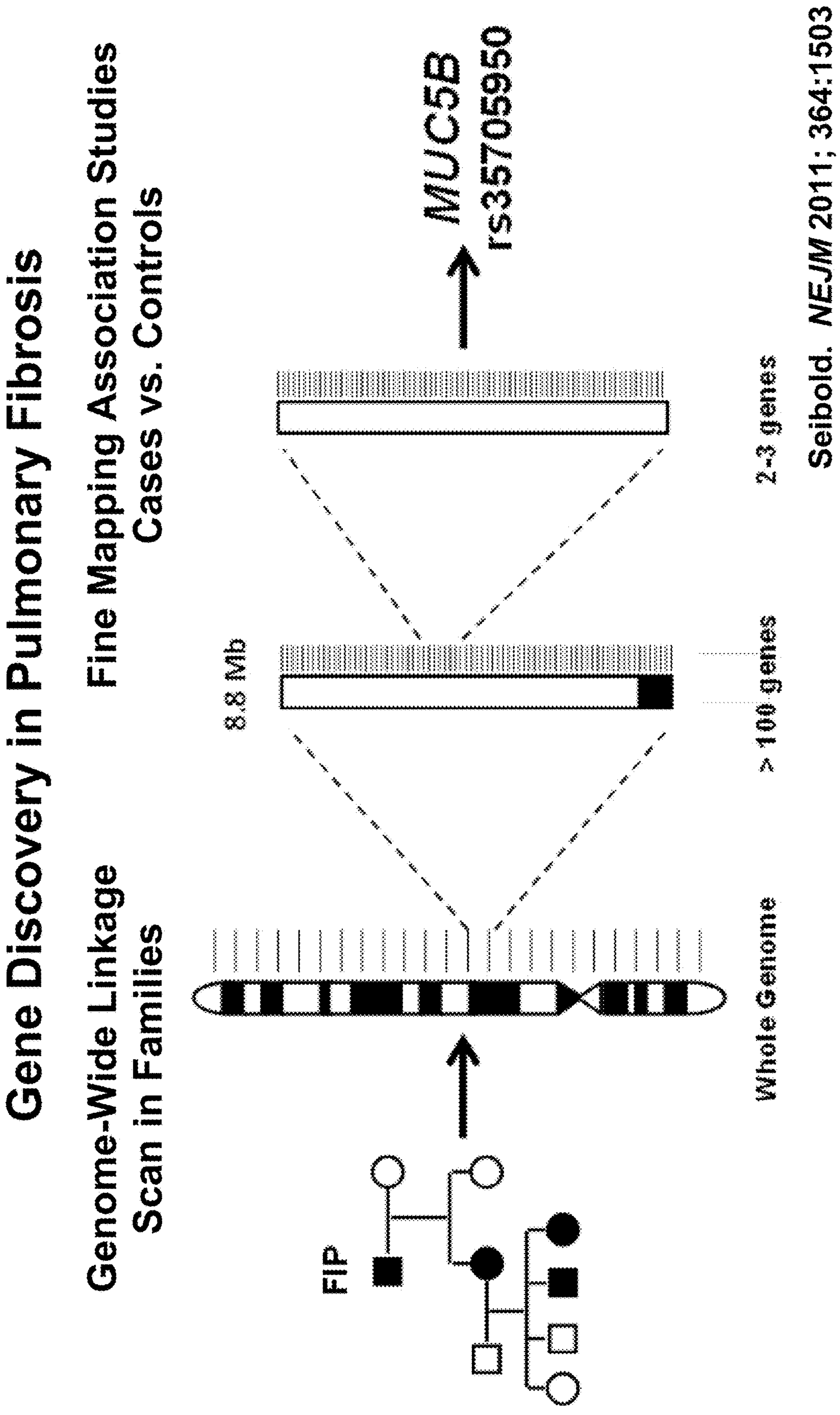
FIG. 8 outlines a genome wide linkage scan in families with interstitial lung disease, where the rs3570950 polymorphism was found to be predictive.
Figure 9:
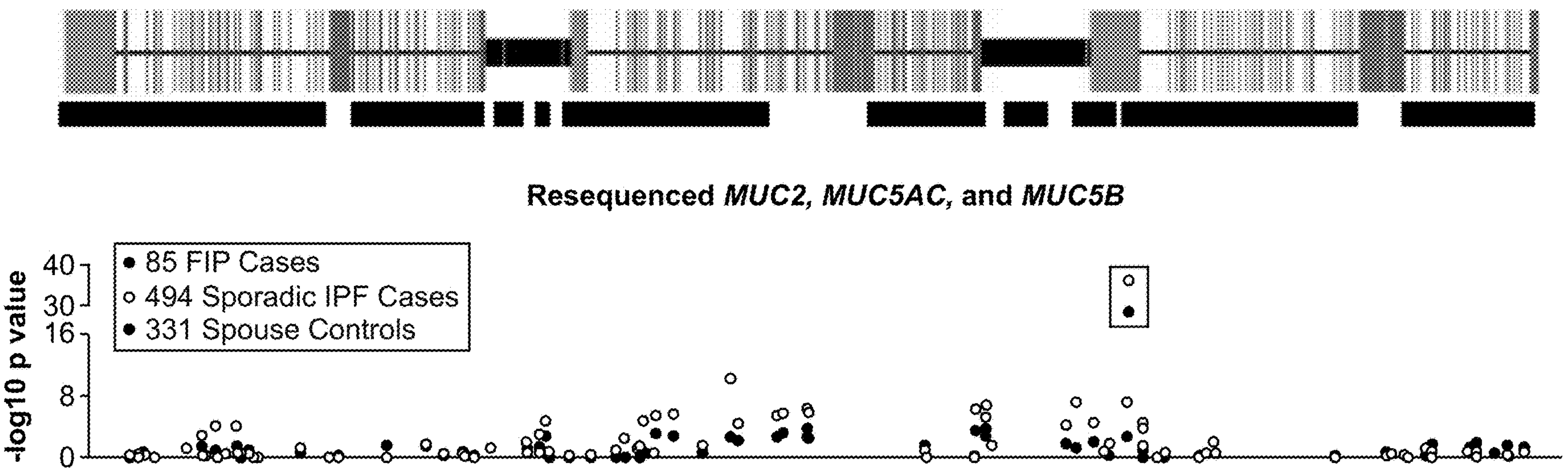
FIG. 9 shows odds ratios of SNPs in MUC2, MUC5AC, and MUC5B being associated with interstitial lung disease.
Figure 11:
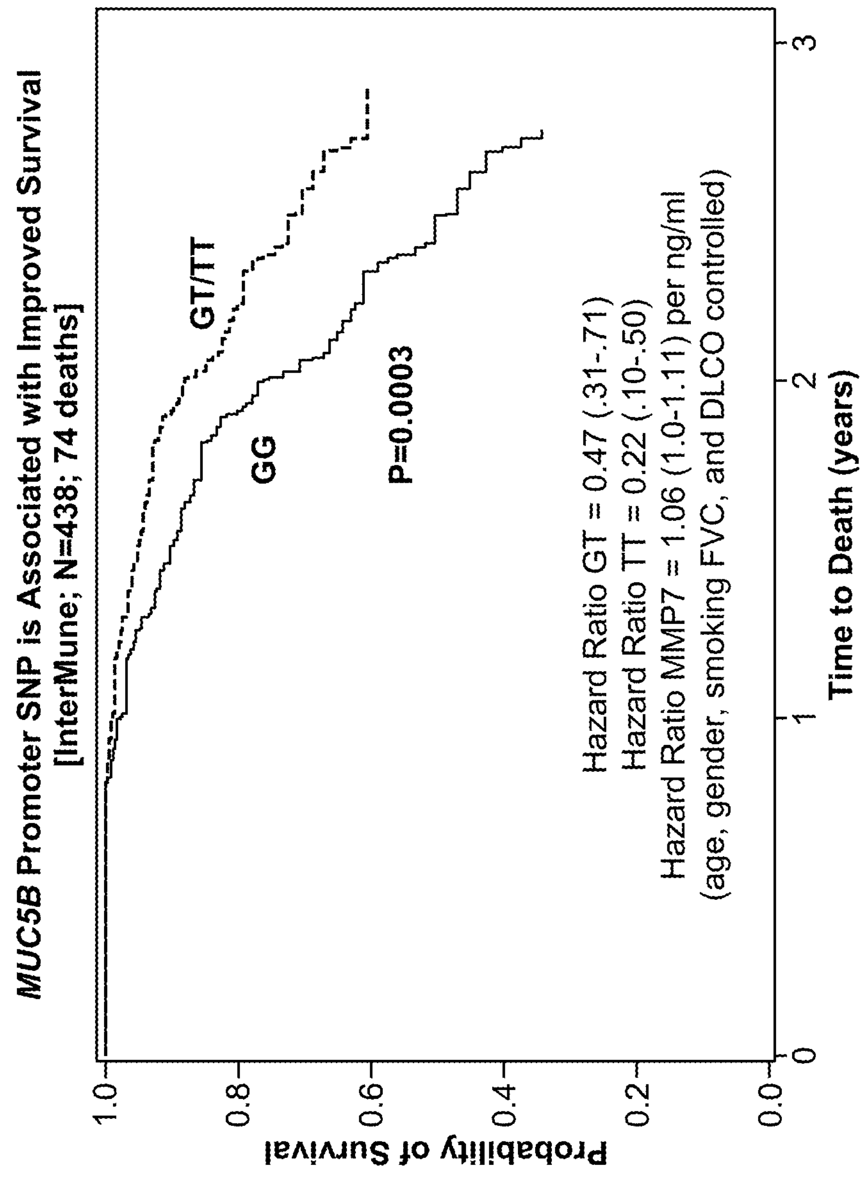
FIG. 11 shows the increased duration of survival associated with interstitial lung disease patients carrying the rs3570950 SNP.
Figure 13:
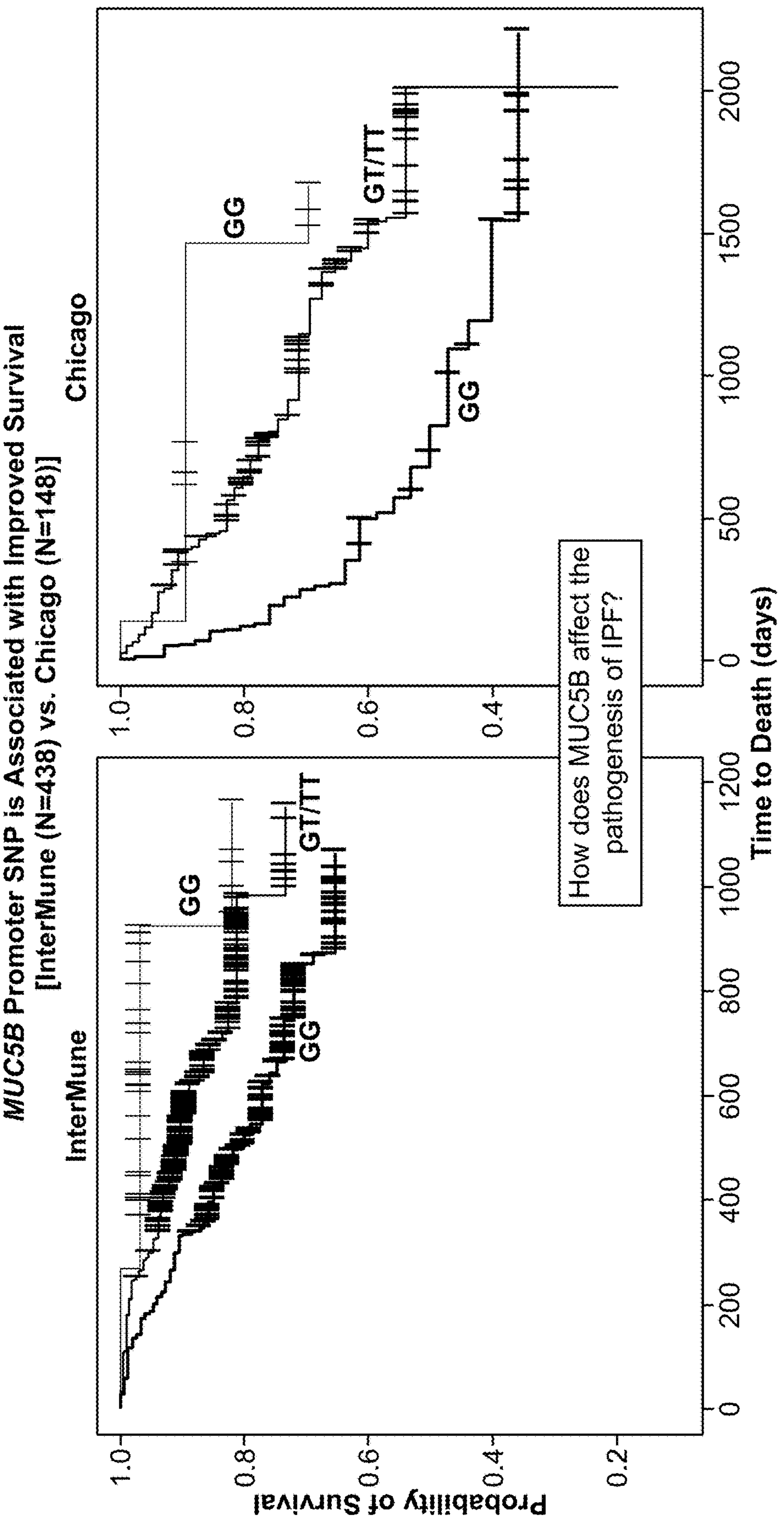
FIG. 13 compares different study groups for increased duration of survival associated with interstitial lung disease patients carrying the rs3570950 SNP.
Figure 14:
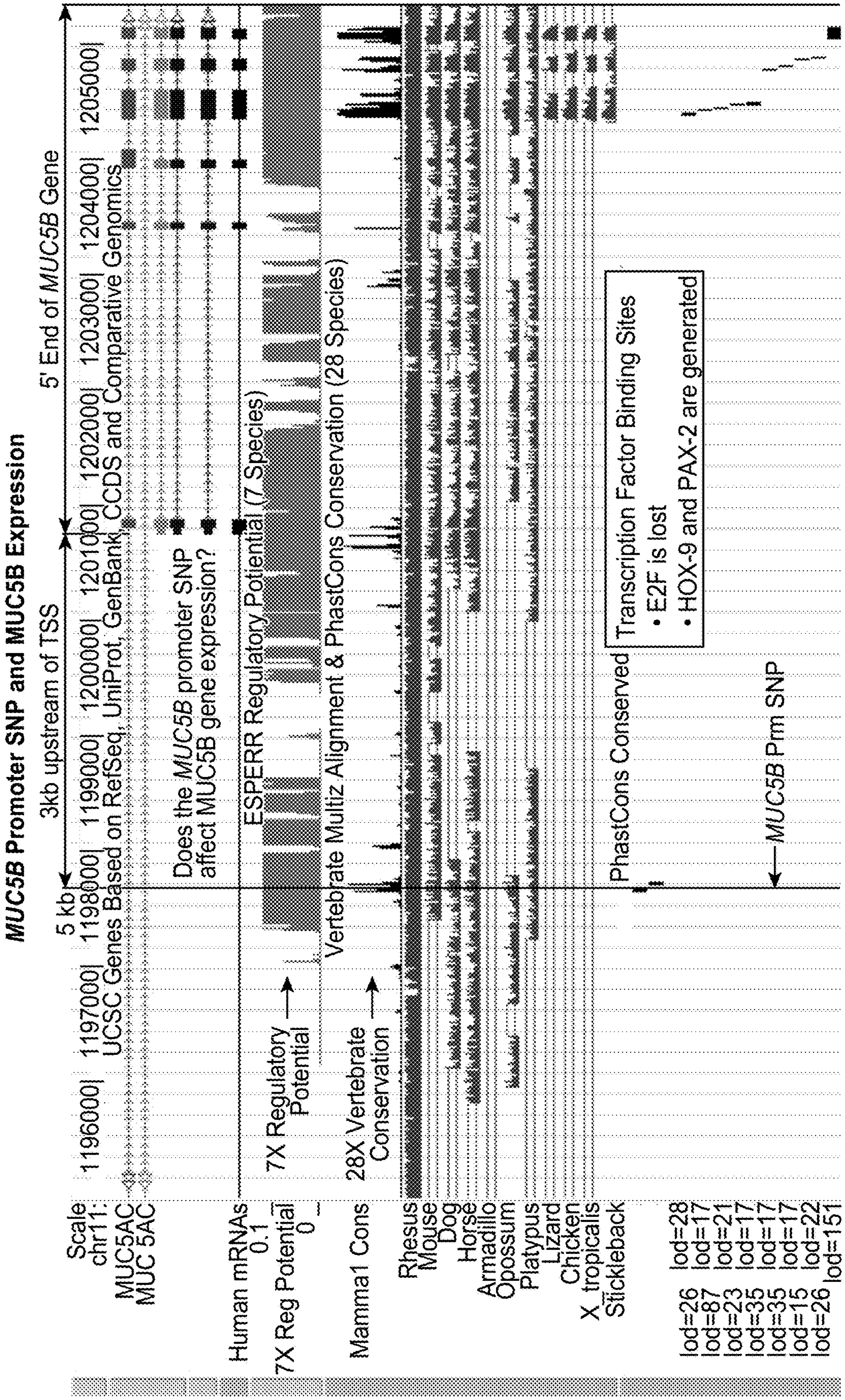
FIG. 14 shows the structure of the MUC5B gene and the effect of the rs3570950 SNP.
Figure 15:
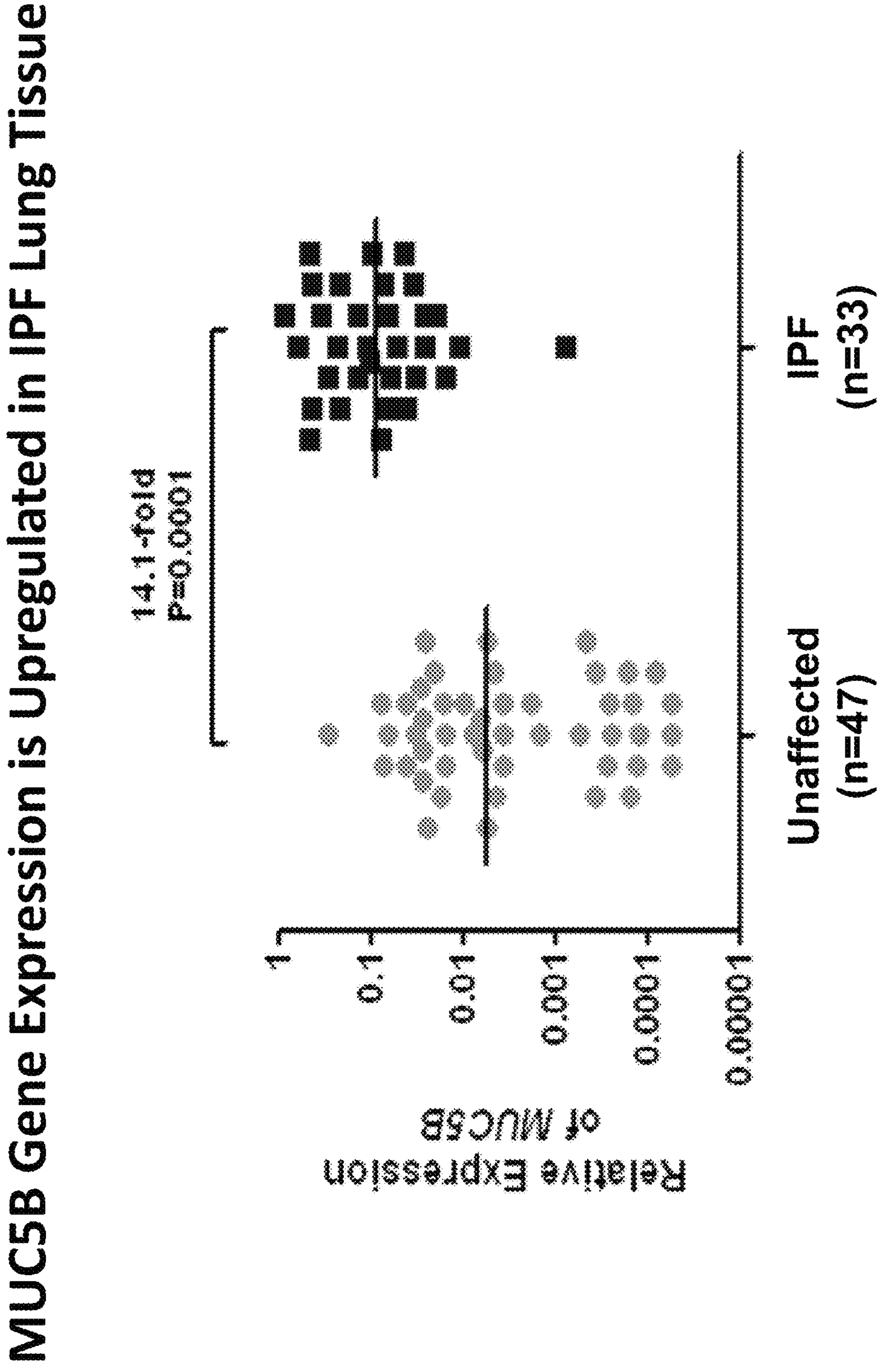
FIG. 15 compares MUC5B expression in normal vs IPF lung tissue.
Figure 16:
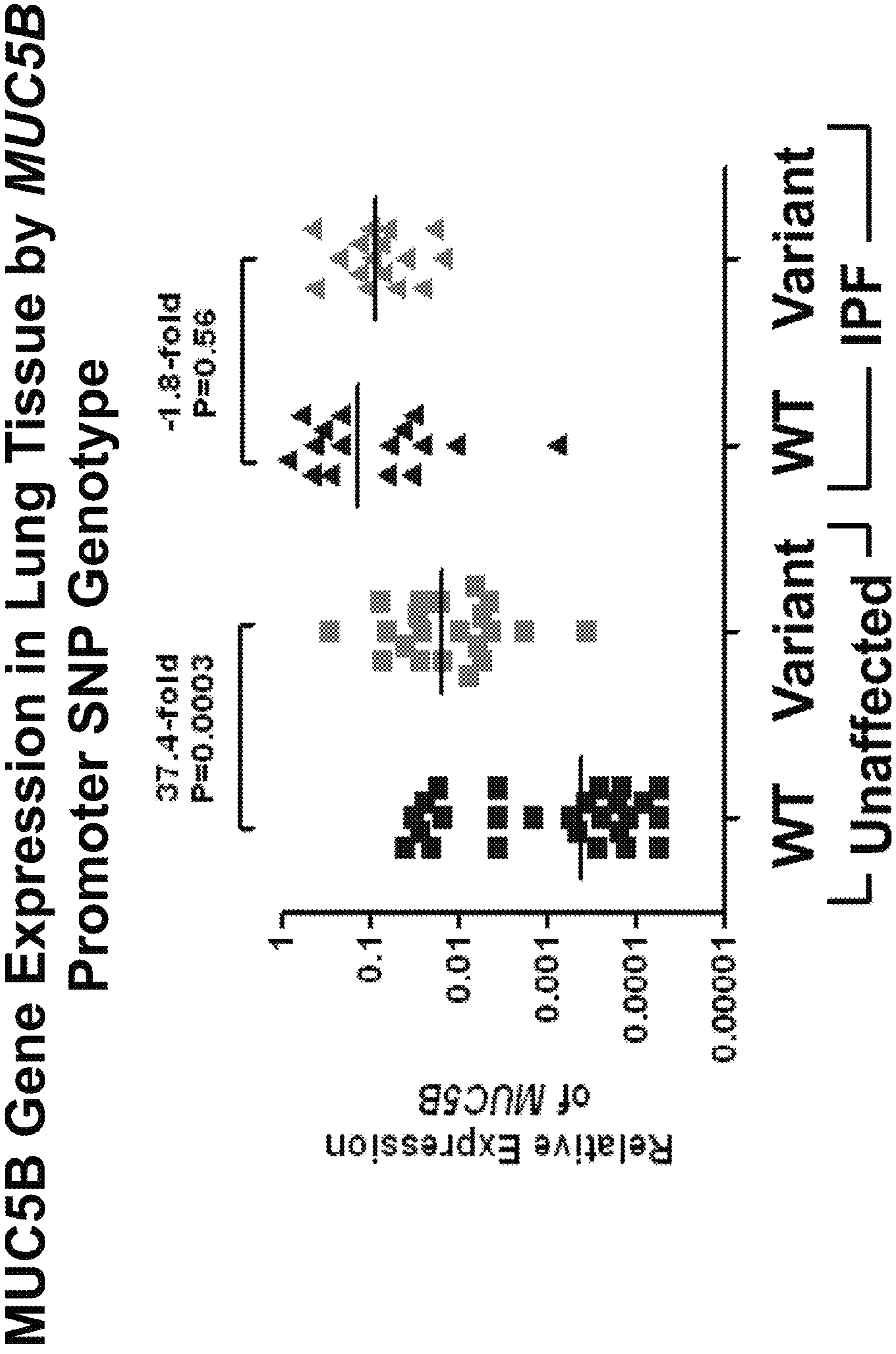
FIG. 16 shows MUC5B expression in normal vs IPF lung tissue in individuals carrying wild type (GG) vs variant MUC5B (GT or TT) genes.
Figure 17:
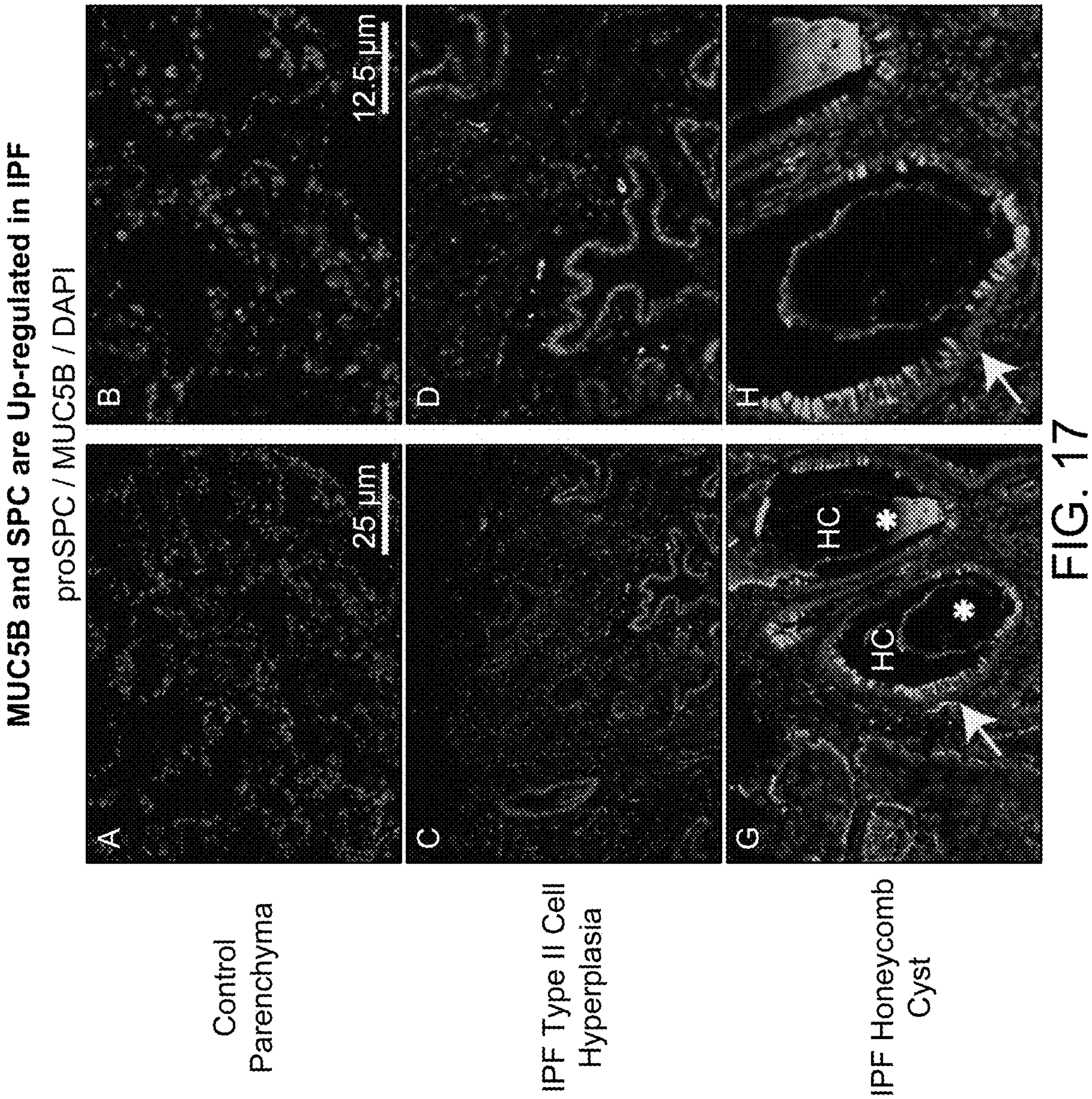
FIG. 17 shows that expression of MUC5B and surfactant protein C (SP(C) is upregulated in IPF lung tissue.
Figure 18:
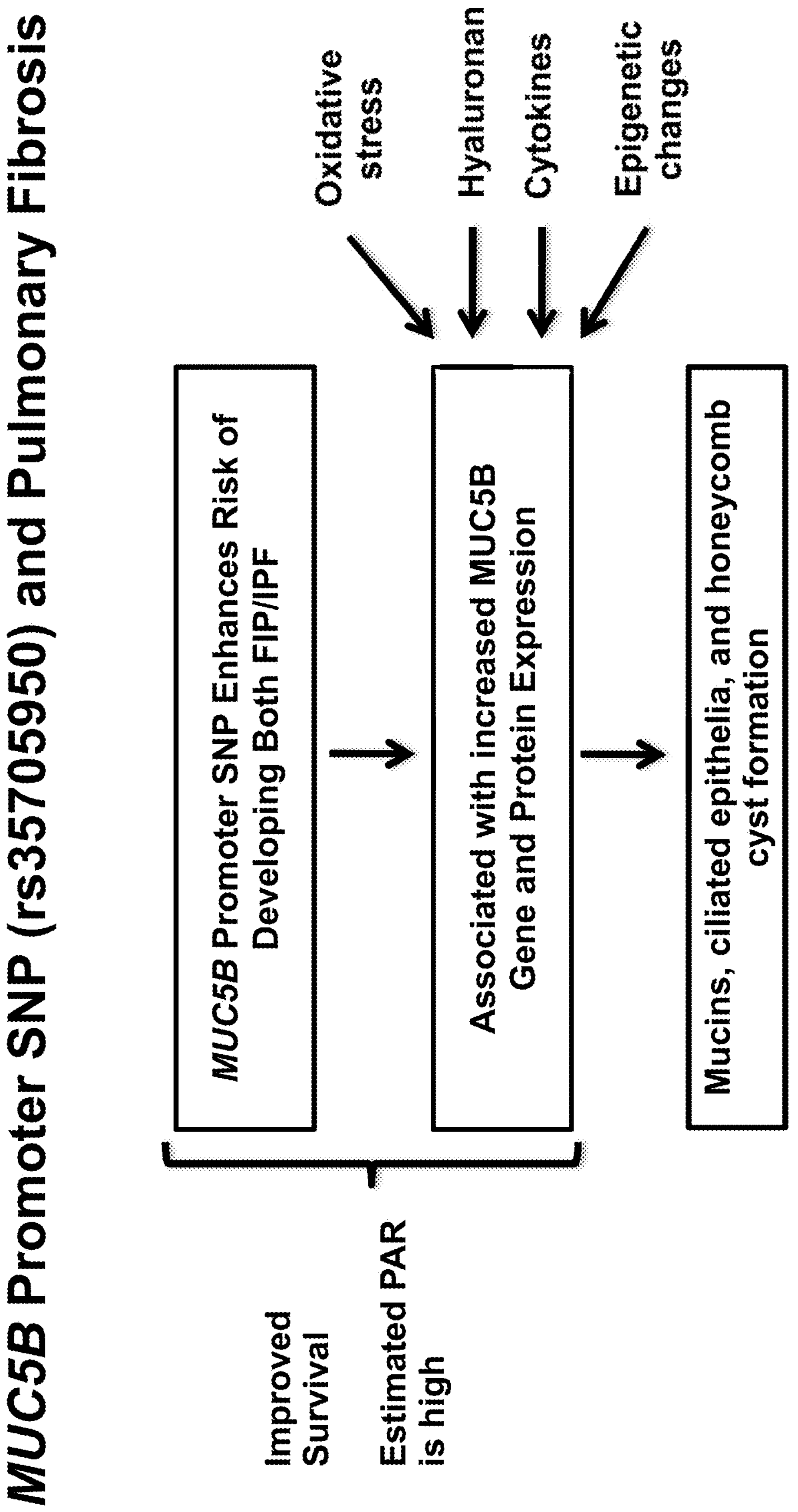
FIG. 18 outlines effects associated with the MUC5B rs3570950 SNP.
Figure 19:
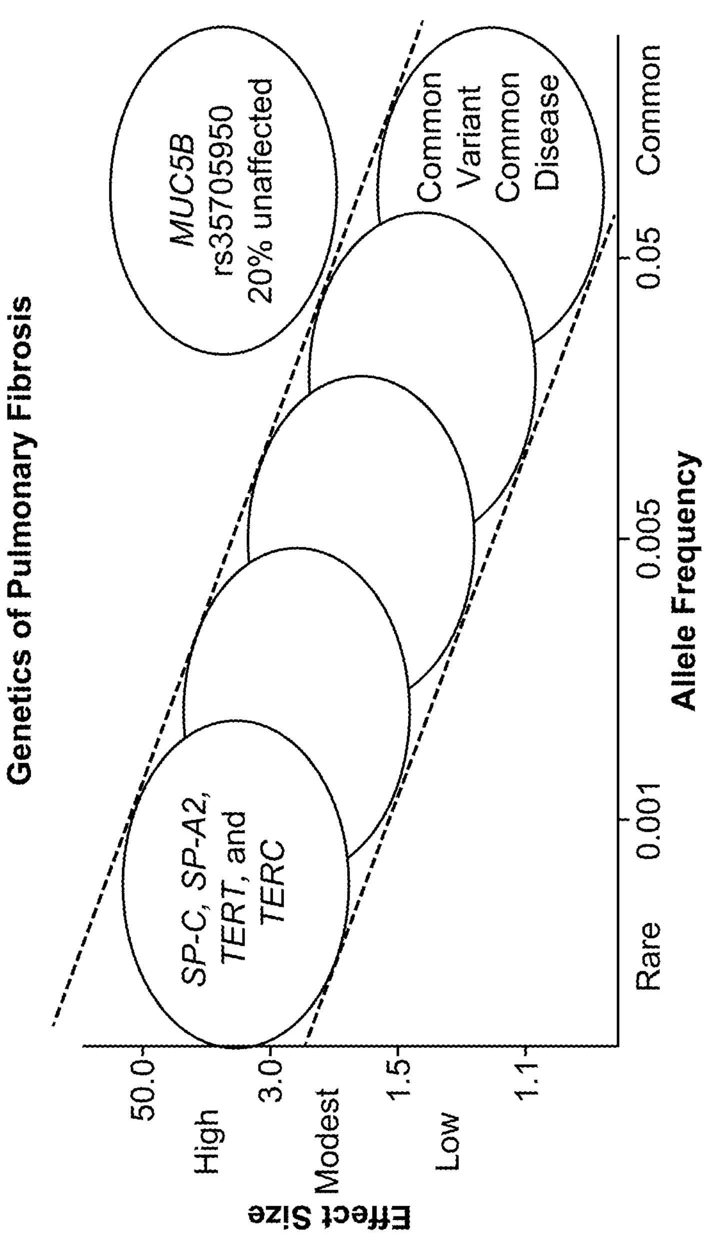
FIG. 19 compares effects of genetics for genes associated with pulmonary fibrosis.
Figure 20:
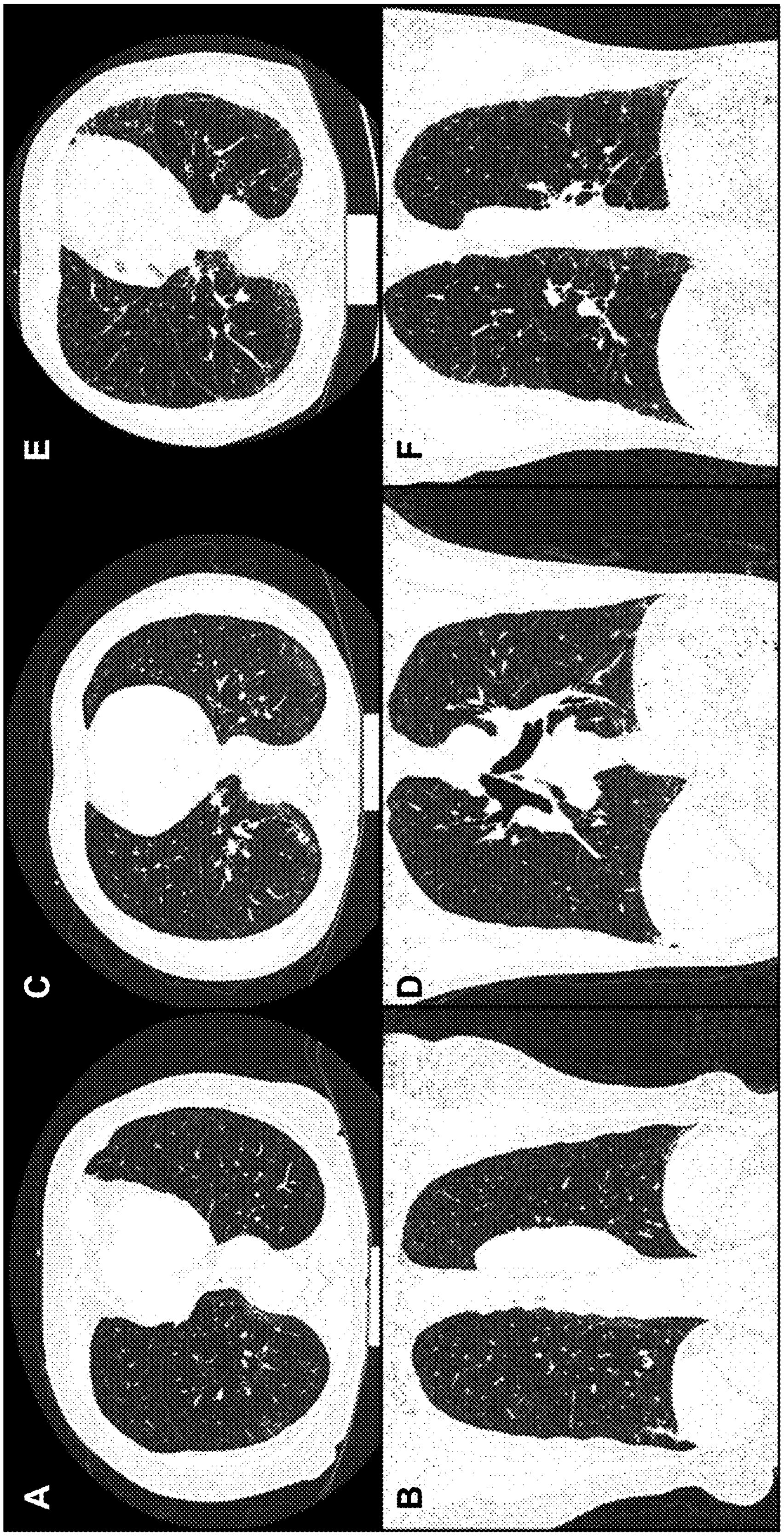
FIG. 20 shows fibrotic lung tissue in patients carrying the rs3570950 SNP.
Figure 22:
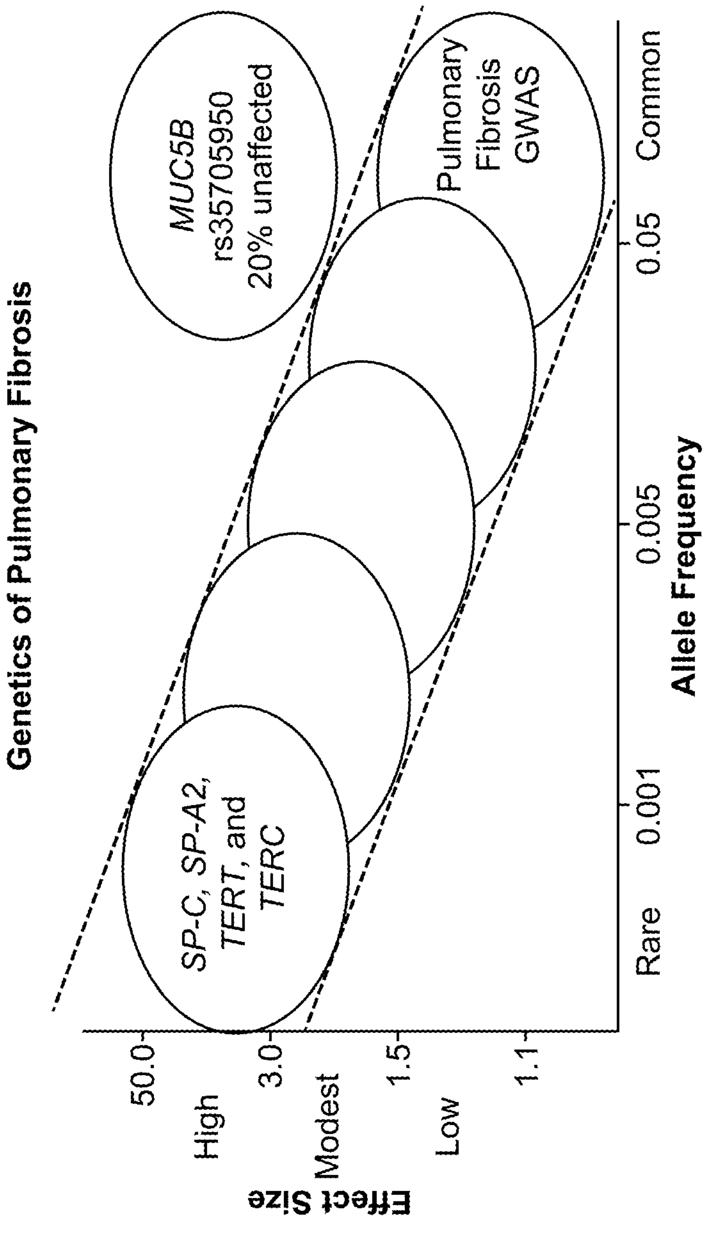
FIG. 22 compares effects of genetics for genes associated with pulmonary fibrosis.
Figure 23:
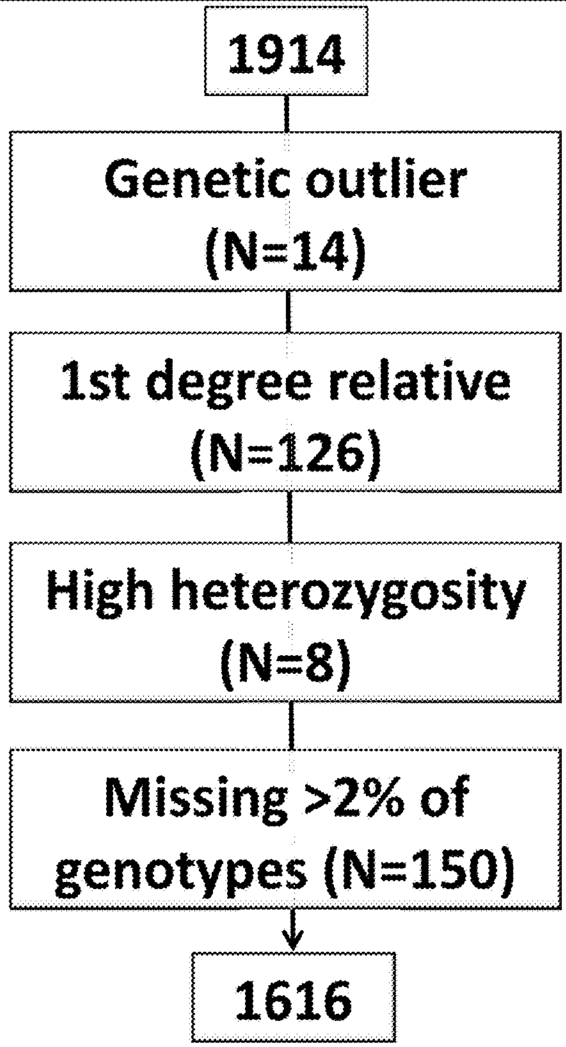
FIG. 23 outlines genome wide association study (GWAS) for associating genetic markers with various interstitial lung diseases.
Figure 24:
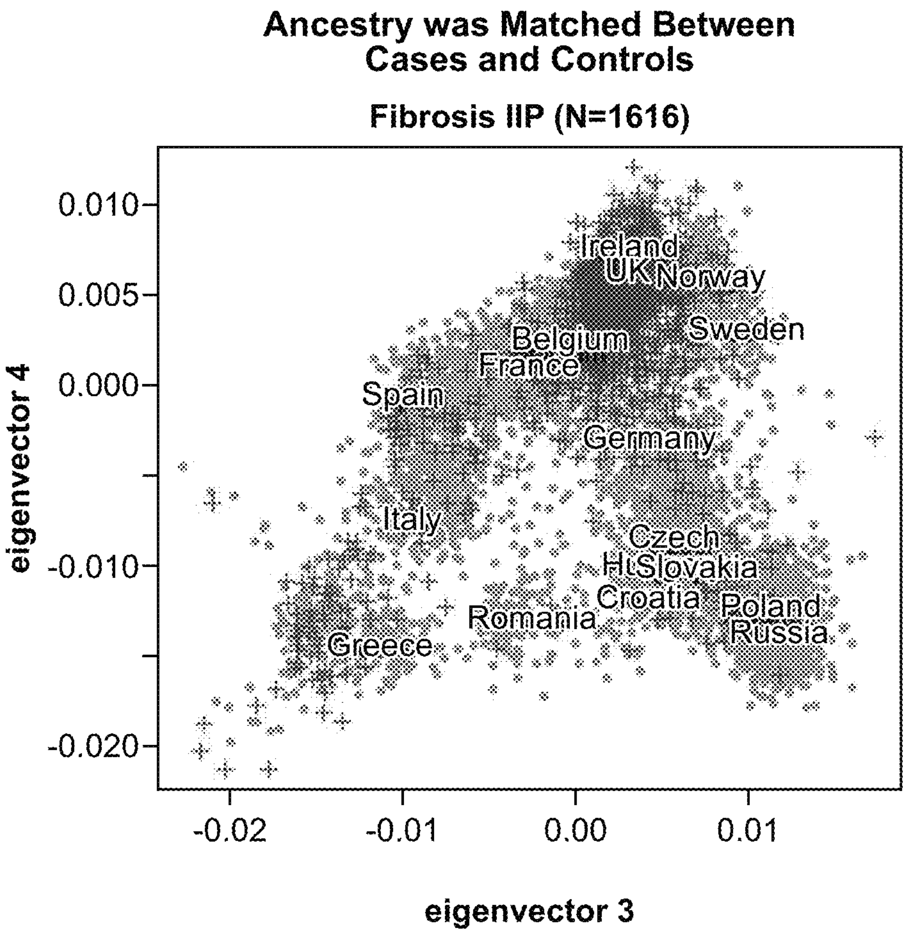
FIG. 24 shows geographic origin of individuals considered in the study.
Figure 25:
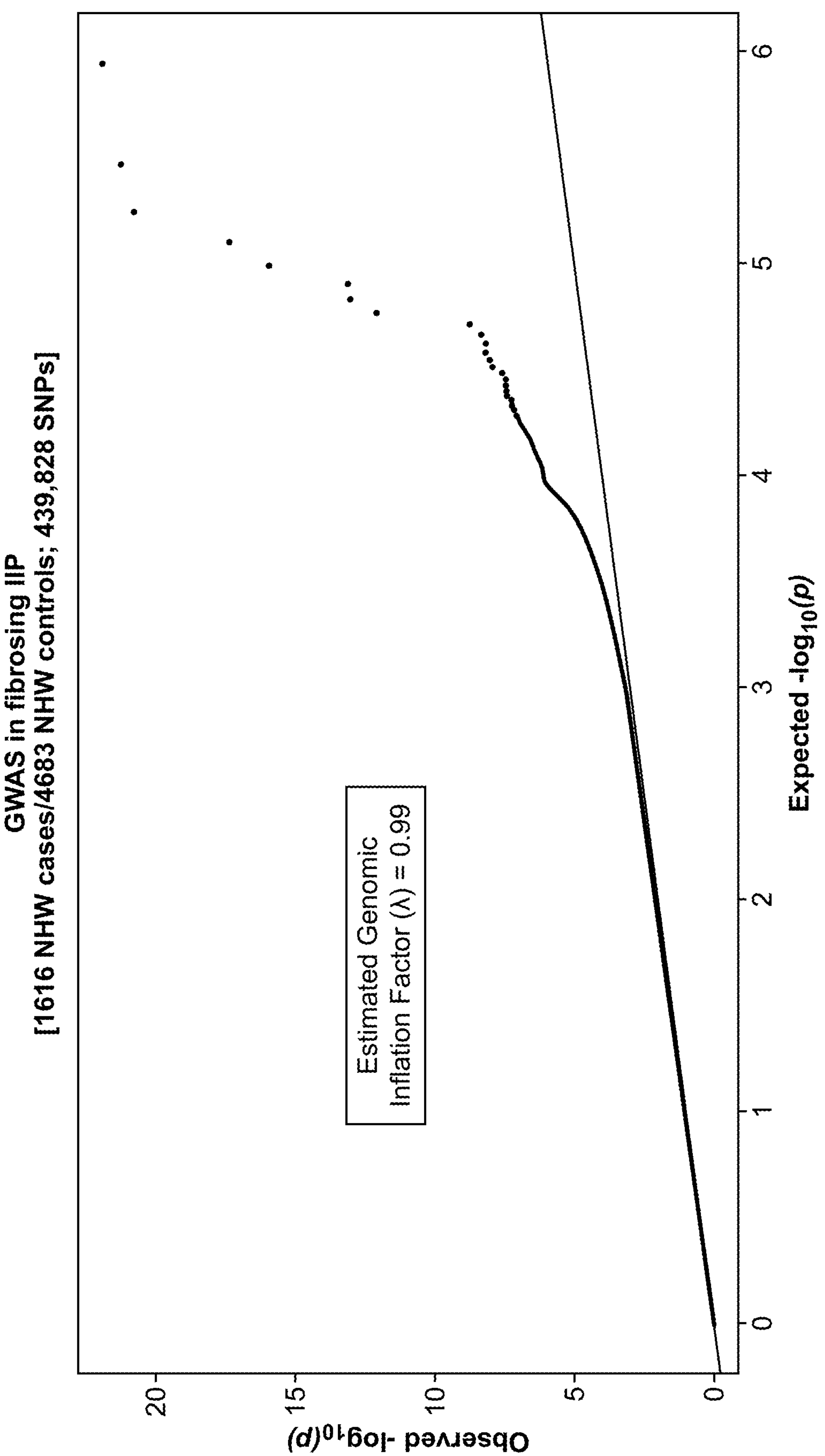
FIG. 25 shows an overview of GWAS results.
Figure 26:
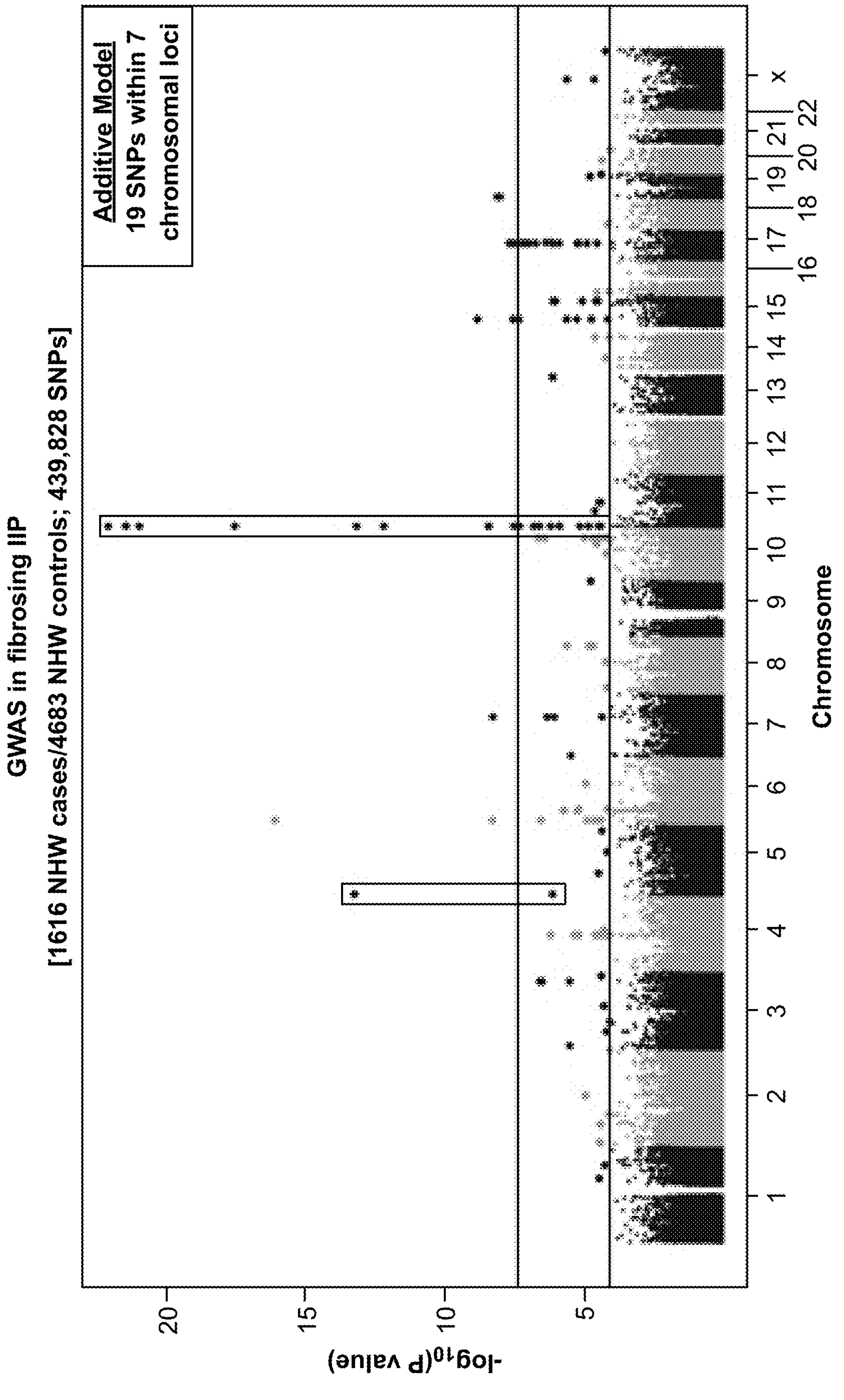
FIG. 26 shows genetic location of SNPs associated with interstitial lung disease.
Figure 28:
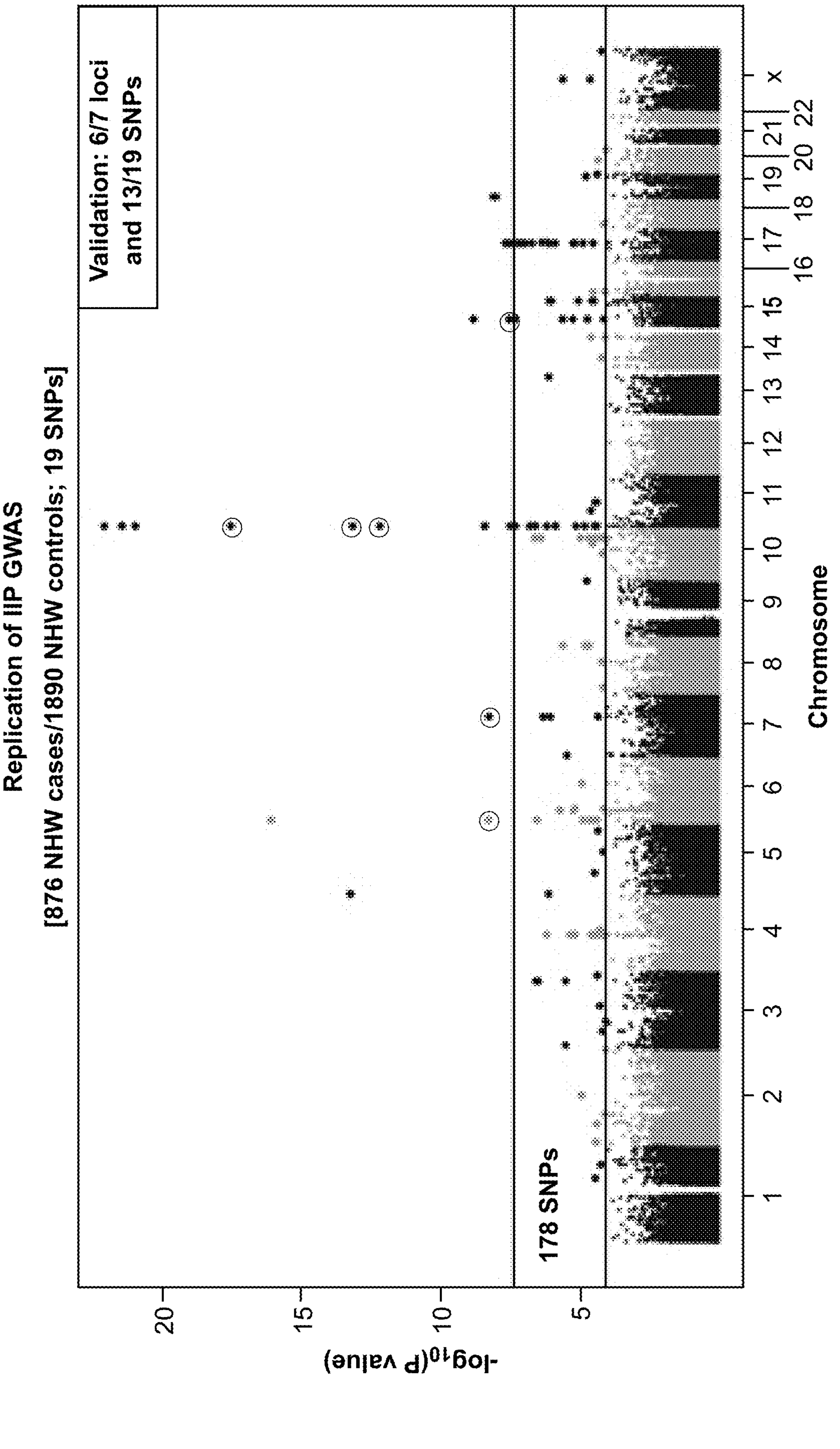
FIG. 28 shows genetic location of SNPs associated with interstitial lung disease in the replication population.
Figure 29:
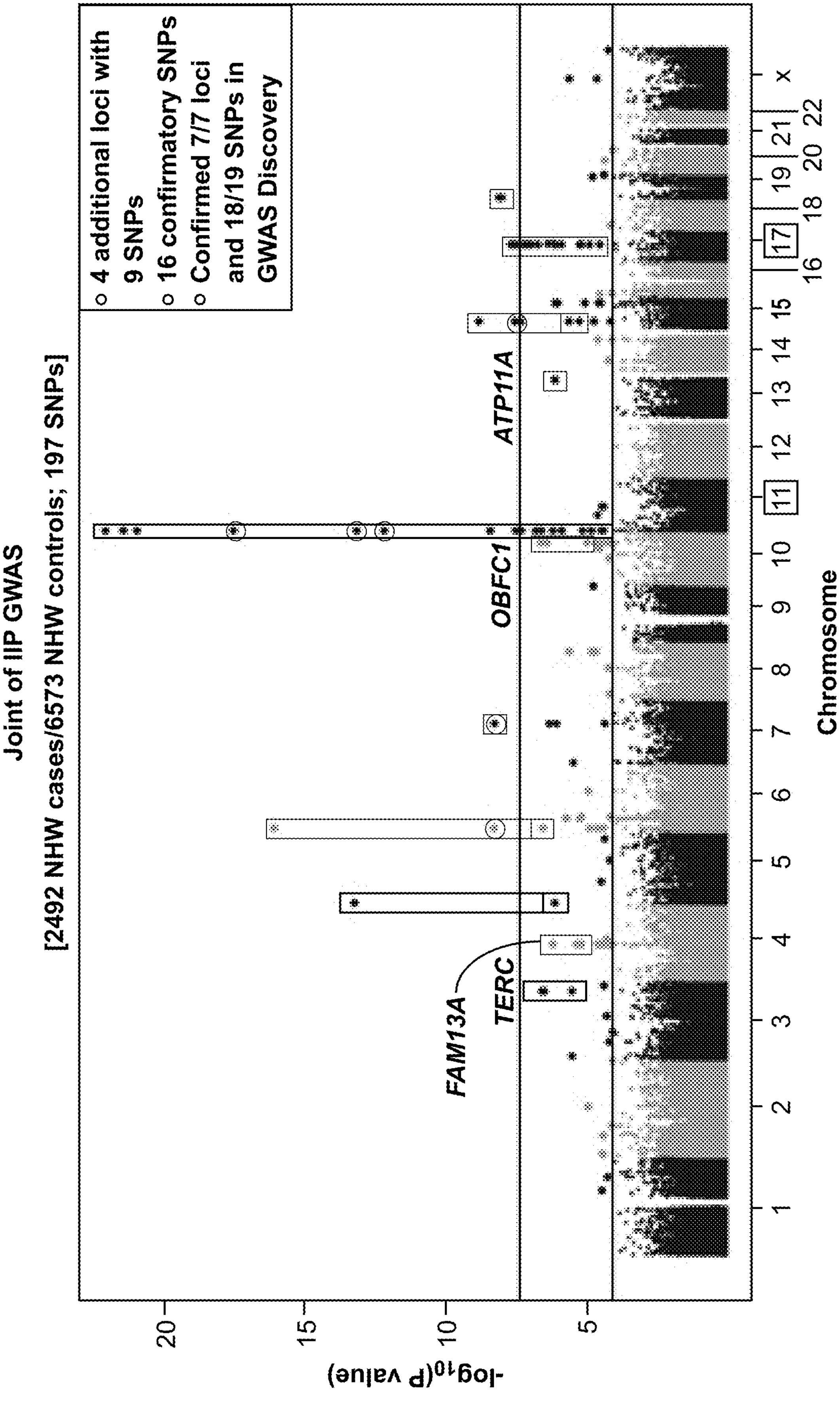
FIG. 29 shows combined results of GWAS studies and the locations of SNPs associated with interstitial lung disease.
Figure 30:
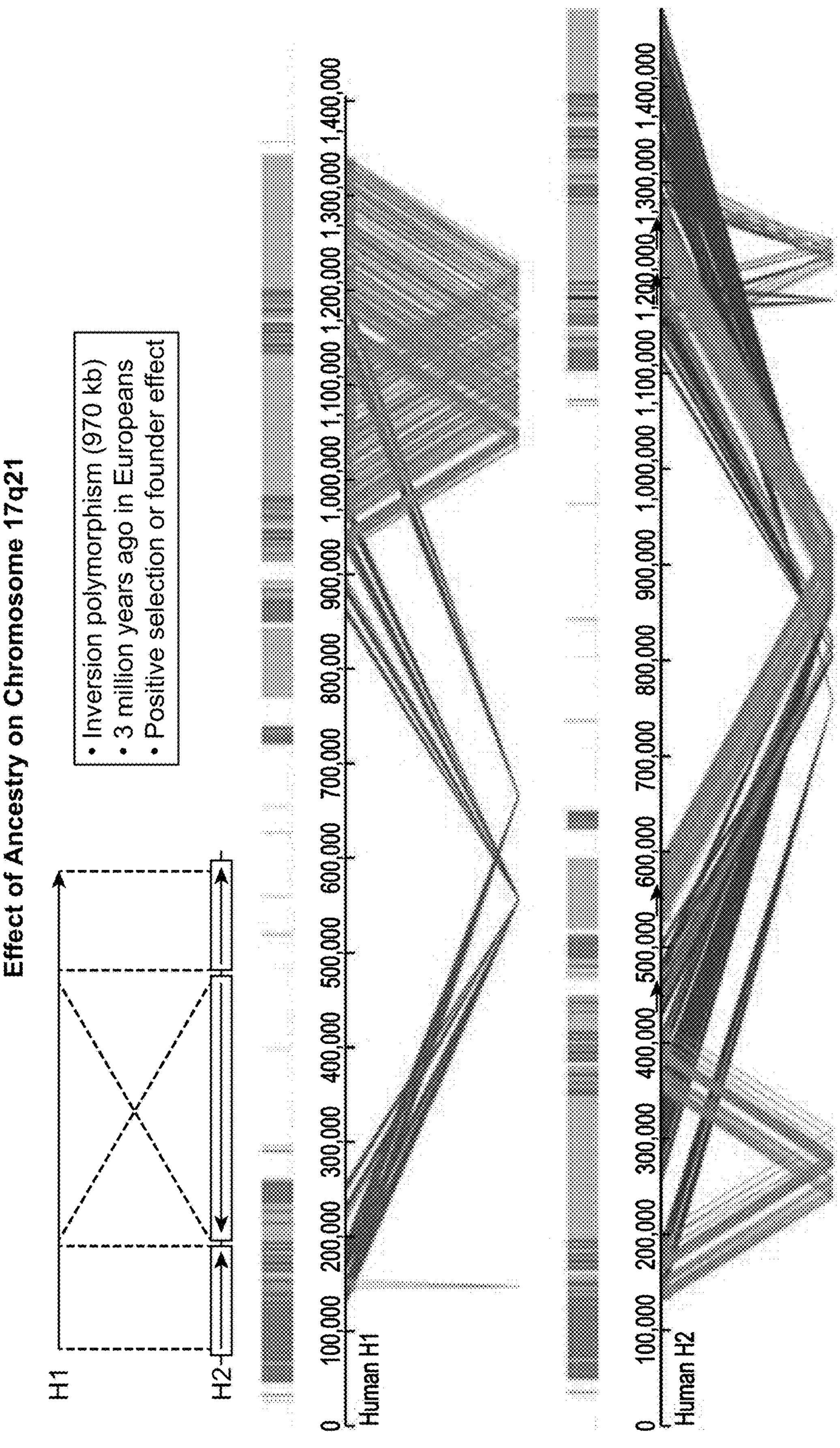
FIG. 30 shows the effect of ancestry on SNPs in chromosome 17q21.
Figure 33:
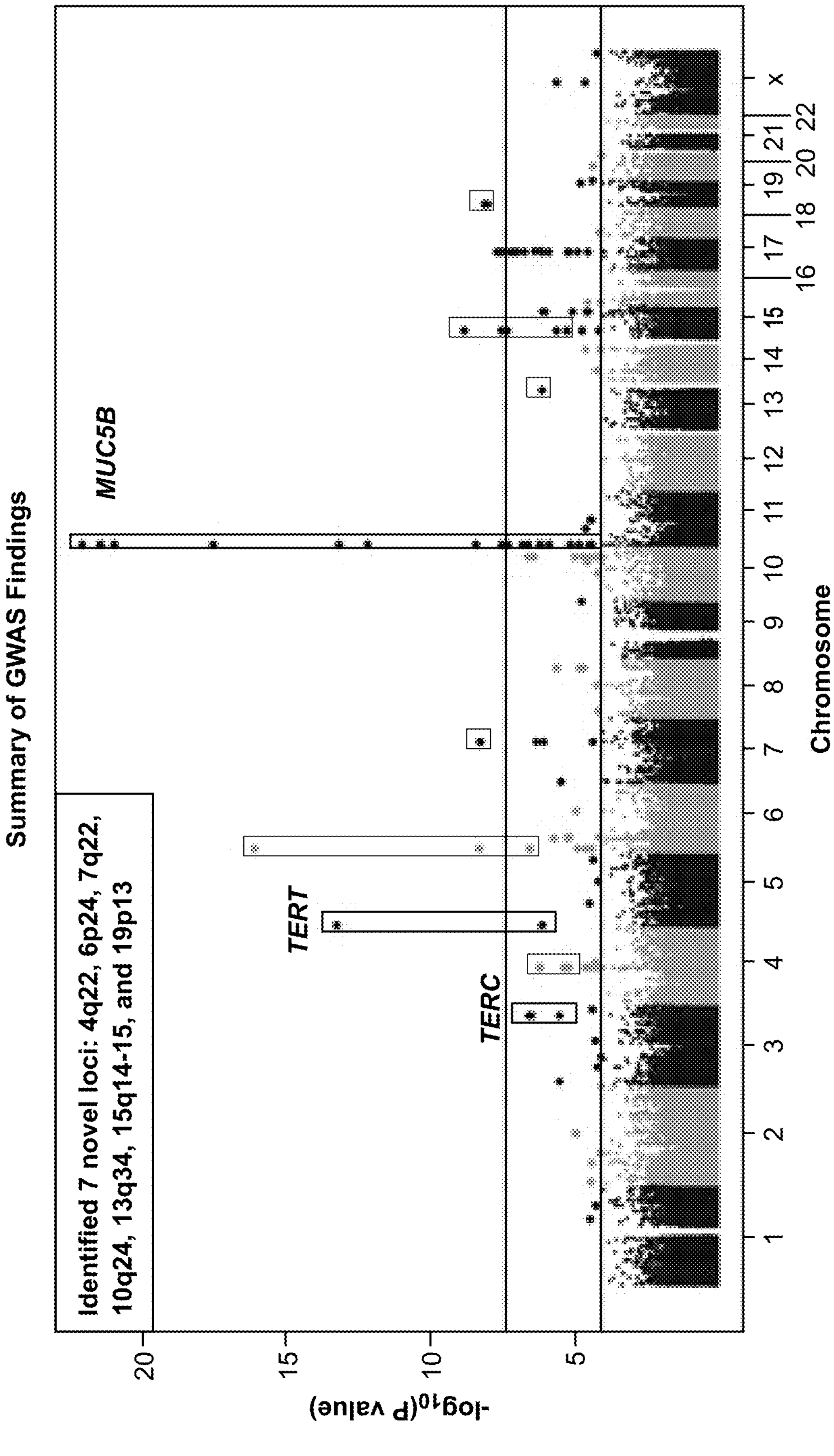
FIG. 33 summarizes the interstitial lung disease GWAS findings in terms of SNP location.
Figure 34:
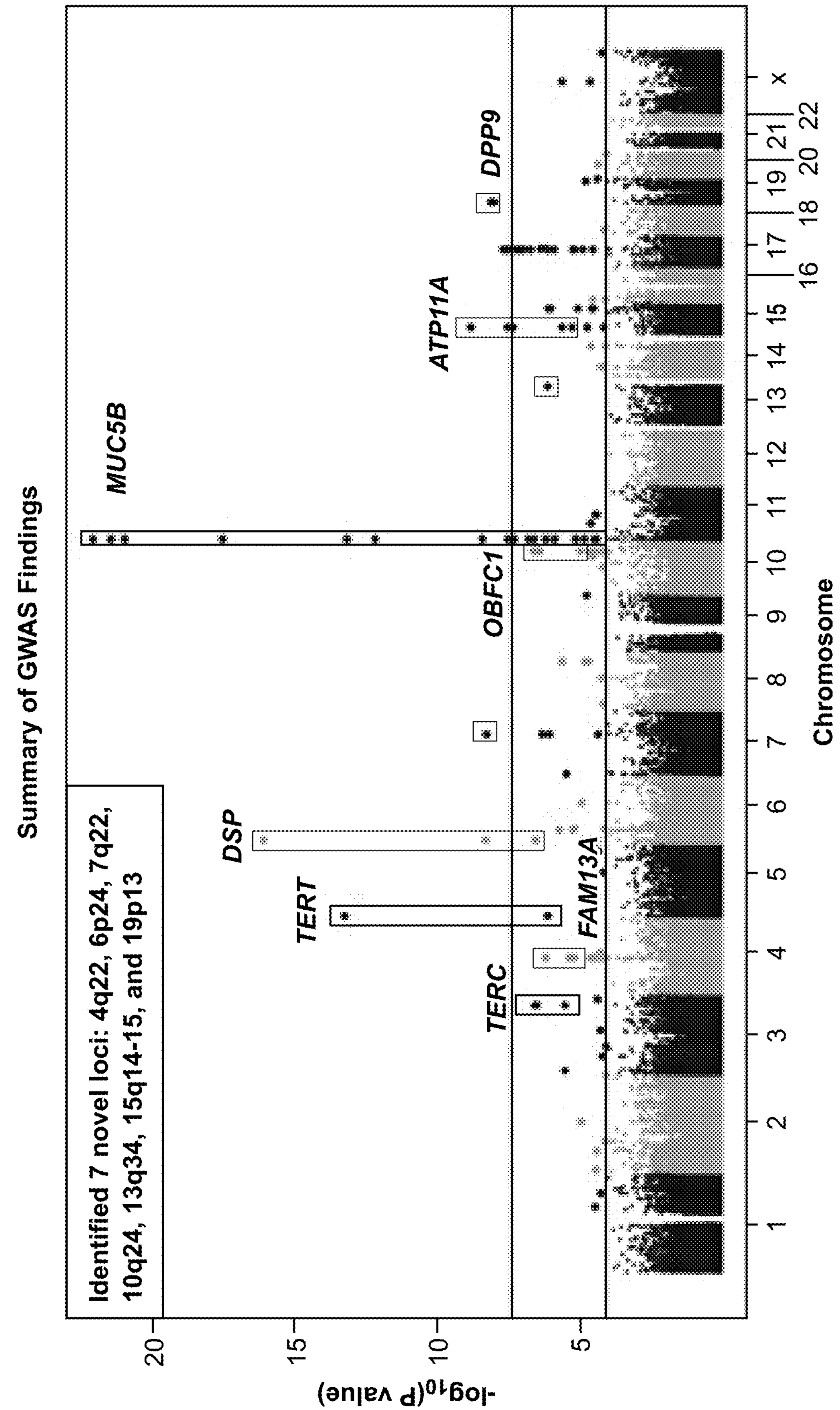
FIG. 34 summarizes the interstitial lung disease GWAS findings in terms of SNP location.
Figure 35:
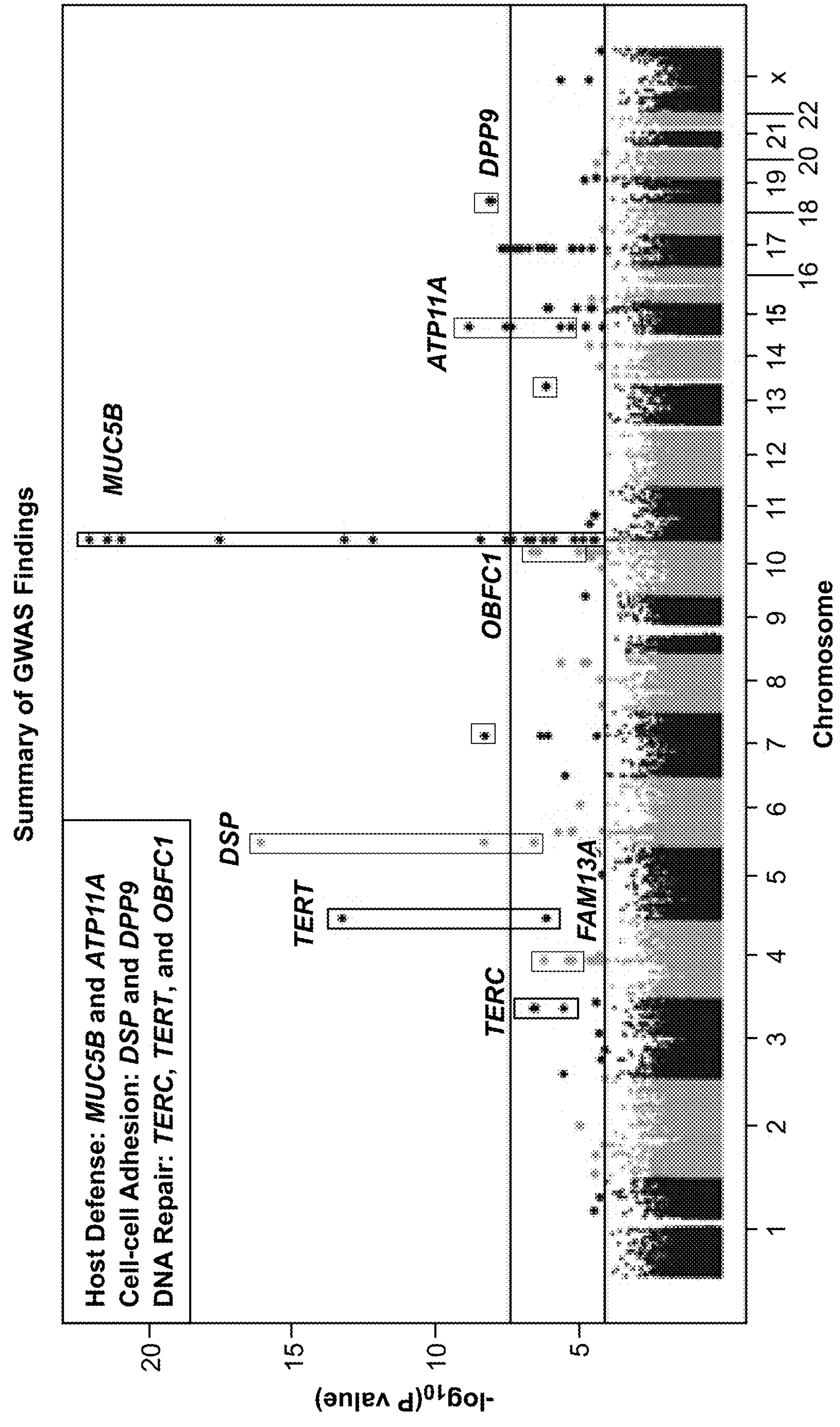
FIG. 35 summarizes the interstitial lung disease GWAS findings in terms of gene function.

The most highly associated SNP in the GWAS discovery, rs868903 (PGWAS=1.3×10-22; PMcta=9.2×10-26), is in the promoter of the MUC5B gene at chromosome 11p15, which we have reported to be associated with IPF and FIP and has been confirmed in other studies. Ten additional SNPs in the MUC5B region, including SNPs in the MUC2 and TOLLIP genes were also genome-wide significant in the joint analysis and not in strong LD with rs868903 (FIG. 2(*d*). The SNPs rs2736100 (PMcta=1.7×10-19) and rs2853676 (PMcta=3.3×10-8) at chromosome 5p15 are in the TERT gene (FIG. 2(*a*) and rs1881984 (PMeta=4.5×10-8) is near the TERC gene (FIG. 3(*a*); rare mutations in TERT and TERC have been reported to be associated with FIP and IPF, and rs2736100 has previously been reported in the TERT gene. The remaining 8 genome-wide significant loci are novel IIP loci (FIG. 6). Five of the association signals on chromosomes 4q22, 6p24, 10q24, 13q34, and 19p13 appear localized to single genes. SNP rs2609255 (PMeta=2.2×10-11) is in the FAM13A gene (family with sequence similarity 13, member (A) at chromosome 4q22 (FIG. 3(*b*). SNPs rs10484326 (PMcta=5.5×10-9) and rs2076295 (PMcta=1.1×10-19) are in the DSP gene (desmoplakin) at chromosome 6p24 (FIG. 2(*b*). SNPs rs10748858 (PMeta=2.7×10-8), rs2067832 (PMeta=3.7×10-8), and rs11191865 (PMeta=2.4×10-8) are in the OBFC1 gene (oligonucleotide-binding fold containing 1) at chromosome 10q24 (FIG. 3(*c*). SNP rs1278769 (PMeta=6.7×10-9) is in the ATP11A gene (ATPase, class VI, type 11(A) at chromosome 13q34 (FIG. 3(*d*). SNPs rs12610495 (PMcta=1.7×10-12) and rs2109069 (PMeta=2.4×10-11) are in the DPP9 gene (dipeptidyl-peptidase 9) at chromosome 19p13 (FIG. 2*g*). The other three chromosomal regions (7q22, 15q14-15, and 17q21) have either no significant SNP in any gene or SNPs with significant associations in multiple genes (Table 1 and FIG. 2*c*, 2*e*, 2*f*). The estimated odds ratios (OR) for all of the genome-wide significant SNPs range from ~1.1 to ~1.6 (Table 1; ORs for MAF that are less than 1 correspond to ORs for major allele in same rang(e).

Investigation of Adjusted Models for Genome-Wide Significant SNPs

To adjust for the previously discovered the MUC5B promoter SNP (rs35705950; not on the Illumina 660 Quad beadchip), we genotyped a subset of the GWAS discovery cases on the same platform and at the same time as the replication cases for the SNPs in Table 1. We combined the raw genotypes from these cases (n=859) with the replication cases and controls for joint analyses.

To assess the evidence for multiple independent association signals within each region, we tested for association with each SNP in a given region after adjusting for the most significant SNP in that region based on the meta-analysis. For the chromosome 11p15 region, we adjusted for rs35705950 given our prior findings and the strength of the association we observed between rs35705950 and IIP in our current study population (OR [95% CI]: 4.51 [3.91, 5.21], PJoint=7.21×10-95). After adjustment for rs35705950, only one of the SNPs at 11p15 (rs4077759) remained nominally associated with IIP (P=0.03; Table 2) while rs35705950 remained highly significant in all models, suggesting that the associations we observed with other SNPs were due to weak LD with rs35705950 (see FIG. 6 for LD among the SNPs). The reductions in significance of SNPs in the other regions after adjustment for the top SNP were consistent with the LD among the SNPs (Table 6) and do not provide evidence for multiple association signals. Of note is that SNP rs1881984 near the TERC gene is no longer significant after adjustment for SNP rs6793295 in the LRRC34 gene.

Finally, we adjusted for age in addition to sex for all of the genome-wide significant SNPs; with the exception of rs7942850 on chromosome 11 (Page-adjusted=0.06), all SNPs remained significant after adjustment (Table 6).

Expression of Key Genes in Lung Tissue

We measured expression of DPP9, DSP, FAM13A, IVD, MUC5B, MUC2, DISP2, OBFC1, WNT3, and WNT9B in lung tissue from 100 cases of IPF and 94 controls using quantitative PCR and validated Taqman Genotyping Assays (Applied Biosystems, Foster, City, C(A) to test for differences between cases and controls and to test for association between the genotypes at the most-highly associated SNPs in each gene with expression of that gene. We confirmed our results from a smaller study that MUC5B is more highly expressed in lung tissue of cases compared to controls (P=5.6×10-11) but consistent with our previous findings for rs35705950 among cases of IPF, rs868903 was not associated with expression of MUC5B. DSP was more highly expressed in cases compared to controls (P=0.0002), and expression differed by genotype at rs2076295 (P=0.002); relative expression of DSP increased with the number of copies of the putative at-risk allele (FIG. 4). There are two isoforms of desmoplakin generated by alternative splicing. rs2076295 is contained in a binding site for transcription factor PU.1, which has been implicated in alternative splicing of target genes; however, we saw no evidence for a differential effect of rs2076295 genotype on expression of the primary isoform compared to the alternative isoform. There was nominal evidence for higher expression of DPP9 in cases compared to controls (P=0.03), but neither rs12610495 (P=0.46) nor rs2109069 (P=0.72) were associated with DPP9 expression. Neither FAM13A, IVD, nor OBFC1 differed in expression between cases and controls or by genotype (all P>0.12); MUC2, DISP2, WNT3, and WNT9B showed little or no expression in these lung samples.

Percent Variation in Disease Risk Explained by GWAS SNPs

We estimated the percent of disease risk explained by all the 439,828 GWAS SNPs tested for association using a variance components model across a range of prevalence estimates for IIP (50 per 100,000 to 100 per 100,000). We found that the GWAS SNPs accounted for an estimated 30% (s.c. 2%) to 33% (s.c. 3%) of the risk of IIP. Since we did not include the MUC5B promoter SNP (rs35705950) in this analysis, this is a conservative estimate of the contribution of common SNPs to the risk of IIP.

Discussion

These findings provide convincing evidence that common genetic variation is an important contributor to risk of interstitial lung diseases such as IIP. We have identified 8 novel genetic risk loci (4922, 6p24, 7922, 10q24, 13q34, 15q14-15, 17q21, and 19p13), and confirmed the role of risk variants in three previously reported genes/loci (TERC [3q26], TERT [5p15], and MUC5B [11p15]) in IIP. Prior to this report, the only two genes with a reproducibly IIP-associated common variant were TERT and MUC5B. In aggregate, the common risk variants associated with IIP suggest that this disease is primarily mediated by defects in host defense, cell-cell adhesion, and early cell senescence. Moreover, these findings can be used to guide intervention trials in this complex disease.

Secreted mucins (MUC5(B) in the distal small airways appear to play a role in the development of IIP. The data do not suggest a strong effect of SNPs in other genes (MUC2 or TOLLIP) in the 11p15 region after accounting for the effect of the MUC5B promoter SNP rs35705950 we have previously identified as a key risk factor for IIP. The rs868903 SNP in the promoter of the MUC5B gene that was one of the most strongly associated SNPs in the GWAS, replication, and meta-analysis is not in strong LD (r2-0.13) with rs35705950 and is closer to the transcription start site for MUC5B than rs35705950 (3 kb vs. 1.5 kb, respectively). Although lung tissue from patients with IIP has higher concentrations of MUC5B than controls, neither of these MUC5B promoter variants appear to be entirely responsible for the increased expression of MUC5B in patients with IIP, suggesting that other gene variants or environmental toxins play a role in this disease. Dysregulated lung mucins likely initiate or exacerbate fibroproliferation through one of the following mechanisms: 1) altered mucosal host defense; 2) interference with alveolar repair; or 3) direct cell toxicity (endoplasmic reticulum stress or apoptosis) stimulating a fibroproliferative response initiated by excess production of the lung mucins.

Genes that maintain the length of telomeres appear to play a role in the development of IIP. Prior to this report, the associations between pulmonary fibrosis and TERT and TERC involved rare variants of TERT and TERC and a common variant of TERT. Mutations in these genes are associated with shortened telomeres in alveolar epithelial cells, suggesting that these gene variants may increase the risk of pulmonary fibrosis through enhanced apoptosis or necrosis of alveolar epithelia. Moreover, dyskeratosis congenita, a congenital disorder that resembles premature aging and frequently involves pulmonary fibrosis, was associated with mutations in TERT and TERC. This GWAS identified common variants in TERT and near TERC, and in another gene that influences telomere length, OBFC1 (Pmeta=2.4×10-08). A common variant in OBFC1 has been associated with telomere length in two GWAS studies of human leukocyte telomere length in the general population. It appears that risk associated with these genes is not limited to rare variants, but represents common risk variation. In aggregate, these findings underscore the importance of telomere length and early cell senescence in the pathogenesis of pulmonary fibrosis.

The results implicate alterations in cell-cell adhesion on risk of developing IIP. Variants in the DSP gene were strongly associated with IIP and the expression of DSP in the lung tissue of patients with IIP. The DSP gene encodes the protein desmoplakin, a component of the desmosome, an adhesive intercellular molecule that tightly links adjacent cells and forms a dynamic structure with other proteins (plakogobin and plakophilins) that tether the cytoskeleton to the cell membrane. Desmosomes are particularly important for maintaining the integrity of tissues that experience mechanical stress (such as the peripheral portions of the lung), and there is strong evidence that perturbation of the desmosome disrupts epithelial homeostasis. Mutations in DSP have been associated with arrhythmogenic right ventricular dysplasia, keratodermas, and alopecia, directly implicating desmoplakin in diseases with loss of tissue integrity. More specifically, mutations in DSP have been associated with cardiac interstitial fibrosis based on over-expression in mouse cardiac tissue. An additional potential mechanism for the involvement of DSP is through alterations in the wnt/β-catenin signaling pathway which have been consistently observed in pulmonary fibrosis. Desmoplakin has been shown to influence the wnt/β-catenin signaling pathway through regulation of another component of the desmosome, γ-catenin. These studies and the finding that over-expression of DSP in IIP is associated with the variant allele of rs2076295, provide a strong biomechanical or biologic rationale for the role of genetic variation in DSP contributing to pulmonary fibrosis.

The results implicate other cell adhesion molecules on risk of IIP development. The DPP9 gene is a member of the same protein family as fibroblast activation protein, which has been shown to be expressed in fibroblastic foci but not in adjacent healthy lung in IPF. DPP9 is expressed in epithelia and has been shown to alter cell adhesion in human embryonic kidney cells. In addition, the catenin cadherinassociated protein alpha 3 (CTNNA3) gene was nearly significant in the joint analysis (Pmeta=9.8×10-07), is located at 10q22, and is a cell adhesion molecule that physically interacts with β-catenin and mediates cell adhesion. In aggregate, these findings suggest that pulmonary fibrosis is be caused by defects in cell-cell adhesion or defects in the cytoskeleton that are unable to accommodate the stress associated with mechanical stretch of the lung.

FAM13A is a signal transduction gene that is responsive to hypoxia and a SNP (rs7671167) in that gene has recently been found to be protective in chronic obstructive lung disease. The other genome-wide significant loci are not as well localized to a single gene, although interesting candidates emerge. There are several markers associated with IIP which are all in strong LD at chromosome 17q21 spanning 1.14 Mb. An obvious candidate among those genes is the WNT3 gene given the alterations in wnt signaling observed in IIP; however, we found no evidence for WNT3 expression in the lung. 17q21 is a structurally complex genetic region with a large (>1 M(b) inversion polymorphism and disease-associated smaller copy number variants (CNVs). Interestingly, the genes LRRC37A and LRRC37A2 in this region are in the same family as the LRRC34 gene on chromosome 3, adjacent to the TERC gene, which had one of the strongest association signals in the replication samples. In both the chromosome 17q21 region and the complex mucin region on chromosome 11p15, it is likely that deep sequencing and array-based copy number measurement followed by functional testing of putative genes/alleles/CNVs will be necessary to further characterize the genetic architecture of these observed associations with IIP. While it has been proposed that pulmonary fibrosis results from activation of developmental pathways or aberrant lung repair, the findings suggest that these mechanisms are secondary to a primary defect in host defense or cell-cell adhesion. Since genes involved in the integrity of lung epithelia (DSP, DPP9, and CTNNA3) and lung mucins (MUC5(B) are genetic risk variants, defects in these mechanisms likely are primary contributors to the development of pulmonary fibrosis. Given the importance of environmental exposures (e.g., exposure to cigarette smoke, asbestos, and silic(a) in the development of other forms of interstitial lung disease, it is logical that common inhaled particles, such as those associated with cigarette smoke or air pollution, over years cause exaggerated interstitial injury in persons who have defects in lung host defense or cell-cell adhesion. Shortened telomeres and subsequent early cell senescence likely alter host defense or may enhance the 'host defense challenge' to the lung, analogous to asbestos or cigarette smoke. Thus, excessive lung injury either through enhanced environmental exposure, endogenous defects in critical homeostatic mechanisms, or subtle defects in host defense may, over years, lead to the development of pulmonary fibrosis. More attention should be directed to host defense and cell-cell adhesion when considering drugable targets for this complex disease.

The present findings should substantially influence future genetic, diagnostic, and pharmacologic studies of IIP. The cumulative GWAS SNPs reported here explain approximately one-third of the variability in risk of developing IIP, suggesting that further examination of common variation with larger cohorts is warranted in addition to studies of rare variation, epigenetic features, and gene-environment interactions. While the clinical manifestations of these diseases have been well defined, it is becoming increasingly clear that each type of IIP is caused by multiple gene variants that likely have distinct prognoses and may respond differently to pharmacologic intervention. Consequently, genotyping IIP subjects in future therapeutic trials may inform drug development by identifying agents that are effective in selective patients. In fact, the lack of attention to pharmacogenetic approaches in IIP trials may explain why few agents have been found to alter the course of these diseases. Moreover, the genetic heterogeneity of IIP suggests that characterization of genetic variants is helpful in redefining the types of IIP so that we can provide more accurate prognostic information for patients and their families.

It is understood that the examples and embodiments described herein are for illustrative purposes only and that various modifications or changes in light thereof will be suggested to persons skilled in the art and are to be included within the spirit and purview of this application and scope of the appended claims. All publications, patents, patent applications, websites and databases cited herein are incorporated by reference in their entireties for all purposes.

TABLE 1

Genome-wide Significant Loci in Discovery GWAS (GWAS P-value <5 × $10^{-8}$)

| | | | | Discovery GWAS | | | | Replication | | | | |
|---|---|---|---|---|---|---|---|---|---|---|---|---|
| | Position[a] | Gene[b] | Minor Allele | MAF Case | MAF Control | OR (95% CI) | P-value[c] | MAF Case | MAF Control | OR (95% CI) | P-value[c] | Meta-Analysis P-value[c] |
| Additive Model GWAS (P-value <5 × $10^{-8}$) | | | | | | | | | | | | |
| Chr. 5p15 | | | | | | | | | | | | |
| rs2736100 | 1339516 | TERT | C | 0.43 | 0.51 | 0.73 (0.67, 0.79) | 7.60e−14 | 0.43 | 0.50 | 0.74 (0.66, 0.85) | 5.59e−06 | 2.27e−18 |
| Chr. 6p24 | | | | | | | | | | | | |
| rs2076295 | 7508231 | DSP | T | 0.54 | 0.44 | 1.43 (1.32, 1.55) | 1.14e−16 | 0.52 | 0.46 | 1.26 (1.11, 1.42) | 3.00e−04 | 4.74e−19 |
| rs3778337 | 7510884 | DSP | A | 0.35 | 0.28 | 1.31 (1.20, 1.43) | 6.41e−09 | 0.32 | 0.30 | 1.08 (0.95, 1.24) | 0.25 | 4.01e−08 |
| Chr. 7q22 | | | | | | | | | | | | |
| rs4727443 | 99431282 | | A | 0.46 | 0.39 | 1.30 (1.20, 1.41) | 6.72e−09 | 0.42 | 0.40 | 1.12 (0.98, 1.27) | 0.088 | 7.18e−09 |
| Chr. 11p15 | | | | | | | | | | | | |
| rs868903 | 1199266 | | T | 0.38 | 0.49 | 0.64 (0.59, 0.70) | 1.26e−22 | 0.40 | 0.48 | 0.74 (0.65, 0.84) | 4.25e−06 | 9.27e−27 |

TABLE 1-continued

Genome-wide Significant Loci in Discovery GWAS (GWAS P-value <5 × $10^{-8}$)

| | Position[a] | Gene[b] | Minor Allele | Discovery GWAS MAF Case | MAF Control | OR (95% CI) | P-value[c] | Replication MAF Case | MAF Control | OR (95% CI) | P-value[c] | Meta-Analysis P-value[c] |
|---|---|---|---|---|---|---|---|---|---|---|---|---|
| rs7934606 | 1083945 | MUC2 | C | 0.52 | 0.42 | 1.52 (1.40, 1.65) | 5.46e−22 | 0.51 | 0.40 | 1.59 (1.40, 1.81) | 9.38e−13 | 4.80e−33 |
| rs6421972 | 1086494 | MUC2 | C | 0.52 | 0.42 | 1.51 (1.39, 1.64) | 1.62e−21 | 0.51 | 0.40 | 1.59 (1.40, 1.80) | 1.09e−12 | 1.70e−32 |
| rs7480563 | 1091649 | MUC2 | C | 0.42 | 0.51 | 0.69 (0.64, 0.75) | 4.17e−18 | 0.45 | 0.50 | 0.83 (0.73, 0.94) | 0.0036 | 8.75e−19 |
| rs7942850 | 1058900 | | C | 0.46 | 0.38 | 1.38 (1.27, 1.50) | 9.29e−14 | 0.42 | 0.39 | 1.16 (1.02, 1.32) | 0.026 | 8.87e−14 |
| rs4077759 | 1095976 | | C | 0.30 | 0.37 | 0.74 (0.67, 0.80) | 8.47e−13 | 0.33 | 0.36 | 0.87 (0.76, 0.99) | 0.032 | 8.16e−13 |
| rs2334659 | 1313639 | | A | 0.12 | 0.16 | 0.71 (0.63, 0.80) | 4.71e−09 | 0.12 | 0.17 | 0.68 (0.56, 0.81) | 3.67e−05 | 8.01e−13 |
| rs7122936 | 1331032 | | C | 0.33 | 0.40 | 0.76 (0.69, 0.82) | 3.69e−08 | 0.33 | 0.39 | 0.76 (0.67, 0.87) | 6.18e−05 | 1.05e−11 |
| Chr. 15q14-15 | | | | | | | | | | | | |
| rs2034650 | 38504594 | | G | 0.42 | 0.49 | 0.77 (0.71, 0.84) | 1.86e−09 | 0.40 | 0.47 | 0.74 (0.65, 0.83) | 1.74e−06 | 2.06e−14 |
| rs1992272 | 38446262 | DISP2 | T | 0.29 | 0.35 | 0.78 (0.71, 0.85) | 3.49e−08 | 0.27 | 0.33 | 0.77 (0.67, 0.88) | 2.00e−04 | 2.96e−11 |
| Chr. 17q21 | | | | | | | | | | | | |
| rs1981997 | 41412603 | MAPT | A | 0.17 | 0.23 | 0.71 (0.64, 0.78) | 2.52e−08 | 0.17 | 0.22 | 0.72 (0.61, 0.85) | 7.02e−05 | 7.95e−12 |
| rs17563986 | 41347100 | MAPT | G | 0.17 | 0.23 | 0.71 (0.64, 0.78) | 3.39e−08 | 0.17 | 0.22 | 0.68 (0.61, 0.85) | 9.32e−05 | 1.39e−11 |
| rs8070723 | 41436901 | MAPT | G | 0.17 | 0.23 | 0.71 (0.64, 0.79) | 3.87e−08 | 0.18 | 0.22 | 0.74 (0.63, 0.87) | 0.00027 | 4.21e−11 |
| Chr. 19p13 | | | | | | | | | | | | |
| rs12610495 | 4668672 | DPP9 | G | 0.34 | 0.29 | 1.29 (1.18, 1.41) | 9.57e−09 | 0.34 | 0.28 | 1.32 (1.15, 1.51) | 5.14e−05 | 2.24e−12 |
| rs2109069 | 4670443 | DPP9 | A | 0.36 | 0.31 | 1.28 (1.18, 1.40) | 1.22e−08 | 0.35 | 0.30 | 1.24 (1.09, 1.42) | 0.0013 | 6.49e−11 |
| Recessive Model GWAS (P-value <5 × $10^{-8}$) | | | | | | | | | | | | |
| Chr. 8p23 | | | | | | | | | | | | |
| rs1379326 | 4605218 | CSMD1 | C | 0.29 | 0.26 | 1.78 (1.45, 2.19) | 5.74e−09 | 0.28 | 0.26 | 1.21 (0.87, 1.68) | 0.25 | 3.75e−08 |

[a]Based on NCBI Build 36,
[b]Name of gene if SNP falls in coding region of gene,
[c]Adjusted for sex
MAF: Minor allele frequency; minor allele defined as minor allele in combined case and control group;
OR: Odds ratio for the minor allele;
CI: Confidence Interval

TABLE 2

Genome-wide Significant Loci from Meta-analysis (GWAS $5 \times 10^{-8}$ < P-value <.0001 and Meta-analysis P-value <$5 \times 10^{-8}$)

| | Position[a] | Gene[b] | Minor Allele | Discovery GWAS MAF Case | Discovery GWAS MAF Control | Discovery GWAS OR (95% Cl) | Discovery GWAS P-value[c] | Replication MAF Case | Replication MAF Control | Replication OR (95% Cl) | Replication P-value[c] | Meta-Analysis P-value[c] |
|---|---|---|---|---|---|---|---|---|---|---|---|---|
| Chr. 3q26 | | | | | | | | | | | | |
| rs1881984 | 170947153 | | G | 0.39 | 0.33 | 1.26 (1.16, 1.37) | 3.60e−06 | 0.38 | 0.33 | 1.21 (1.06, 1.38) | 0.0049 | 6.09e−08 |
| rs10936599 | 170974795 | MYNN | T | 0.30 | 0.24 | 1.30 (1.19, 1.43) | 3.90e−07 | 0.30 | 0.24 | 1.35 (1.17, 1.55) | 2.58e−05 | 5.77e−11 |
| rs1997392 | 170992346 | | T | 0.32 | 0.26 | 1.30 (1.19, 1.42) | 3.71e−07 | 0.33 | 0.26 | 1.34 (1.17, 1.53) | 2.77e−05 | 5.81e−11 |
| rs6793295 | 171001149 | LRRC34 | C | 0.32 | 0.26 | 1.30 (1.19, 1.42) | 3.20e−07 | 0.33 | 0.26 | 1.37 (1.20, 1.56) | 5.34e−06 | 1.30e−11 |
| Chr. 4q22 | | | | | | | | | | | | |
| rs2609255 | 90030218 | FAM13A | G | 0.26 | 0.21 | 1.29 (1.18, 1.42) | 5.27e−06 | 0.28 | 0.21 | 1.47 (1.27, 1.70) | 2.40e−07 | 3.17e−11 |
| Chr. 5p15 | | | | | | | | | | | | |
| rs2853676 | 1341547 | TERT | T | 0.23 | 0.28 | 0.77 (0.70, 0.84) | 8.93e−07 | 0.24 | 0.26 | 0.86 (0.75, 0.99) | 0.043 | 1.77e−07 |
| Chr. 6p24 | | | | | | | | | | | | |
| rs10484326 | 7503317 | DSP | C | 0.20 | 0.25 | 0.77 (0.70, 0.85) | 3.41e−07 | 0.22 | 0.24 | 0.84 (0.73, 0.98) | 0.025 | 5.45e−09 |
| Chr. 10q24 | | | | | | | | | | | | |
| rs10748858 | 105629504 | OBFC1 | G | 0.36 | 0.41 | 0.81 (0.74, 0.88) | 1.24e−05 | 0.35 | 0.40 | 0.80 (0.70, 0.91) | 9.00e−4 | 4.37e−08 |
| rs2067832 | 105633124 | OBFC1 | G | 0.45 | 0.5 | 0.80 (0.74, 0.87) | 4.73e−07 | 0.46 | 0.49 | 0.86 (0.76, 0.97) | 0.017 | 3.28e−08 |
| rs11191865 | 105662832 | OBFC1 | G | 0.45 | 0.51 | 0.80 (0.74, 0.87) | 2.82e−07 | 0.46 | 0.50 | 0.86 (0.76, 0.97) | 0.017 | 2.11e−08 |
| Chr. 11p15 | | | | | | | | | | | | |
| rs2301160 | 1053767 | | C | 0.48 | 0.43 | 1.25 (1.15, 1.35) | 1.90e−07 | 0.47 | 0.42 | 1.20 (1.06, 1.36) | 0.0043 | 3.15e−09 |
| rs3829223 | 1256982 | TOLLIP | C | 0.43 | 0.49 | 0.78 (0.72, 0.84) | 7.52e−07 | 0.45 | 0.50 | 0.82 (0.72, 0.93) | 0.0015 | 4.12e−09 |
| rs2857476 | 1237710 | MUC5B | C | 0.44 | 0.50 | 0.78 (0.71, 0.84) | 1.62e−06 | 0.46 | 0.51 | 0.85 (0.75, 0.96) | 0.01 | 6.02e−08 |
| Chr. 13q34 | | | | | | | | | | | | |
| rs1278769 | 112584628 | ATP11A | A | 0.20 | 0.24 | 0.79 (0.72, 0.88) | 9.11e−07 | 0.20 | 0.24 | 0.80 (0.68, 0.92) | 0.0029 | 9.56e−09 |

TABLE 2-continued

Genome-wide Significant Loci from Meta-analysis (GWAS $5 \times 10^{-8}$ < P-value <.0001 and Meta-analysis P-value <$5 \times 10^{-8}$)

| | | | | Discovery GWAS | | | | Replication | | | | |
|---|---|---|---|---|---|---|---|---|---|---|---|---|
| | Position[a] | Gene[b] | Minor Allele | MAF Case | MAF Control | OR (95% Cl) | P-value[c] | MAF Case | MAF Control | OR (95% Cl) | P-value[c] | Meta-Analysis P-value[c] |
| Chr. 15q14-15 | | | | | | | | | | | | |
| rs1007177 | 38439130 | DISP2 | A | 0.29 | 0.34 | 0.78 (0.71, 0.85) | 5.59e−08 | 0.27 | 0.33 | 0.75 (0.66, 0.87) | 7.94e−05 | 2.01e−11 |
| rs10518693 | 38487314 | IVD | T | 0.44 | 0.39 | 1.23 (1.14, 1.34) | 2.93e−06 | 0.47 | 0.41 | 1.30 (1.14, 1.48) | 6.52e−05 | 1.07e−09 |
| Chr. 17q21 | | | | | | | | | | | | |
| rs393152 | 41074926 | CRHR1, C17orf69 | G | 0.17 | 0.23 | 0.72 (0.65, 0.80) | 9.26e−08 | 0.19 | 0.22 | 0.82 (0.70, 0.96) | 0.016 | 7.27e−09 |
| rs12373139 | 41279910 | IMP5 | A | 0.17 | 0.22 | 0.71 (0.64, 0.79) | 7.07e−08 | 0.17 | 0.22 | 0.72 (0.61, 0.85) | 8.81e−05 | 2.80e−11 |
| rs17690703 | 41281077 | LOC100128977 | T | 0.21 | 0.26 | 0.78 (0.71, 0.86) | 3.42e−05 | 0.21 | 0.25 | 0.79 (0.68, 0.92) | 0.0027 | 3.24e−07 |
| rs2532274 | 41602941 | KIAA1267 | G | 0.17 | 0.23 | 0.72 (0.65, 0.80) | 1.29e−07 | 0.18 | 0.23 | 0.73 (0.62, 0.85) | 9.79e−05 | 5.71e−11 |
| rs2532269 | 41605885 | KIAA1267 | C | 0.17 | 0.23 | 0.71 (0.64, 0.79) | 9.61e−08 | 0.17 | 0.22 | 0.71 (0.60, 0.83) | 2.71e−05 | 1.37e−11 |
| rs2668692 | 41648797 | KIAA1267 | A | 0.17 | 0.22 | 0.71 (0.64, 0.79) | 1.04e−07 | 0.17 | 0.22 | 0.72 (0.61, 0.85) | 7.64e−05 | 3.66e−11 |
| rs169201 | 42145386 | NSF | G | 0.16 | 0.21 | 0.71 (0.64, 0.79) | 2.33e−07 | 0.16 | 0.20 | 0.74 (0.63, 0.88) | 0.00051 | 4.63e−10 |
| rs199533 | 42184098 | NSF | A | 0.16 | 0.21 | 0.72 (0.64, 0.80) | 5.19e−07 | 0.16 | 0.20 | 0.74 (0.62, 0.87) | 0.00035 | 7.38e−10 |
| rs415430 | 42214305 | WNT3 | C | 0.16 | 0.21 | 0.72 (0.65, 0.80) | 7.86e−07 | 0.17 | 0.21 | 0.77 (0.65, 0.91) | 0.0021 | 6.03e−09 |

[a]Based on NCBI Build 36,
[b]Name of gene if SNP falls in coding region of gene,
[c]Adjusted for sex
MAF: Minor allele frequency; minor allele defined as minor allele in combined case and control group;
OR: Odds ratio for the minor allele;
CI: Confidence Interval

TABLE 3

Genotype counts and Hardy-Weinberg Equilibrium (HWE) P-values among cases and controls in the discovery set for all 198 SNPs taken into replication set.

| Chr. | | | Cases | | | | Controls | | | |
|---|---|---|---|---|---|---|---|---|---|---|
| SNP | Position[a] | Alleles[b] | Minor[c] | Hets[d] | Major[e] | HWE P[f] | Minor[c] | Hets[d] | Major[e] | HWE P[f] |
| Chr. 1 | | | | | | | | | | |
| rs12128329 | 64698479 | A/G | 207 | 783 | 625 | 0.12 | 525 | 1983 | 1991 | 0.37 |
| rs1995785 | 161599245 | A/G | 81 | 503 | 1031 | 0.06 | 127 | 1304 | 3065 | 0.43 |
| rs6428467 | 196777745 | C/A | 62 | 532 | 1022 | 0.54 | 125 | 1250 | 3125 | 1.00 |
| rs7525504 | 221934254 | G/A | 240 | 841 | 534 | <0.01 | 879 | 2181 | 1437 | 0.32 |
| rs3738383 | 221972155 | G/A | 41 | 556 | 1019 | <0.01 | 239 | 1532 | 2728 | 0.21 |
| Chr. 2 | | | | | | | | | | |
| rs17247006 | 2511991 | A/G | 30 | 423 | 1163 | 0.28 | 79 | 960 | 3459 | 0.19 |
| rs10495536 | 6498196 | A/G | 49 | 458 | 1109 | 0.86 | 159 | 1496 | 2842 | 0.03 |
| rs2354382 | 51680424 | C/T | 19 | 305 | 1287 | 0.79 | 30 | 679 | 3774 | 1.00 |
| rs1879219 | 76771091 | G/A | 180 | 689 | 746 | 0.28 | 593 | 2068 | 1825 | 0.85 |
| rs1369523 | 125855752 | T/C | 56 | 458 | 1101 | 0.35 | 204 | 1468 | 2815 | 0.47 |
| rs1836676 | 125858674 | A/G | 57 | 458 | 1100 | 0.27 | 205 | 1468 | 2809 | 0.47 |
| rs10174598 | 140429825 | C/T | 271 | 714 | 631 | <0.01 | 580 | 2101 | 1815 | 0.48 |
| rs12469218 | 148949526 | A/G | 97 | 522 | 996 | 0.01 | 162 | 1469 | 2868 | 0.12 |
| rs7578722 | 169761122 | C/T | 154 | 613 | 848 | 0.01 | 274 | 1782 | 2442 | 0.03 |
| rs4668123 | 169761751 | T/C | 154 | 613 | 849 | 0.01 | 274 | 1782 | 2441 | 0.03 |
| rs2302696 | 169761826 | T/C | 158 | 620 | 838 | 0.01 | 284 | 1808 | 2408 | 0.02 |
| rs11687903 | 169765968 | G/T | 167 | 635 | 813 | 0.01 | 310 | 1860 | 2326 | 0.02 |
| rs2284675 | 169767205 | A/G | 166 | 632 | 814 | 0.01 | 303 | 1861 | 2333 | 0.01 |
| rs9646792 | 176546391 | A/C | 348 | 732 | 536 | <0.01 | 773 | 2239 | 1487 | 0.17 |
| rs13415895 | 240625254 | C/A | 67 | 540 | 1009 | 0.65 | 145 | 1333 | 3006 | 0.88 |
| Chr. 3 | | | | | | | | | | |
| rs13091584 | 7380044 | C/T | 391 | 878 | 347 | <0.01 | 1074 | 2212 | 1211 | 0.31 |
| rs12638703 | 9227998 | T/C | 43 | 494 | 1078 | 0.15 | 93 | 1135 | 3268 | 0.68 |
| rs1532898 | 44897145 | C/A | 189 | 674 | 753 | 0.05 | 346 | 1856 | 2298 | 0.29 |
| rs6798211 | 69670985 | T/C | 26 | 409 | 1181 | 0.19 | 113 | 1303 | 3083 | 0.08 |
| rs697954 | 109117605 | G/A | 374 | 774 | 468 | 0.12 | 1165 | 2248 | 1079 | 0.95 |
| rs1881984 | 170947153 | G/A | 245 | 759 | 611 | 0.71 | 488 | 2013 | 1985 | 0.52 |
| rs10936599 | 170974795 | T/C | 143 | 669 | 804 | 0.81 | 260 | 1668 | 2572 | 0.66 |
| rs1997392 | 170992346 | T/C | 162 | 706 | 748 | 0.86 | 317 | 1735 | 2448 | 0.70 |
| rs6793295 | 171001149 | C/T | 162 | 711 | 743 | 0.69 | 320 | 1740 | 2440 | 0.67 |
| rs9844738 | 185664502 | T/C | 96 | 566 | 954 | 0.33 | 332 | 1760 | 2405 | 0.68 |
| Chr. 4 | | | | | | | | | | |
| rs4518326 | 13069051 | A/G | 16 | 415 | 1183 | <0.01 | 107 | 1078 | 3309 | 0.09 |
| rs16877848 | 25584209 | T/C | 20 | 428 | 1168 | <0.01 | 138 | 1173 | 3187 | 0.02 |
| rs340199 | 86569707 | C/A | 216 | 678 | 722 | 0.01 | 632 | 2126 | 1730 | 0.61 |
| rs2869358 | 86600804 | G/A | 180 | 681 | 754 | 0.17 | 528 | 2140 | 1826 | 0.01 |
| rs4488910 | 87581858 | C/T | 27 | 363 | 1226 | 1.00 | 117 | 1188 | 3194 | 0.61 |
| rs6830970 | 89996104 | G/A | 156 | 686 | 774 | 0.82 | 596 | 2053 | 1849 | 0.50 |
| rs2609255 | 90030218 | G/T | 121 | 602 | 891 | 0.18 | 222 | 1445 | 2816 | 0.04 |
| rs10019681 | 90051555 | T/C | 58 | 509 | 1047 | 0.75 | 251 | 1645 | 2602 | 0.71 |
| rs2869967 | 90088355 | C/T | 210 | 707 | 699 | 0.14 | 769 | 2139 | 1592 | 0.27 |
| rs7671167 | 90103002 | T/C | 326 | 776 | 506 | 0.36 | 1177 | 2201 | 1114 | 0.19 |
| rs1921679 | 90109807 | T/C | 124 | 681 | 811 | 0.27 | 494 | 1989 | 2017 | 0.92 |
| rs16996143 | 90116382 | A/G | 124 | 679 | 810 | 0.27 | 501 | 1981 | 2010 | 0.71 |
| rs11737182 | 90117499 | T/C | 124 | 682 | 810 | 0.25 | 499 | 1990 | 2011 | 0.84 |
| rs6849143 | 90147512 | T/C | 219 | 726 | 671 | 0.31 | 790 | 2120 | 1589 | 0.07 |
| rs12505696 | 90150093 | T/C | 277 | 754 | 585 | 0.22 | 584 | 2001 | 1911 | 0.10 |
| rs6828137 | 90278457 | T/G | 300 | 780 | 536 | 0.58 | 1042 | 2169 | 1287 | 0.03 |
| rs756345 | 90292237 | A/G | 167 | 669 | 779 | 0.20 | 587 | 2059 | 1850 | 0.72 |
| rs11727778 | 102641245 | C/T | 88 | 581 | 947 | 1.00 | 169 | 1450 | 2881 | 0.45 |
| rs2130910 | 187823204 | C/T | 378 | 764 | 474 | 0.04 | 1148 | 2279 | 1071 | 0.37 |
| Chr. 5 | | | | | | | | | | |
| rs2736100 | 1339516 | C/A | 329 | 731 | 556 | <0.01 | 1154 | 2287 | 1059 | 0.27 |
| rs2853676 | 1341547 | T/C | 80 | 571 | 964 | 0.78 | 340 | 1803 | 2356 | 0.88 |
| rs30364 | 55865133 | T/G | 319 | 790 | 507 | 0.72 | 1012 | 2264 | 1211 | 0.47 |
| rs9326761 | 108497343 | G/A | 160 | 756 | 700 | 0.03 | 431 | 1830 | 2239 | 0.05 |
| rs2217649 | 108502065 | G/A | 90 | 614 | 912 | 0.35 | 205 | 1490 | 2805 | 0.69 |
| rs13385 | 139693062 | A/G | 75 | 523 | 1018 | 0.45 | 241 | 1677 | 2582 | 0.15 |
| rs31874 | 140349502 | C/T | 135 | 601 | 880 | 0.03 | 416 | 1904 | 2180 | 1.00 |
| rs702390 | 140422393 | A/G | 298 | 727 | 591 | 0.01 | 890 | 2264 | 1346 | 0.28 |
| rs31850 | 140459806 | G/A | 367 | 759 | 490 | 0.03 | 1118 | 2256 | 1126 | 0.88 |
| rs2963163 | 161634659 | T/C | 6 | 202 | 1408 | 0.84 | 28 | 727 | 3743 | 0.30 |
| Chr. 6 | | | | | | | | | | |
| rs4959432 | 7336920 | G/A | 10 | 247 | 1359 | 0.87 | 23 | 531 | 3946 | 0.26 |
| rs10484325 | 7502047 | C/T | 52 | 513 | 1051 | 0.30 | 108 | 1208 | 3182 | 0.65 |

TABLE 3-continued

Genotype counts and Hardy-Weinberg Equilibrium (HWE) P-values among cases and controls in the discovery set for all 198 SNPs taken into replication set.

| Chr. | | | Cases | | | | Controls | | | |
|---|---|---|---|---|---|---|---|---|---|---|
| SNP | Position[a] | Alleles[b] | Minor[c] | Hets[d] | Major[e] | HWE P[f] | Minor[c] | Hets[d] | Major[e] | HWE P[f] |
| rs10484326 | 7503317 | C/T | 68 | 520 | 1028 | 0.82 | 288 | 1666 | 2546 | 0.50 |
| rs2076295 | 7508231 | G/T | 479 | 777 | 359 | 0.19 | 889 | 2219 | 1385 | 1.00 |
| rs3778337 | 7510884 | A/G | 200 | 718 | 698 | 0.47 | 346 | 1869 | 2285 | 0.19 |
| rs2076302 | 7515962 | A/G | 65 | 474 | 1073 | 0.16 | 246 | 1561 | 2688 | 0.33 |
| rs3134603 | 32233980 | A/G | 34 | 432 | 1150 | 0.45 | 72 | 949 | 3476 | 0.44 |
| rs3134943 | 32255739 | T/C | 30 | 445 | 1139 | 0.09 | 76 | 973 | 3449 | 0.45 |
| rs3132946 | 32298006 | A/G | 27 | 436 | 1152 | 0.05 | 71 | 944 | 3485 | 0.44 |
| rs9267992 | 32328375 | G/A | 34 | 454 | 1128 | 0.14 | 81 | 1008 | 3410 | 0.51 |
| rs3129860 | 32509057 | A/G | 38 | 464 | 1111 | 0.21 | 75 | 1006 | 3409 | 0.95 |
| rs9271366 | 32694832 | G/A | 38 | 459 | 1119 | 0.28 | 76 | 1008 | 3415 | 0.84 |
| rs6911621 | 35637003 | T/C | 125 | 687 | 803 | 0.20 | 488 | 2009 | 2000 | 0.64 |
| rs2766535 | 35799760 | A/G | 422 | 803 | 390 | 0.84 | 984 | 2240 | 1274 | 1.00 |
| rs961918 | 100762389 | C/T | 169 | 660 | 787 | 0.08 | 342 | 1711 | 2447 | 0.08 |
| rs1932103 | 130461745 | A/G | 14 | 343 | 1259 | 0.09 | 46 | 746 | 3706 | 0.22 |
| Chr. 7 | | | | | | | | | | |
| rs13225346 | 1833442 | C/T | 381 | 821 | 414 | 0.52 | 855 | 2252 | 1379 | 0.24 |
| rs7783715 | 1889911 | T/C | 287 | 753 | 576 | 0.14 | 594 | 2162 | 1735 | 0.05 |
| rs4994763 | 1895349 | C/T | 298 | 763 | 546 | 0.28 | 643 | 2176 | 1653 | 0.09 |
| rs962060 | 31361662 | C/T | 41 | 504 | 1071 | 0.04 | 124 | 1157 | 3218 | 0.11 |
| rs2283017 | 99412694 | G/A | 331 | 792 | 493 | 0.69 | 711 | 2109 | 1673 | 0.29 |
| rs4727443 | 99431282 | A/C | 338 | 813 | 465 | 0.65 | 711 | 2121 | 1657 | 0.45 |
| rs941289 | 99516427 | G/A | 184 | 710 | 722 | 0.65 | 397 | 1820 | 2282 | 0.22 |
| rs2261360 | 99530929 | T/G | 146 | 658 | 812 | 0.44 | 284 | 1633 | 2582 | 0.24 |
| rs720547 | 123862730 | G/A | 104 | 632 | 880 | 0.56 | 226 | 1563 | 2707 | 1.00 |
| Chr. 8 | | | | | | | | | | |
| rs1379326 | 4605218 | C/T | 164 | 621 | 831 | <0.01 | 269 | 1824 | 2405 | <0.01 |
| rs9650356 | 15796632 | A/G | 54 | 548 | 1014 | 0.05 | 138 | 1273 | 3088 | 0.64 |
| rs17577994 | 20930275 | A/G | 174 | 632 | 810 | <0.01 | 354 | 1813 | 2331 | 0.97 |
| rs10504290 | 60315650 | A/G | 62 | 397 | 1157 | <0.01 | 91 | 1200 | 3203 | 0.09 |
| rs6471845 | 61011882 | T/G | 215 | 706 | 695 | 0.10 | 672 | 2174 | 1652 | 0.33 |
| rs979564 | 79738714 | T/C | 81 | 555 | 980 | 0.83 | 151 | 1403 | 2943 | 0.33 |
| rs279968 | 94129515 | C/A | 396 | 750 | 470 | 0.01 | 891 | 2346 | 1262 | <0.01 |
| rs1467044 | 120956222 | G/A | 298 | 753 | 561 | 0.11 | 967 | 2211 | 1305 | 0.59 |
| rs11781657 | 120958423 | G/T | 298 | 754 | 564 | 0.10 | 965 | 2218 | 1314 | 0.61 |
| rs9987332 | 121003144 | A/G | 254 | 749 | 613 | 0.32 | 852 | 2179 | 1468 | 0.39 |
| rs7005380 | 121023054 | A/G | 166 | 695 | 755 | 0.73 | 617 | 2051 | 1831 | 0.27 |
| Chr. 9 | | | | | | | | | | |
| rs7022345 | 7163752 | A/G | 27 | 454 | 1135 | 0.01 | 158 | 1303 | 3038 | 0.21 |
| rs2820917 | 7182313 | A/G | 19 | 432 | 1165 | <0.01 | 125 | 1186 | 3188 | 0.24 |
| rs10963084 | 17394464 | T/C | 152 | 607 | 857 | <0.01 | 281 | 1824 | 2394 | 0.01 |
| rs541131 | 137692055 | G/A | 278 | 804 | 534 | 0.41 | 627 | 2140 | 1732 | 0.43 |
| Chr. 10 | | | | | | | | | | |
| rs2441727 | 67894892 | G/A | 6 | 217 | 1391 | 0.57 | 8 | 471 | 4010 | 0.15 |
| rs10997263 | 68052141 | C/A | 232 | 791 | 593 | 0.23 | 601 | 1982 | 1917 | 0.01 |
| rs10822856 | 68053979 | C/T | 231 | 788 | 595 | 0.27 | 600 | 1974 | 1920 | 0.01 |
| rs2901088 | 92431533 | T/C | 166 | 708 | 741 | 0.91 | 566 | 2141 | 1790 | 0.06 |
| rs1936606 | 92432636 | T/C | 166 | 708 | 742 | 0.91 | 565 | 2139 | 1788 | 0.06 |
| rs1936602 | 92435233 | T/C | 247 | 764 | 605 | 0.83 | 807 | 2277 | 1412 | 0.04 |
| rs2902638 | 105626979 | C/T | 125 | 679 | 812 | 0.33 | 262 | 1670 | 2567 | 0.69 |
| rs10748858 | 105629504 | G/T | 221 | 721 | 674 | 0.21 | 772 | 2145 | 1582 | 0.34 |
| rs2067832 | 105633124 | G/A | 335 | 777 | 502 | 0.29 | 1138 | 2258 | 1103 | 0.81 |
| rs1980653 | 105644154 | A/G | 334 | 778 | 501 | 0.31 | 1138 | 2256 | 1103 | 0.83 |
| rs11191865 | 105662832 | G/A | 340 | 774 | 502 | 0.19 | 1159 | 2235 | 1105 | 0.68 |
| rs9419958 | 105665936 | T/C | 18 | 319 | 1279 | 0.80 | 73 | 1125 | 3302 | 0.04 |
| rs9420907 | 105666455 | C/A | 18 | 319 | 1279 | 0.80 | 73 | 1124 | 3302 | 0.04 |
| rs7074532 | 105692032 | G/T | 167 | 680 | 769 | 0.36 | 327 | 1776 | 2395 | 0.97 |
| rs7073827 | 105698783 | C/T | 183 | 704 | 728 | 0.54 | 361 | 1837 | 2287 | 0.80 |
| Chr. 11 | | | | | | | | | | |
| rs10751635 | 1052990 | G/A | 380 | 804 | 431 | 0.92 | 824 | 2183 | 1483 | 0.69 |
| rs2301160 | 1053767 | C/T | 379 | 808 | 429 | 1.00 | 826 | 2185 | 1482 | 0.69 |
| rs7942850 | 1058900 | C/T | 346 | 801 | 469 | 0.92 | 642 | 2156 | 1702 | 0.34 |
| rs2071174 | 1063712 | C/T | 121 | 677 | 818 | 0.25 | 497 | 2016 | 1979 | 0.64 |
| rs7396030 | 1073364 | A/G | 41 | 431 | 1140 | 1.00 | 199 | 1423 | 2862 | 0.20 |
| rs7103978 | 1078815 | G/A | 2 | 218 | 1396 | 0.03 | 42 | 764 | 3694 | 0.73 |
| rs7934606 | 1083945 | T/C | 430 | 825 | 361 | 0.37 | 794 | 2179 | 1521 | 0.78 |
| rs6421972 | 1086494 | T/C | 428 | 820 | 363 | 0.45 | 794 | 2178 | 1518 | 0.81 |
| rs7480563 | 1091649 | C/T | 270 | 811 | 535 | 0.22 | 1165 | 2220 | 1092 | 0.59 |
| rs4077759 | 1095976 | C/T | 153 | 675 | 788 | 0.64 | 614 | 2107 | 1775 | 0.80 |

TABLE 3-continued

Genotype counts and Hardy-Weinberg Equilibrium (HWE) P-values among cases and controls in the discovery set for all 198 SNPs taken into replication set.

| Chr. | | | Cases | | | | Controls | | | |
|---|---|---|---|---|---|---|---|---|---|---|
| SNP | Position[a] | Alleles[b] | Minor[c] | Hets[d] | Major[e] | HWE P[f] | Minor[c] | Hets[d] | Major[e] | HWE P[f] |
| rs6421966 | 1116979 | G/T | 32 | 410 | 1174 | 0.69 | 140 | 1292 | 3044 | 0.84 |
| rs868903 | 1199266 | T/C | 219 | 788 | 604 | 0.14 | 1057 | 2260 | 1172 | 0.63 |
| rs2735727 | 1214035 | A/G | 232 | 773 | 611 | 0.64 | 885 | 2186 | 1415 | 0.45 |
| rs2857476 | 1237710 | C/T | 296 | 836 | 484 | 0.06 | 1156 | 2219 | 1123 | 0.37 |
| rs12417955 | 1240803 | G/A | 295 | 830 | 490 | 0.09 | 1151 | 2202 | 1130 | 0.24 |
| rs3829223 | 1256982 | C/T | 298 | 800 | 517 | 0.72 | 1110 | 2211 | 1155 | 0.42 |
| rs3793964 | 1258558 | T/C | 171 | 682 | 763 | 0.33 | 656 | 2081 | 1760 | 0.31 |
| rs2334659 | 1313639 | A/G | 20 | 349 | 1247 | 0.48 | 127 | 1218 | 3153 | 0.48 |
| rs7122936 | 1331032 | C/A | 168 | 733 | 713 | 0.34 | 710 | 2129 | 1653 | 0.57 |
| rs7944761 | 1361414 | C/T | 256 | 775 | 585 | 1.00 | 891 | 2242 | 1362 | 0.59 |
| rs4752744 | 1674842 | G/A | 13 | 286 | 1317 | 0.67 | 23 | 599 | 3878 | 1.00 |
| rs11036021 | 40668015 | T/G | 438 | 818 | 360 | 0.58 | 1051 | 2206 | 1238 | 0.27 |
| rs2736601 | 61462097 | T/C | 11 | 248 | 1357 | 1.00 | 19 | 539 | 3942 | 0.90 |
| rs2727267 | 61462692 | A/G | 11 | 248 | 1357 | 1.00 | 19 | 539 | 3942 | 0.90 |
| Chr. 12 | | | | | | | | | | |
| rs12310569 | 6567614 | A/G | 46 | 483 | 1087 | 0.44 | 113 | 1115 | 3270 | 0.13 |
| rs10845459 | 12099918 | G/A | 335 | 844 | 436 | 0.05 | 1147 | 2193 | 1157 | 0.10 |
| Chr. 13 | | | | | | | | | | |
| rs1278760 | 112579676 | T/C | 166 | 748 | 702 | 0.12 | 633 | 2073 | 1773 | 0.50 |
| rs1278769 | 112584628 | A/G | 62 | 535 | 1018 | 0.44 | 270 | 1647 | 2565 | 0.81 |
| Chr. 14 | | | | | | | | | | |
| rs12879458 | 45894992 | T/C | 58 | 476 | 1080 | 0.56 | 104 | 1157 | 3237 | 0.95 |
| rs10139381 | 46152755 | C/T | 76 | 621 | 919 | 0.03 | 363 | 1736 | 2389 | 0.06 |
| rs2781413 | 97038740 | C/T | 110 | 598 | 904 | 0.43 | 412 | 1807 | 2275 | 0.05 |
| rs1552126 | 97063843 | C/T | 317 | 835 | 464 | 0.10 | 790 | 2147 | 1560 | 0.28 |
| Chr. 15 | | | | | | | | | | |
| rs1007177 | 38439130 | A/G | 145 | 650 | 821 | 0.33 | 550 | 1997 | 1949 | 0.28 |
| rs1992272 | 38446262 | T/C | 149 | 644 | 823 | 0.17 | 558 | 1994 | 1946 | 0.18 |
| rs2289332 | 38471072 | G/A | 249 | 715 | 650 | 0.03 | 809 | 2149 | 1540 | 0.22 |
| rs11636361 | 38475120 | G/A | 262 | 720 | 634 | 0.02 | 849 | 2174 | 1470 | 0.38 |
| rs10518693 | 38487314 | T/C | 331 | 756 | 529 | 0.04 | 714 | 2073 | 1713 | 0.04 |
| rs2034650 | 38504594 | G/A | 304 | 751 | 558 | 0.07 | 1090 | 2193 | 1215 | 0.11 |
| rs603104 | 38544327 | A/C | 285 | 785 | 544 | 0.96 | 960 | 2235 | 1301 | 1.00 |
| rs1849210 | 52413032 | G/A | 96 | 514 | 1006 | 0.01 | 159 | 1483 | 2856 | 0.05 |
| rs351219 | 72276260 | C/T | 187 | 795 | 634 | 0.01 | 675 | 2063 | 1756 | 0.09 |
| rs6496932 | 83626571 | A/C | 46 | 432 | 1136 | 0.52 | 178 | 1371 | 2938 | 0.25 |
| rs1828481 | 83641916 | C/A | 315 | 763 | 538 | 0.14 | 637 | 2126 | 1735 | 0.75 |
| rs7172789 | 83644521 | C/T | 315 | 761 | 539 | 0.12 | 636 | 2122 | 1732 | 0.75 |
| rs11858744 | 83684068 | T/C | 315 | 758 | 539 | 0.10 | 636 | 2118 | 1736 | 0.82 |
| rs16977252 | 83727844 | G/A | 152 | 660 | 804 | 0.34 | 286 | 1712 | 2502 | 0.78 |
| rs6496044 | 83868310 | G/A | 260 | 729 | 627 | 0.05 | 491 | 2022 | 1986 | 0.50 |
| rs10520597 | 83971259 | A/G | 228 | 730 | 658 | 0.26 | 439 | 1995 | 2065 | 0.18 |
| rs11633855 | 96054298 | C/T | 246 | 722 | 648 | 0.06 | 528 | 2082 | 1887 | 0.21 |
| rs1441479 | 96057306 | C/T | 241 | 724 | 651 | 0.09 | 516 | 2076 | 1890 | 0.14 |
| Chr. 16 | | | | | | | | | | |
| rs17139255 | 6047175 | G/T | 61 | 498 | 1057 | 0.81 | 115 | 1233 | 3148 | 0.70 |
| rs1548857 | 6576606 | A/C | 9 | 230 | 1375 | 1.00 | 19 | 493 | 3988 | 0.35 |
| rs4843650 | 86240987 | G/A | 223 | 802 | 591 | 0.07 | 794 | 2172 | 1530 | 0.62 |
| Chr. 17 | | | | | | | | | | |
| rs393152 | 41074926 | G/A | 56 | 439 | 1121 | 0.11 | 243 | 1549 | 2707 | 0.27 |
| rs417968 | 41084159 | G/A | 72 | 541 | 1003 | 1.00 | 328 | 1688 | 2484 | 0.08 |
| rs1635291 | 41107696 | G/A | 62 | 507 | 1047 | 0.94 | 298 | 1629 | 2570 | 0.07 |
| rs7215239 | 41123556 | C/T | 60 | 506 | 1050 | 1.00 | 294 | 1629 | 2572 | 0.10 |
| rs12373139 | 41279910 | A/G | 55 | 433 | 1127 | 0.11 | 240 | 1534 | 2721 | 0.21 |
| rs17690703 | 41281077 | T/C | 78 | 523 | 1015 | 0.33 | 339 | 1638 | 2511 | <0.01 |
| rs17563986 | 41347100 | G/A | 54 | 434 | 1127 | 0.13 | 242 | 1539 | 2711 | 0.23 |
| rs1981997 | 41412603 | A/G | 54 | 433 | 1128 | 0.13 | 241 | 1544 | 2715 | 0.27 |
| rs8070723 | 41436901 | G/A | 54 | 436 | 1126 | 0.15 | 241 | 1546 | 2713 | 0.29 |
| rs7225002 | 41544850 | G/A | 201 | 735 | 679 | 0.91 | 761 | 2164 | 1572 | 0.73 |
| rs2532274 | 41602941 | G/A | 57 | 449 | 1107 | 0.17 | 247 | 1578 | 2664 | 0.50 |
| rs2532269 | 41605885 | C/T | 55 | 439 | 1117 | 0.16 | 243 | 1551 | 2697 | 0.31 |
| rs2668692 | 41648797 | A/G | 54 | 425 | 1121 | 0.09 | 241 | 1497 | 2704 | 0.08 |
| rs183211 | 42143493 | A/G | 52 | 503 | 1061 | 0.46 | 277 | 1592 | 2631 | 0.08 |
| rs169201 | 42145386 | G/A | 42 | 422 | 1152 | 0.64 | 216 | 1466 | 2814 | 0.17 |
| rs7224296 | 42155230 | G/A | 89 | 556 | 971 | 0.44 | 379 | 1738 | 2381 | 0.02 |
| rs199533 | 42184098 | A/G | 42 | 423 | 1147 | 0.71 | 212 | 1469 | 2817 | 0.24 |
| rs415430 | 42214305 | C/T | 40 | 435 | 1139 | 0.93 | 207 | 1488 | 2797 | 0.62 |

TABLE 3-continued

Genotype counts and Hardy-Weinberg Equilibrium (HWE) P-values among cases and controls in the discovery set for all 198 SNPs taken into replication set.

| Chr. | | | Cases | | | | Controls | | | |
|---|---|---|---|---|---|---|---|---|---|---|
| SNP | Position[a] | Alleles[b] | Minor[c] | Hets[d] | Major[e] | HWE P[f] | Minor[c] | Hets[d] | Major[e] | HWE P[f] |
| Chr. 18 | | | | | | | | | | |
| rs367024 | 10388673 | T/C | 54 | 505 | 1057 | 0.57 | 128 | 1171 | 3201 | 0.10 |
| Chr. 19 | | | | | | | | | | |
| rs12610495 | 4668672 | G/A | 210 | 691 | 715 | 0.04 | 377 | 1875 | 2247 | 0.64 |
| rs2109069 | 4670443 | A/G | 233 | 707 | 673 | 0.04 | 426 | 1944 | 2123 | 0.55 |
| rs10417008 | 54895365 | C/T | 43 | 416 | 1157 | 0.45 | 156 | 1371 | 2966 | 0.92 |
| rs306477 | 61181585 | T/C | 336 | 814 | 464 | 0.58 | 797 | 2165 | 1531 | 0.52 |
| Chr. 20 | | | | | | | | | | |
| rs2145275 | 6521455 | T/C | 336 | 754 | 526 | 0.03 | 751 | 2190 | 1557 | 0.71 |
| rs6088520 | 32596025 | T/C | 333 | 817 | 466 | 0.48 | 1070 | 2322 | 1106 | 0.03 |
| rs4810223 | 59179191 | T/G | 88 | 564 | 964 | 0.62 | 168 | 1379 | 2950 | 0.66 |
| Chr. 21 | | | | | | | | | | |
| rs2823529 | 16271144 | C/T | 63 | 408 | 1144 | <0.01 | 102 | 1208 | 3189 | 0.34 |
| rs2830234 | 26754202 | G/T | 277 | 839 | 500 | 0.02 | 744 | 2111 | 1643 | 0.14 |
| Chr. 23 | | | | | | | | | | |
| rs7879375 | 79014847 | A/G | 9 | 122 | 395 | 1.00 | 26 | 415 | 1861 | 0.57 |
| rs3903350 | 79032104 | A/G | 12 | 136 | 378 | 1.00 | 34 | 471 | 1797 | 0.61 |
| rs5924874 | 150037033 | G/A | 104 | 264 | 158 | 0.79 | 391 | 1098 | 809 | 0.57 |

[a]Genomic position based on NCBI Build 36
[b]Minor allele in cases listed first.
[c]Minor: Count of minor allele subjects
[d]Het: Count of heterozygous subjects
[e]Major: Count of major allele (more frequent allele) homozygous subjects
[f]P-value for HWE goodness-of-fit test

TABLE 4

Genotype counts and Hardy-Weinberg Equilibrium (HWE) P-values among cases and controls in the replication set for all SNPs successfully genotyped in replication.

| Chr. | | | Cases | | | | Controls | | | |
|---|---|---|---|---|---|---|---|---|---|---|
| SNP | Position[a] | Alleles[b] | Minor[c] | Hets[d] | Major[e] | HWE P[f] | Minor[c] | Hets[d] | Major[e] | HWE P[f] |
| Chr. 1 | | | | | | | | | | |
| rs12128329 | 64698479 | A/G | 101 | 383 | 391 | 0.65 | 232 | 874 | 779 | 0.61 |
| rs1995785 | 161599245 | T/C | 43 | 271 | 556 | 0.18 | 75 | 582 | 1202 | 0.66 |
| rs6428467 | 196777745 | C/A | 45 | 257 | 572 | 0.03 | 67 | 593 | 1224 | 0.71 |
| rs7525504 | 221934254 | G/A | 177 | 426 | 266 | 0.78 | 393 | 870 | 603 | 0.02 |
| Rs17596 | 223905532 | G/A | 53 | 317 | 504 | 0.71 | 105 | 666 | 1116 | 0.65 |
| Chr. 2 | | | | | | | | | | |
| rs17247006 | 2511991 | T/C | 17 | 178 | 654 | 0.27 | 34 | 404 | 1420 | 0.40 |
| rs10495536 | 6498196 | A/G | 45 | 288 | 541 | 0.42 | 64 | 545 | 1280 | 0.53 |
| rs2354382 | 51680424 | C/T | 11 | 147 | 715 | 0.25 | 19 | 321 | 1544 | 0.59 |
| rs1879219 | 76771091 | C/T | 115 | 396 | 354 | 0.83 | 238 | 844 | 790 | 0.61 |
| rs1369523 | 125855752 | T/C | 36 | 280 | 557 | 0.92 | 83 | 566 | 1237 | 0.08 |
| rs1836676 | 125858674 | T/C | 36 | 280 | 559 | 0.92 | 83 | 566 | 1238 | 0.08 |
| rs10174598 | 140429825 | C/T | 135 | 395 | 342 | 0.25 | 269 | 913 | 696 | 0.28 |
| rs12469218 | 148949526 | A/G | 36 | 295 | 541 | 0.68 | 79 | 606 | 1197 | 0.83 |
| rs7578722 | 169761122 | C/T | 62 | 323 | 482 | 0.43 | 126 | 738 | 991 | 0.51 |
| rs2302696 | 169761826 | A/G | 68 | 339 | 468 | 0.55 | 136 | 757 | 991 | 0.64 |
| rs11687903 | 169765968 | G/T | 71 | 354 | 446 | 0.93 | 140 | 770 | 973 | 0.49 |
| rs2284675 | 169767205 | T/C | 70 | 353 | 450 | 0.93 | 141 | 763 | 981 | 0.69 |
| rs9646792 | 176546391 | A/C | 183 | 415 | 275 | 0.27 | 337 | 953 | 596 | 0.21 |
| rs13415895 | 240625254 | C/A | 36 | 278 | 558 | 0.83 | 49 | 589 | 1242 | 0.04 |
| Chr. 3 | | | | | | | | | | |
| rs13091584 | 7380044 | C/T | 195 | 436 | 239 | 0.95 | 486 | 925 | 474 | 0.43 |
| rs12638703 | 9227998 | T/C | 18 | 242 | 612 | 0.38 | 34 | 500 | 1352 | 0.13 |
| rs1532898 | 44897145 | C/A | 77 | 326 | 328 | 0.80 | 155 | 678 | 804 | 0.48 |
| rs6798211 | 69670985 | T/C | 29 | 238 | 608 | 0.34 | 68 | 521 | 1299 | 0.09 |
| rs697954 | 109117605 | T/C | 194 | 449 | 231 | 0.42 | 427 | 954 | 496 | 0.46 |
| rs1881984 | 170947153 | C/T | 127 | 391 | 333 | 0.51 | 198 | 839 | 819 | 0.46 |

TABLE 4-continued

Genotype counts and Hardy-Weinberg Equilibrium (HWE) P-values among cases and controls in the replication set for all SNPs successfully genotyped in replication.

| Chr. | | | Cases | | | | Controls | | | |
|---|---|---|---|---|---|---|---|---|---|---|
| SNP | Position[a] | Alleles[b] | Minor[c] | Hets[d] | Major[e] | HWE P[f] | Minor[c] | Hets[d] | Major[e] | HWE P[f] |
| rs10936599 | 170974795 | T/C | 97 | 331 | 448 | <0.01 | 89 | 717 | 1078 | 0.03 |
| rs1997392 | 170992346 | A/G | 107 | 360 | 403 | 0.07 | 117 | 752 | 1014 | 0.17 |
| rs6793295 | 171001149 | C/T | 114 | 357 | 404 | 0.01 | 117 | 753 | 1018 | 0.17 |
| rs9844738 | 185664502 | T/C | 51 | 331 | 494 | 0.72 | 137 | 732 | 1018 | 0.72 |
| Chr. 4 | | | | | | | | | | |
| rs4518326 | 13069051 | A/G | 22 | 219 | 630 | 0.60 | 33 | 477 | 1372 | 0.30 |
| rs16877848 | 25584209 | T/C | 26 | 225 | 625 | 0.31 | 59 | 534 | 1297 | 0.63 |
| rs340199 | 86569707 | C/A | 130 | 395 | 347 | 0.31 | 237 | 940 | 707 | 0.01 |
| rs4488910 | 87581858 | C/T | 22 | 217 | 637 | 0.50 | 45 | 483 | 1361 | 0.79 |
| rs6830970 | 89996104 | G/A | 95 | 366 | 411 | 0.31 | 199 | 863 | 821 | 0.23 |
| rs2609255 | 90030218 | G/T | 62 | 359 | 454 | 0.50 | 70 | 670 | 1148 | 0.02 |
| rs10019681 | 90051555 | T/C | 36 | 313 | 527 | 0.24 | 98 | 659 | 1127 | 0.90 |
| rs2869967 | 90088355 | C/T | 126 | 392 | 350 | 0.34 | 251 | 907 | 701 | 0.13 |
| rs7671167 | 90103002 | T/C | 177 | 439 | 255 | 0.68 | 413 | 973 | 486 | 0.08 |
| rs1921679 | 90109807 | T/C | 74 | 378 | 418 | 0.42 | 199 | 823 | 860 | 0.92 |
| rs16996143 | 90116382 | A/G | 74 | 385 | 414 | 0.26 | 204 | 825 | 857 | 0.79 |
| rs11737182 | 90117499 | T/C | 74 | 384 | 417 | 0.30 | 202 | 826 | 859 | 0.88 |
| rs6849143 | 90147512 | T/C | 120 | 415 | 338 | 0.72 | 269 | 915 | 694 | 0.26 |
| rs12505696 | 90150093 | T/C | 135 | 398 | 343 | 0.28 | 238 | 924 | 727 | 0.04 |
| rs6828137 | 90278457 | T/G | 162 | 440 | 261 | 0.37 | 357 | 936 | 555 | 0.30 |
| rs756345 | 90292237 | T/C | 96 | 376 | 396 | 0.64 | 196 | 876 | 802 | 0.06 |
| rs11727778 | 102641245 | C/T | 30 | 274 | 570 | 0.74 | 75 | 645 | 1169 | 0.27 |
| Chr. 5 | | | | | | | | | | |
| rs2736100 | 1339516 | G/T | 152 | 434 | 275 | 0.40 | 474 | 924 | 470 | 0.64 |
| rs2853676 | 1341547 | A/G | 51 | 297 | 520 | 0.34 | 133 | 722 | 1020 | 0.72 |
| rs30364 | 55865133 | A/C | 193 | 455 | 224 | 0.20 | 402 | 955 | 525 | 0.43 |
| rs9326761 | 108497343 | G/A | 76 | 374 | 418 | 0.57 | 171 | 802 | 904 | 0.74 |
| rs2217649 | 108502065 | C/T | 31 | 294 | 529 | 0.25 | 72 | 642 | 1132 | 0.11 |
| rs13385 | 139693062 | T/C | 40 | 297 | 536 | 1.00 | 89 | 677 | 1121 | 0.32 |
| rs31874 | 140349502 | C/T | 72 | 312 | 488 | 0.04 | 149 | 782 | 954 | 0.54 |
| rs702390 | 140422393 | T/C | 176 | 398 | 299 | 0.04 | 345 | 935 | 605 | 0.64 |
| rs31850 | 140459806 | C/T | 217 | 421 | 235 | 0.31 | 430 | 954 | 499 | 0.55 |
| rs2963163 | 161634659 | A/G | 2 | 129 | 738 | 0.22 | 8 | 281 | 1581 | 0.27 |
| Chr. 6 | | | | | | | | | | |
| rs4959432 | 7336920 | G/A | 9 | 133 | 729 | 0.28 | 8 | 259 | 1602 | 0.61 |
| rs10484325 | 7502047 | C/T | 34 | 280 | 555 | 0.92 | 33 | 545 | 1302 | <0.01 |
| rs10484326 | 7503317 | C/T | 46 | 273 | 554 | 0.12 | 117 | 671 | 1097 | 0.28 |
| rs2076295 | 7508231 | G/T | 253 | 412 | 211 | 0.09 | 413 | 924 | 552 | 0.49 |
| rs3778337 | 7510884 | A/G | 80 | 391 | 404 | 0.31 | 165 | 792 | 922 | 0.83 |
| rs2076302 | 7515962 | A/G | 33 | 257 | 583 | 0.50 | 103 | 615 | 1169 | 0.07 |
| rs3134603 | 32233980 | T/C | 21 | 197 | 658 | 0.20 | 40 | 408 | 1442 | 0.08 |
| rs3134943 | 32255739 | A/G | 20 | 207 | 648 | 0.48 | 40 | 401 | 1446 | 0.06 |
| rs3132946 | 32298006 | A/G | 15 | 209 | 651 | 0.78 | 34 | 384 | 1469 | 0.13 |
| rs9267992 | 32328375 | G/A | 16 | 214 | 641 | 0.78 | 35 | 412 | 1435 | 0.41 |
| rs6911621 | 35637003 | T/C | 96 | 356 | 421 | 0.12 | 189 | 810 | 884 | 0.87 |
| rs961918 | 100762389 | G/A | 72 | 355 | 446 | 0.93 | 127 | 769 | 993 | 0.20 |
| rs1932103 | 130461745 | T/C | 10 | 161 | 704 | 0.85 | 19 | 343 | 1522 | 1.00 |
| Chr. 7 | | | | | | | | | | |
| rs13225346 | 1833442 | C/T | 198 | 408 | 260 | 0.12 | 373 | 941 | 559 | 0.54 |
| rs7783715 | 1889911 | T/C | 145 | 390 | 333 | 0.10 | 273 | 887 | 722 | 1.00 |
| rs4994763 | 1895349 | C/T | 143 | 404 | 329 | 0.32 | 295 | 900 | 692 | 0.92 |
| rs962060 | 31361662 | G/A | 21 | 228 | 620 | 1.00 | 55 | 497 | 1327 | 0.31 |
| rs2283017 | 99412694 | G/A | 173 | 388 | 314 | 0.01 | 269 | 940 | 679 | 0.05 |
| rs4727443 | 99431282 | A/C | 171 | 394 | 311 | 0.02 | 278 | 938 | 668 | 0.08 |
| rs941289 | 99516427 | G/A | 83 | 353 | 434 | 0.37 | 154 | 824 | 897 | 0.07 |
| rs2261360 | 99530929 | A/C | 65 | 313 | 495 | 0.13 | 111 | 713 | 1061 | 0.58 |
| rs720547 | 123862730 | G/A | 51 | 303 | 520 | 0.45 | 107 | 650 | 1131 | 0.30 |
| Chr. 8 | | | | | | | | | | |
| rs1379326 | 4605218 | G/A | 70 | 344 | 457 | 0.67 | 135 | 709 | 1029 | 0.40 |
| rs9650356 | 15796632 | A/G | 17 | 278 | 580 | 0.01 | 69 | 553 | 1267 | 0.36 |
| rs17577994 | 20930275 | A/G | 83 | 345 | 447 | 0.17 | 149 | 746 | 985 | 0.65 |
| rs10504290 | 60315650 | A/G | 14 | 236 | 626 | 0.15 | 35 | 490 | 1360 | 0.27 |
| rs6471845 | 61011882 | T/G | 136 | 400 | 338 | 0.35 | 265 | 866 | 753 | 0.52 |
| rs979564 | 79738714 | A/G | 28 | 288 | 557 | 0.24 | 77 | 597 | 1206 | 0.77 |
| rs279968 | 94129515 | C/A | 190 | 444 | 240 | 0.59 | 378 | 962 | 548 | 0.25 |
| rs1467044 | 120956222 | G/A | 164 | 416 | 292 | 0.49 | 400 | 940 | 538 | 0.82 |
| rs9987332 | 121003144 | A/G | 143 | 336 | 320 | <0.01 | 346 | 741 | 621 | <0.01 |
| rs7005380 | 121023054 | A/G | 87 | 395 | 389 | 0.40 | 259 | 856 | 771 | 0.40 |

TABLE 4-continued

Genotype counts and Hardy-Weinberg Equilibrium (HWE) P-values among cases and controls in the replication set for all SNPs successfully genotyped in replication.

| Chr. | | | Cases | | | | Controls | | | |
|---|---|---|---|---|---|---|---|---|---|---|
| SNP | Position[a] | Alleles[b] | Minor[c] | Hets[d] | Major[e] | HWE P[f] | Minor[c] | Hets[d] | Major[e] | HWE P[f] |
| Chr. 9 | | | | | | | | | | |
| rs7022345 | 7163752 | A/G | 24 | 250 | 600 | 0.81 | 57 | 567 | 1258 | 0.53 |
| rs2820917 | 7182313 | T/C | 20 | 222 | 629 | 0.89 | 47 | 527 | 1306 | 0.50 |
| rs10963084 | 17394464 | T/C | 72 | 323 | 476 | 0.10 | 153 | 709 | 1015 | 0.07 |
| rs541131 | 137692055 | C/T | 142 | 386 | 326 | 0.13 | 294 | 905 | 648 | 0.47 |
| Chr. 10 | | | | | | | | | | |
| rs2441727 | 67894892 | G/A | 14 | 127 | 731 | 0.01 | 15 | 228 | 1641 | 0.04 |
| rs10997263 | 68052141 | C/A | 104 | 403 | 367 | 0.71 | 233 | 893 | 761 | 0.25 |
| rs10822856 | 68053979 | C/T | 103 | 397 | 362 | 0.76 | 232 | 888 | 756 | 0.27 |
| rs2901088 | 92431533 | T/C | 122 | 381 | 371 | 0.14 | 239 | 881 | 768 | 0.62 |
| rs1936606 | 92432636 | A/G | 122 | 382 | 370 | 0.14 | 237 | 884 | 765 | 0.48 |
| rs1936602 | 92435233 | A/G | 177 | 410 | 286 | 0.19 | 344 | 933 | 605 | 0.67 |
| rs2902638 | 105626979 | C/T | 56 | 329 | 472 | 0.93 | 123 | 667 | 1040 | 0.26 |
| rs10748858 | 105629504 | G/T | 113 | 385 | 375 | 0.37 | 284 | 920 | 677 | 0.34 |
| rs2067832 | 105633124 | C/T | 182 | 437 | 252 | 0.79 | 461 | 940 | 480 | 1.00 |
| rs1980653 | 105644154 | T/C | 177 | 433 | 240 | 0.49 | 455 | 931 | 465 | 0.82 |
| rs11191865 | 105662832 | G/A | 186 | 436 | 252 | 0.95 | 469 | 940 | 476 | 0.93 |
| rs9420907 | 105666455 | C/A | 19 | 188 | 654 | 0.23 | 33 | 453 | 1384 | 0.63 |
| rs7074532 | 105692032 | G/T | 67 | 364 | 440 | 0.51 | 139 | 789 | 953 | 0.17 |
| rs7073827 | 105698783 | C/T | 85 | 377 | 412 | 1.00 | 169 | 808 | 910 | 0.62 |
| Chr. 11 | | | | | | | | | | |
| rs10751635 | 1052990 | G/A | 188 | 415 | 260 | 0.37 | 357 | 895 | 612 | 0.37 |
| rs2301160 | 1053767 | C/T | 186 | 424 | 256 | 0.68 | 342 | 909 | 628 | 0.67 |
| rs7942850 | 1058900 | G/A | 144 | 427 | 294 | 0.62 | 274 | 909 | 685 | 0.36 |
| rs2071174 | 1063712 | C/T | 98 | 370 | 405 | 0.35 | 183 | 834 | 863 | 0.40 |
| rs7396030 | 1073364 | T/C | 38 | 270 | 562 | 0.46 | 79 | 604 | 1185 | 0.83 |
| rs7103978 | 1078815 | C/T | 6 | 121 | 746 | 0.63 | 12 | 308 | 1567 | 0.57 |
| rs7934606 | 1083945 | A/G | 220 | 450 | 204 | 0.42 | 295 | 920 | 673 | 0.53 |
| rs6421972 | 1086494 | A/G | 220 | 448 | 206 | 0.50 | 291 | 918 | 676 | 0.50 |
| rs7480563 | 1091649 | G/A | 195 | 406 | 266 | 0.10 | 462 | 936 | 476 | 0.96 |
| rs4077759 | 1095976 | C/T | 117 | 359 | 400 | 0.01 | 229 | 900 | 755 | 0.12 |
| rs6421966 | 1116979 | C/A | 34 | 236 | 593 | 0.10 | 63 | 562 | 1250 | 1.00 |
| rs868903 | 1199266 | T/C | 152 | 410 | 310 | 0.44 | 420 | 947 | 509 | 0.64 |
| rs2857476 | 1237710 | C/T | 186 | 435 | 250 | 0.95 | 490 | 922 | 468 | 0.41 |
| rs12417955 | 1240803 | G/A | 183 | 434 | 251 | 0.89 | 479 | 913 | 465 | 0.49 |
| rs3829223 | 1256982 | C/T | 171 | 438 | 266 | 0.73 | 471 | 935 | 470 | 0.89 |
| rs2334659 | 1313639 | T/C | 8 | 198 | 651 | 0.12 | 56 | 502 | 1285 | 0.40 |
| rs7122936 | 1331032 | C/A | 85 | 408 | 370 | 0.08 | 286 | 894 | 686 | 0.88 |
| rs7944761 | 1361414 | C/T | 137 | 435 | 294 | 0.29 | 385 | 942 | 555 | 0.71 |
| rs4752744 | 1674842 | G/A | 10 | 141 | 724 | 0.31 | 8 | 272 | 1605 | 0.41 |
| rs11036021 | 40668015 | T/G | 218 | 429 | 228 | 0.59 | 435 | 915 | 539 | 0.23 |
| rs2736601 | 61462097 | A/G | 4 | 124 | 745 | 0.81 | 16 | 251 | 1618 | 0.09 |
| rs2727267 | 61462692 | A/G | 5 | 111 | 684 | 0.80 | 17 | 223 | 1532 | 0.01 |
| Chr. 12 | | | | | | | | | | |
| rs12310569 | 6567614 | A/G | 25 | 236 | 606 | 0.71 | 48 | 477 | 1355 | 0.42 |
| rs10845459 | 12099918 | G/A | 224 | 446 | 205 | 0.59 | 443 | 954 | 488 | 0.61 |
| Chr. 13 | | | | | | | | | | |
| rs1278769 | 112584628 | A/G | 38 | 278 | 551 | 0.68 | 119 | 666 | 1096 | 0.19 |
| Chr. 14 | | | | | | | | | | |
| rs12879458 | 45894992 | T/C | 19 | 261 | 591 | 0.12 | 45 | 494 | 1346 | 1.00 |
| rs10139381 | 46152755 | C/T | 56 | 330 | 478 | 1.00 | 142 | 754 | 975 | 0.86 |
| rs2781413 | 97038740 | C/T | 60 | 337 | 475 | 1.00 | 144 | 741 | 997 | 0.69 |
| Chr. 15 | | | | | | | | | | |
| rs1007177 | 38439130 | T/C | 75 | 356 | 444 | 0.74 | 188 | 861 | 835 | 0.13 |
| rs1992272 | 38446262 | A/G | 77 | 355 | 439 | 0.68 | 189 | 854 | 834 | 0.17 |
| rs2289332 | 38471072 | C/T | 121 | 399 | 338 | 0.88 | 286 | 928 | 634 | 0.08 |
| rs10518693 | 38487314 | T/C | 182 | 396 | 263 | 0.16 | 297 | 907 | 631 | 0.36 |
| rs2034650 | 38504594 | C/T | 179 | 378 | 317 | <0.01 | 422 | 933 | 533 | 0.75 |
| rs1849210 | 52413032 | C/T | 36 | 278 | 549 | 0.92 | 89 | 615 | 1142 | 0.58 |
| rs351219 | 72276260 | C/T | 133 | 417 | 325 | 1.00 | 268 | 845 | 775 | 0.12 |
| rs6496932 | 83626571 | A/C | 34 | 271 | 569 | 0.83 | 58 | 606 | 1221 | 0.10 |
| rs1828481 | 83641916 | C/A | 151 | 397 | 328 | 0.11 | 292 | 915 | 681 | 0.63 |
| rs7172789 | 83644521 | C/T | 147 | 393 | 332 | 0.10 | 291 | 912 | 680 | 0.63 |
| rs11858744 | 83684068 | T/C | 149 | 393 | 330 | 0.09 | 287 | 914 | 684 | 0.53 |
| rs16977252 | 83727844 | G/A | 78 | 310 | 488 | 0.01 | 135 | 689 | 1057 | 0.13 |
| rs6496044 | 83868310 | G/A | 130 | 378 | 365 | 0.05 | 214 | 831 | 834 | 0.76 |

TABLE 4-continued

Genotype counts and Hardy-Weinberg Equilibrium (HWE) P-values among cases and controls in the replication set for all SNPs successfully genotyped in replication.

| Chr. | | | Cases | | | | Controls | | | |
|---|---|---|---|---|---|---|---|---|---|---|
| SNP | Position[a] | Alleles[b] | Minor[c] | Hets[d] | Major[e] | HWE P[f] | Minor[c] | Hets[d] | Major[e] | HWE P[f] |
| rs10520597 | 83971259 | A/G | 116 | 358 | 399 | 0.02 | 202 | 805 | 871 | 0.43 |
| rs11633855 | 96054298 | C/T | 107 | 364 | 401 | 0.09 | 209 | 889 | 783 | 0.08 |
| rs1441479 | 96057306 | C/T | 103 | 360 | 410 | 0.09 | 211 | 878 | 790 | 0.17 |
| Chr. 16 | | | | | | | | | | |
| rs17139255 | 6047175 | G/T | 26 | 251 | 587 | 1.00 | 49 | 555 | 1266 | 0.23 |
| rs1548857 | 6576606 | A/C | 13 | 103 | 759 | <0.01 | 10 | 233 | 1647 | 0.58 |
| rs4843650 | 86240987 | G/A | 142 | 436 | 291 | 0.33 | 333 | 911 | 643 | 0.74 |
| Chr. 17 | | | | | | | | | | |
| rs393152 | 41074926 | G/A | 35 | 259 | 579 | 0.38 | 79 | 672 | 1132 | 0.11 |
| rs417968 | 41084159 | C/T | 47 | 308 | 494 | 1.00 | 107 | 731 | 1012 | 0.10 |
| rs7215239 | 41123556 | C/T | 40 | 290 | 546 | 0.84 | 97 | 719 | 1071 | 0.10 |
| rs12373139 | 41279910 | A/G | 26 | 233 | 617 | 0.46 | 81 | 668 | 1137 | 0.18 |
| rs17690703 | 41281077 | T/C | 40 | 276 | 559 | 0.41 | 108 | 737 | 1040 | 0.14 |
| rs17563986 | 41347100 | G/A | 26 | 233 | 617 | 0.46 | 82 | 668 | 1138 | 0.20 |
| rs1981997 | 41412603 | A/G | 25 | 235 | 615 | 0.62 | 81 | 668 | 1134 | 0.18 |
| rs8070723 | 41436901 | G/A | 28 | 240 | 605 | 0.47 | 85 | 662 | 1136 | 0.38 |
| rs7225002 | 41544850 | G/A | 111 | 377 | 380 | 0.26 | 309 | 892 | 680 | 0.56 |
| rs2532274 | 41602941 | C/T | 28 | 247 | 594 | 0.72 | 88 | 688 | 1108 | 0.17 |
| rs2532269 | 41605885 | G/A | 25 | 235 | 611 | 0.71 | 85 | 673 | 1122 | 0.23 |
| rs2668692 | 41648797 | T/C | 26 | 235 | 614 | 0.54 | 82 | 675 | 1131 | 0.14 |
| rs183211 | 42143493 | A/G | 37 | 264 | 535 | 0.52 | 98 | 643 | 1067 | 0.95 |
| rs169201 | 42145386 | G/A | 25 | 218 | 632 | 0.24 | 69 | 626 | 1194 | 0.25 |
| rs7224296 | 42155230 | G/A | 72 | 304 | 498 | 0.01 | 150 | 779 | 952 | 0.61 |
| rs199533 | 42184098 | T/C | 23 | 221 | 619 | 0.52 | 68 | 622 | 1161 | 0.20 |
| rs415430 | 42214305 | G/A | 25 | 230 | 619 | 0.53 | 69 | 641 | 1180 | 0.12 |
| Chr. 18 | | | | | | | | | | |
| rs367024 | 10388673 | T/C | 25 | 267 | 582 | 0.43 | 58 | 514 | 1310 | 0.36 |
| Chr. 19 | | | | | | | | | | |
| rs12610495 | 4668672 | G/A | 104 | 380 | 383 | 0.54 | 143 | 767 | 959 | 0.57 |
| rs2109069 | 4670443 | A/G | 107 | 401 | 367 | 0.94 | 175 | 793 | 917 | 0.87 |
| rs10417008 | 54895365 | C/T | 25 | 227 | 620 | 0.45 | 53 | 536 | 1298 | 0.87 |
| rs306477 | 61181585 | A/G | 165 | 429 | 282 | 0.95 | 368 | 928 | 591 | 0.93 |
| Chr. 20 | | | | | | | | | | |
| rs2145275 | 6521455 | T/C | 155 | 378 | 280 | 0.17 | 291 | 852 | 618 | 0.96 |
| rs6088520 | 32596025 | T/C | 181 | 419 | 268 | 0.49 | 441 | 910 | 522 | 0.27 |
| rs4810223 | 59179191 | T/G | 46 | 306 | 522 | 0.92 | 91 | 602 | 1195 | 0.18 |
| Chr. 21 | | | | | | | | | | |
| rs2823529 | 16271144 | C/T | 25 | 241 | 609 | 0.81 | 47 | 490 | 1343 | 0.79 |
| rs2830234 | 26754202 | G/T | 146 | 430 | 299 | 0.73 | 307 | 916 | 666 | 0.81 |
| Chr.23 | | | | | | | | | | |
| rs7879375 | 79014847 | A/G | 1 | 49 | 223 | 0.49 | 8 | 184 | 781 | 0.60 |
| rs5924874 | 150037033 | G/A | 53 | 128 | 95 | 0.39 | 183 | 454 | 341 | 0.15 |

[a]Genomic position based on NCBI Build 36
[b]Minor allele in cases listed first.
[c]Minor: Count of minor allele subjects
[d]Het: Count of heterozygous subjects
[e]Major: Count of major allele (more frequent allele) homozygous subjects
[f]P-value for HWE goodness-of-fit test

TABLE 5

Association information for all 198 SNPs chosen for replication. Blank Replication and Joint columns correspond to SNPs not successfully genotyped in replication

| | Discovery GWAS | | | | Replication | | | | |
|---|---|---|---|---|---|---|---|---|---|
| Chr. SNP | MAF Case | MAF Control | OR (95% CI) | P-value | MAF Case | MAF Control | OR (95% CI) | P-value | Joint P-value |
| Chr. 1 | | | | | | | | | |
| rs12128329 | 0.37 | 0.34 | 1.26 (1.12, 1.41) | 8.81e−05 | 0.33 | 0.35 | 0.87 (0.74, 1.03) | 0.10 | 0.024 |

TABLE 5-continued

Association information for all 198 SNPs chosen for replication. Blank Replication and Joint columns correspond to SNPs not successfully genotyped in replication

| | Discovery GWAS | | | | Replication | | | | |
|---|---|---|---|---|---|---|---|---|---|
| Chr. SNP | MAF Case | MAF Control | OR (95% CI) | P-value | MAF Case | MAF Control | OR (95% CI) | P-value | Joint P-value |
| rs1995785 | 0.21 | 0.17 | 1.22 (1.1, 1.35) | 4.05e−05 | 0.21 | 0.20 | 1.04 (0.91, 1.21) | 0.54 | 0.00021 |
| rs6428467 | 0.20 | 0.17 | 1.25 (1.13, 1.39) | 6.45e−05 | 0.20 | 0.19 | 1.06 (0.92, 1.22) | 0.43 | 0.0002 |
| rs7525504 | 0.41 | 0.44 | 0.72 (0.62, 0.85) | 6.21e−05 | 0.45 | 0.44 | 0.98 (0.8, 1.2) | 0.81 | 0.00065 |
| rs3738383 | 0.20 | 0.22 | 0.46 (0.33, 0.64) | 3.75e−06 | | | | | |
| Chr. 2 | | | | | | | | | |
| rs17247006 | 0.15 | 0.12 | 1.30 (1.14, 1.48) | 4.76e−05 | 0.12 | 0.13 | 0.96 (0.79, 1.17) | 0.70 | 0.0019 |
| rs10495536 | 0.17 | 0.20 | 0.81 (0.73, 0.9) | 4.30e−05 | 0.22 | 0.18 | 1.25 (1.09, 1.45) | 0.0018 | 0.12 |
| rs2354382 | 0.11 | 0.08 | 1.34 (1.17, 1.54) | 4.54e−05 | 0.10 | 0.10 | 1.00 (0.83, 1.22) | 0.97 | 0.0008 |
| rs1879219 | 0.32 | 0.36 | 0.84 (0.77, 0.92) | 9.17e−05 | 0.36 | 0.35 | 1.04 (0.93, 1.18) | 0.47 | 0.0054 |
| rs1369523 | 0.18 | 0.21 | 0.80 (0.72, 0.89) | 1.31e−05 | 0.20 | 0.19 | 1.05 (0.91, 1.21) | 0.52 | 0.0014 |
| rs1836676 | 0.18 | 0.21 | 0.80 (0.72, 0.89) | 1.33e−05 | 0.20 | 0.19 | 1.05 (0.91, 1.21) | 0.53 | 0.0014 |
| rs10174598 | 0.39 | 0.36 | 1.41 (1.21, 1.66) | 2.74e−05 | 0.38 | 0.39 | 1.11 (0.89, 1.4) | 0.36 | 7.53e−05 |
| rs12469218 | 0.22 | 0.20 | 1.74 (1.34, 2.26) | 5.06e−05 | 0.21 | 0.20 | 0.96 (0.64, 1.45) | 0.86 | 0.0013 |
| rs7578722 | 0.29 | 0.26 | 1.65 (1.34, 2.04) | 7.16e−06 | 0.26 | 0.27 | 1.00 (0.73, 1.39) | 0.95 | 0.00021 |
| rs4668123 | 0.28 | 0.26 | 1.65 (1.34, 2.03) | 7.42e−06 | | | | | |
| rs2302696 | 0.29 | 0.26 | 1.63 (1.33, 2.01) | 1.02e−05 | 0.27 | 0.27 | 1.04 (0.77, 1.42) | 0.79 | 0.00017 |
| rs11687903 | 0.30 | 0.28 | 1.59 (1.3, 1.94) | 3.61e−05 | 0.28 | 0.28 | 1.08 (0.8, 1.47) | 0.60 | 0.00024 |
| rs2284675 | 0.30 | 0.27 | 1.62 (1.32, 1.98) | 1.75e−05 | 0.28 | 0.28 | 1.05 (0.78, 1.43) | 0.74 | 0.00022 |
| rs9646792 | 0.44 | 0.42 | 1.33 (1.15, 1.53) | 3.65e−05 | 0.45 | 0.43 | 1.16 (0.94, 1.42) | 0.16 | 2.92e−05 |
| rs13415895 | 0.21 | 0.18 | 1.21 (1.09, 1.34) | 9.83e−05 | 0.20 | 0.18 | 1.13 (0.97, 1.31) | 0.11 | 3.93e−05 |
| Chr. 3 | | | | | | | | | |
| rs13091584 | 0.51 | 0.48 | 1.34 (1.17, 1.53) | 3.15e−05 | 0.47 | 0.50 | 0.88 (0.73, 1.06) | 0.17 | 0.0092 |
| rs12638703 | 0.18 | 0.15 | 1.29 (1.15, 1.44) | 3.53e−06 | 0.16 | 0.15 | 1.06 (0.9, 1.25) | 0.48 | 2.67e−05 |
| rs1532898 | 0.33 | 0.28 | 1.20 (1.1, 1.31) | 7.37e−05 | 0.33 | 0.30 | 1.14 (0.99, 1.3) | 0.061 | 1.58e−05 |
| rs6798211 | 0.14 | 0.17 | 0.79 (0.7, 0.88) | 9.67e−05 | 0.17 | 0.17 | 1.00 (0.86, 1.17) | 0.97 | 0.0016 |
| rs697954 | 0.47 | 0.51 | 0.86 (0.8, 0.94) | 6.14e−05 | 0.48 | 0.48 | 0.99 (0.88, 1.11) | 0.83 | 0.0016 |
| rs1881984 | 0.39 | 0.33 | 1.26 (1.16, 1.37) | 3.60e−06 | 0.38 | 0.33 | 1.20 (1.06, 1.36) | 0.0035 | 4.53e−08 |
| rs10936599 | 0.30 | 0.24 | 1.30 (1.19, 1.43) | 3.90e−07 | 0.30 | 0.24 | 1.34 (1.17, 1.52) | 1.17e−05 | 2.51e−11 |
| rs1997392 | 0.32 | 0.26 | 1.30 (1.19, 1.42) | 3.71e−07 | 0.33 | 0.26 | 1.37 (1.21, 1.55) | 1.05e−06 | 3.20e−12 |
| rs6793295 | 0.32 | 0.26 | 1.30 (1.19, 1.42) | 3.20e−07 | 0.33 | 0.26 | 1.39 (1.23, 1.58) | 2.37e−07 | 8.33e−13 |
| rs9844738 | 0.23 | 0.27 | 0.82 (0.74, 0.9) | 4.99e−05 | 0.25 | 0.27 | 0.91 (0.8, 1.04) | 0.16 | 3.81e−05 |
| Chr. 4 | | | | | | | | | |
| rs4518326 | 0.14 | 0.14 | 0.39 (0.23, 0.66) | 7.79e−05 | 0.15 | 0.14 | 1.55 (0.88, 2.7) | 0.13 | 0.019 |
| rs16877848 | 0.14 | 0.16 | 0.38 (0.23, 0.61) | 2.34e−05 | 0.16 | 0.17 | 0.98 (0.61, 1.58) | 0.93 | 0.00046 |
| rs340199 | 0.34 | 0.38 | 0.77 (0.69, 0.87) | 3.52e−05 | 0.38 | 0.38 | 0.89 (0.76, 1.06) | 0.19 | 3.62e−05 |
| rs2869358 | 0.32 | 0.36 | 0.78 (0.69, 0.87) | 3.35e−05 | | | | | |

TABLE 5-continued

Association information for all 198 SNPs chosen for replication. Blank Replication and Joint columns correspond to SNPs not successfully genotyped in replication

| | Discovery GWAS | | | | Replication | | | | |
|---|---|---|---|---|---|---|---|---|---|
| Chr. SNP | MAF Case | MAF Control | OR (95% CI) | P-value | MAF Case | MAF Control | OR (95% CI) | P-value | Joint P-value |
| rs4488910 | 0.13 | 0.16 | 0.80 (0.71, 0.9) | 8.68e−05 | 0.15 | 0.15 | 0.96 (0.82, 1.13) | 0.64 | 0.00051 |
| rs6830970 | 0.31 | 0.36 | 0.80 (0.73, 0.87) | 6.66e−05 | 0.32 | 0.33 | 0.91 (0.8, 1.03) | 0.12 | 3.23e−05 |
| rs2609255 | 0.26 | 0.21 | 1.29 (1.18, 1.42) | 5.27e−06 | 0.28 | 0.21 | 1.43 (1.25, 1.64) | 2.56e−07 | 2.20e−11 |
| rs10019681 | 0.19 | 0.24 | 0.77 (0.7, 0.85) | 3.73e−05 | 0.22 | 0.23 | 0.94 (0.82, 1.09) | 0.42 | 0.00013 |
| rs2869967 | 0.35 | 0.41 | 0.79 (0.73, 0.86) | 7.54e−06 | 0.37 | 0.38 | 0.95 (0.85, 1.08) | 0.45 | 4.28e−05 |
| rs7671167 | 0.44 | 0.51 | 0.79 (0.73, 0.85) | 7.59e−07 | 0.46 | 0.48 | 0.89 (0.79, 1.0) | 0.06 | 2.96e−07 |
| rs1921679 | 0.29 | 0.33 | 0.82 (0.75, 0.89) | 8.49e−05 | 0.30 | 0.32 | 0.89 (0.79, 1.01) | 0.082 | 2.52e−05 |
| rs16996143 | 0.29 | 0.33 | 0.81 (0.74, 0.89) | 4.72e−05 | 0.31 | 0.33 | 0.90 (0.79, 1.02) | 0.088 | 1.64e−05 |
| rs11737182 | 0.29 | 0.33 | 0.81 (0.74, 0.89) | 5.42e−05 | 0.30 | 0.33 | 0.89 (0.79, 1.01) | 0.08 | 1.65e−05 |
| rs6849143 | 0.36 | 0.41 | 0.81 (0.75, 0.88) | 2.93e−05 | 0.38 | 0.39 | 0.94 (0.83, 1.06) | 0.31 | 6.26e−05 |
| rs12505696 | 0.40 | 0.35 | 1.25 (1.15, 1.36) | 5.35e−06 | 0.38 | 0.37 | 1.04 (0.93, 1.18) | 0.49 | 3.81e−05 |
| rs6828137 | 0.43 | 0.47 | 0.84 (0.77, 0.91) | 4.19e−05 | 0.44 | 0.45 | 0.97 (0.86, 1.09) | 0.63 | 0.00029 |
| rs756345 | 0.31 | 0.36 | 0.81 (0.74, 0.88) | 5.73e−05 | 0.33 | 0.34 | 0.94 (0.83, 1.07) | 0.35 | 0.00013 |
| rs11727778 | 0.23 | 0.20 | 1.24 (1.12, 1.37) | 6.16e−05 | 0.19 | 0.21 | 0.86 (0.74, 1.0) | 0.043 | 0.035 |
| rs2130910 | 0.47 | 0.51 | 0.76 (0.67, 0.86) | 9.30e−05 | | | | | |
| Chr. 5 | | | | | | | | | |
| rs2736100 | 0.43 | 0.51 | 0.73 (0.67, 0.79) | 7.60e−14 | 0.43 | 0.50 | 0.74 (0.65, 0.83) | 4.05e−07 | 1.71e−19 |
| rs2853676 | 0.23 | 0.28 | 0.77 (0.7, 0.84) | 8.93e−07 | 0.23 | 0.26 | 0.84 (0.73, 0.96) | 0.0088 | 3.31e−08 |
| rs30364 | 0.44 | 0.48 | 0.85 (0.79, 0.93) | 3.80e−05 | 0.48 | 0.47 | 1.06 (0.94, 1.19) | 0.35 | 0.0047 |
| rs9326761 | 0.33 | 0.30 | 1.28 (1.14, 1.44) | 2.68e−05 | 0.30 | 0.30 | 1.00 (0.85, 1.18) | 0.98 | 0.00057 |
| rs2217649 | 0.25 | 0.21 | 1.21 (1.1, 1.33) | 7.65e−05 | 0.21 | 0.21 | 0.98 (0.85, 1.14) | 0.83 | 0.0019 |
| rs13385 | 0.21 | 0.24 | 0.79 (0.7, 0.89) | 6.49e−05 | 0.22 | 0.23 | 0.88 (0.74, 1.04) | 0.12 | 3.27e−05 |
| rs31874 | 0.27 | 0.30 | 0.78 (0.7, 0.88) | 7.08e−05 | 0.26 | 0.29 | 0.80 (0.68, 0.94) | 0.0077 | 1.73e−06 |
| rs702390 | 0.41 | 0.45 | 0.74 (0.66, 0.84) | 2.96e−06 | 0.43 | 0.43 | 0.88 (0.74, 1.04) | 0.14 | 3.11e−06 |
| rs31850 | 0.46 | 0.50 | 0.77 (0.67, 0.87) | 8.39e−05 | 0.49 | 0.48 | 0.97 (0.81, 1.17) | 0.75 | 0.00069 |
| rs2963163 | 0.07 | 0.09 | 0.72 (0.62, 0.85) | 5.04e−05 | 0.08 | 0.08 | 0.96 (0.77, 1.2) | 0.72 | 0.00043 |
| Chr. 6 | | | | | | | | | |
| rs4959432 | 0.08 | 0.06 | 1.34 (1.15, 1.56) | 4.64e−05 | 0.09 | 0.07 | 1.23 (1.0, 1.52) | 0.052 | 8.56e−06 |
| rs10484325 | 0.19 | 0.16 | 1.27 (1.15, 1.42) | 2.92e−05 | 0.20 | 0.16 | 1.32 (1.13, 1.54) | 0.00038 | 4.67e−08 |
| rs10484326 | 0.20 | 0.25 | 0.77 (0.7, 0.85) | 3.41e−07 | 0.21 | 0.24 | 0.82 (0.71, 0.94) | 0.0038 | 5.45e−09 |
| rs2076295 | 0.54 | 0.44 | 1.43 (1.32, 1.55) | 1.14e−16 | 0.52 | 0.46 | 1.26 (1.13, 1.42) | 6.28e−05 | 1.08e−19 |
| rs3778337 | 0.35 | 0.28 | 1.31 (1.2, 1.43) | 6.41e−09 | 0.31 | 0.30 | 1.07 (0.95, 1.22) | 0.28 | 7.91e−08 |
| rs2076302 | 0.19 | 0.23 | 0.79 (0.71, 0.87) | 1.54e−05 | 0.18 | 0.22 | 0.83 (0.72, 0.95) | 0.0094 | 4.96e−07 |
| rs3134603 | 0.15 | 0.12 | 1.38 (1.21, 1.57) | 4.73e−05 | 0.14 | 0.13 | 1.04 (0.86, 1.26) | 0.67 | 0.00036 |
| rs3134943 | 0.16 | 0.13 | 1.37 (1.2, 1.56) | 2.76e−05 | 0.14 | 0.13 | 1.12 (0.93, 1.35) | 0.25 | 4.29e−05 |
| rs3132946 | 0.15 | 0.12 | 1.38 (1.21, 1.57) | 2.58e−05 | 0.14 | 0.12 | 1.19 (0.98, 1.44) | 0.077 | 8.36e−06 |

TABLE 5-continued

Association information for all 198 SNPs chosen for replication. Blank Replication and Joint columns correspond to SNPs not successfully genotyped in replication

| | Discovery GWAS | | | | Replication | | | | |
|---|---|---|---|---|---|---|---|---|---|
| Chr. SNP | MAF Case | MAF Control | OR (95% CI) | P-value | MAF Case | MAF Control | OR (95% CI) | P-value | Joint P-value |
| rs9267992 | 0.16 | 0.13 | 1.37 (1.2, 1.55) | 3.38e−05 | 0.14 | 0.13 | 1.16 (0.96, 1.4) | 0.12 | 1.85e−05 |
| rs3129860 | 0.17 | 0.13 | 1.37 (1.23, 1.54) | 2.26e−06 | | | | | |
| rs9271366 | 0.17 | 0.13 | 1.35 (1.21, 1.51) | 6.72e−06 | | | | | |
| rs6911621 | 0.29 | 0.33 | 0.82 (0.75, 0.89) | 7.79e−06 | 0.31 | 0.32 | 0.98 (0.86, 1.1) | 0.70 | 0.00011 |
| rs2766535 | 0.51 | 0.47 | 1.18 (1.09, 1.28) | 8.43e−05 | | | | | |
| rs961918 | 0.31 | 0.27 | 1.22 (1.12, 1.33) | 1.38e−05 | 0.29 | 0.27 | 1.08 (0.95, 1.23) | 0.26 | 2.62e−05 |
| rs1932103 | 0.11 | 0.09 | 1.31 (1.14, 1.51) | 6.11e−05 | 0.10 | 0.10 | 1.03 (0.84, 1.26) | 0.79 | 0.00061 |
| Chr. 7 | | | | | | | | | |
| rs13225346 | 0.49 | 0.44 | 1.23 (1.13, 1.33) | 3.96e−06 | 0.46 | 0.45 | 1.03 (0.92, 1.16) | 0.61 | 4.82e−05 |
| rs7783715 | 0.41 | 0.37 | 1.43 (1.23, 1.67) | 8.71e−06 | 0.39 | 0.38 | 1.13 (0.9, 1.41) | 0.29 | 2.26e−05 |
| rs4994763 | 0.42 | 0.39 | 1.38 (1.18, 1.6) | 7.92e−05 | 0.39 | 0.39 | 0.99 (0.8, 1.24) | 0.95 | 0.0014 |
| rs962060 | 0.18 | 0.16 | 1.28 (1.13, 1.45) | 8.90e−05 | 0.16 | 0.16 | 0.97 (0.81, 1.16) | 0.71 | 0.0028 |
| rs2283017 | 0.45 | 0.39 | 1.25 (1.16, 1.36) | 5.87e−07 | 0.42 | 0.39 | 1.12 (1.0, 1.26) | 0.051 | 1.91e−07 |
| rs4727443 | 0.46 | 0.39 | 1.30 (1.2, 1.41) | 6.72e−09 | 0.42 | 0.40 | 1.11 (0.98, 1.24) | 0.093 | 1.17e−08 |
| rs941289 | 0.33 | 0.29 | 1.20 (1.1, 1.31) | 5.10e−05 | 0.30 | 0.30 | 0.97 (0.86, 1.1) | 0.67 | 0.0022 |
| rs2261360 | 0.29 | 0.24 | 1.26 (1.15, 1.38) | 1.02e−06 | 0.25 | 0.25 | 1.02 (0.9, 1.17) | 0.72 | 2.72e−05 |
| rs720547 | 0.26 | 0.22 | 1.28 (1.14, 1.44) | 6.39e−05 | 0.23 | 0.23 | 1.01 (0.85, 1.19) | 0.95 | 0.00095 |
| Chr. 8 | | | | | | | | | |
| rs1379326 | 0.29 | 0.26 | 1.78 (1.45, 2.19) | 5.74e−09 | 0.28 | 0.26 | 1.17 (0.86, 1.59) | 0.32 | 9.56e−08 |
| rs9650356 | 0.20 | 0.17 | 1.23 (1.11, 1.36) | 7.76e−05 | 0.18 | 0.18 | 0.95 (0.81, 1.1) | 0.47 | 0.005 |
| rs17577994 | 0.30 | 0.28 | 1.42 (1.17, 1.72) | 5.97e−05 | 0.29 | 0.28 | 1.20 (0.9, 1.59) | 0.22 | 6.87e−05 |
| rs10504290 | 0.16 | 0.15 | 1.96 (1.41, 2.73) | 8.65e−05 | 0.15 | 0.15 | 0.85 (0.45, 1.6) | 0.61 | 0.0036 |
| rs6471845 | 0.35 | 0.39 | 0.77 (0.68, 0.86) | 6.35e−05 | 0.38 | 0.37 | 1.05 (0.89, 1.25) | 0.53 | 0.0036 |
| rs979564 | 0.22 | 0.19 | 1.23 (1.11, 1.36) | 6.92e−05 | 0.20 | 0.20 | 1.00 (0.87, 1.16) | 0.99 | 0.0011 |
| rs279968 | 0.48 | 0.46 | 1.35 (1.18, 1.55) | 1.18e−05 | 0.47 | 0.46 | 1.14 (0.93, 1.39) | 0.21 | 1.65e−05 |
| rs1467044 | 0.42 | 0.46 | 0.84 (0.77, 0.91) | 1.90e−05 | 0.43 | 0.46 | 0.88 (0.78, 0.99) | 0.03 | 2.08e−06 |
| rs11781657 | 0.42 | 0.46 | 0.84 (0.77, 0.91) | 1.83e−05 | | | | | |
| rs9987332 | 0.39 | 0.43 | 0.84 (0.77, 0.91) | 2.50e−05 | 0.39 | 0.42 | 0.92 (0.81, 1.03) | 0.14 | 1.72e−05 |
| rs7005380 | 0.32 | 0.37 | 0.80 (0.73, 0.87) | 2.92e−06 | 0.33 | 0.36 | 0.86 (0.76, 0.97) | 0.015 | 1.71e−07 |
| Chr. 9 | | | | | | | | | |
| rs7022345 | 0.16 | 0.18 | 0.45 (0.3, 0.69) | 3.54e−05 | 0.17 | 0.18 | 0.96 (0.59, 1.58) | 0.88 | 0.00054 |
| rs2820917 | 0.15 | 0.16 | 0.42 (0.25, 0.68) | 9.57e−05 | 0.15 | 0.17 | 0.96 (0.56, 1.64) | 0.87 | 0.001 |
| rs10963084 | 0.28 | 0.27 | 1.59 (1.29, 1.95) | 4.12e−05 | 0.27 | 0.27 | 1.00 (0.74, 1.35) | 0.99 | 0.00079 |
| rs541131 | 0.42 | 0.38 | 1.19 (1.1, 1.29) | 1.99e−05 | 0.39 | 0.40 | 0.94 (0.84, 1.06) | 0.32 | 0.0036 |
| Chr. 10 | | | | | | | | | |
| rs2441727 | 0.07 | 0.05 | 1.35 (1.15, 1.6) | 7.33e−05 | 0.09 | 0.07 | 1.35 (1.1, 1.66) | 0.0041 | 9.80e−07 |

TABLE 5-continued

Association information for all 198 SNPs chosen for replication. Blank Replication and Joint columns correspond to SNPs not successfully genotyped in replication

| | Discovery GWAS | | | | Replication | | | | |
|---|---|---|---|---|---|---|---|---|---|
| Chr. SNP | MAF Case | MAF Control | OR (95% CI) | P-value | MAF Case | MAF Control | OR (95% CI) | P-value | Joint P-value |
| rs10997263 | 0.39 | 0.35 | 1.30 (1.16, 1.46) | 7.92e−05 | 0.35 | 0.36 | 0.93 (0.79, 1.1) | 0.38 | 0.0066 |
| rs10822856 | 0.39 | 0.35 | 1.30 (1.15, 1.46) | 8.57e−05 | 0.35 | 0.36 | 0.93 (0.78, 1.09) | 0.37 | 0.0071 |
| rs2901088 | 0.32 | 0.36 | 0.82 (0.75, 0.9) | 3.40e−05 | 0.36 | 0.36 | 0.99 (0.88, 1.12) | 0.92 | 0.00057 |
| rs1936606 | 0.32 | 0.36 | 0.82 (0.75, 0.9) | 3.23e−05 | 0.36 | 0.36 | 1.00 (0.88, 1.12) | 0.97 | 0.00063 |
| rs1936602 | 0.39 | 0.43 | 0.77 (0.68, 0.87) | 6.25e−05 | 0.44 | 0.43 | 0.97 (0.82, 1.16) | 0.75 | 0.00055 |
| rs2902638 | 0.29 | 0.24 | 1.24 (1.13, 1.36) | 2.50e−05 | 0.26 | 0.25 | 1.03 (0.9, 1.17) | 0.71 | 0.00025 |
| rs10748858 | 0.36 | 0.41 | 0.81 (0.74, 0.88) | 1.24e−05 | 0.35 | 0.40 | 0.81 (0.72, 0.91) | 0.00055 | 2.65e−08 |
| rs2067832 | 0.45 | 0.50 | 0.80 (0.74, 0.87) | 4.73e−07 | 0.46 | 0.49 | 0.87 (0.77, 0.97) | 0.016 | 3.67e−08 |
| rs1980653 | 0.45 | 0.50 | 0.80 (0.74, 0.87) | 4.65e−07 | 0.46 | 0.50 | 0.87 (0.77, 0.98) | 0.021 | 5.02e−08 |
| rs11191865 | 0.45 | 0.51 | 0.80 (0.74, 0.87) | 2.82e−07 | 0.46 | 0.50 | 0.87 (0.77, 0.97) | 0.017 | 2.44e−08 |
| rs9419958 | 0.11 | 0.14 | 0.75 (0.66, 0.85) | 8.46e−05 | | | | | |
| rs9420907 | 0.11 | 0.14 | 0.75 (0.66, 0.85) | 9.32e−05 | 0.13 | 0.14 | 0.95 (0.8, 1.13) | 0.58 | 0.00045 |
| rs7074532 | 0.31 | 0.27 | 1.22 (1.12, 1.33) | 6.47e−05 | 0.29 | 0.28 | 1.01 (0.89, 1.15) | 0.84 | 0.00072 |
| rs7073827 | 0.33 | 0.29 | 1.22 (1.12, 1.33) | 4.01e−05 | 0.31 | 0.30 | 1.05 (0.93, 1.19) | 0.44 | 0.00014 |
| Chr. 11 | | | | | | | | | |
| rs10751635 | 0.48 | 0.43 | 1.25 (1.15, 1.35) | 1.86e−07 | 0.46 | 0.43 | 1.12 (1.0, 1.26) | 0.049 | 6.97e−08 |
| rs2301160 | 0.48 | 0.43 | 1.25 (1.15, 1.35) | 1.90e−07 | 0.46 | 0.42 | 1.16 (1.03, 1.3) | 0.013 | 1.24e−08 |
| rs7942850 | 0.46 | 0.38 | 1.38 (1.27, 1.5) | 9.29e−14 | 0.41 | 0.39 | 1.11 (0.98, 1.25) | 0.093 | 1.71e−12 |
| rs2071174 | 0.28 | 0.34 | 0.79 (0.72, 0.86) | 3.10e−07 | 0.32 | 0.32 | 1.02 (0.9, 1.16) | 0.75 | 6.40e−05 |
| rs7396030 | 0.16 | 0.20 | 0.74 (0.66, 0.82) | 5.90e−08 | 0.20 | 0.20 | 0.99 (0.86, 1.15) | 0.92 | 7.10e−06 |
| rs7103978 | 0.07 | 0.09 | 0.71 (0.61, 0.83) | 1.69e−05 | 0.08 | 0.09 | 0.85 (0.68, 1.05) | 0.12 | 1.07e−05 |
| rs7934606 | 0.52 | 0.42 | 1.52 (1.4, 1.65) | 5.46e−22 | 0.51 | 0.40 | 1.56 (1.39, 1.76) | 1.49e−13 | 6.87e−34 |
| rs6421972 | 0.52 | 0.42 | 1.51 (1.39, 1.64) | 1.62e−21 | 0.51 | 0.40 | 1.57 (1.39, 1.77) | 9.94e−14 | 1.44e−33 |
| rs7480563 | 0.42 | 0.51 | 0.69 (0.64, 0.75) | 4.17e−18 | 0.46 | 0.50 | 0.87 (0.78, 0.98) | 0.018 | 2.95e−17 |
| rs4077759 | 0.30 | 0.37 | 0.74 (0.67, 0.8) | 8.47e−13 | 0.34 | 0.36 | 0.91 (0.81, 1.03) | 0.14 | 2.14e−11 |
| rs6421966 | 0.15 | 0.18 | 0.79 (0.71, 0.89) | 4.73e−05 | 0.18 | 0.18 | 0.98 (0.84, 1.14) | 0.77 | 0.00048 |
| rs868903 | 0.38 | 0.49 | 0.64 (0.59, 0.7) | 1.26e−22 | 0.41 | 0.48 | 0.77 (0.69, 0.87) | 1.49e−05 | 9.18e−26 |
| rs2735727 | 0.38 | 0.44 | 0.79 (0.73, 0.86) | 8.58e−06 | | | | | |
| rs2857476 | 0.44 | 0.50 | 0.78 (0.71, 0.84) | 1.62e−06 | 0.46 | 0.51 | 0.85 (0.76, 0.96) | 0.0074 | 4.68e−08 |
| rs12417955 | 0.44 | 0.50 | 0.78 (0.71, 0.84) | 1.48e−06 | 0.46 | 0.50 | 0.85 (0.76, 0.96) | 0.0076 | 4.46e−08 |
| rs3829223 | 0.43 | 0.49 | 0.78 (0.72, 0.84) | 7.52e−07 | 0.45 | 0.50 | 0.81 (0.72, 0.91) | 0.0003 | 9.07e−10 |
| rs3793964 | 0.32 | 0.38 | 0.77 (0.71, 0.84) | 7.77e−07 | | | | | |
| rs2334659 | 0.12 | 0.16 | 0.71 (0.63, 0.8) | 4.71e−09 | 0.12 | 0.17 | 0.70 (0.59, 0.84) | 5.84e−05 | 1.22e−12 |
| rs7122936 | 0.33 | 0.40 | 0.76 (0.69, 0.82) | 3.69e−08 | 0.33 | 0.39 | 0.78 (0.69, 0.88) | 6.37e−05 | 1.02e−11 |
| rs7944761 | 0.40 | 0.45 | 0.81 (0.74, 0.88) | 3.98e−05 | 0.41 | 0.45 | 0.84 (0.75, 0.95) | 0.0042 | 5.55e−07 |
| rs4752744 | 0.10 | 0.07 | 1.36 (1.18, 1.57) | 4.42e−05 | 0.09 | 0.08 | 1.24 (1.01, 1.52) | 0.044 | 6.84e−06 |

TABLE 5-continued

Association information for all 198 SNPs chosen for replication. Blank Replication and Joint columns correspond to SNPs not successfully genotyped in replication

| | Discovery GWAS | | | | Replication | | | | |
|---|---|---|---|---|---|---|---|---|---|
| Chr. SNP | MAF Case | MAF Control | OR (95% CI) | P-value | MAF Case | MAF Control | OR (95% CI) | P-value | Joint P-value |
| rs11036021 | 0.52 | 0.48 | 1.20 (1.1, 1.3) | 2.85e−05 | 0.49 | 0.47 | 1.08 (0.96, 1.21) | 0.19 | 2.99e−05 |
| rs2736601 | 0.08 | 0.06 | 1.37 (1.18, 1.6) | 4.66e−05 | 0.08 | 0.08 | 1.01 (0.81, 1.25) | 0.96 | 0.00079 |
| rs2727267 | 0.08 | 0.06 | 1.37 (1.18, 1.6) | 4.21e−05 | 0.08 | 0.07 | 1.04 (0.83, 1.3) | 0.75 | 0.00042 |
| Chr. 12 | | | | | | | | | |
| rs12310569 | 0.18 | 0.15 | 1.29 (1.14, 1.46) | 8.70e−05 | 0.16 | 0.15 | 1.13 (0.94, 1.35) | 0.19 | 7.21e−05 |
| rs10845459 | 0.47 | 0.50 | 0.75 (0.65, 0.86) | 5.05e−05 | 0.51 | 0.49 | 1.14 (0.94, 1.38) | 0.17 | 0.011 |
| Chr. 13 | | | | | | | | | |
| rs1278760 | 0.33 | 0.37 | 0.69 (0.58, 0.83) | 4.79e−05 | | | | | |
| rs1278769 | 0.20 | 0.24 | 0.79 (0.72, 0.88) | 9.11e−07 | 0.20 | 0.24 | 0.80 (0.7, 0.92) | 0.002 | 6.72e−09 |
| Chr. 14 | | | | | | | | | |
| rs12879458 | 0.18 | 0.15 | 1.24 (1.11, 1.38) | 6.84e−05 | 0.17 | 0.15 | 1.14 (0.98, 1.34) | 0.096 | 2.52e−05 |
| rs10139381 | 0.24 | 0.27 | 0.58 (0.45, 0.75) | 7.43e−05 | 0.26 | 0.28 | 0.82 (0.59, 1.14) | 0.24 | 9.11e−05 |
| rs2781413 | 0.25 | 0.29 | 0.83 (0.76, 0.91) | 2.91e−05 | 0.26 | 0.27 | 0.95 (0.83, 1.08) | 0.42 | 0.00011 |
| rs1552126 | 0.45 | 0.41 | 1.18 (1.09, 1.28) | 9.45e−05 | | | | | |
| Chr. 15 | | | | | | | | | |
| rs1007177 | 0.29 | 0.34 | 0.78 (0.71, 0.85) | 5.59e−08 | 0.29 | 0.33 | 0.83 (0.73, 0.94) | 0.0046 | 1.26e−09 |
| rs1992272 | 0.29 | 0.35 | 0.78 (0.71, 0.85) | 3.49e−08 | 0.29 | 0.33 | 0.85 (0.75, 0.96) | 0.01 | 2.16e−09 |
| rs2289332 | 0.38 | 0.42 | 0.84 (0.77, 0.91) | 2.14e−05 | 0.37 | 0.41 | 0.88 (0.78, 0.99) | 0.036 | 2.80e−06 |
| rs11636361 | 0.38 | 0.43 | 0.83 (0.76, 0.9) | 6.53e−06 | | | | | |
| rs10518693 | 0.44 | 0.39 | 1.23 (1.14, 1.33) | 2.93e−06 | 0.45 | 0.41 | 1.20 (1.07, 1.36) | 0.0022 | 2.32e−08 |
| rs2034650 | 0.42 | 0.49 | 0.77 (0.71, 0.84) | 1.86e−09 | 0.42 | 0.47 | 0.82 (0.74, 0.93) | 0.00098 | 9.76e−12 |
| rs603104 | 0.42 | 0.46 | 0.84 (0.77, 0.91) | 8.14e−05 | | | | | |
| rs1849210 | 0.22 | 0.20 | 1.67 (1.29, 2.17) | 8.65e−05 | 0.20 | 0.21 | 0.84 (0.56, 1.25) | 0.39 | 0.0068 |
| rs351219 | 0.36 | 0.38 | 0.71 (0.6, 0.85) | 3.91e−05 | 0.39 | 0.37 | 1.10 (0.88, 1.39) | 0.41 | 0.0039 |
| rs6496932 | 0.16 | 0.19 | 0.80 (0.72, 0.89) | 3.65e−05 | 0.19 | 0.19 | 1.04 (0.9, 1.21) | 0.58 | 0.0023 |
| rs1828481 | 0.43 | 0.38 | 1.25 (1.15, 1.36) | 1.11e−06 | 0.40 | 0.40 | 1.00 (0.89, 1.13) | 0.93 | 5.56e−05 |
| rs7172789 | 0.43 | 0.38 | 1.25 (1.15, 1.36) | 1.12e−06 | 0.39 | 0.40 | 0.98 (0.87, 1.11) | 0.79 | 0.00013 |
| rs11858744 | 0.43 | 0.38 | 1.25 (1.15, 1.36) | 9.74e−07 | 0.40 | 0.39 | 1.00 (0.89, 1.13) | 0.98 | 5.97e−05 |
| rs16977252 | 0.30 | 0.25 | 1.24 (1.14, 1.36) | 3.36e−05 | 0.27 | 0.25 | 1.04 (0.92, 1.19) | 0.50 | 0.00016 |
| rs6496044 | 0.39 | 0.33 | 1.25 (1.15, 1.36) | 1.03e−05 | 0.37 | 0.34 | 1.13 (1.0, 1.27) | 0.045 | 1.95e−06 |
| rs10520597 | 0.37 | 0.32 | 1.24 (1.14, 1.35) | 3.05e−05 | 0.34 | 0.32 | 1.04 (0.93, 1.18) | 0.49 | 0.00014 |
| rs11633855 | 0.38 | 0.35 | 1.38 (1.17, 1.63) | 9.68e−05 | 0.33 | 0.35 | 1.08 (0.84, 1.39) | 0.56 | 0.00043 |
| rs1441479 | 0.37 | 0.35 | 1.38 (1.17, 1.63) | 8.39e−05 | 0.32 | 0.35 | 1.02 (0.79, 1.31) | 0.89 | 0.00099 |
| Chr. 16 | | | | | | | | | |
| rs17139255 | 0.19 | 0.16 | 1.25 (1.12, 1.38) | 3.45e−05 | 0.18 | 0.17 | 1.02 (0.88, 1.2) | 0.76 | 0.00037 |
| rs1548857 | 0.08 | 0.06 | 1.32 (1.13, 1.54) | 9.21e−05 | 0.07 | 0.07 | 1.11 (0.89, 1.38) | 0.35 | 0.00019 |

TABLE 5-continued

Association information for all 198 SNPs chosen for replication. Blank Replication and Joint columns correspond to SNPs not successfully genotyped in replication

| | Discovery GWAS | | | | Replication | | | | |
|---|---|---|---|---|---|---|---|---|---|
| Chr. SNP | MAF Case | MAF Control | OR (95% CI) | P-value | MAF Case | MAF Control | OR (95% CI) | P-value | Joint P-value |
| rs4843650 | 0.39 | 0.42 | 0.74 (0.63, 0.87) | 8.65e−05 | 0.41 | 0.42 | 0.94 (0.76, 1.18) | 0.61 | 0.00046 |
| Chr. 17 | | | | | | | | | |
| rs393152 | 0.17 | 0.23 | 0.72 (0.65, 0.8) | 9.26e−08 | 0.19 | 0.22 | 0.82 (0.71, 0.95) | 0.0075 | 3.50e−09 |
| rs417968 | 0.21 | 0.26 | 0.77 (0.7, 0.85) | 1.57e−05 | 0.24 | 0.26 | 0.91 (0.79, 1.04) | 0.16 | 1.50e−05 |
| rs1635291 | 0.20 | 0.25 | 0.75 (0.68, 0.83) | 1.49e−06 | | | | | |
| rs7215239 | 0.19 | 0.25 | 0.75 (0.68, 0.82) | 9.18e−07 | 0.21 | 0.24 | 0.84 (0.73, 0.97) | 0.017 | 6.96e−08 |
| rs12373139 | 0.17 | 0.22 | 0.71 (0.64, 0.79) | 7.07e−08 | 0.16 | 0.22 | 0.67 (0.58, 0.79) | 4.65e−07 | 2.68e−13 |
| rs17690703 | 0.21 | 0.26 | 0.78 (0.71, 0.86) | 3.42e−05 | 0.20 | 0.25 | 0.75 (0.65, 0.86) | 4.98e−05 | 1.04e−08 |
| rs17563986 | 0.17 | 0.23 | 0.71 (0.64, 0.78) | 3.39e−08 | 0.16 | 0.22 | 0.68 (0.58, 0.79) | 4.95e−07 | 1.27e−13 |
| rs1981997 | 0.17 | 0.23 | 0.71 (0.64, 0.78) | 2.52e−08 | 0.16 | 0.22 | 0.67 (0.58, 0.79) | 4.74e−07 | 8.87e−14 |
| rs8070723 | 0.17 | 0.23 | 0.71 (0.64, 0.79) | 3.87e−08 | 0.17 | 0.22 | 0.71 (0.61, 0.83) | 8.06e−06 | 1.61e−12 |
| rs7225002 | 0.35 | 0.41 | 0.79 (0.72, 0.86) | 7.60e−06 | 0.34 | 0.40 | 0.79 (0.7, 0.89) | 8.11e−05 | 3.04e−09 |
| rs2532274 | 0.17 | 0.23 | 0.72 (0.65, 0.8) | 1.29e−07 | 0.17 | 0.23 | 0.70 (0.6, 0.81) | 2.99e−06 | 2.43e−12 |
| rs2532269 | 0.17 | 0.23 | 0.71 (0.64, 0.79) | 9.61e−08 | 0.16 | 0.22 | 0.66 (0.57, 0.77) | 1.63e−07 | 1.61e−13 |
| rs2668692 | 0.17 | 0.22 | 0.71 (0.64, 0.79) | 1.04e−07 | 0.16 | 0.22 | 0.67 (0.58, 0.78) | 3.35e−07 | 3.12e−13 |
| rs183211 | 0.19 | 0.24 | 0.75 (0.68, 0.83) | 6.95e−06 | 0.20 | 0.23 | 0.84 (0.73, 0.97) | 0.019 | 4.96e−07 |
| rs169201 | 0.16 | 0.21 | 0.71 (0.64, 0.79) | 2.33e−07 | 0.15 | 0.20 | 0.70 (0.6, 0.82) | 8.97e−06 | 1.16e−11 |
| rs7224296 | 0.23 | 0.28 | 0.78 (0.71, 0.86) | 3.48e−05 | 0.26 | 0.29 | 0.87 (0.77, 0.99) | 0.038 | 4.71e−06 |
| rs199533 | 0.16 | 0.21 | 0.72 (0.64, 0.8) | 5.19e−07 | 0.15 | 0.20 | 0.70 (0.59, 0.81) | 6.18e−06 | 1.99e−11 |
| rs415430 | 0.16 | 0.21 | 0.72 (0.65, 0.8) | 7.86e−07 | 0.16 | 0.21 | 0.72 (0.62, 0.84) | 3.88e−05 | 1.48e−10 |
| Chr. 18 | | | | | | | | | |
| rs367024 | 0.19 | 0.16 | 1.23 (1.11, 1.37) | 8.30e−05 | 0.18 | 0.17 | 1.09 (0.94, 1.27) | 0.26 | 0.00011 |
| Chr. 19 | | | | | | | | | |
| rs12610495 | 0.34 | 0.29 | 1.29 (1.18, 1.41) | 9.57e−09 | 0.34 | 0.28 | 1.30 (1.15, 1.47) | 3.94e−05 | 1.68e−12 |
| rs2109069 | 0.36 | 0.31 | 1.28 (1.18, 1.4) | 1.22e−08 | 0.35 | 0.30 | 1.25 (1.1, 1.41) | 0.00045 | 2.42e−11 |
| rs10417008 | 0.16 | 0.19 | 0.79 (0.71, 0.88) | 1.92e−05 | 0.16 | 0.17 | 0.93 (0.8, 1.09) | 0.39 | 6.73e−05 |
| rs306477 | 0.46 | 0.42 | 1.19 (1.1, 1.29) | 5.00e−05 | 0.43 | 0.44 | 0.96 0.86, 1.08) | 0.51 | 0.0034 |
| Chr. 20 | | | | | | | | | |
| rs2145275 | 0.44 | 0.41 | 1.36 (1.18, 1.57) | 5.23e−05 | 0.42 | 0.41 | 1.18 (0.94, 1.47) | 0.15 | 3.43e−05 |
| rs6088520 | 0.46 | 0.50 | 0.85 (0.78, 0.92) | 5.27e−05 | 0.45 | 0.48 | 0.90 (0.8, 1.01) | 0.067 | 1.31e−05 |
| rs4810223 | 0.23 | 0.19 | 1.25 (1.13, 1.38) | 9.58e−05 | 0.23 | 0.21 | 1.13 (0.98, 1.29) | 0.089 | 3.08e−05 |
| Chr. 21 | | | | | | | | | |
| rs2823529 | 0.17 | 0.16 | 1.86 (1.35, 2.57) | 9.90e−05 | 0.17 | 0.16 | 1.13 (0.68, 1.86) | 0.64 | 0.00055 |
| rs2830234 | 0.43 | 0.40 | 1.29 (1.14, 1.46) | 9.42e−06 | 0.41 | 0.41 | 1.05 (0.89, 1.25) | 0.57 | 7.87e−05 |
| Chr. 23 | | | | | | | | | |
| rs7879375 | 0.13 | 0.10 | 1.40 (1.21, 1.63) | 2.68e−05 | 0.11 | 0.10 | 1.05 (0.83, 1.32) | 0.68 | 0.00025 |

TABLE 5-continued

Association information for all 198 SNPs chosen for replication. Blank Replication and Joint columns correspond to SNPs not successfully genotyped in replication

| | Discovery GWAS | | | | Replication | | | | |
|---|---|---|---|---|---|---|---|---|---|
| Chr. SNP | MAF Case | MAF Control | OR (95% CI) | P-value | MAF Case | MAF Control | OR (95% CI) | P-value | Joint P-value |
| rs3903350 | 0.15 | 0.11 | 1.42 (1.23, 1.63) | 2.94e−06 | | | | | |
| rs5924874 | 0.44 | 0.40 | 1.19 (1.07, 1.31) | 6.77e−05 | 0.43 | 0.42 | 1.08 (0.94, 1.24) | 0.30 | 0.00012 |

MAF: Minor allele frequency; minor allele defined as minor allele in combined case and control group;
OR: Odds ratio for the minor allele;
CI: Confidence Interval

TABLE 6

Adjusted Association information for all 181 SNPs successfully genotyped in replication using joint genotypes from subset of GWAS cases, all replication cases and all replication controls.

| | | Joint Analysis[a] | | Joint Analysis Adjusted for top SNP[b] | | Joint Analysis Adjusted for age[c] | |
|---|---|---|---|---|---|---|---|
| | Gene[b] | OR (95% CI) | P-value | OR (95% CI) | P-value | OR (95% CI) | P-value |
| Chr. 5p15 | | | | | | | |
| rs2736100 | TERT | 0.75 (0.677, 0.822) | 3.39e−09 | N/A | N/A | 0.76 (0.685, 0.839) | 7.49e−08 |
| Chr. 6p24 | | | | | | | |
| rs2076295 | DSP | 1.30 (1.184, 1.431) | 5.33e−08 | N/A | N/A | 1.29 (1.170, 1.425) | 3.74e−07 |
| Chr. 7q22 | | | | | | | |
| rs4727443 | | 1.19 (1.082, 1.315) | 4.06e−04 | N/A | N/A | 1.18 (1.068, 1.308) | 1.25e−03 |
| Chr. 11p15 | | | | | | | |
| rs868903 | | 0.74 (0.666, 0.810) | 5.74e−10 | 1.04 (0.934, 1.162) | 0.46 | 0.75 (0.681, 0.834) | 4.25e−08 |
| rs7934606 | MUC2 | 1.61 (1.459, 1.778) | 3.47e−21 | 1.06 (0.944, 1.182) | 0.34 | 1.57 (1.413, 1.735) | 9.90e−18 |
| rs6421972 | MUC2 | 1.62 (1.464, 1.784) | 1.85e−21 | 1.06 (0.944, 1.183) | 0.34 | 1.57 (1.415, 1.737) | 8.51e−18 |
| rs7480563 | MUC2 | 0.82 (0.747, 0.906) | 7.10e−05 | 1.10 (0.988, 1.225) | 0.08 | 0.85 (0.772, 0.942) | 1.78e−03 |
| rs7942850 | | 1.15 (1.042, 1.271) | 5.63e−03 | 0.94 (0.846, 1.054) | 0.31 | 1.10 (0.995, 1.224) | 0.06 |
| rs4077759 | | 0.87 (0.782, 0.957) | 4.86e−03 | 1.13 (1.015, 1.268) | 0.03 | 0.90 (0.809, 0.998) | 0.05 |
| rs2334659 | | 0.72 (0.626, 0.828) | 3.99e−06 | 0.89 (0.766, 1.034) | 0.13 | 0.75 (0.649, 0.869) | 1.21e−04 |
| rs7122936 | | 0.79 (0.716, 0.877) | 7.23e−06 | 1.01 (0.905, 1.130) | 0.85 | 0.80 (0.719, 0.888) | 3.10e−05 |
| Chr. 15q14-15 | | | | | | | |
| rs2034650 | | 0.84 (0.765, 0.924) | 3.38e−04 | N/A | N/A | 0.84 (0.756, 0.921) | 3.35e.04 |
| rs1992272 | DISP2 | 0.85 (0.763, 0.940) | 1.83e−03 | 0.93 (0.804, 1.080) | 0.35 | 0.84 (0.754, 0.938) | 1.79e−03 |
| Chr. 17q21 | | | | | | | |
| rs1981997 | MAPT | 0.69 (0.604, 0.776) | 2.90e−09 | N/A | N/A | 0.71 (0.621, 0.805) | 1.63e−07 |
| rs17563986 | MAPT | 0.69 (0.605, 0.776) | 2.72e−09 | 0.68 (0.171, 2.704) | 0.58 | 0.71 (0.621, 0.804) | 1.37e−07 |
| rs8070723 | MAPT | 0.70 (0.617, 0.791) | 1.38e−08 | 1.69 (0.720, 3.939) | 0.23 | 0.72 (0.636, 0.822) | 7.63e−07 |
| Chr. 19p13 | | | | | | | |
| rs12610495 | DPP9 | 1.35 (1.214, 1.495) | 1.99e−08 | N/A | N/A | 1.32 (1.185, 1.471) | 4.34e−07 |
| rs2109069 | DPP9 | 1.31 (1.179, 1.446) | 3.01e−07 | 0.88 (0.641, 1.208) | 0.43 | 1.28 (1.154, 1.427) | 3.92e−06 |

TABLE 6-continued

Adjusted Association information for all 181 SNPs successfully genotyped in replication using joint genotypes from subset of GWAS cases, all replication cases and all replication controls.

| | | Joint Analysis[a] | | Joint Analysis Adjusted for top SNP[b] | | Joint Analysis Adjusted for age[c] | |
|---|---|---|---|---|---|---|---|
| | Gene[b] | OR (95% CI) | P-value | OR (95% CI) | P-value | OR (95% CI) | P-value |
| Chr. 3q26 | | | | | | | |
| rs1881984 | | 1.21 (1.089, 1.335) | 3.07e−04 | 0.93 (0.794, 1.081) | 0.33 | 1.17 (1.052, 1.300) | 3.65e−03 |
| rs10936599 | MYNN | 1.35 (1.212, 1.507) | 6.29e−08 | 0.94 (0.708, 1.250) | 0.67 | 1.34 (1.197, 1.502) | 3.93e−07 |
| rs1997392 | | 1.37 (1.231, 1.524) | 6.87e−09 | 0.52 (0.139, 1.966) | 0.34 | 1.37 (1.228, 1.532) | 2.08e−08 |
| rs6793295 | LRRC34 | 1.38 (1.242, 1.535) | 2.32e−09 | N/A | N/A | 1.38 (1.238, 1.543) | 8.26e−09 |
| Chr. 4q22 | | | | | | | |
| rs2609255 | FAM13A | 1.32 (1.179, 1.481) | 1.66e−06 | N/A | N/A | 1.29 (1.144, 1.451) | 2.90e−05 |
| Chr. 5p15 | | | | | | | |
| rs2853676 | TERT | 0.83 (0.742, 0.928) | 1.05e−03 | 0.94 (0.83, 1.06) | 0.32 | 0.86 (0.753, 0.950) | 4.61e−03 |
| Chr. 6p24 | | | | | | | |
| rs10484326 | DSP | 0.78 (0.699, 0.880) | 3.60e−05 | 0.90 (0.76, 1.03) | 0.11 | 0.79 (0.703, 0.892) | 1.23e−04 |
| Chr. 10q24 | | | | | | | |
| rs10748858 | OBFC1 | 0.84 (0.761, 0.929) | 6.36e−04 | 0.88 (0.751, 1.040) | 0.14 | 0.84 (0.758, 0.933) | 1.04e−03 |
| rs2067832 | OBFC1 | 0.86 (0.781, 0.947) | 2.08e−03 | 1.25 (0.533, 2.915) | 0.61 | 0.88 (0.799, 0.976) | 0.02 |
| rs11191865 | OBFC1 | 0.86 (0.780, 0.945) | 1.80e−03 | N/A | N/A | 0.88 (0.798, 0.974) | 0.01 |
| Chr. 11p15 | | | | | | | |
| rs2301160 | | 1.17 (1.062, 1.288) | 1.49e−03 | 1.02 (0.920, 1.136) | 0.68 | 1.13 (1.025, 1.254) | 0.01 |
| rs3829223 | TOLLIP | 0.78 (0.706, 0.858) | 4.14e−07 | 1.03 (0.927, 1.150) | 0.56 | 0.79 (0.713, 0.872) | 3.78e−06 |
| rs2857476 | MUC5B | 0.82 (0.747, 0.907) | 7.90e−05 | 1.10 (0.990, 1.228) | 0.07 | 0.84 (0.759, 0.928) | 6.27e−04 |
| Chr. 13q34 | | | | | | | |
| rs1278769 | ATP11A | 0.80 (0.708, 0.893) | 1.06e−04 | N/A | N/A | 0.78 (0.695, 0.885) | 7.90e−05 |
| Chr. 15q14-15 | | | | | | | |
| rs1007177 | DISP2 | 0.84 (0.753, 0.929) | 8.26e−04 | 0.93 (0.80, 1.07) | 0.32 | 0.84 (0.749, 0.930) | 1.12e−03 |
| rs10518693 | IVD | 1.14 (1.037, 1.262) | 7.12e−03 | 1.00 (0.87, 1.17) | 0.95 | 1.15 (1.041, 1.276) | 6.42e−03 |
| Chr. 17q21 | | | | | | | |
| rs393152 | CRHR1, C17orf69 | 0.77 (0.683, 0.872) | 3.40e−05 | 4.29 (2.315, 7.940) | 3.67e−06 | 0.82 (0.721, 0.930) | 2.03e−03 |
| rs12373139 | IMP5 | 0.69 (0.604, 0.776) | 2.93e−09 | 0.71 (0.173, 2.882) | 0.63 | 0.71 (0.622, 0.806) | 1.79e−07 |
| rs17690703 | | 0.76 (0.676, 0.853) | 3.37e−06 | 1.18 (0.920, 1.506) | 0.19 | 0.77 (0.682, 0.869) | 2.20e−05 |
| rs2532274 | KIAA1267 | 0.69 (0.613, 0.784) | 5.68e−09 | 0.90 (0.553, 1.462) | 0.67 | 0.72 (0.635, 0.820) | 5.61e−07 |
| rs2532269 | KIAA1267 | 0.67 (0.590, 0.758) | 2.63e−10 | 0.42 (0.190, 0.938) | 0.03 | 0.69 (0.607, 0.786) | 1.99e−08 |
| rs2668692 | KIAA1267 | 0.68 (0.599, 0.769) | 1.13e−09 | 0.37 (0.127, 1.104) | 0.07 | 0.70 (0.616, 0.798) | 7.20e−08 |
| rs169201 | NSF | 0.71 (0.622, 0.804) | 1.23e−07 | 1.08 (0.778, 1.507) | 0.64 | 0.73 (0.639, 0.834) | 3.48e−06 |
| rs199533 | NSF | 0.71 (0.625, 0.809) | 2.31e−07 | 1.09 (0.792, 1.499) | 0.60 | 0.74 (0.647, 0.846) | 1.00e−05 |

TABLE 6-continued

Adjusted Association information for all 181 SNPs successfully genotyped in replication using joint genotypes from subset of GWAS cases, all replication cases and all replication controls.

| | | Joint Analysis[a] | | Joint Analysis Adjusted for top SNP[b] | | Joint Analysis Adjusted for age[c] | |
|---|---|---|---|---|---|---|---|
| | Gene[b] | OR (95% CI) | P-value | OR (95% CI) | P-value | OR (95% CI) | P-value |
| rs415430 | WNT3 | 0.72 (0.633, 0.817) | 3.83e−07 | 1.05 (0.800, 1.381) | 0.72 | 0.75 (0.659, 0.858) | 2.20e−05 |

[a]Based on joint analysis of GWAS and replication cases compared to controls to allow for adjustment for rs35705950, which is not on GWAS panel and age; GWAS cases were re-genotyped for Table 1 SNPs and rs35705950 using same platform and at same time as replication cases and controls.
bEach SNP was tested for association in a logistic regression model that also included the most highly associated SNP from the meta-analysis at that locus. The exception is chromosome 11p15, where each SNP was tested for association in a logistic regression model that also included rs35705950.

What is claimed is:

1. A method of detecting a single nucleotide polymorphism (SNP) in a subject having interstitial lung disease, the method comprising detecting an A allele of an rs3778337 SNP in a DSP gene, a C allele of a rs10484326 SNP in a DSP gene, or a combination thereof, in a first biological sample obtained from the subject.

2. The method of claim 1, comprising detecting an A allele of rs3778337 SNP in the DSP gene.

3. The method of claim 1, comprising detecting a C allele of rs10484326 SNP in the DSP gene.

4. The method of claim 1, comprising detecting an A allele of rs3778337 SNP in the DSP gene and a C allele of rs10484326 SNP in the DSP gene.

5. The method of claim 1, wherein the interstitial lung disease is a fibrotic lung disease.

6. The method of claim 1, wherein the interstitial lung disease is idiopathic pulmonary fibrosis, familial interstitial pneumonia, or idiopathic interstitial pneumonia.

7. The method of claim 1, wherein the first biological sample is blood.

8. The method of claim 1, wherein the subject is undergoing treatment for interstitial lung disease.

9. A method of detecting a single nucleotide polymorphism (SNP) in a subject having interstitial lung disease, the method comprising detecting:

(i) an A allele of an rs3778337 SNP in a DSP gene, a C allele of a rs10484326 SNP in a DSP gene, or a combination thereof, and (ii) a first level of expression of a DSP gene, in a first biological sample obtained from the subject.

10. The method of claim 9, comprising detecting an A allele of rs3778337 SNP in the DSP gene.

11. The method of claim 9, comprising detecting a C allele of rs10484326 SNP in the DSP gene.

12. The method of claim 9, comprising detecting an A allele of rs3778337 SNP in the DSP gene and a C allele of rs10484326 SNP in the DSP gene.

13. The method of claim 9, further comprising obtaining a second biological sample from the subject and detecting a level of expression of the DSP gene in the second biological sample; wherein the second biological sample from the subject is obtained at a later time than the first biological sample.

14. The method of claim 9, wherein the subject is undergoing treatment for interstitial lung disease.

15. The method of claim 9, wherein the interstitial lung disease is a fibrotic lung disease.

16. The method of claim 9, wherein the interstitial lung disease is idiopathic pulmonary fibrosis, familial interstitial pneumonia, or idiopathic interstitial pneumonia.

* * * * *